US007470675B2

(12) United States Patent
Horton et al.

(10) Patent No.: US 7,470,675 B2

(45) Date of Patent: Dec. 30, 2008

(54) METHODS FOR TREATING CANCER USING INTERFERON-ω-EXPRESSING POLYNUCLEOTIDES

(75) Inventors: Holly Horton, San Diego, CA (US); Suezanne Parker, San Diego, CA (US); Marston Manthorpe, San Diego, CA (US); Philip L. Felgner, San Diego, CA (US); Jukka Hartikka, San Diego, CA (US)

(73) Assignee: Vical Incorporated, San Diego, CA (US)

(*) Notice: Subject to any disclaimer, the term of this patent is extended or adjusted under 35 U.S.C. 154(b) by 0 days.

(21) Appl. No.: 11/709,868

(22) Filed: Feb. 23, 2007

(65) Prior Publication Data

US 2007/0225243 A1 Sep. 27, 2007

Related U.S. Application Data

(63) Continuation of application No. 09/557,907, filed on Apr. 21, 2000, now Pat. No. 7,268,120, which is a continuation-in-part of application No. 09/196,313, filed on Nov. 20, 1998, now abandoned.

(60) Provisional application No. 60/100,820, filed on Sep. 15, 1998, provisional application No. 60/079,914, filed on Mar. 30, 1998, provisional application No. 60/067,087, filed on Nov. 20, 1997.

(51) Int. Cl.

| | |
|---|---|
| ***A01K 54/04*** | (2006.01) |
| ***A61K 37/715*** | (2006.01) |

(52) U.S. Cl. ...................................... 514/44; 424/93.21

(58) Field of Classification Search .................... 514/44

See application file for complete search history.

(56) References Cited

U.S. PATENT DOCUMENTS

| | | | |
|---|---|---|---|
| 4,897,355 | A | 1/1990 | Eppstein et al. |
| 4,946,787 | A | 8/1990 | Eppstein et al. |
| 5,049,386 | A | 9/1991 | Eppstein et al. |
| 5,120,832 | A | 6/1992 | Goeddel et al. |
| 5,229,272 | A | 7/1993 | Paul et al. |
| 5,231,176 | A | 7/1993 | Goeddel et al. |
| 5,264,618 | A | 11/1993 | Felgner et al. |
| 5,268,169 | A | 12/1993 | Brandely et al. |
| 5,314,995 | A | 5/1994 | Fell, Jr. et al. |
| 5,349,053 | A | 9/1994 | Landolfi |
| 5,459,127 | A | 10/1995 | Felgner et al. |
| 5,578,475 | A | 11/1996 | Jessee |
| 5,580,859 | A | 12/1996 | Felgner et al. |
| 5,589,466 | A | 12/1996 | Felgner et al. |
| 5,641,665 | A | 6/1997 | Hobart et al. |
| 5,676,954 | A | 10/1997 | Brigham |
| 5,693,622 | A | 12/1997 | Wolff et al. |
| 5,703,055 | A | 12/1997 | Felgner et al. |
| 5,827,703 | A | 10/1998 | Debs et al. |
| 5,861,397 | A | 1/1999 | Wheeler |
| 5,910,488 | A | 6/1999 | Nabel et al. |
| 5,994,317 | A | 11/1999 | Wheeler |
| 6,022,874 | A | 2/2000 | Wheeler |
| 6,147,055 | A | 11/2000 | Hobart et al. |
| 6,214,804 | B1 | 4/2001 | Felgner et al. |
| 6,228,844 | B1 | 5/2001 | Wolff et al. |
| 6,399,588 | B1 | 6/2002 | Hobart et al. |
| 6,413,942 | B1 | 7/2002 | Felgner et al. |
| 6,586,409 | B1 | 7/2003 | Wheeler |
| 6,670,332 | B1 | 12/2003 | Wheeler |
| 6,673,776 | B1 | 1/2004 | Felgner et al. |
| 6,696,424 | B1 | 2/2004 | Wheeler |
| 6,706,694 | B1 | 3/2004 | Wolff et al. |
| 6,867,195 | B1 | 3/2005 | Felgner et al. |
| 6,875,748 | B2 | 4/2005 | Manthorpe et al. |
| 7,250,404 | B2 | 7/2007 | Felgner et al. |
| 2003/0186913 | A1 | 10/2003 | Wolff et al. |
| 2003/0203863 | A1 | 10/2003 | Hobart et al. |
| 2004/0023911 | A1 | 2/2004 | Felgner et al. |
| 2004/0132683 | A1 | 7/2004 | Felgner et al. |

FOREIGN PATENT DOCUMENTS

| | | | |
|---|---|---|---|
| CA | 1 169 793 | | 6/1984 |
| EP | 0 170 204 | A2 | 2/1986 |
| EP | 0 465 529 | A1 | 4/1998 |
| WO | WO 90/11092 | A1 | 10/1990 |
| WO | WO 91/14438 | A1 | 10/1991 |

(Continued)

OTHER PUBLICATIONS

Horton, Cancer Research, Aug. 15, 1999, vol. 59, p. 4064-4068.*

(Continued)

*Primary Examiner*—Michael C. Wilson

(74) *Attorney, Agent, or Firm*—Sterne, Kessler, Goldstein & Fox P.L.L.C.

(57) ABSTRACT

The present invention provides a pharmaceutical composition, comprising a non-infectious, non-integrating polynucleotide construct comprising a polynucleotide encoding an interferon ω and one or more cationic compounds. The present invention also provides methods of treating cancer in a mammal, comprising administering into a tissue of the mammal a non-infectious, non-integrating polynucleotide construct comprising a polynucleotide encoding a cytokine. In addition, the present invention also relates to the methodology for selective transfection of malignant cells with polynucleotides expressing therapeutic or prophylactic molecules in intra-cavity tumor bearing mammals. More specifically, the present invention provides a methodology for the suppression of an intra-cavity dissemination of malignant cells, such as intraperitoneal dissemination. Furthermore, the invention relates to compositions and methods to deliver polynucleotides encoding polypeptides to vertebrate cells in vivo, where the composition comprises an aqueous solution of sodium phosphate.

30 Claims, 30 Drawing Sheets

FOREIGN PATENT DOCUMENTS

| | | | |
|---|---|---|---|
| WO | WO 94/29469 | A2 | 12/1994 |
| WO | WO 95/09917 | A1 | 4/1995 |
| WO | WO 95/14381 | A1 | 6/1995 |
| WO | WO 95/14651 | A1 | 6/1995 |
| WO | WO 95/17373 | A1 | 6/1995 |
| WO | WO 96/18372 | A2 | 6/1996 |
| WO | WO 96/26179 | A1 | 8/1996 |
| WO | WO 96/40962 | A1 | 12/1996 |
| WO | WO 96/40963 | A1 | 12/1996 |
| WO | WO 96/41873 | A1 | 12/1996 |
| WO | WO 97/00085 | A1 | 1/1997 |
| WO | WO 97/00241 | A1 | 1/1997 |
| WO | WO 97/30089 | A1 | 8/1997 |
| WO | WO 98/08947 | A1 | 3/1998 |
| WO | WO 99/26663 | A2 | 6/1999 |
| WO | WO 99/64615 | | 12/1999 |

OTHER PUBLICATIONS

Acsadi, G., et al., "Direct Gene Transfer and Expression into Rat Heart in Vivo," *New Biol.* 3:71-81, W.B. Saunders (1991).

Adachi, T., et al., "Tumoricidal effect of human macrophage-colony-stimulating factor against human-ovarian-carcinoma-bearing athymic mice and its therapeutic effect when combined with cisplatin," *Cancer Immunol. Immunother*. 37:1-6, Springer-Verlag (1993).

Adolf, G.R., "Monoclonal Antibodies and Enzyme Immunoassays Specific for Human Interferon (INF) ω1: Evidence that IFN-ω1 is a Component of Human Leukocyte IFN," *Virology 175*:410-417, Elsevier Science Ltd. (1990).

Adolf, G.R., et al., "Human interferon ω1: isolation of the gene, expression in Chinese hamster ovary cells and characterization of the recombinant protein," *Biochim. Biophys. Acta 1089*:167-174, Elsevier Science Ltd. (1991).

Adolf, G.R., "Human interferon omega-a review," *Multiple Sclerosis 1*:S44-S47, SAGE Publications (1995).

Almadrones, L., et al., "Arterial, Peritoneal, and Intraventricular Access Devices," *Sem. Oncol. Nursing 11*:194-202, W.B. Saunders (1995).

Aihara, H. and Miyazaki, J.-I., "Gene transfer into muscle by electroporation in vivo," *Nature Biotechnol.* 16:867-870, Nature America Publishing (Sep. 1998).

Aoki, K., et al., "Gene Therapy for Peritoneal Dissemination of Pancreatic Cancer by Liposome-Mediated Transfer of Herpes Simplex Virus Thymidine Kinase Gene," *Human Gene Therapy 8*:1105-1113, Mary Ann Liebert, Inc. (Jun. 1997).

Baron, S., et al., "The Interferons. Mechanisms of Action and Clinical Applications," *JAMA 266*:1375-1383, American Medical Association (1991).

Bast, Jr., R.C., et al., "Immunotherapy of a Murine Ovarian Carcinoma with *Corynebacterium parvum* and Specific *Heteroantiserum*. I. Activation of Peritoneal Cells to Mediate Antibody-Dependent Cytotoxicity," *J. Immunol.* 123:1945-1951, American Association of Immunologists (1979).

Beatty, J.D., et al., "Liposomes as immune adjuvants: T cell dependence," *Surgery 96*:345-351, Mosby-Year Book (1984).

Belldegrun, A., et al., "Human Renal Carcinoma Line Transfected With Interleukin-2 and/or Interferon α Gene(s): Implications for Live Cancer Vaccines," *J. Natl. Cancer Inst.* 85:207-216, Oxford University Press (1993).

Beller, U., et al., "Phase IB Study of Low-Dose Intraperitoneal Recombinant Interleukin-2 in Patients with Refractory Advanced Ovarian Cancer: Rationale and Preliminary Report," *Gynecol. Oncol.* 34:407-412, Academic Press (1989).

Benedetti Panici, P., et al., "Recombinant interleukin-2 continuous infusion in ovarian cancer patients with minimal residual disease at second-look," *Cancer Treatment Rev 16*(*Suppl. A*):123-127, Academic Press (1989).

Berek, J.S., et al., "Immunotherapy with Biochemically Dissociated Fractions of *Propionibacterium acnes* in a Murine Ovarian Cancer Model," *Cancer Res.* 44:1871-1875, American Association for Cancer Research (1984).

Bramson, J., et al., "Construction of a Double Recombinant Adenovirus Vector Expressing a Heterodimeric Cytokine: In Vitro and In Vivo Production of Biologically Active Interleukin-12," *Hum. Gene Ther.* 7:333-342, Mary Ann Liebert, Inc. (Feb. 1996).

Brunda, M.J., et al., "Antitumor and Antimetastatic Activity of Interleukin 12 against Murine Tumors," *J. Exp. Med.* 178:1223-1230, The Rockefeller University Press (1993).

Budker, V., et al., "The efficient expression of intravascularly delivered DNA in rat muscle," *Gene Ther.* 5:272-276, Nature Publishing Group (1998).

Capon, D.J., et al., "Two Distinct Families of Human and Bovine Interferon-α Genes Are Coordinately Expressed and Encode Functional Polypeptides," *Mol. Cell. Biol.* 5:768-779, American Society of Microbiology (1985).

Chapman, P.B., et al., "A phase I trial of intraperitoneal recombinant interleukin 2 in patients with ovarian carcinoma," *Investig. New Drugs 6*:179-188, Kluwer Academic Publishers (1988).

Chen, Y., et al., "DNA Vaccines Encoding Full-Length or Truncated Neu Induce Protective Immunity against Neu-Expressing Mammary Tumors," *Canc. Res.* 58:1965-1971, American Association for Cancer Research (May 1998).

Childers, J.M., et al., "Laparoscopic Surgical Staging of Ovarian Cancer," *Gynecol. Oncol.* 59:25-33, Academic Press (1995).

Clement, P.B., "Reactive Tumor-Like Lesions of the Peritoneum," *Am. J. Clin. Pathol.* 103:673-676, J.B. Lippincott Company (1995).

Coll, J.-L., et al., "Long-term survival of immunocompetent rats with intraperitoneal colon carcinoma tumors using herpes simplex thymidine kinase/genciclovir and IL-2 treatments," *Gene Ther.* 4:1160-1166, Nature Publishing Group (Nov. 1997).

Cordell, B., et al., "Isolation and Characterization of a Cloned Rat Insulin Gene," *Cell 18*:533-543, Cell Press (1979).

Crystal, R.G., "Transfer of genes to Humans: Early lessons and obstacles to success," *Science 270*:404-410, American Assn. for the Advancement of Science (1995).

Dalgleish, A.G. and Souberbielle B.E., "The development of therapeutic vaccines for the management of malignant melanoma," *Cancer Surv.* 26:289-319, Cold Spring Harbor Press (1996).

Danko, I., et al., "Pharmacological enhancement of in vivo foreign gene expression in muscle," *Gene Ther.* 1:114-121, Nature Publishing Group (1994).

Davis, H.L., et al., "Direct Gene Transfer into Skeletal Muscle In Vivo: Factors Affecting Efficiency of Transfer and Stability of Expression," *Hum. Gene Ther.* 4:151-159, M.A. Liebert (1993).

Deonarain, M.P., "Ligand-targeted receptor-mediated vectors for gene delivery," *Exp. Opin. Ther. Patients 8*:53-69, Informa Healthcare (1998).

Desnick, R.J. and Schuchman, E.H., "Gene therapy for genetic diseases," *Acta Paediatr. Jpn.* 40:191-203, Blackwell Scientific (Jun. 1998).

Doh, S.G., et al., "Spatial-temporal patterns of gene expression in mouse skeletal muscle after injection of lacZ plasmid DNA," *Gene Ther.* 4:648-663, (1997).

Dougherty, G.J., et al., "Inhibitory effect of locally produced and exogenous interleukin-6 on tumor growth in vivo," *Cancer Immunol. Immunother.* 38:339-345, Springer-Verlag (1994).

Edwards, R.P., et al., "Comparison of Toxicity and Survival Following Intraperitoneal Recombinant Interleukin-2 for Persistent Ovarian Cancer After Platinum: Twenty-Four-Hour Versus 7-Day Infusion," *J. Clin. Oncol.* 15:3399-3407, American Society of Clinical Oncology (Nov. 1997).

Feinstein, S.I., et al., "Family of Human α-Interferon-Like Sequences," *Mol. Cell. Biol.* 5:510-517, American Society for Microbiology (1985).

Felgner, P.L., et al., "Lipofection: A highly efficient, lipid-mediated DNA-transfection procedure," *Proc. Natl. Acad. Sci. USA 84*:7413-7417, National Academy of Sciences (1987).

Felgner, P.L. and Ringold, G.M., "Cationic liposome-mediated transfection," *Nature 337*:387-388, Nature Publishing Group (1989).

Felgner, J.H., et al., "Enhanced Gene Delivery and Mechanism Studies with a Novel Series of Cationic Lipid Formulations," *J. Biol. Chem.* 269:2550-2561, American Society for Biochemistry and Molecular Biology (1994).
Ferrantini, M., et al., "$\alpha^1$-Interferon Gene Transfer into Metastatic Friend Leukemia Cells Abrogated Tumorigenicity in Immunocompetent Mice: Antitumor Therapy by Means of Interferon-producing Cells," *Cancer Res.* 53:1107-1112, American Association for Cancer Research (1993).
Ferrantini, M., et al., "IFN-$\alpha$1 Gene Expression into a Metaastatic Murine Adenocarcinoma (TS/A) results in $CD8^+$ T Cell-Mediated Tumor Rejection and Development of Antitumor-Immunity. Comparative Studies with IFN-$\gamma$-Producing TS/A Cells," *J. Immunol.* 153:4604-4615, The American Association of Immunologists (1994).
Fjeld, J.G., et al., "Radio-immunotargeting in experimental animal models of intraperitoneal cancer," *Acta Obstet. Gynecol. Scand. Suppl.* 71:105-111, Scandinavian University Press (1992).
Flores, I., et al., "Human Interferon Omega ($\omega$) Binds to the $\alpha/\beta$ Receptor," *J. Biol. Chem.* 266:19875-19877, The American Society for Biochemistry and Molecular Biology, Inc. (1991).
Forstner, R., et al., "Ovarian Cancer Recurrence: Value of MR Imaging," *Radiology 196*:715-720, Radiological Society of North America (1995).
Freedman, R.S., et al., "Intraperitoneal Adoptive Immunotherapy of Ovarian Carcinoma with Tumor-Infiltrating Lymphocytes and Low-Dose Recombinant Interleukin-2: A Pilot Trial," *J. Immunother.* 16:198-210, Raven Press, Ltd. (1994).
Friedman, R.M., "Pharmacology of Interferons in Humans," in: *Interferons: A Primer*, Academic Press, New York, pp. 104-115 (1981).
Galvani, D.W. and Cawley, J.C., "Pharmacology of INF$\alpha$," in "Cytokine Therapy," Galvani, D.W. and Cawley, J.C., eds., Press Syndicate of the Cambridge University, New York City, NY, pp. 114-115 (1992).
Gough, N.M., et al., "Structure and expression of the mRNA for murine granulocyte-macrophage colony stimulating factor," *EMBO J.* 4:645-653, IRL Press Limited (1985).
Gould-Fogerite, S., et al., "Chimerasome-mediated gene transfer in vitro and in vivo," *Gene 84*:429-438, Elsevier Science Publishers B.V. (1989).
Gramazinski, R.A., et al., "Immune response to a Hepatitis B DNA Vaccine in Aotus Monkeys: A Comparison of Vaccine Forumlation, Route, and Method of Administration," *Mol. Med.* 4:109-118, The Feinstein Institute for Medical Research (1998).
Hamilton, T.C., "Ovarian Cancer, Part I: Biology," in *Curr Probl Cancer*, Mosby-Year Book, Inc., St. Louis, MO, pp. 3-57 (1992).
Hartikka, J., et al., "An Improved Plasmid DNA Expression Vector for Direct Injection into Skeletal Muscle," *Hum Gene Ther.* 7:1205-1217, M.A. Liebert (Jun. 1996).
Hauptmann, R. and Swetly, P., "A novel class of human type I interferons," *Nucl. Acids Res.* 13:4739-4749, IRL Press (1985).
Henderson, et al., "Therapeutic potential of cytokine manipulation," Trends in Pharmacological Science 13:145-152, (1992).
Hersh, E.M., and Stopeck, A.T., "Advances in the Biological Therapy and Gene Therapy for Malignant Disease," *Clin. Canc. Res.* 3:2623-2629, American Association for Cancer Research (Dec. 1997).
Horton, H.M., et al., "A gene therapy for cancer using intramuscular injection of plasmid DNA encoding interferon $\alpha$," *Proc. Natl. Acad. Sci. USA* 96:1553-1558, National Academy of Sciences (1999).
Hsu, M.J. and Juliano, R.L., "Interactions of Liposomes with the Reticuloendothelial System. II. Nonspecific and Receptor-Mediated Uptake of Liposomes by Mouse Peritoneal Macrophages," *Biochim. et Biophys. Acta 720*:411-419, Elsevier Biomedical Press (1982).
Huang, H., et al., "Gene therapy for hepatocellular carcinoma: long-term remission of primary and metastatic tumors in mice by interleukin-2 gene therapy in vivo," *Gene Ther.* 3:980-987, Nature Publishing Group (Nov. 1996).
Imakawa, K., et al., "Interferon-like sequence of ovine trophoblast protein secreted by embryonic trophectoderm," *Nature 330*:337-379, Nature Publishing Group (1987).
Irvine, K.R., et al., "Cytokine Enhancement of DNA Immunization Leads to Effective Treatment of Established Pulmonary Metastases," *J. Immunol.* 156:238-245, The American Association of Immunologists (Jan. 1996).
Jiao, S., et al., "Direct Gene Transfer into Nonhuman Primate Myofibers In Vivo," *Hum. Gene Ther.* 3:21-33, Mary Ann Liebert, Inc. (1992).
Jones, G.J. and Itri, L.M., "Safety and Tolerance of Recombinant Interferon Alfa-2a (Roferon®-A) in Cancer Patients," *Cancer 57*:1709-1715, Wiley (1986).
Kaido, T., et al., "IFN-$\alpha_1$ gene transfection completely abolishes the tumorigenicity of murine B16 melanoma cells in allogenic DBA/2 mice and decreases their tumorigenicity in syngeneic C57BL/6 mice," *Int. J. Cancer 60*:221-229, Wiley- Liss, Inc. (1995).
Kariko, K., et al., "Phosphate-enhanced transfection of cationic lipid-complexed mRNA and plasmid DNA," *Biochim. Biophys. Acta 1369*:320-334, Elsevier Science Ltd. (1998).
Kashima, N., et al., "Unique structure of murine interleukin-2 as deduced from cloned cDNAs," *Nature 313*:402-404, Nature Publishing Group (1985).
Kataoka, A., et al., "A Study on the Distribution of Metastases at Autopsy in 70 Patients with Ovarian Cancer," *Acta Obstet Gynaecol Jpn 46*:337-344, Japan Society of Obstetrics and Gynecology (1994).
Kichler, A., et al., "Influence of the DNA complexation medium on the transfection efficiency of lipospermine/DNA particles," *Gene Ther.* 5:855-860, Nature Publishing Group (1998).
Kigawa, J., et al., "Retroperitoneal Lymphadenectomy, Including the Para-aortic Nodes in Patients with Stage III Ovarian Cancer," *Am. J. Clin. Oncol.* 17:230-233, Raven Press, Ltd. (1994).
Kikuchi, Y., et al., "Effects of granulocyte-colony-stimulating factor and interleukin-2 on ascites formation and the survival time of nude mice bearing human ovarian cancer cells," *Cancer Immunol. Immunother.* 43:257-261, Springer-Verlag (Dec. 1996).
Knapp, R.C. and Berkowitz, R.S., "*Corynebacterium parvum* as an immunotherapeutic agent in an ovarian cancer model," *Am. J. Obstet. Gynecol.* 128:782-786, The C.V. Mosby Company (1977).
Kubeš, M., et al., "Cross-Species Antiviral and Antiproliferative Activity of Human Interferon-$\omega$," *J. Interferon Res.* 14:57-59, Mary Ann Liebert, Inc. (1994).
Labhasetwar, V., et al., "A DNA Controlled-Release Coating for Gene transfer: transfection in Skeletal and cardiac Muscle," *J. Pharma. Sci.* 87:1347-1350, Wiley (Nov. 1998).
Lawson, C.M., et al., "In Vivo Expression of an Interferon-$\alpha$ Gene by Intramuscular Injection of Naked DNA," *J. Interferon and Cytokine Res.* 17:255-261, Mary Ann Liebert, Inc. (May 1997).
Levy, M.Y., et al., "Characterization of plasmid DNA transfer into mouse skeletal muscle: evaluation of uptake mechanism, expression and secretion of gene products into blood," *Gene Ther.* 3:201-211, Nature Publishing Group (1996).
Lissoni, P., et al., "Intracavitary administration of interleukin-2 as palliative therapy for neoplastic effusions," *Tumori 78*:118-120, Casa Editrice Ambrosiana (1992).
Lotze, M.T., et al., "Intraperitoneal Administration of Interleukin-2 in Patients with Cancer," *Arch. Surg.* 121:1373-1379, American Medical Assn. (1986).
Malone, R.W., et al., "Cationic liposome-mediated RNA transfection," *Proc. Natl. Acad. Sci. USA 86*:6077-6081, National Academy of Sciences (1989).
Mandl, C.W., et al., "In vitro-synthesized infectious RNA as an attenuated live vaccine in a flavivirus model," *Nat. Med.* 4:1438-1440, Nature America Inc. (Dec. 1998).
Manthorpe, M., et al., "Gene Therapy by Intramuscular Injection of Plasmid DNA: Studies on Firefly Luciferase Gene Expression in Mice," *Hum Gene Ther.* 4:419-431, M.A. Liebert (1993).
Markman, M., et al., "Phase I Trial of Intraperitoneal Taxol: A Gynecoloic Oncology Group Study," *J. Clin. Oncol.* 10:1485-1491, American Society of Clinical Oncology (1992).
Marshall, E., "Cancer Trial of Interleukin-12 Halted," *Science 268*:1555, American Association for the Advancement of Science (1995).
Mathiesen, I., "Electropermeabilization of skeletal muscle enhances gene transfer in vivo," *Gene Ther.* 6:508-514, Nature Publishing Group (1999).

Miller, N. and Vile, R., "Targeted vectors for gene therapy," *FASEB J.* 9:190-199, The Federation of American Societies for Experimental Biology (1995).
Mir, L.M., et al., "Long term, high level in vivo gene expression after electric pulse-mediated gene transfer into skeletal muscle," *C R Acad Sci III.* 321:893-899, Editions Scientifiques et Médicales Elsevier (1998).
Mir, L.M., et al., "High-efficiency gene transfer into skeletal muscle mediated by electric pulses," *Proc. Natl. Acad. Sci. USA 96*:4262-4267, National Academy of Sciences (Apr. 1999).
Moelling, K., "Naked DNA—the poor man's gene therapy?" *Gene Ther.* 5:573-574, Stockton Press (May 1998).
Mumper, R.J., et al., "Polyvinyl Derivatives as Novel Interactive Polymers for Controlled Gene Delivery to Muscle," *Pharma. Res.* 13:701-709, Kluwer Academic (1996).
Mumper, R.J., et al., "Protective interactive noncondensing (PINC) polymers for enhanced plasmid distribution and expression in rat skeletal muscle," *J. Controlled Release 52*:191-203, Elsevier Science Ltd. (1998).
Naumann, R.W., et al., "The Groshong Catheter as an Intraperitoneal Access Device in the treatment of Ovarian Cancer patients," *Gynecol. Oncol.* 50:291-293, Academic Press (1993).
Nicolau, C., et al., "In vivo expression of rat insulin after intravenous administration of the liposome-entrapped gene for rat insulin I," *Proc. Natl. Acad. Sci. USA 80*:1068-1072, National Academy of Sciences (1983).
Nieroda, C., et al., "Interferon-ω Augments Major Histocompatibility and Human Tumor-Associated Antigen Expression," *Mol. Cell. Different.* 4:335-351, CRC Press (1996).
Norman, J., et al., "Adjuvants for Plasmid DNA vaccines," in *Methods in Molecular medicine* vol. 29, DNA Vaccines: Methods and Protocols, Lowrie, D.B., Whalen, R.G., Humana Press Inc., Totowa, N.J. pp. 185-196, (1999).
Ogura, H., et al., "Implantation of Genetically Manipulated Fibroblasts into Mice as Antitumor α-Interferon Therapy," *Cancer Res.* 50:5102-5106, American Association for Cancer Research (Aug. 1990).
Okamoto, T., et al., "Induction of antibody response to human tumor antigens by gene therapy using a fusigenic viral liposome vaccine," *Gene Therapy 4*:969-976, Stockton Press(1997).
Ottow, R.T., et al., "Immunotherapy of Intraperitoneal Cancer with Interleukin 2 and Lymphokine-Activated Killer Cells reduces Tumor Load and Prolongs Survival in Murine Models," *Cell. Immunol.* 104:366-376, Academic Press (1987).
Parker, S.E., et al., "Cancer gene Therapy Using Plasmid DNA: Safety Evaluation in rodents and Non-human Primates," *Hum. Gene. Ther.* 6:575-590, M.A. Liebert (1995).
Pestka, S. and Langer, J.A., "Interferons and their actions," *Ann. Rev. Biochem.* 56:727-777, Annual Reviews (1987).
Porgador, A., et al., "Interleukin 6 Gene Transfection into Lewis Lung Carcinoma Tumor Cells Suppresses the Malignant Phenotype and Confers Immunotherapeutic Competence against Parental Metastatic Cells," *Cancer Res.* 52:3679-3686, American Association for Cancer Research (1992).
Qin, Y.-J., et al., "Gene Suture-A Novel method for Intramuscular Gene Transfer and its Application in Hypertension Therapy," *Life Sciences 65*:2193-2203, Pergamon Press (1999).
Quesada, J.R., et al., "Treatment of Hairy Cell Leukemia with recombinant α-Interferon," *Blood 68*:493-497, American Society of Hematology (1986).
Rakhmilevich, A.L., et al., "Cytokine Gene Therapy of Cancer Using Gene Gun Technology: Superior Antitumor Activity of Interleukin-12," *Hum. Gene Ther.* 8:1303-1311, Mary Ann Liebert, Inc. (Jul. 1997).
Rakhmilevich, A.L., et al., "Gene gun-mediated skin transfection with interleukin 12 gene results in regression of established primary and metastatic murine tumors," *Proc. Natl. Acad. Sci. USA 93*:6291-6296, National Academy of Sciences (Jun. 1996).
Rammensee, H.-G., et al., "Protein-specific cytotoxic T lymphocytes. Recognition or transfectants expressing intracellular, membrane-associated of secreted forms of β-galactosidase," *Immunogenet.* 30:296-302, Springer-Verlag (1989).
Raz, E., et al., "Systemic immunological effects of cytokine genes injected into skeletal muscle," *Proc. Natl. Acad. Sci. USA 90*:4523-4527, National Academy of Sciences (1993).
Raz, E., et al., "Modulation of disease activity in murine systemic lupus erythematosus by cytokine gene delivery," *Lupus 4*:286-292, SAGE Publications (1995).
Rizzuto, G., et al., "Efficient and regulated erythropoietin production by naked DNA injection and muscle electroporation," *Proc. Natl. Acad. Sci. USA 96*:6417-6422, National Academy of Sciences (May 1999).
Ross, G., et al., "Gene Therapy in the United States: A Five-year Status report," *Hum. Gene Ther.* 7:1781-1790, Mary Ann Liebert, Inc. (Sep. 1996).
Roth, J.A. and Cristiano, R.J., Gene Therapy for cancer; What have we done and where are we going? *J. Natl. Cancer Inst.* 89:21-39, Oxford University Press (1997).
Rubin, J., et al., "Phase I study of immunotherapy of hepatic metastases of colorectal carcinoma by direct gene transfer of an allogeneic histocompatibility antigen, HLA-B7," *Gene Ther.* 4:419-425, Nature Publishing Group (May 1997).
Saffran, D.C., et al., "Immunotherapy of established tumors in mice by intratumoral injection of interleukin-2 plasmid DNA: Induction of CD8 T-cell immunity," *Cancer Gene Ther.* 5:321-330, Nature Publishing Group (Sep.-Oct. 1998).
San, H., et al., "Safety and Short-term Toxicity of a Novel Cationic Lipid Formulation for Human Gene therapy," *Hum. Gene Ther.* 4:781-788, Mary Ann Liebert, Inc. (1993).
Santodonato, L., et al., "Cure of Mice with Established Metastatic Friend Leukemia Cell Tumors by a Combined Therapy with Tumor Cells Expressing Both Interferon-α1 and Herpes Simplex Thymidine Kinase Followed by Ganciclovir," *Hum. Gene Ther.* 7:1-10, Mary Ann Liebert, Inc. (Jan. 1996).
Santodonato, L., et al., "local and systemic antitumor response after combined therapy of mouse metastatic tumors with tumor cells expressinf IFN-α and HSVtk: perspectives for the generation of cancer vaccines," *Gene Ther.* 4:1246-1255, Nature Publishing Group (Nov. 1997).
Sedlacek, H.H., et al., "Vaccination for treatment of tumors: A critical comment," *Crit Rev Oncog 5*:555-587, Begell House (1994).
Smith, B.F., et al., "Humoral and cellular immune responses of dogs immunized with a nucleic acid vaccine encoding human carcinoembryonic antigen," *Gene Ther.* 5:865-868, Nature Publishing Group (1998).
Son, K., "Cisplatin-based interferon γ gene therapy of murine ovarian carcinoma," *Cancer Gene Ther.* 4:391-396, Nature Publishing Group (Nov.-Dec. 1997).
Sparano, J.A., et al., "Phase II Trials of High-Dose Interleukin-2 and Lymphokine-Activated Killer Cells in Advanced Breast Carcinoma of the Lung, Ovary, and Pancreas and Other Tumors," *J. Immunother.* 16:216-223, Raven Press (1994).
Steis, R.G., et al., "Intraperitoneal Lymphokine-Activated Killer-Cell and interleukin-2 Therapy for Malignancies Limited to the Peritoneal cavity," *J. Clin. Oncol.* 8:1618-1629, American Society of Clinical Oncology (1990).
Stewart, H.J., et al., "Interferon sequence homolgy and receptor binding activity of ovine trophoblast antiluteolytic protein," *J. Endocrinol.* 115:R13-R15, Society for Endocrinology (1987).
Stewart, J.A., et al., "Phase I Trial of Intraperitoneal Recombinant Interleukin-2/Lymphokine-activated Killer Cells in Patients with Ovarian Cancer," *Cancer Res.* 50:6302-6310, American Association for Cancer Research (1990).
Stopeck, A.T., et al., "Phase I Study of Direct gene Transfer of an Allogeneic Histocompatibility Antigen, HLA-B7, in Patients With Metastatic Melanoma," *J. Clin. Oncol.* 15:341-349, American Society of Clinical Oncology (Jan. 1997).
Sugaya, S., et al., "Inhibition of Tumor Growth by Direct Intratumoral Gene Transfer of Herpes Simplex Virus Thymidine Kinase Gene with DNA-Liposome Complexes," *Hum. Gene Ther.*, 7:223-230, Mary Ann Liebert, Inc. (Jan. 1996).
Sun, W.H., et al., "In vivo cytokine gene transfer by gene gun reduces tumor growth in mice," *Proc. Natl. Acad. Sci. USA 92*:2889-2893, National Academy of Sciences (1995).

Sutcliffe, J.G., "Nucleotide sequence of the ampicillin resistance gene of *Escherichia coli* plasmid pBR322," *Proc. Natl. Acad. Sci. USA 75*:3737-3741, National Academy of Sciences (1978).

Szala, S., et al., "The use of cationic liposomes DC-CHOL/DOPE and DDAB/DOPE for direct transfer of *Escherichia coli* cytosine deaminase gene into growing melanoma tumors," *Gene Ther*. 3:1026-1031, Nature Publishing Group (Nov. 1996).

Tan, J., et al., "Injection of Complementary DNA Encoding Interleukin-12 Inhibits Tumor Establishment at a Distant Site in a Murine Renal Carcinoma Model," *Canc. Res*. 56:3399-3403, American Association for Cancer Research (Aug. 1996).

Thomason, D.B. and Booth, F.W., "Stable incorporation of a bacterial gene into adult rat akeletal muscle in vivo," *Am J Physiol*. 258:C578-C581, American Physiological Society (Mar. 1990).

Tokui, M., et al., "Intramuscular Injection of Expression Plasmid DNA Is an Effective Means of Long-Term Systemic Delivery of Interleukin-5," *Biochem. Biophys. Res. Comm*. 233:527-531, Academic Press (Apr. 1997).

Tone, Y., et al., "Structure and chromosomal location of the mouse interleukin-12 p35 and p40 subunit genes," *Eur. J. Immunol*. 26:1222-1227, VCH Verlagsgesellschaft (Jun. 1996).

Urba, W.J., et al., "Intraperitoneal Lymphokine-Activated Killer Cell/Interleukin-2 Therapy in Patients with Intra-abdominal Cancer: Immunologic Considerations," *J. Natl. Cancer Inst*. 81:602-611, Oxford University Press (1989).

Vanhaelen, C.P.J. and Fischer, R.I., "Requirements for Successful Immunotherapy and Chemoimmunotherapy of a Murine Model of Ovarian Cancer," *Cancer Res*. 41:980-983, American Association for Cancer Research (1981).

Verma, I.M. and Somia, N., "Gene therapy-promises, problems and prospects," *Nature 389*:239-242, Nature Publishing Group (1997).

Vitadello, M., et al., "Gene Transfer in Regenerating Muscle," *Hum. Gene Ther*. 5:11-18, Mary Ann Liebert, Inc. (1994).

Welander, C.E., "Overview of preclinical and clinical studies of interferon alfa-2b in combination with cytotoxic drugs," *Investigational New Drugs 5*:S47-59, Kluwer Academic (1987) (abstract).

Wells, D.J., "Improved gene transfer by direct plasmid injection associated with regeneration in mouse skeletal muscle," *FEBS Letters 332*:179-182, Elsevier Science B.V. (Oct. 1993).

West, W.H., et al., "Constant-infusion recombinant interleukin-2 in adoptive immunotherapy of advanced cancer," *New Engl. J. Med*. 316:898-905, Massachusetts Medical Society (1987).

Wheeler, C.J., et al., "A novel cationic lipid greatly enhances plasmid DNA delivery and expression in mouse lung," *Proc. Natl. Acad. Sci. USA 93*:11454-11459, National Academy of Sciences (Oct. 1996).

Winnacker, E.-L., "7 Expression Vectors in Prokaryotes," in *From Genes to Clones*, Weller, M.G., eds., Weinheim, Germany, pp. 290-293 (1987).

Wolff, J.A., et al., "Conditions Affecting Direct Gene transfer into Rodent Muscle In Vivo," *BioTechniques 11*:474-485, Informa Healthcare USA, Inc. (1991).

Wigginton, J.M., et al., "Administration of Interleukin 12 With Pulse Interleukin 2 and the Rapid and Complete Eradication of Murine Renal Carcinoma," *J. Natl. Canc. Inst*. 88:38-43, Oxford University Press (Jan. 1996).

Xiang, Z., and Ertl, H.C.J., "Manipulation of the Immune Response to a Plasmid-Encoded Viral Antigen by Coinoculation with Plasmids Expressing Cytokines," *Immunity 2*:129-135, Cell Press (1995).

Yagi, K., et al., "Interferon-β endogenously produced by intratumoral injection of cationic liposome-encapsulated gene: cytocidal effect of glioma transplanted into nude mouse brain," *Biochem Mol Biol Int*. 32:167-171, Taylor & Francis (1994).

Yankauckas, M.A., et al., "Direct Intratumor Injections of IL-2 Plasmid DNA: An Effective Method for Immunotherapy," J. Cell Biochem. Suppl. 21A:429, Abstr. C6-552 (1995).

Yeow, W.-S., et al., "Antiviral Activities of Individual Murine IFN-α Subtypes In Vivo: Intramuscular Injection of IFN Expression Constructs Reduces Cytomegalovirus Replication," *J. Immunol*. 160:2932-2939, The American Association of Immunologists, Inc. (Mar. 1998).

Yu, D., et al., "Liposome-mediated in vivo E1A gene transfer suppressed dissemination of ovarian cancer cells that overexpress HER-2/*neu," Oncogene 11*:1383-1388, Nature Publishing Group (1995).

Zhang, J.F., et al., "Gene therapy with an adeno-associated virus carrying an interon gene results in tumor growth suppression and regression," Cancer Gene Ther. 3:31-38, Nature Publishing Group (Jan.-Feb. 1996).

Zhang, J.-F., et al., "Treatment of a human breast cancer xenograft with an adenovirus vector containing an interferon gene results in rapid regression due to viral oncolysis and gene therapy," *Proc. Natl. Acad. Sci. USA 93*:4513-4518, National Academy of Sciences (Apr. 1996).

Database EMBASE, Accession No. 1997118387, English abstract of Kinoshita, Y., et al., "The possibility of gene immunotherapy for tumor using in vivo lipofection procedure," *Biotherapy 11*:448-450, Elsevier Science B.V. (1997).

European Search Report for European Patent Application No. EP 03 01 2772, mailed Jun. 21, 2004.

International Search Report for International Patent Application No. PCT/US97/01420, mailed Jun. 2, 1997.

Rosenberg, S.A., "The Immunotherapy and Gene Therapy of Cancer," *J. Clin. Oncol*. 10:180-199, American Society of Clinical Oncology (1992).

* cited by examiner

Figure 2
A
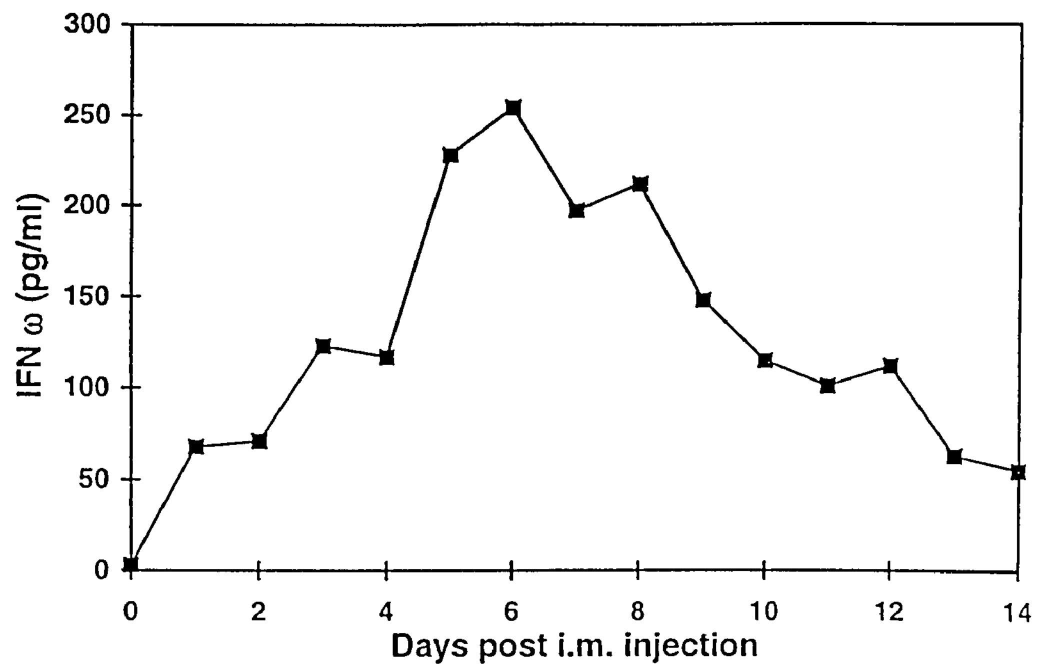
B
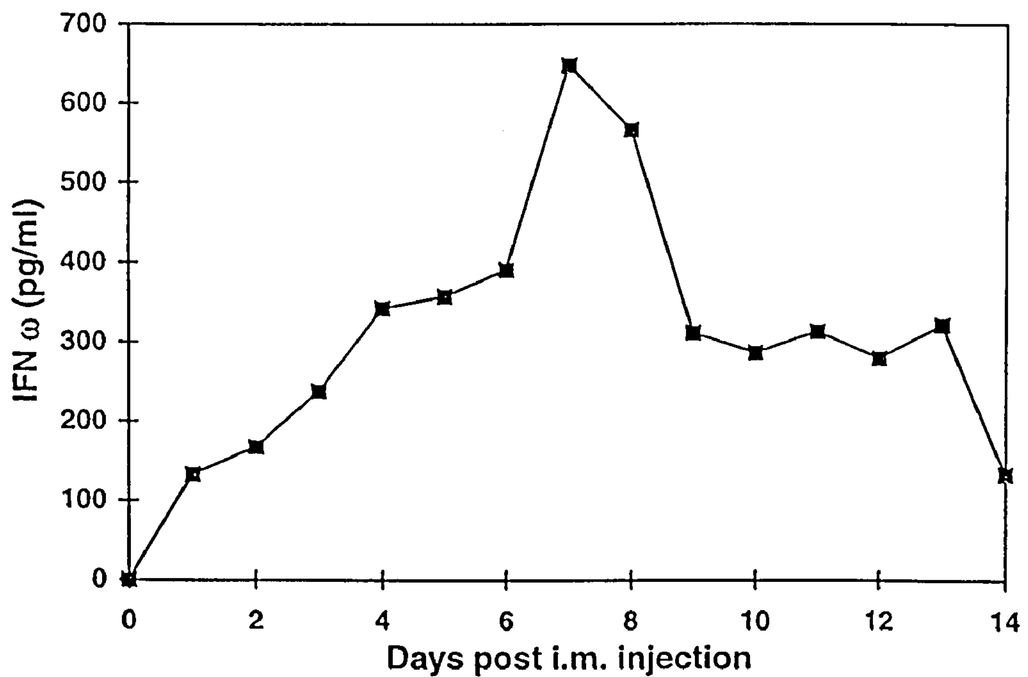

Figure 4
A
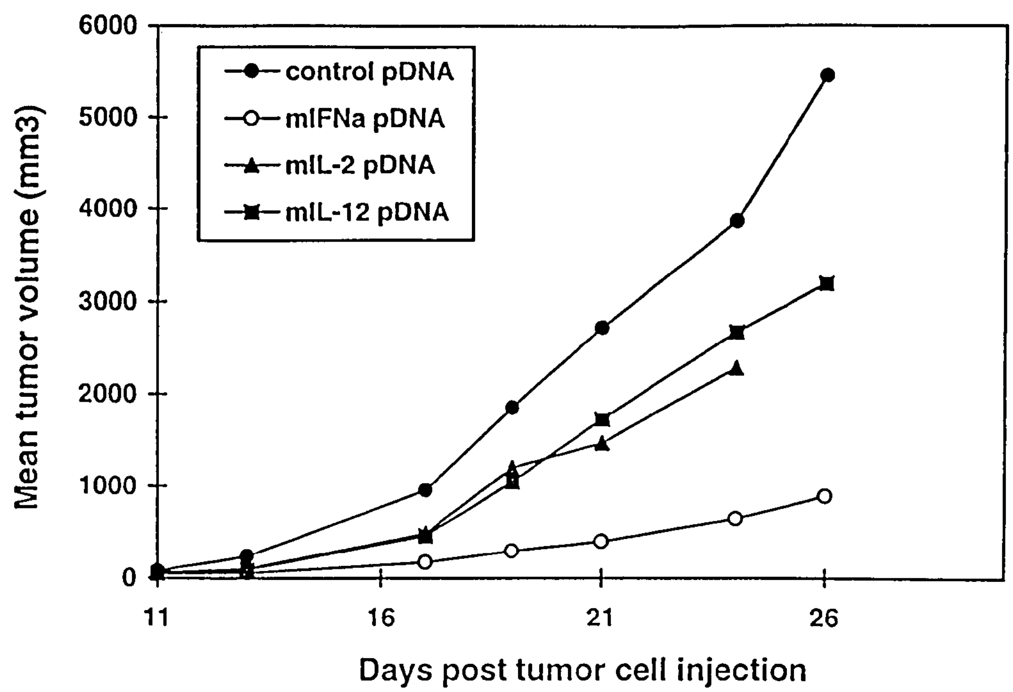
B
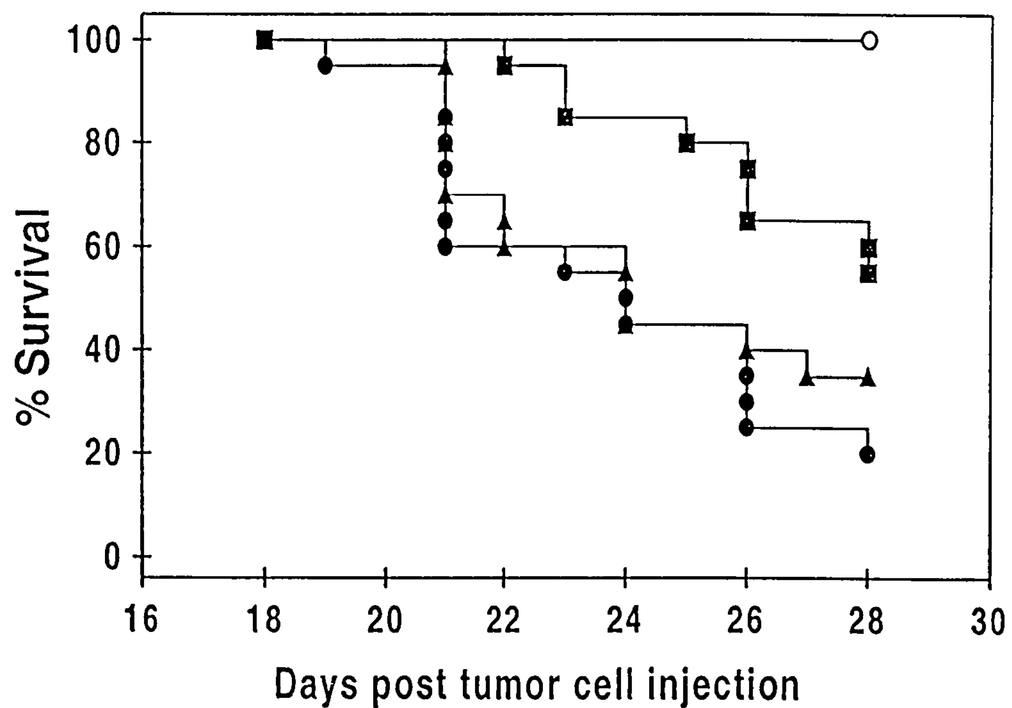

Figure 5
A
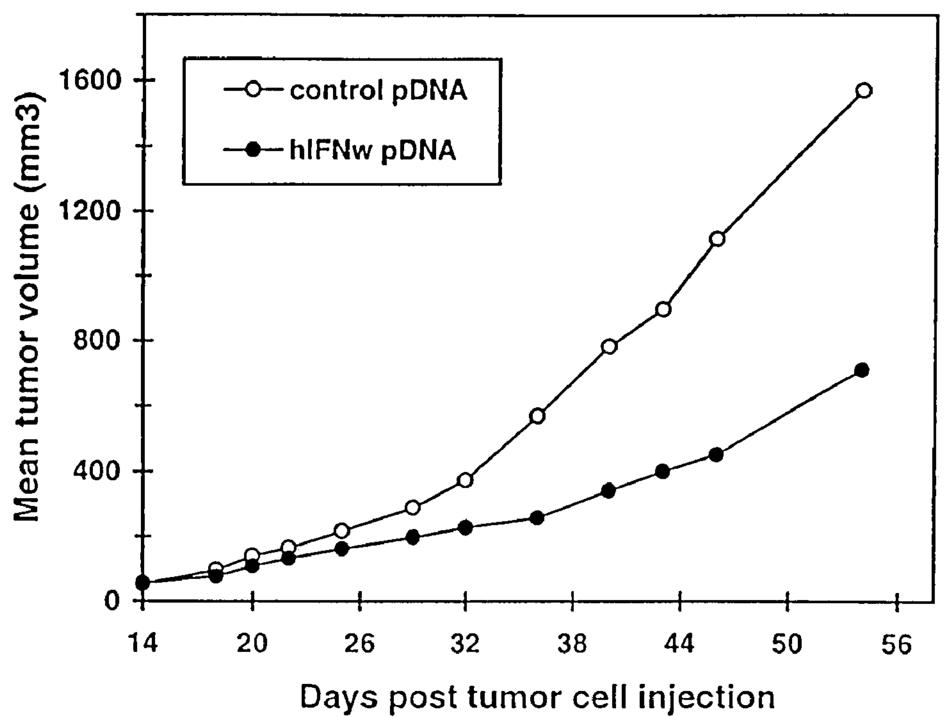
B
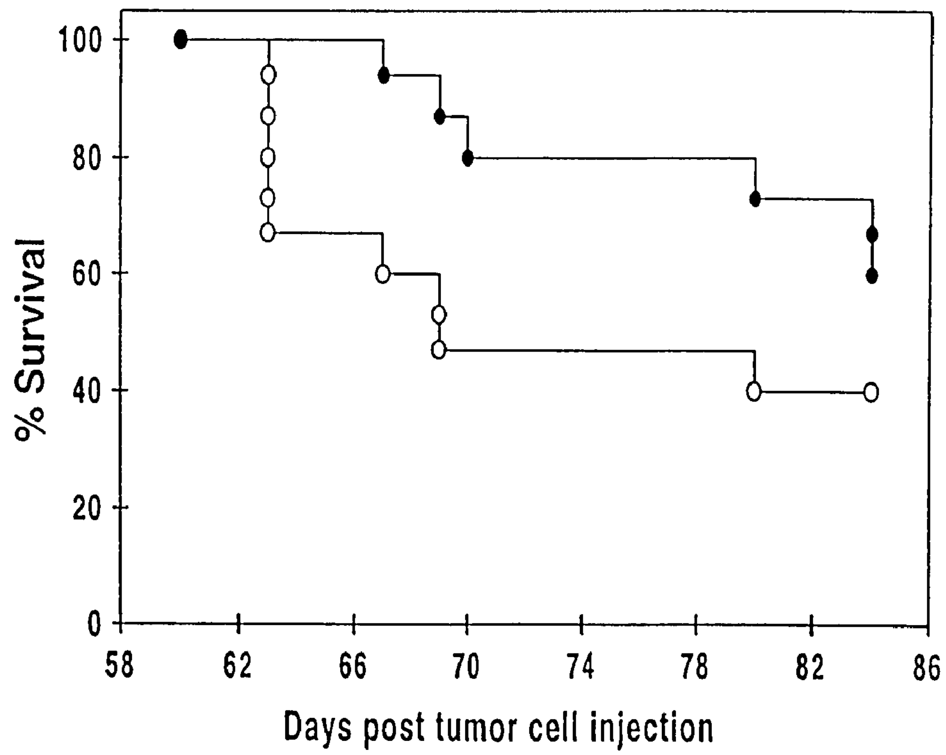

Figure 7
A
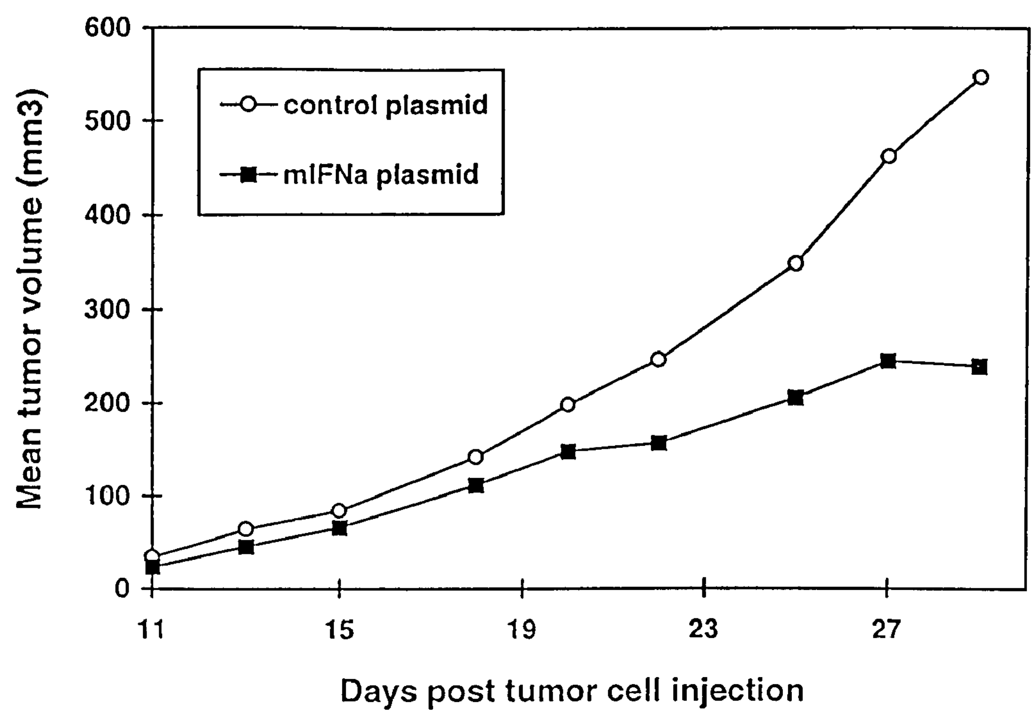
B
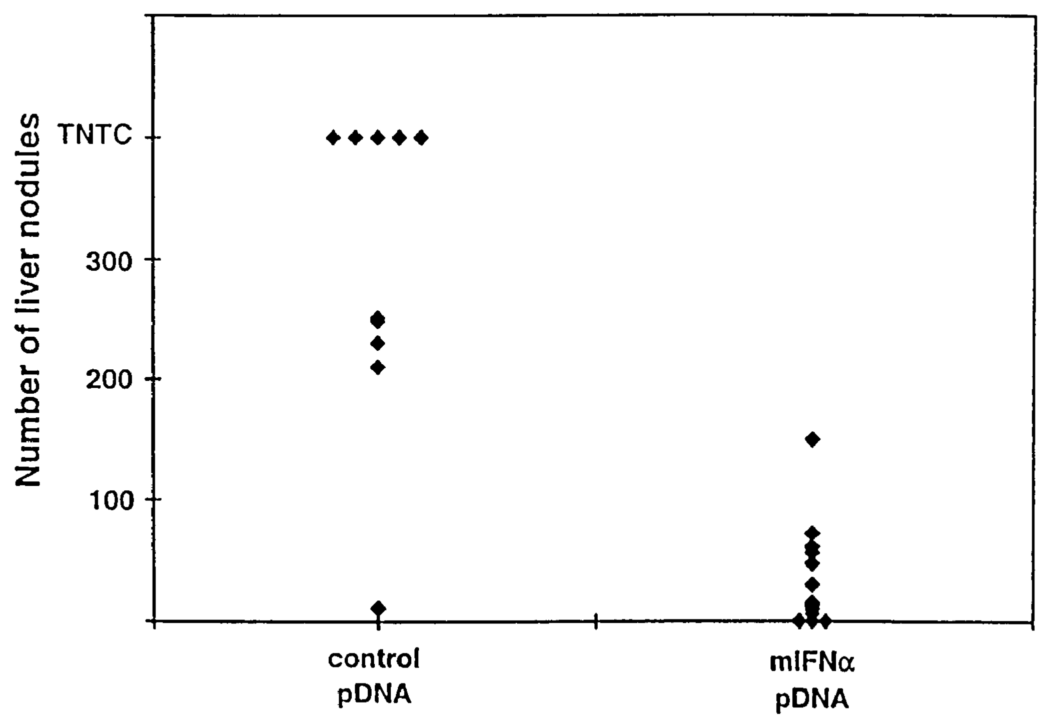

Figure 8
100 µg DNA:
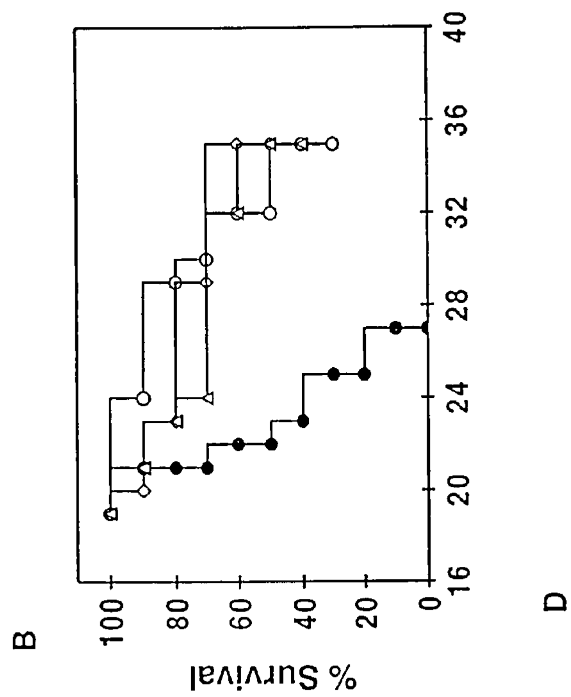
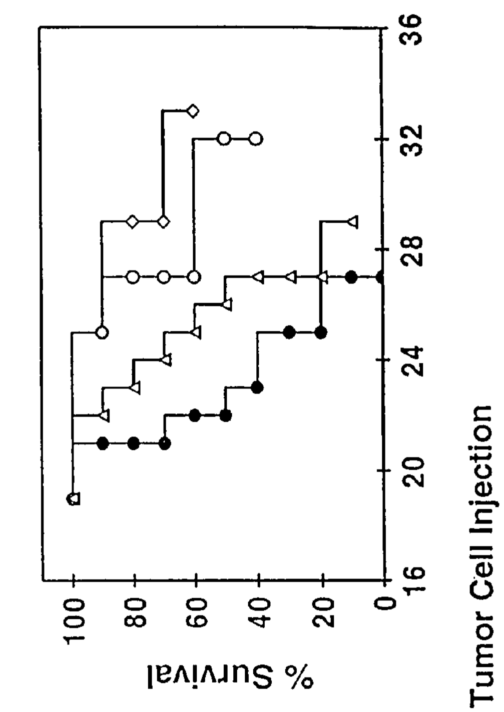
50 µg DNA:
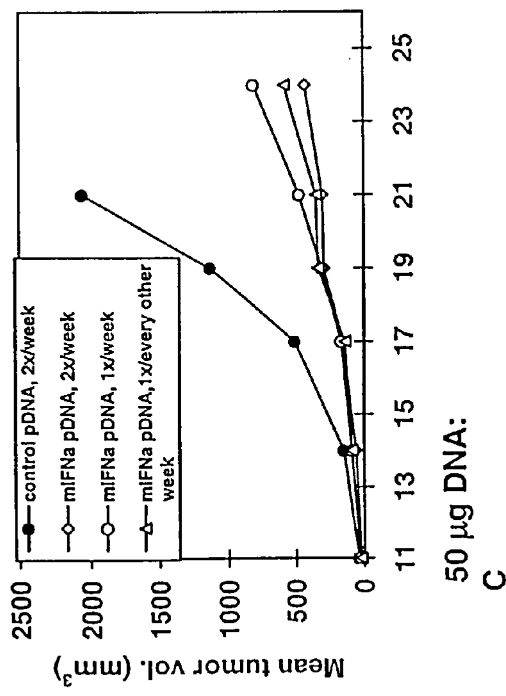
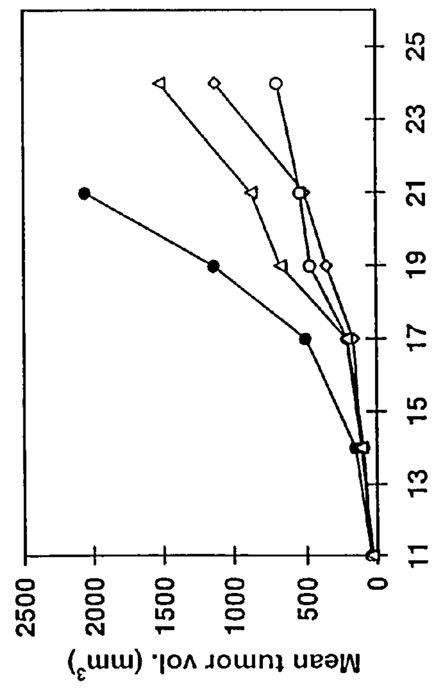

Nude Mice:
A
B
Mean tumor vol. (mm$^3$)
control pDNA
mIFNa pDNA
% Survival
Beige-Nude Mice:
C
D
Days post tumor cell injection Figure 10
A
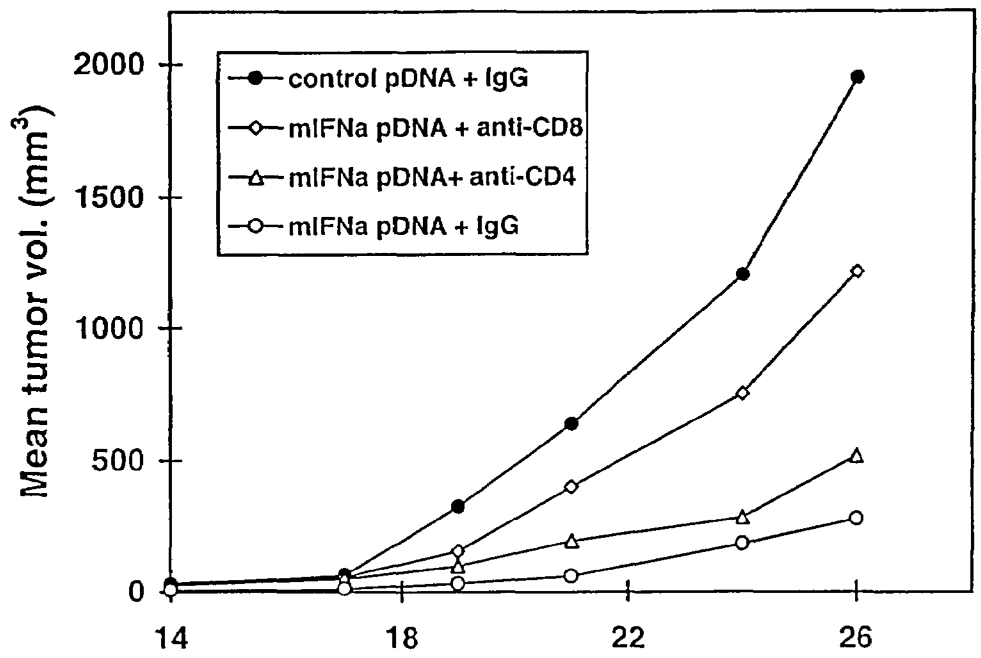
B
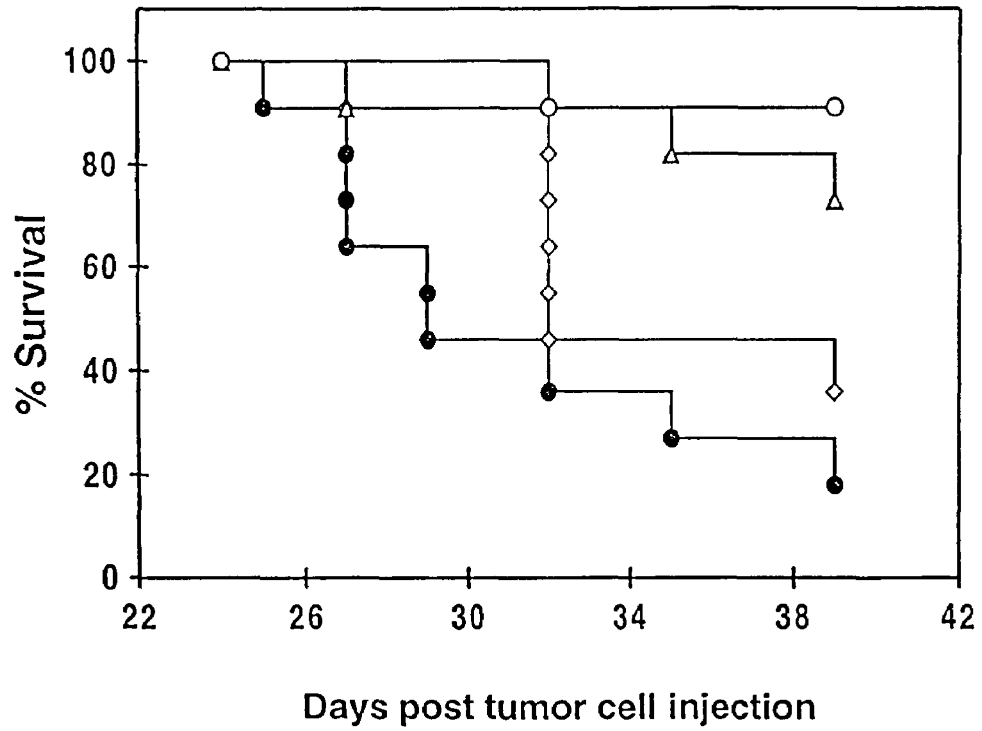

Figure 11
A
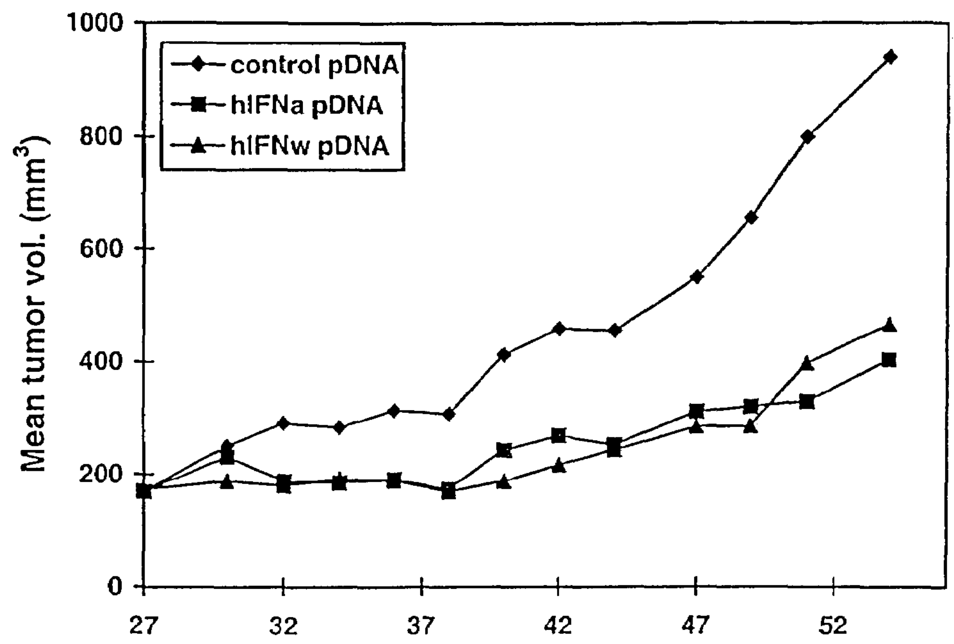
B
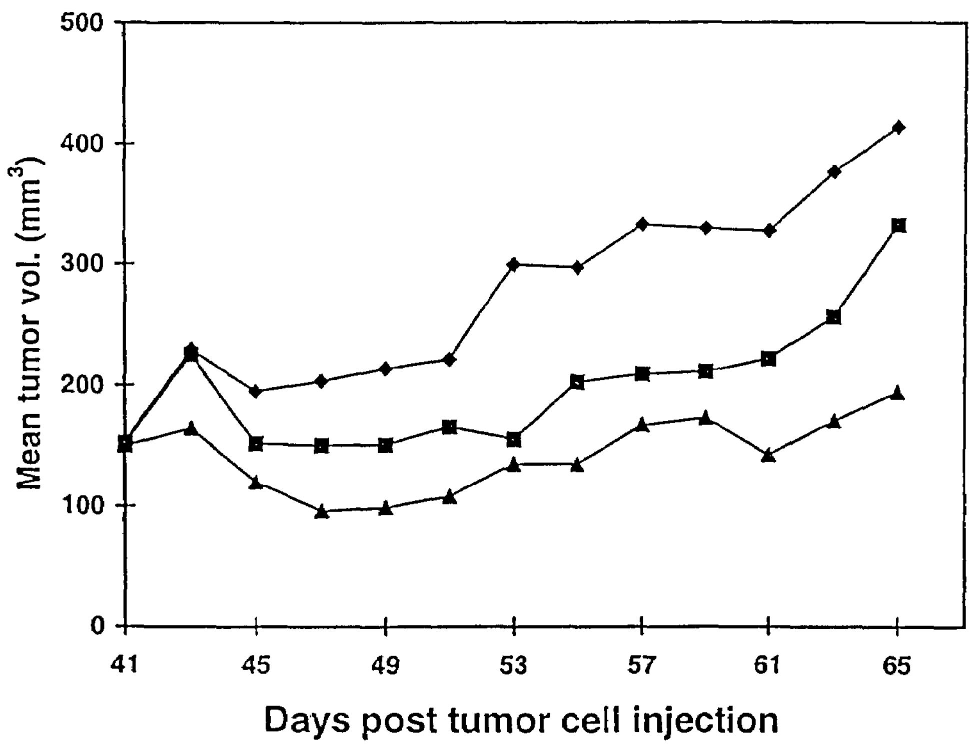

Figure 12
A
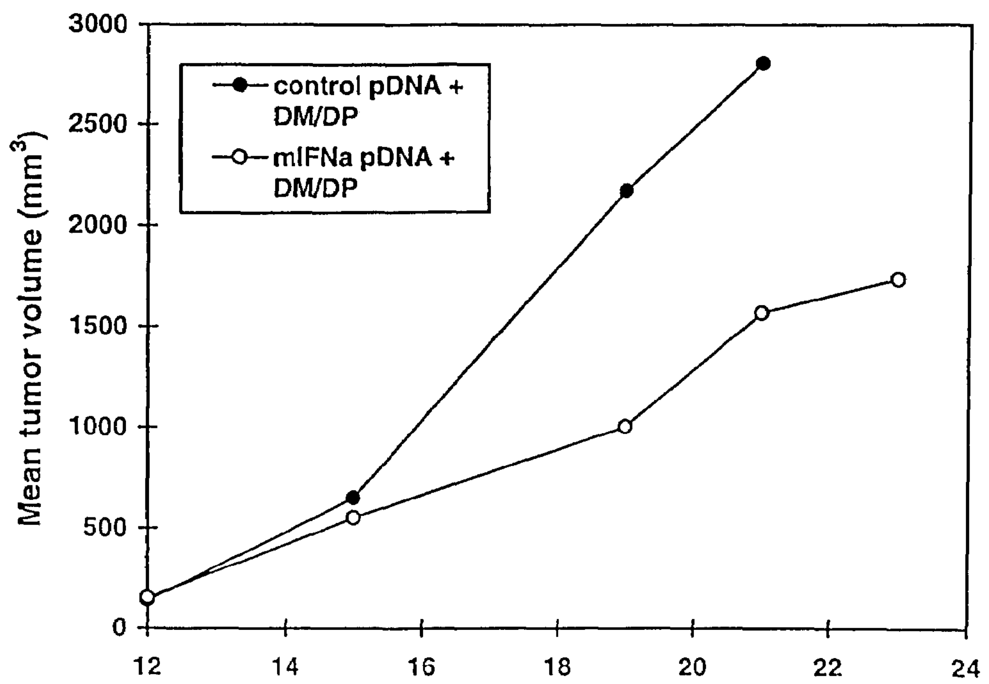
B
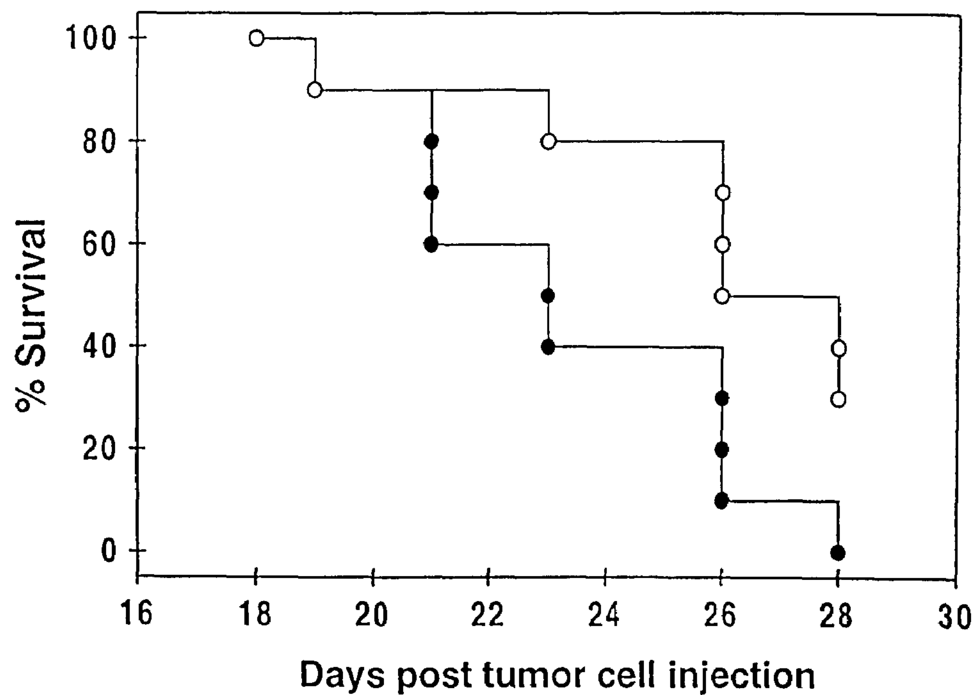

Figure 13
A Day 1 after DNA:lipid
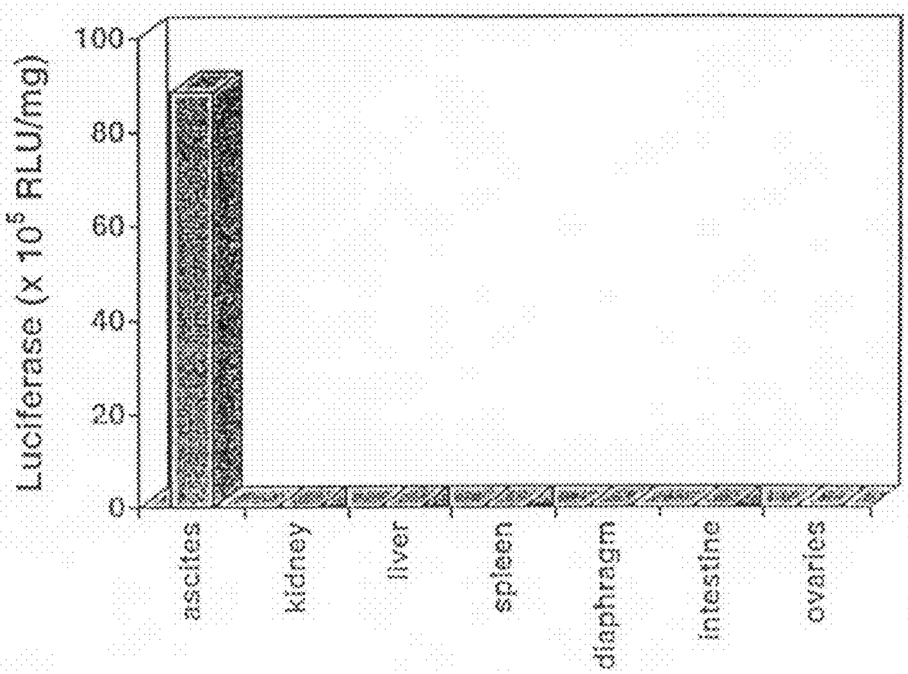
B Day 3 after DNA:lipid
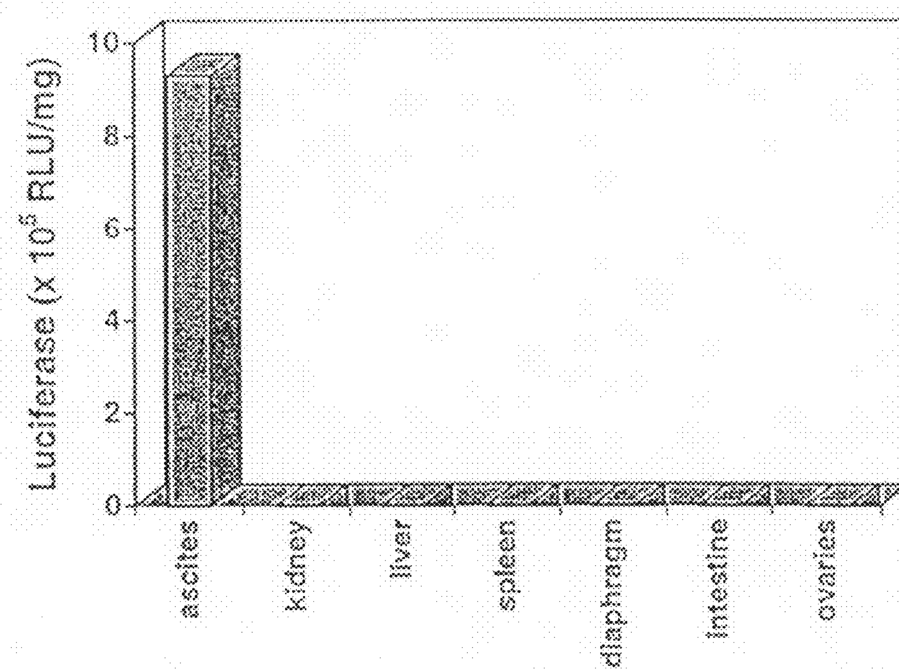

Figure 14
A Ascites
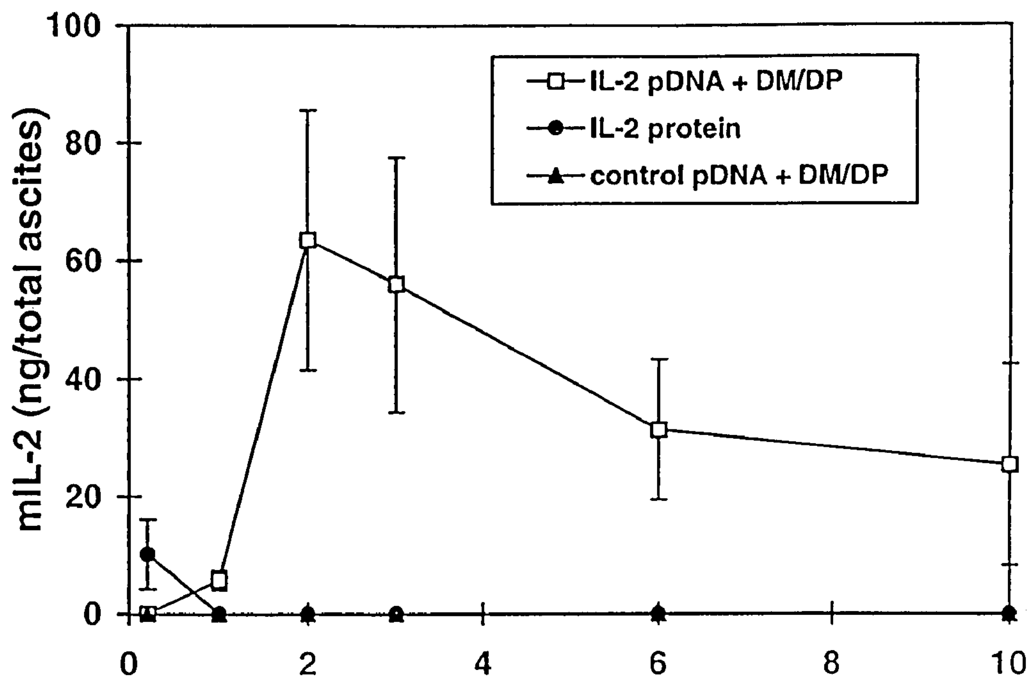
B Serum
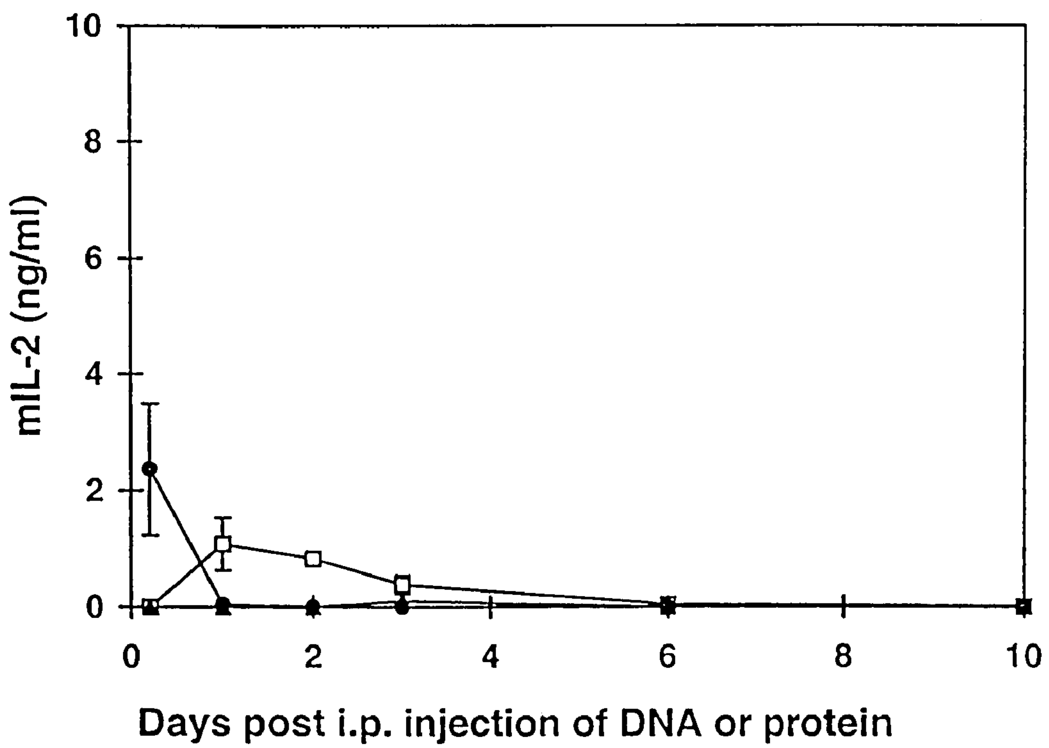

Figure 15
1:1 pDNA:DM/DP
A
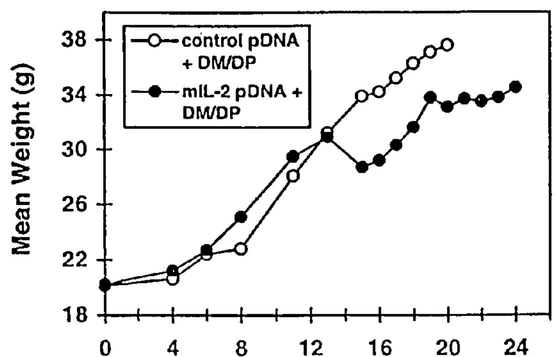
B
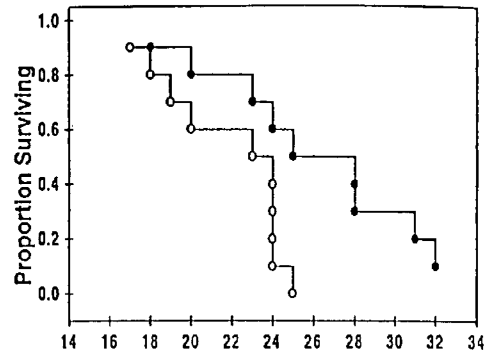
5:1 pDNA:DM/DP
C
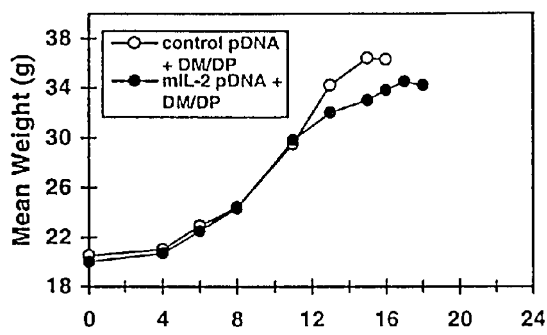
D
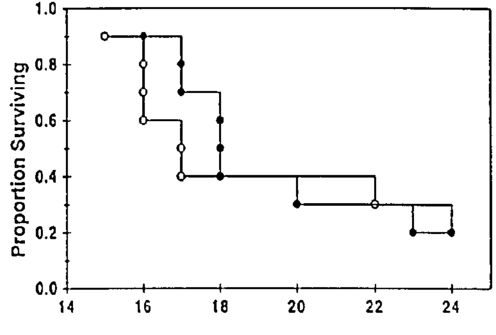
pDNA without DM/DP
E
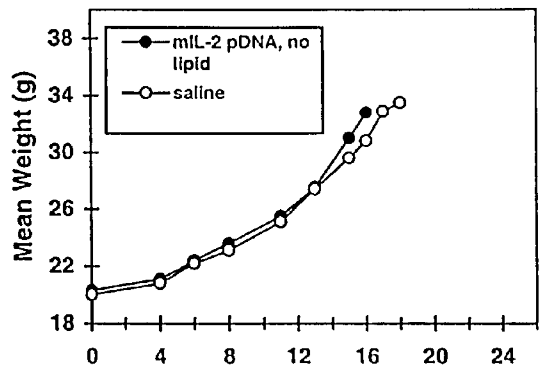
F
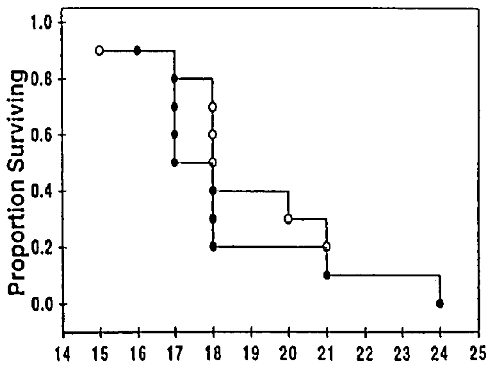
Days post tumor cell injection Figure 16
A
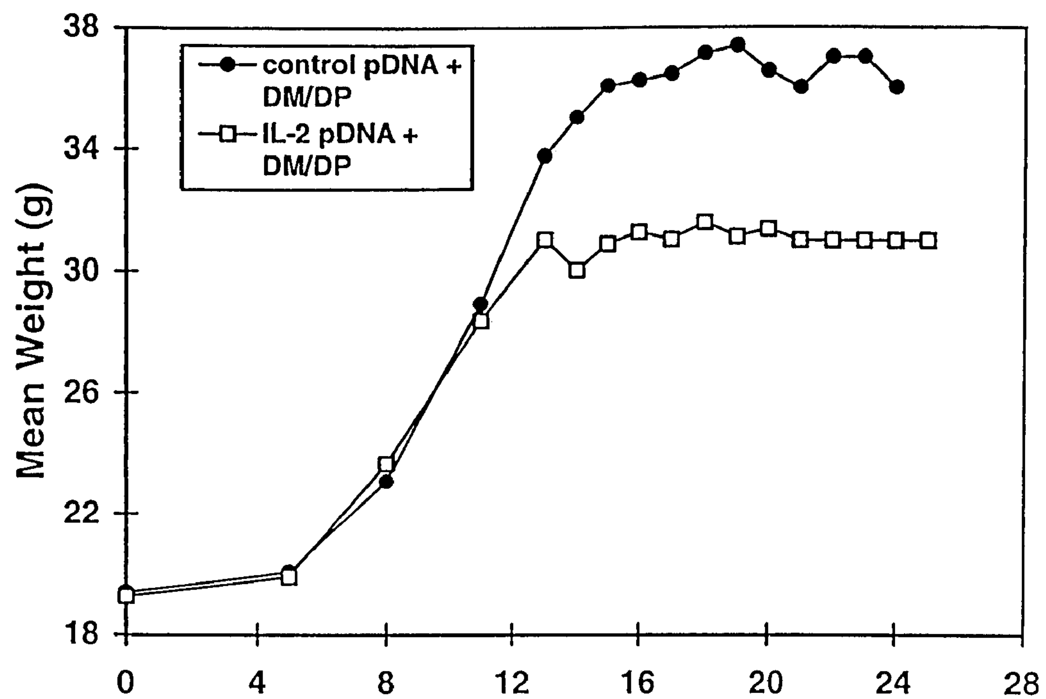
B
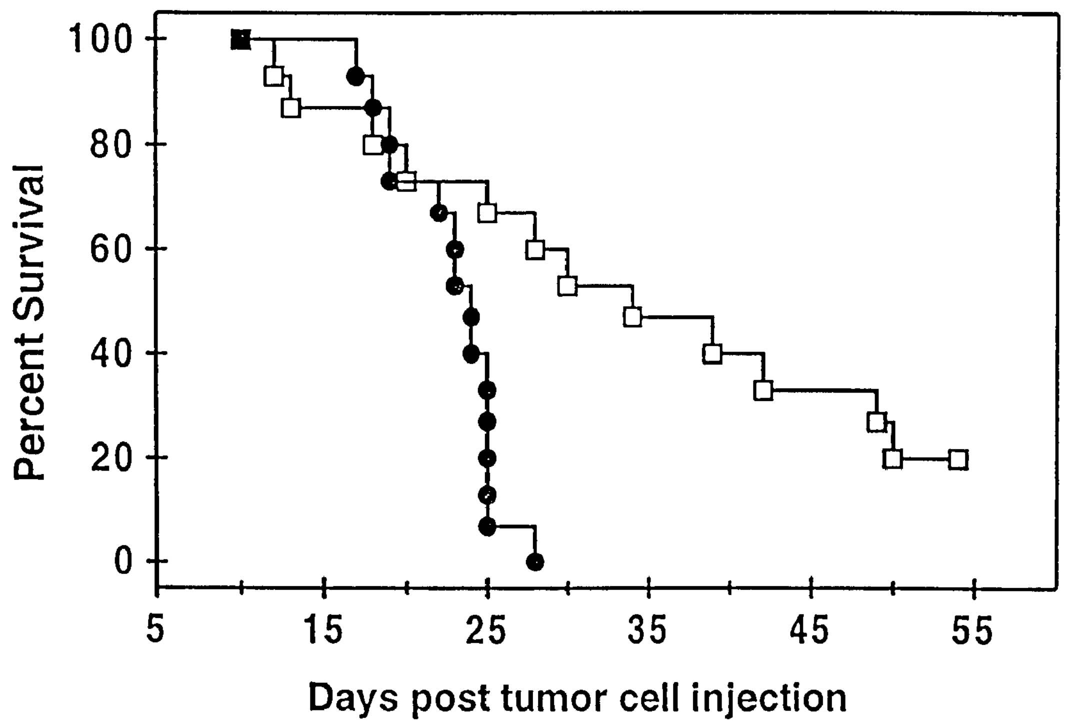

Figure 17
A
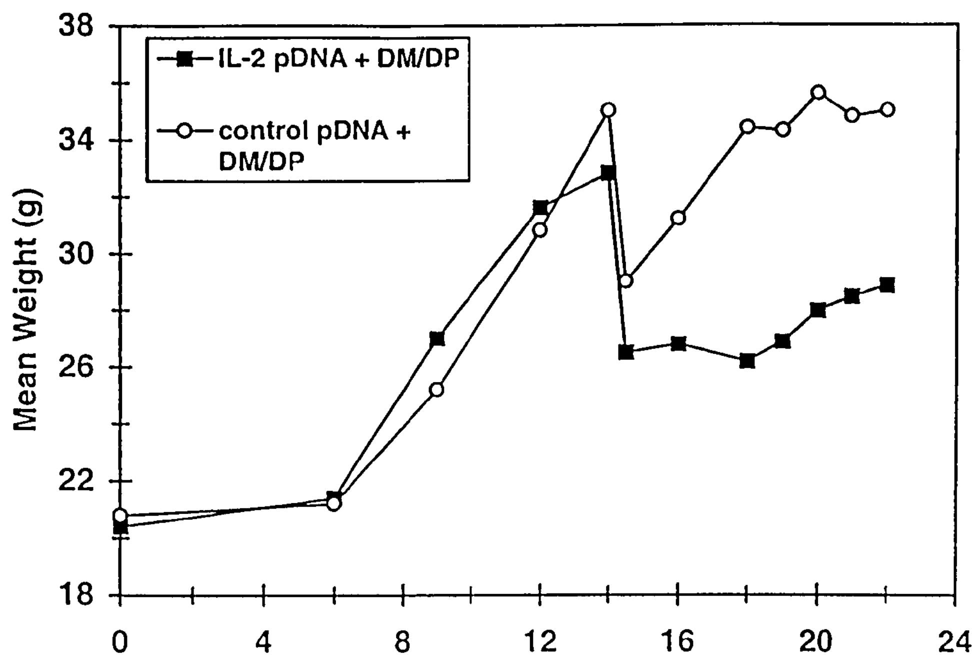
B
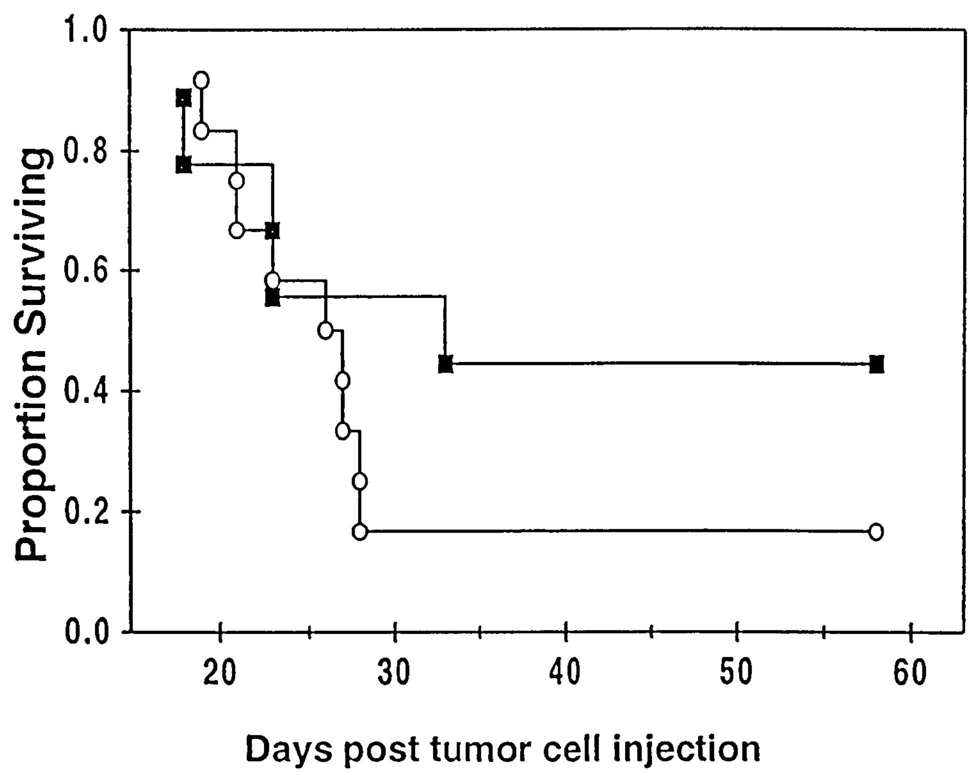

Figure 18
A
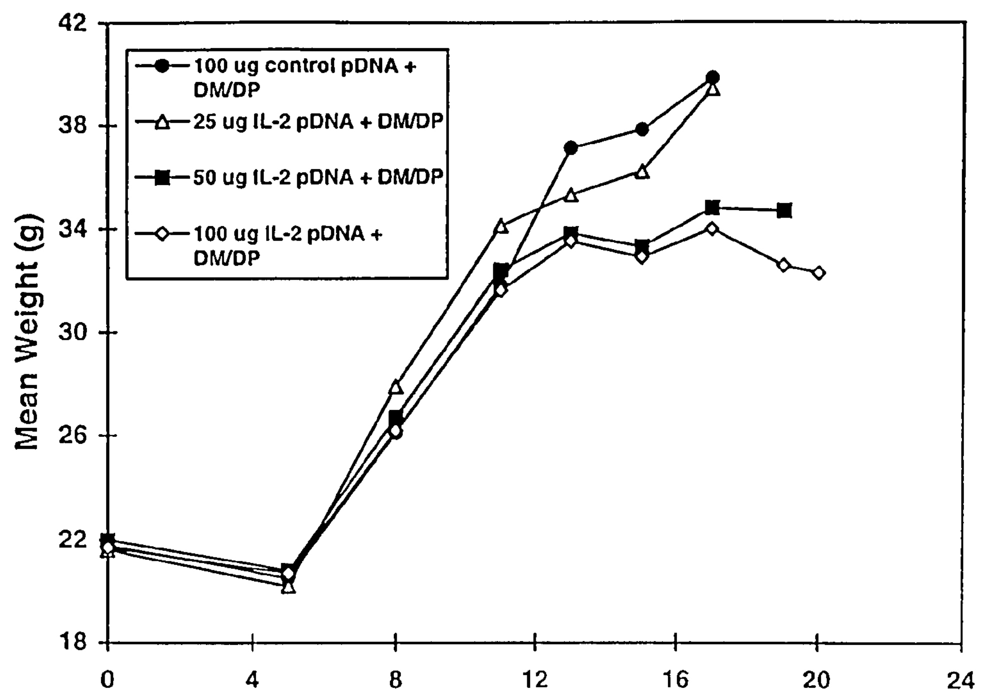
B
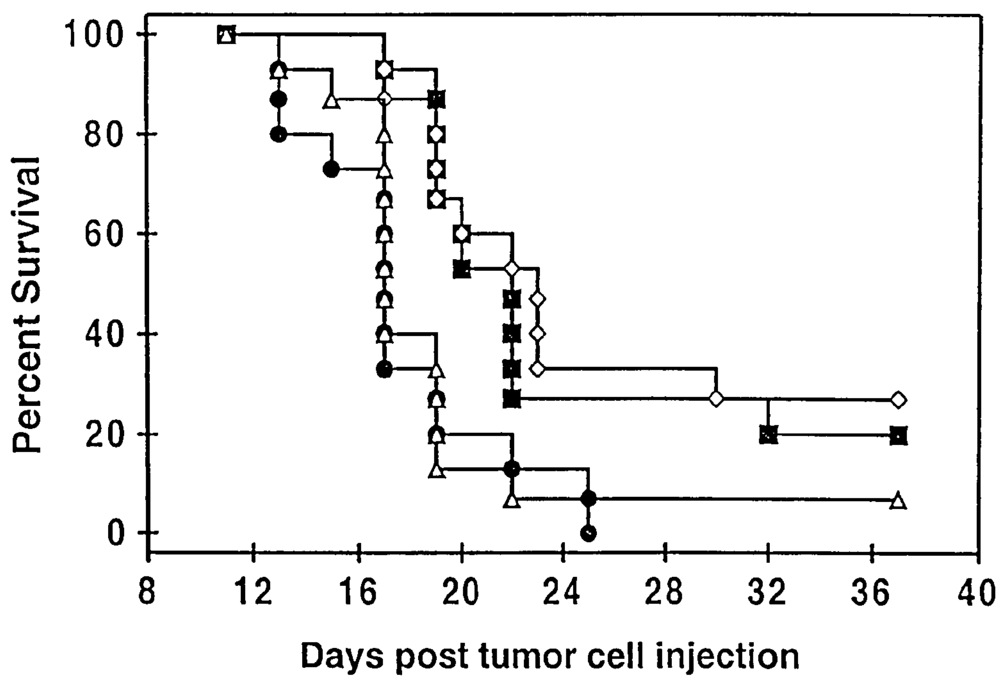

A
B
C
D
E
F
IL-2
IFNγ
GM-CSF
IL-6
TNFα
IL-10
day 7
day 10
day 13
Cytokine (pg/total ascites)
Untreated
Control pDNA
IL-2 pDNA
80000
60000
40000
20000
0
300000
200000
100000
6000
4000
2000
20000
15000
10000
5000
3000
1000

Figure 20
A
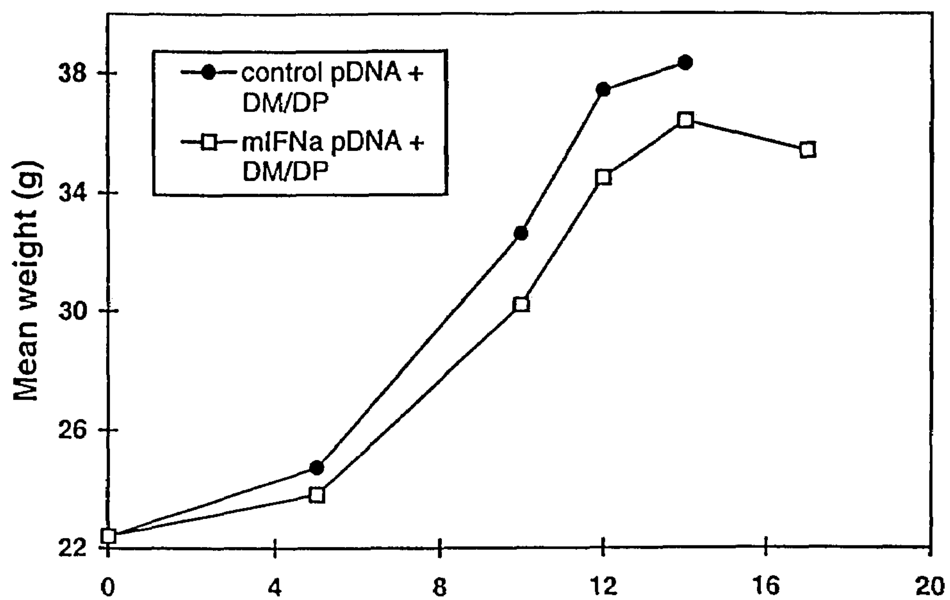
B
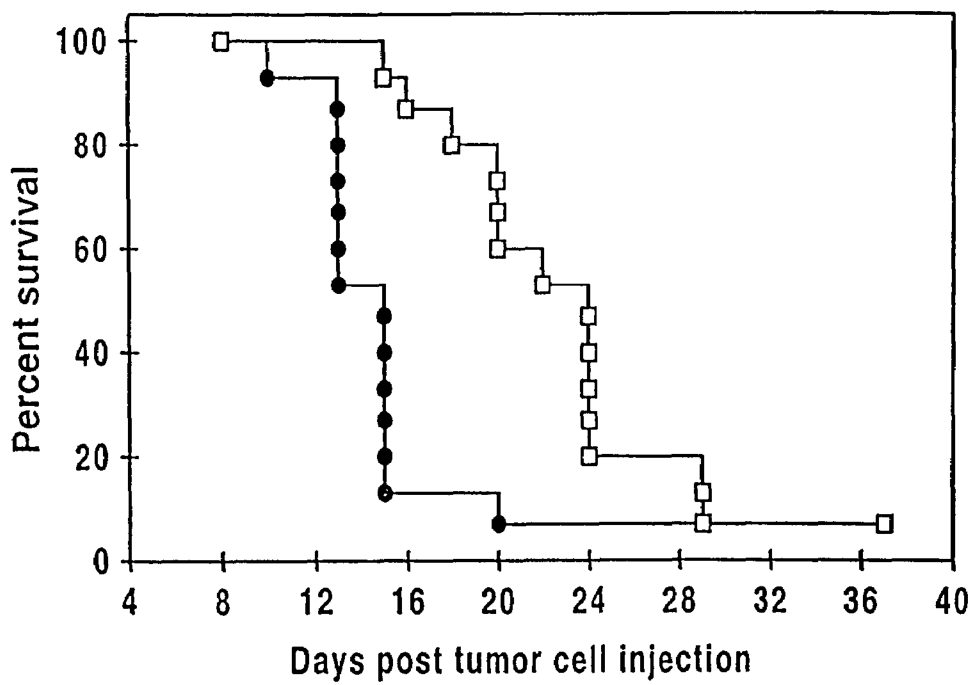

Figure 21

| Plasmid Name | GENE | Parental Plasmid | Promoter/ Enhancer | Terminator |
|---|---|---|---|---|
| VR1223 | Firefly Lux | VR1012* | CMV | BGH |
| VR1255 | Firefly Lux | VR1223 | CMV | mRBG |
| VR1412 | Bacterial LacZ | VR1012* | CMV | BGH |
| VR1418 | Bacterial LacZ | VR1043 | RSV | BGH |
| VR4151 | Human IFN-ω | VR1055 | CMV | mRBG |
| VR3301 | Human SEAP | VR1012* | CMV | BGH |
| VR3502 | Rat preproinsulin | VR1012* | CMV | BGH |
| VR2901 | Mouse EPO | VR1012* | CMV | BGH |
| VR1110 | Mouse IL-2 | VR1012* | CMV | BGH |
| VR4111 | Mouse IFN-α | VR1055 | CMV | mRBG |
| VR4700 | Influenza NP | VR1255** | CMV | mRBG |

Intermediate plasmids

| | | | | |
|---|---|---|---|---|
| VR1012 | none | V1J*** | CMV | BGH |
| VR1055 | none | VR1255 | CMV | mRBG |
| VR1043 | none | VR1343 | RSV | BGH |

SEQUENCE LISTING

```
<160> NUMBER OF SEQ ID NOS: 26

<210> SEQ ID NO 1
<211> LENGTH: 5428
<212> TYPE: DNA
<213> ORGANISM: Homo sapiens

<400> SEQUENCE: 1

tcgcgcgttt cggtgatgac ggtgaaaacc tctgacacat gcagctcccg gagacggtca      60

cagcttgtct gtaagcggat gccgggagca gacaagcccg tcagggcgcg tcagcgggtg     120

ttggcgggtg tcggggctgg cttaactatg cggcatcaga gcagattgta ctgagagtgc     180

accatatgcg gtgtgaaata ccgcacagat gcgtaaggag aaaataccgc atcagattgg     240

ctattggcca ttgcatacgt tgtatccata tcataatatg tacatttata ttggctcatg     300
```

-continued

```
tccaacatta ccgccatgtt gacattgatt attgactagt tattaatagt aatcaattac    360
ggggtcatta gttcatagcc catatatgga gttccgcgtt acataactta cggtaaatgg    420
cccgcctggc tgaccgccca acgacccccg cccattgacg tcaataatga cgtatgttcc    480
catagtaacg ccaataggga ctttccattg acgtcaatgg gtggagtatt tacggtaaac    540
tgcccacttg gcagtacatc aagtgtatca tatgccaagt acgcccccta ttgacgtcaa    600
tgacggtaaa tggcccgcct ggcattatgc ccagtacatg accttatggg actttcctac    660
ttggcagtac atctacgtat tagtcatcgc tattaccatg gtgatgcggt tttggcagta    720
catcaatggg cgtggatagc ggtttgactc acggggattt ccaagtctcc accccattga    780
cgtcaatggg agtttgtttt ggcaccaaaa tcaacgggac tttccaaaat gtcgtaacaa    840
ctccgcccca ttgacgcaaa tgggcggtag gcgtgtacgg tgggaggtct atataagcag    900
agctcgttta gtgaaccgtc agatcgcctg gagacgccat ccacgctgtt ttgacctcca    960
tagaagacac cgggaccgat ccagcctccg cggccgggaa cggtgcattg gaacgcggat   1020
tccccgtgcc aagagtgacg taagtaccgc ctatagactc tataggcaca cccctttggc   1080
tcttatgcat gctatactgt ttttggcttg gggcctatac acccccgctt ccttatgcta   1140
taggtgatgg tatagcttag cctataggtg tgggttattg accattattg accactcccc   1200
tattggtgac gatactttcc attactaatc cataacatgg ctctttgcca caactatctc   1260
tattggctat atgccaatac tctgtccttc agagactgac acggactctg tatttttaca   1320
ggatggggtc ccatttatta tttacaaatt cacatataca acaacgccgt cccccgtgcc   1380
cgcagttttt attaaacata gcgtgggatc tccacgcgaa tctcgggtac gtgttccgga   1440
catgggctct tctccggtag cggcggagct tccacatccg agccctggtc ccatgcctcc   1500
agcggctcat ggtcgctcgg cagctccttg ctcctaacag tggaggccag acttaggcac   1560
agcacaatgc ccaccaccac cagtgtgccg cacaaggccg tggcggtagg gtatgtgtct   1620
gaaaatgagc gtggagattg ggctcgcacg gctgacgcag atggaagact taaggcagcg   1680
gcagaagaag atgcaggcag ctgagttgtt gtattctgat aagagtcaga ggtaactccc   1740
gttgcggtgc tgttaacggt ggagggcagt gtagtctgag cagtactcgt tgctgccgcg   1800
cgcgccacca gacataatag ctgacagact aacagactgt tcctttccat gggtcttttc   1860
tgcagatggc ctcgcccttt gctttactga tggtcctggt ggtgctcagc tgcaagtcaa   1920
gctgctctct gggctgtgat ctccctgaga cccacagcct ggataacagg aggaccttga   1980
tgctcctggc acaaatgagc agaatctctc cttcctcctg tctgatggac agacatgact   2040
ttggatttcc ccaggaggag tttgatggca accagttcca gaaggctcca gccatctctg   2100
tcctccatga gctgatccag cagatcttca acctctttac cacaaaagat tcatctgctg   2160
cttgggatga ggacctccta gacaaattct gcaccgaact ctaccagcag ctgaatgact   2220
tggaagcctg tgtgatgcag gaggagaggg tgggagaaac tcccctgatg aatgcggact   2280
ccatcttggc tgtgaagaaa tacttccgaa gaatcactct ctatctgaca gagaagaaat   2340
acagcccttg tgcctgggag gttgtcagag cagaaatcat gagatccctc tctttatcaa   2400
caaacttgca agaaagatta aggaggaagg aataaggatc cagatctgct gtgccttcta   2460
gttgccagcc atctgttgtt tgcccctccc ccgtgccttc cttgaccctg gaaggtgcca   2520
ctcccactgt cctttcctaa taaaatgagg aaattgcatc gcattgtctg agtaggtgtc   2580
attctattct ggggggtggg gtggggcagc acagcaaggg ggaggattgg gaagacaata   2640
```

-continued

```
gcaggcatgc tggggatgcg gtgggctcta tgggtaccca ggtgctgaag aattgacccg   2700
gttcctcctg ggccagaaag aagcaggcac atccccttct ctgtgacaca ccctgtccac   2760
gcccctggtt cttagttcca gccccactca taggacactc atagctcagg agggctccgc   2820
cttcaatccc acccgctaaa gtacttggag cggtctctcc ctccctcatc agcccaccaa   2880
accaaaccta gcctccaaga gtgggaagaa attaaagcaa gataggctat taagtgcaga   2940
gggagagaaa atgcctccaa catgtgagga agtaatgaga gaaatcatag aatttcttcc   3000
gcttcctcgc tcactgactc gctgcgctcg gtcgttcggc tgcggcgagc ggtatcagct   3060
cactcaaagg cggtaatacg gttatccaca gaatcagggg ataacgcagg aaagaacatg   3120
tgagcaaaag gccagcaaaa ggccaggaac cgtaaaaagg ccgcgttgct ggcgtttttc   3180
cataggctcc gcccccctga cgagcatcac aaaaatcgac gctcaagtca gaggtggcga   3240
aacccgacag gactataaag ataccaggcg tttccccctg gaagctccct cgtgcgctct   3300
cctgttccga ccctgccgct taccggatac ctgtccgcct ttctcccttc gggaagcgtg   3360
gcgctttctc aatgctcacg ctgtaggtat ctcagttcgg tgtaggtcgt tcgctccaag   3420
ctgggctgtg tgcacgaacc ccccgttcag cccgaccgct gcgccttatc cggtaactat   3480
cgtcttgagt ccaacccggt aagacacgac ttatcgccac tggcagcagc cactggtaac   3540
aggattagca gagcgaggta tgtaggcggt gctacagagt tcttgaagtg gtggcctaac   3600
tacggctaca ctagaaggac agtatttggt atctgcgctc tgctgaagcc agttaccttc   3660
ggaaaaagag ttggtagctc ttgatccggc aaacaaacca ccgctggtag cggtggtttt   3720
tttgtttgca agcagcagat tacgcgcaga aaaaaaggat ctcaagaaga tcctttgatc   3780
ttttctacgg ggtctgacgc tcagtggaac gaaaactcac gttaagggat tttggtcatg   3840
agattatcaa aaaggatctt cacctagatc cttttaaatt aaaaatgaag ttttaaatca   3900
atctaaagta tatatgagta aacttggtct gacagttacc aatgcttaat cagtgaggca   3960
cctatctcag cgatctgtct atttcgttca tccatagttg cctgactccg gggggggggg   4020
gcgctgaggt ctgcctcgtg aagaaggtgt tgctgactca taccaggcct gaatcgcccc   4080
atcatccagc cagaaagtga gggagccacg gttgatgaga gctttgttgt aggtggacca   4140
gttggtgatt ttgaactttt gctttgccac ggaacggtct gcgttgtcgg gaagatgcgt   4200
gatctgatcc ttcaactcag caaaagttcg atttattcaa caaagccgcc gtcccgtcaa   4260
gtcagcgtaa tgctctgcca gtgttacaac caattaacca attctgatta gaaaaactca   4320
tcgagcatca aatgaaactg caatttattc atatcaggat tatcaatacc atatttttga   4380
aaaagccgtt tctgtaatga aggagaaaac tcaccgaggc agttccatag gatggcaaga   4440
tcctggtatc ggtctgcgat tccgactcgt ccaacatcaa tacaacctat taatttcccc   4500
tcgtcaaaaa taaggttatc aagtgagaaa tcaccatgag tgacgactga atccggtgag   4560
aatggcaaaa gcttatgcat ttctttccag acttgttcaa caggccagcc attacgctcg   4620
tcatcaaaat cactcgcatc aaccaaaccg ttattcattc gtgattgcgc ctgagcgaga   4680
cgaaatacgc gatcgctgtt aaaaggacaa ttacaaacag gaatcgaatg caaccggcgc   4740
aggaacactg ccagcgcatc aacaatattt tcacctgaat caggatattc ttctaatacc   4800
tggaatgctg ttttcccggg gatcgcagtg gtgagtaacc atgcatcatc aggagtacgg   4860
ataaaatgct tgatggtcgg aagaggcata aattccgtca gccagtttag tctgaccatc   4920
tcatctgtaa catcattggc aacgctacct ttgccatgtt tcagaaacaa ctctggcgca   4980
tcgggcttcc catacaatcg atagattgtc gcacctgatt gcccgacatt atcgcgagcc   5040
```

```
catttatacc catataaatc agcatccatg ttggaattta atcgcggcct cgagcaagac   5100

gtttcccgtt gaatatggct cataacaccc cttgtattac tgtttatgta agcagacagt   5160

tttattgttc atgatgatat atttttatct tgtgcaatgt aacatcagag attttgagac   5220

acaacgtggc tttccccccc cccccattat tgaagcattt atcagggtta ttgtctcatg   5280

agcggataca tatttgaatg tatttagaaa aataaacaaa taggggttcc gcgcacattt   5340

ccccgaaaag tgccacctga cgtctaagaa accattatta tcatgacatt aacctataaa   5400

aataggcgta tcacgaggcc ctttcgtc                                       5428
```

```
<210> SEQ ID NO 2
<211> LENGTH: 5259
<212> TYPE: DNA
<213> ORGANISM: Homo sapiens

<400> SEQUENCE: 2

tcgcgcgttt cggtgatgac ggtgaaaacc tctgacacat gcagctcccg gagacggtca     60

cagcttgtct gtaagcggat gccgggagca gacaagcccg tcagggcgcg tcagcgggtg    120

ttggcgggtg tcggggctgg cttaactatg cggcatcaga gcagattgta ctgagagtgc    180

accatatgcg gtgtgaaata ccgcacagat gcgtaaggag aaaataccgc atcagattgg    240

ctattggcca ttgcatacgt tgtatccata tcataatatg tacatttata ttggctcatg    300

tccaacatta ccgccatgtt gacattgatt attgactagt tattaatagt aatcaattac    360

ggggtcatta gttcatagcc catatatgga gttccgcgtt acataactta cggtaaatgg    420

cccgcctggc tgaccgccca acgacccccg cccattgacg tcaataatga cgtatgttcc    480

catagtaacg ccaataggga ctttccattg acgtcaatgg gtggagtatt tacggtaaac    540

tgcccacttg gcagtacatc aagtgtatca tatgccaagt acgcccccta ttgacgtcaa    600

tgacggtaaa tggcccgcct ggcattatgc ccagtacatg accttatggg actttcctac    660

ttggcagtac atctacgtat tagtcatcgc tattaccatg gtgatgcggt tttggcagta    720

catcaatggg cgtggatagc ggtttgactc acggggattt ccaagtctcc accccattga    780

cgtcaatggg agtttgtttt ggcaccaaaa tcaacgggac tttccaaaat gtcgtaacaa    840

ctccgcccca ttgacgcaaa tgggcggtag gcgtgtacgg tgggaggtct atataagcag    900

agctcgttta gtgaaccgtc agatcgcctg gagacgccat ccacgctgtt ttgacctcca    960

tagaagacac cgggaccgat ccagcctccg cggccgggaa cggtgcattg gaacgcggat   1020

tccccgtgcc aagagtgacg taagtaccgc ctatagactc tataggcaca cccctttggc   1080

tcttatgcat gctatactgt ttttggcttg gggcctatac acccccgctt ccttatgcta   1140

taggtgatgg tatagcttag cctataggtg tgggttattg accattattg accactcccc   1200

tattggtgac gatactttcc attactaatc cataacatgg ctctttgcca caactatctc   1260

tattggctat atgccaatac tctgtccttc agagactgac acggactctg tatttttaca   1320

ggatggggtc ccatttatta tttacaaatt cacatataca acaacgccgt cccccgtgcc   1380

cgcagttttt attaaacata gcgtgggatc tccacgcgaa tctcgggtac gtgttccgga   1440

catgggctct tctccggtag cggcggagct tccacatccg agccctggtc ccatgcctcc   1500

agcggctcat ggtcgctcgg cagctccttg ctcctaacag tggaggccag acttaggcac   1560

agcacaatgc ccaccaccac cagtgtgccg cacaaggccg tggcggtagg gtatgtgtct   1620

gaaaatgagc gtggagattg ggctcgcacg gctgacgcag atggaagact taaggcagcg   1680
```

-continued

```
gcagaagaag atgcaggcag ctgagttgtt gtattctgat aagagtcaga ggtaactccc   1740
gttgcggtgc tgttaacggt ggagggcagt gtagtctgag cagtactcgt tgctgccgcg   1800
cgcgccacca gacataatag ctgacagact aacagactgt tcctttccat gggtcttttc   1860
tgcagatggc ctcgcccttt gctttactga tggtcctggt ggtgctcagc tgcaagtcaa   1920
gctgctctct gggctgtgat ctccctgaga cccacagcct ggataacagg aggaccttga   1980
tgctcctggc acaaatgagc agaatctctc cttcctcctg tctgatggac agacatgact   2040
ttggatttcc ccaggaggag tttgatggca accagttcca gaaggctcca gccatctctg   2100
tcctccatga gctgatccag cagatcttca acctctttac cacaaaagat tcatctgctg   2160
cttgggatga ggacctccta gacaaattct gcaccgaact ctaccagcag ctgaatgact   2220
tggaagcctg tgtgatgcag gaggagaggg tgggagaaac tcccctgatg aatgcggact   2280
ccatcttggc tgtgaagaaa tacttccgaa gaatcactct ctatctgaca gagaagaaat   2340
acagcccttg tgcctgggag gttgtcagag cagaaatcat gagatccctc tctttatcaa   2400
caaacttgca agaaagatta aggaggaagg aataaggatc cagatctact tctggctaat   2460
aaaagatcag agctctagag atctgtgtgt tggttttttg tgtggtaccc aggtgctgaa   2520
gaattgaccc ggttcctcct gggccagaaa gaagcaggca catccccttc tctgtgacac   2580
accctgtcca cgcccctggt tcttagttcc agccccactc ataggacact catagctcag   2640
gagggctccg ccttcaatcc cacccgctaa agtacttgga gcggtctctc cctccctcat   2700
cagcccacca aaccaaacct agcctccaag agtgggaaga aattaaagca agataggcta   2760
ttaagtgcag agggagagaa aatgcctcca acatgtgagg aagtaatgag agaaatcata   2820
gaatttcttc cgcttcctcg ctcactgact cgctgcgctc ggtcgttcgg ctgcggcgag   2880
cggtatcagc tcactcaaag gcggtaatac ggttatccac agaatcaggg gataacgcag   2940
gaaagaacat gtgagcaaaa ggccagcaaa aggccaggaa ccgtaaaaag gccgcgttgc   3000
tggcgttttt ccataggctc cgcccccctg acgagcatca caaaaatcga cgctcaagtc   3060
agaggtggcg aaacccgaca ggactataaa gataccaggc gtttccccct ggaagctccc   3120
tcgtgcgctc tcctgttccg accctgccgc ttaccggata cctgtccgcc tttctccctt   3180
cgggaagcgt ggcgctttct caatgctcac gctgtaggta tctcagttcg gtgtaggtcg   3240
ttcgctccaa gctgggctgt gtgcacgaac cccccgttca gcccgaccgc tgcgccttat   3300
ccggtaacta tcgtcttgag tccaacccgg taagacacga cttatcgcca ctggcagcag   3360
ccactggtaa caggattagc agagcgaggt atgtaggcgg tgctacagag ttcttgaagt   3420
ggtggcctaa ctacggctac actagaagga cagtatttgg tatctgcgct ctgctgaagc   3480
cagttacctt cggaaaaaga gttggtagct cttgatccgg caaacaaacc accgctggta   3540
gcggtggttt ttttgtttgc aagcagcaga ttacgcgcag aaaaaaagga tctcaagaag   3600
atcctttgat cttttctacg gggtctgacg ctcagtggaa cgaaaactca cgttaaggga   3660
ttttggtcat gagattatca aaaaggatct tcacctagat ccttttaaat taaaaatgaa   3720
gttttaaatc aatctaaagt atatatgagt aaacttggtc tgacagttac caatgcttaa   3780
tcagtgaggc acctatctca gcgatctgtc tatttcgttc atccatagtt gcctgactcc   3840
gggggggggg ggcgctgagg tctgcctcgt gaagaaggtg ttgctgactc ataccaggcc   3900
tgaatcgccc catcatccag ccagaaagtg agggagccac ggttgatgag agctttgttg   3960
taggtggacc agttggtgat tttgaacttt tgctttgcca cggaacggtc tgcgttgtcg   4020
ggaagatgcg tgatctgatc cttcaactca gcaaaagttc gatttattca acaaagccgc   4080
```

-continued

```
cgtcccgtca agtcagcgta atgctctgcc agtgttacaa ccaattaacc aattctgatt   4140

agaaaaactc atcgagcatc aaatgaaact gcaatttatt catatcagga ttatcaatac   4200

catatttttg aaaaagccgt ttctgtaatg aaggagaaaa ctcaccgagg cagttccata   4260

ggatggcaag atcctggtat cggtctgcga ttccgactcg tccaacatca atacaaccta   4320

ttaatttccc ctcgtcaaaa ataaggttat caagtgagaa atcaccatga gtgacgactg   4380

aatccggtga gaatggcaaa agcttatgca tttctttcca gacttgttca acaggccagc   4440

cattacgctc gtcatcaaaa tcactcgcat caaccaaacc gttattcatt cgtgattgcg   4500

cctgagcgag acgaaatacg cgatcgctgt taaaaggaca attacaaaca ggaatcgaat   4560

gcaaccggcg caggaacact gccagcgcat caacaatatt ttcacctgaa tcaggatatt   4620

cttctaatac ctggaatgct gttttcccgg ggatcgcagt ggtgagtaac catgcatcat   4680

caggagtacg gataaaatgc ttgatggtcg gaagaggcat aaattccgtc agccagttta   4740

gtctgaccat ctcatctgta acatcattgg caacgctacc tttgccatgt ttcagaaaca   4800

actctggcgc atcgggcttc ccatacaatc gatagattgt cgcacctgat tgcccgacat   4860

tatcgcgagc ccatttatac ccatataaat cagcatccat gttggaattt aatcgcggcc   4920

tcgagcaaga cgtttcccgt tgaatatggc tcataacacc ccttgtatta ctgtttatgt   4980

aagcagacag ttttattgtt catgatgata tatttttatc ttgtgcaatg taacatcaga   5040

gattttgaga cacaacgtgg ctttcccccc ccccccatta ttgaagcatt tatcagggtt   5100

attgtctcat gagcggatac atatttgaat gtatttagaa aaataaacaa ataggggttc   5160

cgcgcacatt tccccgaaaa gtgccacctg acgtctaaga aaccattatt atcatgacat   5220

taacctataa aaataggcgt atcacgaggc cctttcgtc                          5259
```

<210> SEQ ID NO 3
<211> LENGTH: 5480
<212> TYPE: DNA
<213> ORGANISM: Homo sapiens

<400> SEQUENCE: 3

```
tcgcgcgttt cggtgatgac ggtgaaaacc tctgacacat gcagctcccg gagacggtca     60

cagcttgtct gtaagcggat gccgggagca gacaagcccg tcagggcgcg tcagcgggtg    120

ttggcgggtg tcggggctgg cttaactatg cggcatcaga gcagattgta ctgagagtgc    180

accatatgcg gtgtgaaata ccgcacagat gcgtaaggag aaaataccgc atcagattgg    240

ctattggcca ttgcatacgt tgtatccata tcataatatg tacatttata ttggctcatg    300

tccaacatta ccgccatgtt gacattgatt attgactagt tattaatagt aatcaattac    360

ggggtcatta gttcatagcc catatatgga gttccgcgtt acataactta cggtaaatgg    420

cccgcctggc tgaccgccca acgacccccg cccattgacg tcaataatga cgtatgttcc    480

catagtaacg ccaataggga ctttccattg acgtcaatgg gtggagtatt tacggtaaac    540

tgcccacttg gcagtacatc aagtgtatca tatgccaagt acgcccccta ttgacgtcaa    600

tgacggtaaa tggcccgcct ggcattatgc ccagtacatg accttatggg actttcctac    660

ttggcagtac atctacgtat tagtcatcgc tattaccatg gtgatgcggt tttggcagta    720

catcaatggg cgtggatagc ggtttgactc acggggattt ccaagtctcc accccattga    780

cgtcaatggg agtttgtttt ggcaccaaaa tcaacgggac tttccaaaat gtcgtaacaa    840

ctccgcccca ttgacgcaaa tgggcggtag gcgtgtacgg tgggaggtct atataagcag    900
```

-continued

```
agctcgttta gtgaaccgtc agatcgcctg gagacgccat ccacgctgtt ttgacctcca    960
tagaagacac cgggaccgat ccagcctccg cggccgggaa cggtgcattg gaacgcggat   1020
tccccgtgcc aagagtgacg taagtaccgc ctatagactc tataggcaca cccctttggc   1080
tcttatgcat gctatactgt ttttggcttg gggcctatac acccccgctt ccttatgcta   1140
taggtgatgg tatagcttag cctataggtg tgggttattg accattattg accactcccc   1200
tattggtgac gatactttcc attactaatc cataacatgg ctctttgcca caactatctc   1260
tattggctat atgccaatac tctgtccttc agagactgac acggactctg tatttttaca   1320
ggatggggtc ccatttatta tttacaaatt cacatataca acaacgccgt cccccgtgcc   1380
cgcagttttt attaaacata gcgtgggatc tccacgcgaa tctcgggtac gtgttccgga   1440
catgggctct tctccggtag cggcggagct tccacatccg agccctggtc ccatgcctcc   1500
agcggctcat ggtcgctcgg cagctccttg ctcctaacag tggaggccag acttaggcac   1560
agcacaatgc ccaccaccac cagtgtgccg cacaaggccg tggcggtagg gtatgtgtct   1620
gaaaatgagc gtggagattg ggctcgcacg gctgacgcag atggaagact taaggcagcg   1680
gcagaagaag atgcaggcag ctgagttgtt gtattctgat aagagtcaga ggtaactccc   1740
gttgcggtgc tgttaacggt ggagggcagt gtagtctgag cagtactcgt tgctgccgcg   1800
cgcgccacca gacataatag ctgacagact aacagactgt tcctttccat gggtcttttc   1860
tgcagtcacc gtcgtcgaca cgtgtgatca gatatcacca tggccctcct gttccctcta   1920
ctggcagccc tagtgatgac cagctatagc cctgttggat ctctgggctg tgatctgcct   1980
cagaaccatg gcctacttag caggaacacc ttggtgcttc tgcaccaaat gaggagaatc   2040
tcccctttct tgtgtctcaa ggacagaaga gacttcaggt tcccccagga gatggtaaaa   2100
gggagccagt tgcagaaggc ccatgtcatg tctgtcctcc atgagatgct gcagcagatc   2160
ttcagcctct tccacacaga gcgctcctct gctgcctgga acatgaccct cctagaccaa   2220
ctccacactg gacttcatca gcaactgcaa cacctggaga cctgcttgct gcaggtagtg   2280
ggagaaggag aatctgctgg ggcaattagc agccctgcac tgaccttgag gaggtacttc   2340
cagggaatcc gtgtctacct gaaagagaag aaatacagcg actgtgcctg ggaagttgtc   2400
agaatggaaa tcatgaaatc cttgttctta tcaacaaaca tgcaagaaag actgagaagt   2460
aaagatagag acctgggctc atcttgagga tccagatctg ctgtgccttc tagttgccag   2520
ccatctgttg tttgcccctc ccccgtgcct tccttgaccc tggaaggtgc cactcccact   2580
gtcctttcct aataaaatga ggaaattgca tcgcattgtc tgagtaggtg tcattctatt   2640
ctggggggtg gggtggggca gcacagcaag ggggaggatt gggaagacaa tagcaggcat   2700
gctggggatg cggtgggctc tatgggtacc caggtgctga agaattgacc cggttcctcc   2760
tgggccagaa agaagcaggc acatcccctt ctctgtgaca caccctgtcc acgcccctgg   2820
ttcttagttc cagccccact cataggacac tcatagctca ggagggctcc gccttcaatc   2880
ccacccgcta aagtacttgg agcggtctct ccctccctca tcagcccacc aaaccaaacc   2940
tagcctccaa gagtgggaag aaattaaagc aagataggct attaagtgca gagggagaga   3000
aaatgcctcc aacatgtgag gaagtaatga gagaaatcat agaatttctt ccgcttcctc   3060
gctcactgac tcgctgcgct cggtcgttcg gctgcggcga gcggtatcag ctcactcaaa   3120
ggcggtaata cggttatcca cagaatcagg ggataacgca ggaaagaaca tgtgagcaaa   3180
aggccagcaa aaggccagga accgtaaaaa ggccgcgttg ctggcgtttt tccataggct   3240
ccgcccccct gacgagcatc acaaaaatcg acgctcaagt cagaggtggc gaaacccgac   3300
```

-continued

```
aggactataa agataccagg cgtttccccc tggaagctcc ctcgtgcgct ctcctgttcc   3360
gaccctgccg cttaccggat acctgtccgc ctttctccct tcgggaagcg tggcgctttc   3420
tcaatgctca cgctgtaggt atctcagttc ggtgtaggtc gttcgctcca agctgggctg   3480
tgtgcacgaa ccccccgttc agcccgaccg ctgcgcctta tccggtaact atcgtcttga   3540
gtccaacccg gtaagacacg acttatcgcc actggcagca gccactggta acaggattag   3600
cagagcgagg tatgtaggcg gtgctacaga gttcttgaag tggtggccta actacggcta   3660
cactagaagg acagtatttg gtatctgcgc tctgctgaag ccagttacct tcggaaaaag   3720
agttggtagc tcttgatccg gcaaacaaac caccgctggt agcggtggtt tttttgtttg   3780
caagcagcag attacgcgca gaaaaaaagg atctcaagaa gatcctttga tcttttctac   3840
ggggtctgac gctcagtgga acgaaaactc acgttaaggg attttggtca tgagattatc   3900
aaaaaggatc ttcacctaga tccttttaaa ttaaaaatga agttttaaat caatctaaag   3960
tatatatgag taaacttggt ctgacagtta ccaatgctta atcagtgagg cacctatctc   4020
agcgatctgt ctatttcgtt catccatagt tgcctgactc cggggggggg gggcgctgag   4080
gtctgcctcg tgaagaaggt gttgctgact cataccaggc ctgaatcgcc ccatcatcca   4140
gccagaaagt gagggagcca cggttgatga gagctttgtt gtaggtggac cagttggtga   4200
ttttgaactt ttgctttgcc acggaacggt ctgcgttgtc gggaagatgc gtgatctgat   4260
ccttcaactc agcaaaagtt cgatttattc aacaaagccg ccgtcccgtc aagtcagcgt   4320
aatgctctgc cagtgttaca accaattaac caattctgat tagaaaaact catcgagcat   4380
caaatgaaac tgcaatttat tcatatcagg attatcaata ccatattttt gaaaaagccg   4440
tttctgtaat gaaggagaaa actcaccgag gcagttccat aggatggcaa gatcctggta   4500
tcggtctgcg attccgactc gtccaacatc aatacaacct attaatttcc cctcgtcaaa   4560
aataaggtta tcaagtgaga aatcaccatg agtgacgact gaatccggtg agaatggcaa   4620
aagcttatgc atttctttcc agacttgttc aacaggccag ccattacgct cgtcatcaaa   4680
atcactcgca tcaaccaaac cgttattcat tcgtgattgc gcctgagcga gacgaaatac   4740
gcgatcgctg ttaaaaggac aattacaaac aggaatcgaa tgcaaccggc gcaggaacac   4800
tgccagcgca tcaacaatat tttcacctga atcaggatat tcttctaata cctggaatgc   4860
tgttttcccg gggatcgcag tggtgagtaa ccatgcatca tcaggagtac ggataaaatg   4920
cttgatggtc ggaagaggca taaattccgt cagccagttt agtctgacca tctcatctgt   4980
aacatcattg gcaacgctac ctttgccatg tttcagaaac aactctggcg catcgggctt   5040
cccatacaat cgatagattg tcgcacctga ttgcccgaca ttatcgcgag cccatttata   5100
cccatataaa tcagcatcca tgttggaatt taatcgcggc ctcgagcaag acgtttcccg   5160
ttgaatatgg ctcataacac cccttgtatt actgtttatg taagcagaca gttttattgt   5220
tcatgatgat atatttttat cttgtgcaat gtaacatcag agattttgag acacaacgtg   5280
gctttccccc cccccccatt attgaagcat ttatcagggt tattgtctca tgagcggata   5340
catatttgaa tgtatttaga aaaataaaca aataggggtt ccgcgcacat ttccccgaaa   5400
agtgccacct gacgtctaag aaaccattat tatcatgaca ttaacctata aaaataggcg   5460
tatcacgagg ccctttcgtc                                                5480
```

<210> SEQ ID NO 4
<211> LENGTH: 5322
<212> TYPE: DNA

<213> ORGANISM: Homo sapiens

<400> SEQUENCE: 4

```
tcgcgcgttt cggtgatgac ggtgaaaacc tctgacacat gcagctcccg gagacggtca     60
cagcttgtct gtaagcggat gccgggagca gacaagcccg tcagggcgcg tcagcgggtg    120
ttggcgggtg tcggggctgg cttaactatg cggcatcaga gcagattgta ctgagagtgc    180
accatatgcg gtgtgaaata ccgcacagat gcgtaaggag aaaataccgc atcagattgg    240
ctattggcca ttgcatacgt tgtatccata tcataatatg tacatttata ttggctcatg    300
tccaacatta ccgccatgtt gacattgatt attgactagt tattaatagt aatcaattac    360
ggggtcatta gttcatagcc catatatgga gttccgcgtt acataactta cggtaaatgg    420
cccgcctggc tgaccgccca acgacccccg cccattgacg tcaataatga cgtatgttcc    480
catagtaacg ccaataggga ctttccattg acgtcaatgg gtggagtatt tacggtaaac    540
tgcccacttg gcagtacatc aagtgtatca tatgccaagt acgcccccta ttgacgtcaa    600
tgacggtaaa tggcccgcct ggcattatgc ccagtacatg accttatggg actttcctac    660
ttggcagtac atctacgtat tagtcatcgc tattaccatg gtgatgcggt tttggcagta    720
catcaatggg cgtggatagc ggtttgactc acggggattt ccaagtctcc accccattga    780
cgtcaatggg agtttgtttt ggcaccaaaa tcaacgggac tttccaaaat gtcgtaacaa    840
ctccgcccca ttgacgcaaa tgggcggtag gcgtgtacgg tgggaggtct atataagcag    900
agctcgttta gtgaaccgtc agatcgcctg gagacgccat ccacgctgtt ttgacctcca    960
tagaagacac cgggaccgat ccagcctccg cggccgggaa cggtgcattg gaacgcggat   1020
tccccgtgcc aagagtgacg taagtaccgc ctatagactc tataggcaca cccctttggc   1080
tcttatgcat gctatactgt ttttggcttg gggcctatac acccccgctt ccttatgcta   1140
taggtgatgg tatagcttag cctataggtg tgggttattg accattattg accactcccc   1200
tattggtgac gatactttcc attactaatc cataacatgg ctctttgcca caactatctc   1260
tattggctat atgccaatac tctgtccttc agagactgac acggactctg tatttttaca   1320
ggatggggtc ccatttatta tttacaaatt cacatataca acaacgccgt cccccgtgcc   1380
cgcagttttt attaaacata gcgtgggatc tccacgcgaa tctcgggtac gtgttccgga   1440
catgggctct tctccggtag cggcggagct tccacatccg agccctggtc ccatgcctcc   1500
agcggctcat ggtcgctcgg cagctccttg ctcctaacag tggaggccag acttaggcac   1560
agcacaatgc ccaccaccac cagtgtgccg cacaaggccg tggcggtagg gtatgtgtct   1620
gaaaatgagc gtggagattg ggctcgcacg gctgacgcag atggaagact taaggcagcg   1680
gcagaagaag atgcaggcag ctgagttgtt gtattctgat aagagtcaga ggtaactccc   1740
gttgcggtgc tgttaacggt ggagggcagt gtagtctgag cagtactcgt tgctgccgcg   1800
cgcgccacca gacataatag ctgacagact aacagactgt tcctttccat gggtcttttc   1860
tgcagtcacc gtcgtcgaca cgtgtgatca gatatcgcgg ccgctctaga atggccctcc   1920
tgttccctct actggcagcc ctagtgatga ccagctatag ccctgttgga tctctgggct   1980
gtgatctgcc tcagaaccat ggcctactta gcaggaacac cttggtgctt ctgcaccaaa   2040
tgaggagaat ctcccctttc ttgtgtctca aggacagaag agacttcagg ttcccccagg   2100
agatggtaaa agggagccag ttgcagaagg cccatgtcat gtctgtcctc catgagatgc   2160
tgcagcagat cttcagcctc ttccacacag agcgctcctc tgctgcctgg aacatgaccc   2220
tcctagacca actccacact ggacttcatc agcaactgca acacctggag acctgcttgc   2280
```

-continued

```
tgcaggtagt gggagaagga gaatctgctg gggcaattag cagccctgca ctgaccttga   2340
ggaggtactt ccagggaatc cgtgtctacc tgaaagagaa gaaatacagc gactgtgcct   2400
gggaagttgt cagaatggaa atcatgaaat ccttgttctt atcaacaaac atgcaagaaa   2460
gactgagaag taaagataga gacctgggct catcttgagg atccagatct acttctggct   2520
aataaaagat cagagctcta gagatctgtg tgttggtttt ttgtgtggta cccaggtgct   2580
gaagaattga cccggttcct cctgggccag aaagaagcag gcacatcccc ttctctgtga   2640
cacaccctgt ccacgcccct ggttcttagt tccagcccca ctcataggac actcatagct   2700
caggagggct ccgccttcaa tcccacccgc taaagtactt ggagcggtct ctccctccct   2760
catcagccca ccaaaccaaa cctagcctcc aagagtggga agaaattaaa gcaagatagg   2820
ctattaagtg cagagggaga gaaaatgcct ccaacatgtg aggaagtaat gagagaaatc   2880
atagaatttc ttccgcttcc tcgctcactg actcgctgcg ctcggtcgtt cggctgcggc   2940
gagcggtatc agctcactca aaggcggtaa tacggttatc cacagaatca ggggataacg   3000
caggaaagaa catgtgagca aaaggccagc aaaaggccag gaaccgtaaa aaggccgcgt   3060
tgctggcgtt tttccatagg ctccgccccc ctgacgagca tcacaaaaat cgacgctcaa   3120
gtcagaggtg gcgaaacccg acaggactat aaagatacca ggcgtttccc cctggaagct   3180
ccctcgtgcg ctctcctgtt ccgaccctgc cgcttaccgg atacctgtcc gcctttctcc   3240
cttcgggaag cgtggcgctt tctcaatgct cacgctgtag gtatctcagt tcggtgtagg   3300
tcgttcgctc caagctgggc tgtgtgcacg aaccccccgt tcagcccgac cgctgcgcct   3360
tatccggtaa ctatcgtctt gagtccaacc cggtaagaca cgacttatcg ccactggcag   3420
cagccactgg taacaggatt agcagagcga ggtatgtagg cggtgctaca gagttcttga   3480
agtggtggcc taactacggc tacactagaa ggacagtatt tggtatctgc gctctgctga   3540
agccagttac cttcggaaaa agagttggta gctcttgatc cggcaaacaa accaccgctg   3600
gtagcggtgg tttttttgtt tgcaagcagc agattacgcg cagaaaaaaa ggatctcaag   3660
aagatccttt gatcttttct acggggtctg acgctcagtg gaacgaaaac tcacgttaag   3720
ggattttggt catgagatta tcaaaaagga tcttcaccta gatcctttta aattaaaaat   3780
gaagttttaa atcaatctaa agtatatatg agtaaacttg gtctgacagt taccaatgct   3840
taatcagtga ggcacctatc tcagcgatct gtctatttcg ttcatccata gttgcctgac   3900
tccggggggg gggggcgctg aggtctgcct cgtgaagaag gtgttgctga ctcataccag   3960
gcctgaatcg ccccatcatc cagccagaaa gtgagggagc cacggttgat gagagctttg   4020
ttgtaggtgg accagttggt gattttgaac ttttgctttg ccacggaacg gtctgcgttg   4080
tcgggaagat gcgtgatctg atccttcaac tcagcaaaag ttcgatttat tcaacaaagc   4140
cgccgtcccg tcaagtcagc gtaatgctct gccagtgtta caaccaatta accaattctg   4200
attagaaaaa ctcatcgagc atcaaatgaa actgcaattt attcatatca ggattatcaa   4260
taccatattt ttgaaaaagc cgtttctgta atgaaggaga aaactcaccg aggcagttcc   4320
ataggatggc aagatcctgg tatcggtctg cgattccgac tcgtccaaca tcaatacaac   4380
ctattaattt cccctcgtca aaaataaggt tatcaagtga gaaatcacca tgagtgacga   4440
ctgaatccgg tgagaatggc aaaagcttat gcatttcttt ccagacttgt tcaacaggcc   4500
agccattacg ctcgtcatca aaatcactcg catcaaccaa accgttattc attcgtgatt   4560
gcgcctgagc gagacgaaat acgcgatcgc tgttaaaagg acaattacaa acaggaatcg   4620
```

-continued

```
aatgcaaccg gcgcaggaac actgccagcg catcaacaat attttcacct gaatcaggat   4680
attcttctaa tacctggaat gctgttttcc cggggatcgc agtggtgagt aaccatgcat   4740
catcaggagt acggataaaa tgcttgatgg tcggaagagg cataaattcc gtcagccagt   4800
ttagtctgac catctcatct gtaacatcat tggcaacgct acctttgcca tgtttcagaa   4860
acaactctgg cgcatcgggc ttcccataca atcgatagat tgtcgcacct gattgcccga   4920
cattatcgcg agcccattta tacccatata aatcagcatc catgttggaa tttaatcgcg   4980
gcctcgagca agacgtttcc cgttgaatat ggctcataac accccttgta ttactgttta   5040
tgtaagcaga cagttttatt gttcatgatg atatattttt atcttgtgca atgtaacatc   5100
agagattttg agacacaacg tggctttccc cccccccca ttattgaagc atttatcagg   5160
gttattgtct catgagcgga tacatatttg aatgtattta gaaaaataaa caaatagggg   5220
ttccgcgcac atttccccga aaagtgccac ctgacgtcta agaaaccatt attatcatga   5280
cattaaccta taaaaatagg cgtatcacga ggccctttcg tc                        5322
```

<210> SEQ ID NO 5
<211> LENGTH: 5422
<212> TYPE: DNA
<213> ORGANISM: Mus musculus

<400> SEQUENCE: 5

```
tcgcgcgttt cggtgatgac ggtgaaaacc tctgacacat gcagctcccg gagacggtca     60
cagcttgtct gtaagcggat gccgggagca gacaagcccg tcagggcgcg tcagcgggtg    120
ttggcgggtg tcggggctgg cttaactatg cggcatcaga gcagattgta ctgagagtgc    180
accatatgcg gtgtgaaata ccgcacagat gcgtaaggag aaaataccgc atcagattgg    240
ctattggcca ttgcatacgt tgtatccata tcataatatg tacatttata ttggctcatg    300
tccaacatta ccgccatgtt gacattgatt attgactagt tattaatagt aatcaattac    360
ggggtcatta gttcatagcc catatatgga gttccgcgtt acataactta cggtaaatgg    420
cccgcctggc tgaccgccca acgacccccg cccattgacg tcaataatga cgtatgttcc    480
catagtaacg ccaataggga ctttccattg acgtcaatgg gtggagtatt tacggtaaac    540
tgcccacttg gcagtacatc aagtgtatca tatgccaagt acgcccccta ttgacgtcaa    600
tgacggtaaa tggcccgcct ggcattatgc ccagtacatg accttatggg actttcctac    660
ttggcagtac atctacgtat tagtcatcgc tattaccatg gtgatgcggt tttggcagta    720
catcaatggg cgtggatagc ggtttgactc acggggattt ccaagtctcc accccattga    780
cgtcaatggg agtttgtttt ggcaccaaaa tcaacgggac tttccaaaat gtcgtaacaa    840
ctccgcccca ttgacgcaaa tgggcggtag gcgtgtacgg tgggaggtct atataagcag    900
agctcgttta gtgaaccgtc agatcgcctg gagacgccat ccacgctgtt ttgacctcca    960
tagaagacac cgggaccgat ccagcctccg cggccgggaa cggtgcattg gaacgcggat   1020
tccccgtgcc aagagtgacg taagtaccgc ctatagactc tataggcaca cccctttggc   1080
tcttatgcat gctatactgt ttttggcttg gggcctatac acccccgctt ccttatgcta   1140
taggtgatgg tatagcttag cctataggtg tgggttattg accattattg accactcccc   1200
tattggtgac gatactttcc attactaatc cataacatgg ctctttgcca caactatctc   1260
tattggctat atgccaatac tctgtccttc agagactgac acggactctg tatttttaca   1320
ggatggggtc ccatttatta tttacaaatt cacatataca acaacgccgt cccccgtgcc   1380
cgcagttttt attaaacata gcgtgggatc tccacgcgaa tctcgggtac gtgttccgga   1440
```

```
catgggctct tctccggtag cggcggagct tccacatccg agccctggtc ccatgcctcc   1500
agcggctcat ggtcgctcgg cagctccttg ctcctaacag tggaggccag acttaggcac   1560
agcacaatgc ccaccaccac cagtgtgccg cacaaggccg tggcggtagg gtatgtgtct   1620
gaaaatgagc gtggagattg ggctcgcacg gctgacgcag atggaagact taaggcagcg   1680
gcagaagaag atgcaggcag ctgagttgtt gtattctgat aagagtcaga ggtaactccc   1740
gttgcggtgc tgttaacggt ggagggcagt gtagtctgag cagtactcgt tgctgccgcg   1800
cgcgccacca gacataatag ctgacagact aacagactgt tcctttccat gggtcttttc   1860
tgcagatggc taggctctgt gctttcctga tggtcctggc ggtgatgagc tactggccaa   1920
cctgctctct aggatgtgac ctgcctcaga ctcataacct caggaacaag agagccttga   1980
cactcctggt acaaatgagg agactctccc ctctctcctg cctgaaggac aggaaggact   2040
ttggattccc gcaggagaag gtggatgccc agcagatcaa gaaggctcaa gccatccctg   2100
tcctgagtga gctgacccag cagatcctga acatcttcac atcaaaggac tcatctgctg   2160
cttggaatgc aaccctccta gactcattct gcaatgacct ccaccagcag ctcaatgacc   2220
tgcaaggttg tctgatgcag caggtggggg tgcaggaatt tcccctgacc caggaagatg   2280
ccctgctggc tgtgaggaaa tacttccaca ggatcactgt gtacctgaga gagaagaaac   2340
acagcccctg tgcctgggag gtggtcagag cagaagtctg gagagccctg tcttcctctg   2400
ccaatgtgct gggaagactg agagaagaga aatgaagatc tgctgtgcct tctagttgcc   2460
agccatctgt tgtttgcccc tcccccgtgc cttccttgac cctggaaggt gccactccca   2520
ctgtcctttc ctaataaaat gaggaaattg catcgcattg tctgagtagg tgtcattcta   2580
ttctgggggg tggggtgggg cagcacagca agggggagga ttgggaagac aatagcaggc   2640
atgctgggga tgcggtgggc tctatgggta cccaggtgct gaagaattga cccggttcct   2700
cctgggccag aaagaagcag gcacatcccc ttctctgtga cacaccctgt ccacgcccct   2760
ggttcttagt tccagcccca ctcataggac actcatagct caggagggct ccgccttcaa   2820
tcccacccgc taaagtactt ggagcggtct ctccctccct catcagccca ccaaaccaaa   2880
cctagcctcc aagagtggga agaaattaaa gcaagatagg ctattaagtg cagagggaga   2940
gaaaatgcct ccaacatgtg aggaagtaat gagagaaatc atagaatttc ttccgcttcc   3000
tcgctcactg actcgctgcg ctcggtcgtt cggctgcggc gagcggtatc agctcactca   3060
aaggcggtaa tacggttatc cacagaatca ggggataacg caggaaagaa catgtgagca   3120
aaaggccagc aaaaggccag gaaccgtaaa aaggccgcgt tgctggcgtt tttccatagg   3180
ctccgccccc ctgacgagca tcacaaaaat cgacgctcaa gtcagaggtg gcgaaacccg   3240
acaggactat aaagatacca ggcgtttccc cctggaagct ccctcgtgcg ctctcctgtt   3300
ccgaccctgc cgcttaccgg atacctgtcc gcctttctcc cttcgggaag cgtggcgctt   3360
tctcaatgct cacgctgtag gtatctcagt tcggtgtagg tcgttcgctc caagctgggc   3420
tgtgtgcacg aaccccccgt tcagcccgac cgctgcgcct tatccggtaa ctatcgtctt   3480
gagtccaacc cggtaagaca cgacttatcg ccactggcag cagccactgg taacaggatt   3540
agcagagcga ggtatgtagg cggtgctaca gagttcttga agtggtggcc taactacggc   3600
tacactagaa ggacagtatt tggtatctgc gctctgctga agccagttac cttcggaaaa   3660
agagttggta gctcttgatc cggcaaacaa accaccgctg gtagcggtgg tttttttgtt   3720
tgcaagcagc agattacgcg cagaaaaaaa ggatctcaag aagatccttt gatcttttct   3780
```

-continued

```
acggggtctg acgctcagtg gaacgaaaac tcacgttaag ggattttggt catgagatta   3840

tcaaaaagga tcttcaccta gatcctttta aattaaaaat gaagttttaa atcaatctaa   3900

agtatatatg agtaaacttg gtctgacagt taccaatgct taatcagtga ggcacctatc   3960

tcagcgatct gtctatttcg ttcatccata gttgcctgac tccggggggg gggggcgctg   4020

aggtctgcct cgtgaagaag gtgttgctga ctcataccag gcctgaatcg ccccatcatc   4080

cagccagaaa gtgagggagc cacggttgat gagagctttg ttgtaggtgg accagttggt   4140

gattttgaac ttttgctttg ccacggaacg gtctgcgttg tcgggaagat gcgtgatctg   4200

atccttcaac tcagcaaaag ttcgatttat tcaacaaagc cgccgtcccg tcaagtcagc   4260

gtaatgctct gccagtgtta caaccaatta accaattctg attagaaaaa ctcatcgagc   4320

atcaaatgaa actgcaattt attcatatca ggattatcaa taccatattt ttgaaaaagc   4380

cgtttctgta atgaaggaga aaactcaccg aggcagttcc ataggatggc aagatcctgg   4440

tatcggtctg cgattccgac tcgtccaaca tcaatacaac ctattaattt cccctcgtca   4500

aaaataaggt tatcaagtga gaaatcacca tgagtgacga ctgaatccgg tgagaatggc   4560

aaaagcttat gcatttcttt ccagacttgt tcaacaggcc agccattacg ctcgtcatca   4620

aaatcactcg catcaaccaa accgttattc attcgtgatt gcgcctgagc gagacgaaat   4680

acgcgatcgc tgttaaaagg acaattacaa acaggaatcg aatgcaaccg gcgcaggaac   4740

actgccagcg catcaacaat attttcacct gaatcaggat attcttctaa tacctggaat   4800

gctgttttcc cggggatcgc agtggtgagt aaccatgcat catcaggagt acggataaaa   4860

tgcttgatgg tcggaagagg cataaattcc gtcagccagt ttagtctgac catctcatct   4920

gtaacatcat tggcaacgct acctttgcca tgtttcagaa acaactctgg cgcatcgggc   4980

ttcccataca atcgatagat tgtcgcacct gattgcccga cattatcgcg agcccattta   5040

tacccatata aatcagcatc catgttggaa tttaatcgcg gcctcgagca agacgtttcc   5100

cgttgaatat ggctcataac accccttgta ttactgttta tgtaagcaga cagttttatt   5160

gttcatgatg atatattttt atcttgtgca atgtaacatc agagattttg agacacaacg   5220

tggctttccc ccccccccca ttattgaagc atttatcagg gttattgtct catgagcgga   5280

tacatatttg aatgtattta gaaaaataaa caaatagggg ttccgcgcac atttccccga   5340

aaagtgccac ctgacgtcta agaaaccatt attatcatga cattaaccta taaaaatagg   5400

cgtatcacga ggccctttcg tc                                            5422
```

<210> SEQ ID NO 6
<211> LENGTH: 5259
<212> TYPE: DNA
<213> ORGANISM: Mus musculus

<400> SEQUENCE: 6

```
tcgcgcgttt cggtgatgac ggtgaaaacc tctgacacat gcagctcccg gagacggtca     60

cagcttgtct gtaagcggat gccgggagca gacaagcccg tcagggcgcg tcagcgggtg    120

ttggcgggtg tcggggctgg cttaactatg cggcatcaga gcagattgta ctgagagtgc    180

accatatgcg gtgtgaaata ccgcacagat gcgtaaggag aaaataccgc atcagattgg    240

ctattggcca ttgcatacgt tgtatccata tcataatatg tacatttata ttggctcatg    300

tccaacatta ccgccatgtt gacattgatt attgactagt tattaatagt aatcaattac    360

ggggtcatta gttcatagcc catatatgga gttccgcgtt acataactta cggtaaatgg    420
```

-continued

```
cccgcctggc tgaccgccca acgacccccg cccattgacg tcaataatga cgtatgttcc    480
catagtaacg ccaataggga ctttccattg acgtcaatgg gtggagtatt tacggtaaac    540
tgcccacttg gcagtacatc aagtgtatca tatgccaagt acgcccccta ttgacgtcaa    600
tgacggtaaa tggcccgcct ggcattatgc ccagtacatg accttatggg actttcctac    660
ttggcagtac atctacgtat tagtcatcgc tattaccatg gtgatgcggt tttggcagta    720
catcaatggg cgtggatagc ggtttgactc acggggattt ccaagtctcc accccattga    780
cgtcaatggg agtttgtttt ggcaccaaaa tcaacgggac tttccaaaat gtcgtaacaa    840
ctccgcccca ttgacgcaaa tgggcggtag gcgtgtacgg tgggaggtct atataagcag    900
agctcgttta gtgaaccgtc agatcgcctg gagacgccat ccacgctgtt ttgacctcca    960
tagaagacac cgggaccgat ccagcctccg cggccgggaa cggtgcattg gaacgcggat   1020
tccccgtgcc aagagtgacg taagtaccgc ctatagactc tataggcaca cccctttggc   1080
tcttatgcat gctatactgt ttttggcttg gggcctatac acccccgctt ccttatgcta   1140
taggtgatgg tatagcttag cctataggtg tgggttattg accattattg accactcccc   1200
tattggtgac gatactttcc attactaatc cataacatgg ctctttgcca caactatctc   1260
tattggctat atgccaatac tctgtccttc agagactgac acggactctg tatttttaca   1320
ggatggggtc ccatttatta tttacaaatt cacatataca acaacgccgt cccccgtgcc   1380
cgcagttttt attaaacata gcgtgggatc tccacgcgaa tctcgggtac gtgttccgga   1440
catgggctct tctccggtag cggcggagct tccacatccg agccctggtc ccatgcctcc   1500
agcggctcat ggtcgctcgg cagctccttg ctcctaacag tggaggccag acttaggcac   1560
agcacaatgc ccaccaccac cagtgtgccg cacaaggccg tggcggtagg gtatgtgtct   1620
gaaaatgagc gtggagattg ggctcgcacg gctgacgcag atggaagact taaggcagcg   1680
gcagaagaag atgcaggcag ctgagttgtt gtattctgat aagagtcaga ggtaactccc   1740
gttgcggtgc tgttaacggt ggagggcagt gtagtctgag cagtactcgt tgctgccgcg   1800
cgcgccacca gacataatag ctgacagact aacagactgt tcctttccat gggtcttttc   1860
tgcagatggc taggctctgt gctttcctga tggtcctggc ggtgatgagc tactggccaa   1920
cctgctctct aggatgtgac ctgcctcaga ctcataacct caggaacaag agagccttga   1980
cactcctggt acaaatgagg agactctccc ctctctcctg cctgaaggac aggaaggact   2040
ttggattccc gcaggagaag gtggatgccc agcagatcaa gaaggctcaa gccatccctg   2100
tcctgagtga gctgacccag cagatcctga acatcttcac atcaaaggac tcatctgctg   2160
cttggaatgc aaccctccta gactcattct gcaatgacct ccaccagcag ctcaatgacc   2220
tgcaaggttg tctgatgcag caggtggggg tgcaggaatt tcccctgacc caggaagatg   2280
ccctgctggc tgtgaggaaa tacttccaca ggatcactgt gtacctgaga gagaagaaac   2340
acagcccctg tgcctgggag gtggtcagag cagaagtctg gagagccctg tcttcctctg   2400
ccaatgtgct gggaagactg agagaagaga aatgaagatc cagatctact tctggctaat   2460
aaaagatcag agctctagag atctgtgtgt tggttttttg tgtggtaccc aggtgctgaa   2520
gaattgaccc ggttcctcct gggccagaaa gaagcaggca catccccttc tctgtgacac   2580
accctgtcca cgcccctggt tcttagttcc agccccactc ataggacact catagctcag   2640
gagggctccg ccttcaatcc cacccgctaa agtacttgga gcggtctctc cctccctcat   2700
cagcccacca aaccaaacct agcctccaag agtgggaaga aattaaagca agataggcta   2760
ttaagtgcag agggagagaa aatgcctcca acatgtgagg aagtaatgag agaaatcata   2820
```

-continued

```
gaatttcttc cgcttcctcg ctcactgact cgctgcgctc ggtcgttcgg ctgcggcgag   2880

cggtatcagc tcactcaaag gcggtaatac ggttatccac agaatcaggg gataacgcag   2940

gaaagaacat gtgagcaaaa ggccagcaaa aggccaggaa ccgtaaaaag gccgcgttgc   3000

tggcgttttt ccataggctc cgcccccctg acgagcatca caaaaatcga cgctcaagtc   3060

agaggtggcg aaacccgaca ggactataaa gataccaggc gtttccccct ggaagctccc   3120

tcgtgcgctc tcctgttccg accctgccgc ttaccggata cctgtccgcc tttctccctt   3180

cgggaagcgt ggcgctttct caatgctcac gctgtaggta tctcagttcg gtgtaggtcg   3240

ttcgctccaa gctgggctgt gtgcacgaac cccccgttca gcccgaccgc tgcgccttat   3300

ccggtaacta tcgtcttgag tccaacccgg taagacacga cttatcgcca ctggcagcag   3360

ccactggtaa caggattagc agagcgaggt atgtaggcgg tgctacagag ttcttgaagt   3420

ggtggcctaa ctacggctac actagaagga cagtatttgg tatctgcgct ctgctgaagc   3480

cagttacctt cggaaaaaga gttggtagct cttgatccgg caaacaaacc accgctggta   3540

gcggtggttt ttttgtttgc aagcagcaga ttacgcgcag aaaaaaagga tctcaagaag   3600

atcctttgat cttttctacg gggtctgacg ctcagtggaa cgaaaactca cgttaaggga   3660

ttttggtcat gagattatca aaaaggatct tcacctagat ccttttaaat taaaaatgaa   3720

gttttaaatc aatctaaagt atatatgagt aaacttggtc tgacagttac caatgcttaa   3780

tcagtgaggc acctatctca gcgatctgtc tatttcgttc atccatagtt gcctgactcc   3840

gggggggggg ggcgctgagg tctgcctcgt gaagaaggtg ttgctgactc ataccaggcc   3900

tgaatcgccc catcatccag ccagaaagtg agggagccac ggttgatgag agctttgttg   3960

taggtggacc agttggtgat tttgaacttt tgctttgcca cggaacggtc tgcgttgtcg   4020

ggaagatgcg tgatctgatc cttcaactca gcaaaagttc gatttattca acaaagccgc   4080

cgtcccgtca agtcagcgta atgctctgcc agtgttacaa ccaattaacc aattctgatt   4140

agaaaaactc atcgagcatc aaatgaaact gcaatttatt catatcagga ttatcaatac   4200

catatttttg aaaaagccgt ttctgtaatg aaggagaaaa ctcaccgagg cagttccata   4260

ggatggcaag atcctggtat cggtctgcga ttccgactcg tccaacatca atacaaccta   4320

ttaatttccc ctcgtcaaaa ataaggttat caagtgagaa atcaccatga gtgacgactg   4380

aatccggtga gaatggcaaa agcttatgca tttctttcca gacttgttca acaggccagc   4440

cattacgctc gtcatcaaaa tcactcgcat caaccaaacc gttattcatt cgtgattgcg   4500

cctgagcgag acgaaatacg cgatcgctgt taaaaggaca attacaaaca ggaatcgaat   4560

gcaaccggcg caggaacact gccagcgcat caacaatatt ttcacctgaa tcaggatatt   4620

cttctaatac ctggaatgct gttttcccgg ggatcgcagt ggtgagtaac catgcatcat   4680

caggagtacg gataaaatgc ttgatggtcg gaagaggcat aaattccgtc agccagttta   4740

gtctgaccat ctcatctgta acatcattgg caacgctacc tttgccatgt ttcagaaaca   4800

actctggcgc atcgggcttc ccatacaatc gatagattgt cgcacctgat tgcccgacat   4860

tatcgcgagc ccatttatac ccatataaat cagcatccat gttggaattt aatcgcggcc   4920

tcgagcaaga cgtttcccgt tgaatatggc tcataacacc ccttgtatta ctgtttatgt   4980

aagcagacag ttttattgtt catgatgata tatttttatc ttgtgcaatg taacatcaga   5040

gattttgaga cacaacgtgg ctttcccccc ccccccatta ttgaagcatt tatcagggtt   5100

attgtctcat gagcggatac atatttgaat gtatttagaa aaataaacaa ataggggttc   5160
```

```
cgcgcacatt tccccgaaaa gtgccacctg acgtctaaga aaccattatt atcatgacat   5220

taacctataa aaataggcgt atcacgaggc cctttcgtc                          5259


<210> SEQ ID NO 7
<211> LENGTH: 585
<212> TYPE: DNA
<213> ORGANISM: Homo sapiens
<220> FEATURE:
<221> NAME/KEY: CDS
<222> LOCATION: (1)..(585)
<220> FEATURE:
<221> NAME/KEY: sig_peptide
<222> LOCATION: (1)..(69)
<220> FEATURE:
<221> NAME/KEY: mat_peptide
<222> LOCATION: (70)..(585)

<400> SEQUENCE: 7

atg gcc ctc ctg ttc cct cta ctg gca gcc cta gtg atg acc agc tat       48
Met Ala Leu Leu Phe Pro Leu Leu Ala Ala Leu Val Met Thr Ser Tyr
            -20                 -15                 -10

agc cct gtt gga tct ctg ggc tgt gat ctg cct cag aac cat ggc cta       96
Ser Pro Val Gly Ser Leu Gly Cys Asp Leu Pro Gln Asn His Gly Leu
        -5              -1   1               5

ctt agc agg aac acc ttg gtg ctt ctg cac caa atg agg aga atc tcc      144
Leu Ser Arg Asn Thr Leu Val Leu Leu His Gln Met Arg Arg Ile Ser
 10                  15                  20                  25

cct ttc ttg tgt ctc aag gac aga aga gac ttc agg ttc ccc cag gag      192
Pro Phe Leu Cys Leu Lys Asp Arg Arg Asp Phe Arg Phe Pro Gln Glu
                30                  35                  40

atg gta aaa ggg agc cag ttg cag aag gcc cat gtc atg tct gtc ctc      240
Met Val Lys Gly Ser Gln Leu Gln Lys Ala His Val Met Ser Val Leu
            45                  50                  55

cat gag atg ctg cag cag atc ttc agc ctc ttc cac aca gag cgc tcc      288
His Glu Met Leu Gln Gln Ile Phe Ser Leu Phe His Thr Glu Arg Ser
        60                  65                  70

tct gct gcc tgg aac atg acc ctc cta gac caa ctc cac act gga ctt      336
Ser Ala Ala Trp Asn Met Thr Leu Leu Asp Gln Leu His Thr Gly Leu
    75                  80                  85

cat cag caa ctg caa cac ctg gag acc tgc ttg ctg cag gta gtg gga      384
His Gln Gln Leu Gln His Leu Glu Thr Cys Leu Leu Gln Val Val Gly
 90                  95                 100                 105

gaa gga gaa tct gct ggg gca att agc agc cct gca ctg acc ttg agg      432
Glu Gly Glu Ser Ala Gly Ala Ile Ser Ser Pro Ala Leu Thr Leu Arg
                110                 115                 120

agg tac ttc cag gga atc cgt gtc tac ctg aaa gag aag aaa tac agc      480
Arg Tyr Phe Gln Gly Ile Arg Val Tyr Leu Lys Glu Lys Lys Tyr Ser
            125                 130                 135

gac tgt gcc tgg gaa gtt gtc aga atg gaa atc atg aaa tcc ttg ttc      528
Asp Cys Ala Trp Glu Val Val Arg Met Glu Ile Met Lys Ser Leu Phe
        140                 145                 150

tta tca aca aac atg caa gaa aga ctg aga agt aaa gat aga gac ctg      576
Leu Ser Thr Asn Met Gln Glu Arg Leu Arg Ser Lys Asp Arg Asp Leu
    155                 160                 165

ggc tca tct                                                          585
Gly Ser Ser
170


<210> SEQ ID NO 8
<211> LENGTH: 195
<212> TYPE: PRT
<213> ORGANISM: Homo sapiens
```

```
<400> SEQUENCE: 8

Met Ala Leu Leu Phe Pro Leu Leu Ala Ala Leu Val Met Thr Ser Tyr
            -20                 -15                 -10

Ser Pro Val Gly Ser Leu Gly Cys Asp Leu Pro Gln Asn His Gly Leu
        -5                  -1   1               5

Leu Ser Arg Asn Thr Leu Val Leu Leu His Gln Met Arg Arg Ile Ser
 10                  15                  20                  25

Pro Phe Leu Cys Leu Lys Asp Arg Arg Asp Phe Arg Phe Pro Gln Glu
                 30                  35                  40

Met Val Lys Gly Ser Gln Leu Gln Lys Ala His Val Met Ser Val Leu
            45                  50                  55

His Glu Met Leu Gln Gln Ile Phe Ser Leu Phe His Thr Glu Arg Ser
        60                  65                  70

Ser Ala Ala Trp Asn Met Thr Leu Leu Asp Gln Leu His Thr Gly Leu
    75                  80                  85

His Gln Gln Leu Gln His Leu Glu Thr Cys Leu Leu Gln Val Val Gly
 90                  95                 100                 105

Glu Gly Glu Ser Ala Gly Ala Ile Ser Ser Pro Ala Leu Thr Leu Arg
                110                 115                 120

Arg Tyr Phe Gln Gly Ile Arg Val Tyr Leu Lys Glu Lys Lys Tyr Ser
            125                 130                 135

Asp Cys Ala Trp Glu Val Val Arg Met Glu Ile Met Lys Ser Leu Phe
        140                 145                 150

Leu Ser Thr Asn Met Gln Glu Arg Leu Arg Ser Lys Asp Arg Asp Leu
    155                 160                 165

Gly Ser Ser
170


<210> SEQ ID NO 9
<211> LENGTH: 567
<212> TYPE: DNA
<213> ORGANISM: Homo sapiens
<220> FEATURE:
<221> NAME/KEY: CDS
<222> LOCATION: (1)..(567)
<220> FEATURE:
<221> NAME/KEY: sig_peptide
<222> LOCATION: (1)..(69)
<220> FEATURE:
<221> NAME/KEY: mat_peptide
<222> LOCATION: (70)..(567)

<400> SEQUENCE: 9

atg gcc tcg ccc ttt gct tta ctg atg gtc ctg gtg gtg ctc agc tgc       48
Met Ala Ser Pro Phe Ala Leu Leu Met Val Leu Val Val Leu Ser Cys
            -20                 -15                 -10

aag tca agc tgc tct ctg ggc tgt gat ctc cct gag acc cac agc ctg       96
Lys Ser Ser Cys Ser Leu Gly Cys Asp Leu Pro Glu Thr His Ser Leu
        -5                  -1   1               5

gat aac agg agg acc ttg atg ctc ctg gca caa atg agc aga atc tct      144
Asp Asn Arg Arg Thr Leu Met Leu Leu Ala Gln Met Ser Arg Ile Ser
 10                  15                  20                  25

cct tcc tcc tgt ctg atg gac aga cat gac ttt gga ttt ccc cag gag      192
Pro Ser Ser Cys Leu Met Asp Arg His Asp Phe Gly Phe Pro Gln Glu
                 30                  35                  40

gag ttt gat ggc aac cag ttc cag aag gct cca gcc atc tct gtc ctc      240
Glu Phe Asp Gly Asn Gln Phe Gln Lys Ala Pro Ala Ile Ser Val Leu
            45                  50                  55

cat gag ctg atc cag cag atc ttc aac ctc ttt acc aca aaa gat tca      288
```

```
His Glu Leu Ile Gln Gln Ile Phe Asn Leu Phe Thr Thr Lys Asp Ser
        60                  65                  70

tct gct gct tgg gat gag gac ctc cta gac aaa ttc tgc acc gaa ctc      336
Ser Ala Ala Trp Asp Glu Asp Leu Leu Asp Lys Phe Cys Thr Glu Leu
    75                  80                  85

tac cag cag ctg aat gac ttg gaa gcc tgt gtg atg cag gag gag agg      384
Tyr Gln Gln Leu Asn Asp Leu Glu Ala Cys Val Met Gln Glu Glu Arg
 90                  95                 100                 105

gtg gga gaa act ccc ctg atg aat gcg gac tcc atc ttg gct gtg aag      432
Val Gly Glu Thr Pro Leu Met Asn Ala Asp Ser Ile Leu Ala Val Lys
                110                 115                 120

aaa tac ttc cga aga atc act ctc tat ctg aca gag aag aaa tac agc      480
Lys Tyr Phe Arg Arg Ile Thr Leu Tyr Leu Thr Glu Lys Lys Tyr Ser
            125                 130                 135

cct tgt gcc tgg gag gtt gtc aga gca gaa atc atg aga tcc ctc tct      528
Pro Cys Ala Trp Glu Val Val Arg Ala Glu Ile Met Arg Ser Leu Ser
        140                 145                 150

tta tca aca aac ttg caa gaa aga tta agg agg aag gaa                  567
Leu Ser Thr Asn Leu Gln Glu Arg Leu Arg Arg Lys Glu
    155                 160                 165


<210> SEQ ID NO 10
<211> LENGTH: 189
<212> TYPE: PRT
<213> ORGANISM: Homo sapiens

<400> SEQUENCE: 10

Met Ala Ser Pro Phe Ala Leu Leu Met Val Leu Val Val Leu Ser Cys
            -20                 -15                 -10

Lys Ser Ser Cys Ser Leu Gly Cys Asp Leu Pro Glu Thr His Ser Leu
        -5              -1   1               5

Asp Asn Arg Arg Thr Leu Met Leu Leu Ala Gln Met Ser Arg Ile Ser
 10                  15                  20                  25

Pro Ser Ser Cys Leu Met Asp Arg His Asp Phe Gly Phe Pro Gln Glu
                30                  35                  40

Glu Phe Asp Gly Asn Gln Phe Gln Lys Ala Pro Ala Ile Ser Val Leu
            45                  50                  55

His Glu Leu Ile Gln Gln Ile Phe Asn Leu Phe Thr Thr Lys Asp Ser
        60                  65                  70

Ser Ala Ala Trp Asp Glu Asp Leu Leu Asp Lys Phe Cys Thr Glu Leu
    75                  80                  85

Tyr Gln Gln Leu Asn Asp Leu Glu Ala Cys Val Met Gln Glu Glu Arg
 90                  95                 100                 105

Val Gly Glu Thr Pro Leu Met Asn Ala Asp Ser Ile Leu Ala Val Lys
                110                 115                 120

Lys Tyr Phe Arg Arg Ile Thr Leu Tyr Leu Thr Glu Lys Lys Tyr Ser
            125                 130                 135

Pro Cys Ala Trp Glu Val Val Arg Ala Glu Ile Met Arg Ser Leu Ser
        140                 145                 150

Leu Ser Thr Asn Leu Gln Glu Arg Leu Arg Arg Lys Glu
    155                 160                 165


<210> SEQ ID NO 11
<211> LENGTH: 567
<212> TYPE: DNA
<213> ORGANISM: Mus musculus
<220> FEATURE:
<221> NAME/KEY: CDS
<222> LOCATION: (1)..(567)
```

-continued

```
<220> FEATURE:
<221> NAME/KEY: sig_peptide
<222> LOCATION: (1)..(69)
<220> FEATURE:
<221> NAME/KEY: mat_peptide
<222> LOCATION: (70)..(567)

<400> SEQUENCE: 11

atg gct agg ctc tgt gct ttc ctg atg gtc ctg gcg gtg atg agc tac       48
Met Ala Arg Leu Cys Ala Phe Leu Met Val Leu Ala Val Met Ser Tyr
            -20                 -15                 -10

tgg cca acc tgc tct cta gga tgt gac ctg cct cag act cat aac ctc       96
Trp Pro Thr Cys Ser Leu Gly Cys Asp Leu Pro Gln Thr His Asn Leu
         -5                  -1   1               5

agg aac aag aga gcc ttg aca ctc ctg gta caa atg agg aga ctc tcc      144
Arg Asn Lys Arg Ala Leu Thr Leu Leu Val Gln Met Arg Arg Leu Ser
 10                  15                  20                  25

cct ctc tcc tgc ctg aag gac agg aag gac ttt gga ttc ccg cag gag      192
Pro Leu Ser Cys Leu Lys Asp Arg Lys Asp Phe Gly Phe Pro Gln Glu
                 30                  35                  40

aag gtg gat gcc cag cag atc aag aag gct caa gcc atc cct gtc ctg      240
Lys Val Asp Ala Gln Gln Ile Lys Lys Ala Gln Ala Ile Pro Val Leu
             45                  50                  55

agt gag ctg acc cag cag atc ctg aac atc ttc aca tca aag gac tca      288
Ser Glu Leu Thr Gln Gln Ile Leu Asn Ile Phe Thr Ser Lys Asp Ser
         60                  65                  70

tct gct gct tgg aat gca acc ctc cta gac tca ttc tgc aat gac ctc      336
Ser Ala Ala Trp Asn Ala Thr Leu Leu Asp Ser Phe Cys Asn Asp Leu
     75                  80                  85

cac cag cag ctc aat gac ctg caa ggt tgt ctg atg cag cag gtg ggg      384
His Gln Gln Leu Asn Asp Leu Gln Gly Cys Leu Met Gln Gln Val Gly
 90                  95                 100                 105

gtg cag gaa ttt ccc ctg acc cag gaa gat gcc ctg ctg gct gtg agg      432
Val Gln Glu Phe Pro Leu Thr Gln Glu Asp Ala Leu Leu Ala Val Arg
                110                 115                 120

aaa tac ttc cac agg atc act gtg tac ctg aga gag aag aaa cac agc      480
Lys Tyr Phe His Arg Ile Thr Val Tyr Leu Arg Glu Lys Lys His Ser
            125                 130                 135

ccc tgt gcc tgg gag gtg gtc aga gca gaa gtc tgg aga gcc ctg tct      528
Pro Cys Ala Trp Glu Val Val Arg Ala Glu Val Trp Arg Ala Leu Ser
        140                 145                 150

tcc tct gcc aat gtg ctg gga aga ctg aga gaa gag aaa                  567
Ser Ser Ala Asn Val Leu Gly Arg Leu Arg Glu Glu Lys
    155                 160                 165


<210> SEQ ID NO 12
<211> LENGTH: 189
<212> TYPE: PRT
<213> ORGANISM: Mus musculus

<400> SEQUENCE: 12

Met Ala Arg Leu Cys Ala Phe Leu Met Val Leu Ala Val Met Ser Tyr
            -20                 -15                 -10

Trp Pro Thr Cys Ser Leu Gly Cys Asp Leu Pro Gln Thr His Asn Leu
         -5                  -1   1               5

Arg Asn Lys Arg Ala Leu Thr Leu Leu Val Gln Met Arg Arg Leu Ser
 10                  15                  20                  25

Pro Leu Ser Cys Leu Lys Asp Arg Lys Asp Phe Gly Phe Pro Gln Glu
                 30                  35                  40

Lys Val Asp Ala Gln Gln Ile Lys Lys Ala Gln Ala Ile Pro Val Leu
             45                  50                  55
```

```
Ser Glu Leu Thr Gln Gln Ile Leu Asn Ile Phe Thr Ser Lys Asp Ser
        60                  65                  70

Ser Ala Ala Trp Asn Ala Thr Leu Leu Asp Ser Phe Cys Asn Asp Leu
    75                  80                  85

His Gln Gln Leu Asn Asp Leu Gln Gly Cys Leu Met Gln Gln Val Gly
 90                  95                 100                 105

Val Gln Glu Phe Pro Leu Thr Gln Glu Asp Ala Leu Leu Ala Val Arg
                110                 115                 120

Lys Tyr Phe His Arg Ile Thr Val Tyr Leu Arg Glu Lys Lys His Ser
            125                 130                 135

Pro Cys Ala Trp Glu Val Val Arg Ala Glu Val Trp Arg Ala Leu Ser
        140                 145                 150

Ser Ser Ala Asn Val Leu Gly Arg Leu Arg Glu Glu Lys
    155                 160                 165


<210> SEQ ID NO 13
<211> LENGTH: 459
<212> TYPE: DNA
<213> ORGANISM: Homo sapiens
<220> FEATURE:
<221> NAME/KEY: CDS
<222> LOCATION: (1)..(459)
<220> FEATURE:
<221> NAME/KEY: sig_peptide
<222> LOCATION: (1)..(60)
<220> FEATURE:
<221> NAME/KEY: mat_peptide
<222> LOCATION: (61)..(459)

<400> SEQUENCE: 13

atg tac agg atg caa ctc ctg tct tgc att gca cta agt ctt gca ctt       48
Met Tyr Arg Met Gln Leu Leu Ser Cys Ile Ala Leu Ser Leu Ala Leu
-20                 -15                 -10                  -5

gtc aca aac agt gca cct act tca agt tct aca aag aaa aca cag cta       96
Val Thr Asn Ser Ala Pro Thr Ser Ser Ser Thr Lys Lys Thr Gln Leu
             -1   1               5                  10

caa ctg gag cat tta ctt ctg gat tta cag atg att ttg aat gga att      144
Gln Leu Glu His Leu Leu Leu Asp Leu Gln Met Ile Leu Asn Gly Ile
        15                  20                  25

aat aat tac aag aat ccc aaa ctc acc agg atg ctc aca ttt aag ttt      192
Asn Asn Tyr Lys Asn Pro Lys Leu Thr Arg Met Leu Thr Phe Lys Phe
    30                  35                  40

tac atg ccc aag aag gcc aca gaa ctg aaa cat ctt cag tgt cta gaa      240
Tyr Met Pro Lys Lys Ala Thr Glu Leu Lys His Leu Gln Cys Leu Glu
 45                  50                  55                  60

gaa gaa ctc aaa cct ctg gag gaa gtg cta aat tta gct caa agc aaa      288
Glu Glu Leu Lys Pro Leu Glu Glu Val Leu Asn Leu Ala Gln Ser Lys
                65                  70                  75

aac ttt cac tta aga ccc agg gac tta atc agc aat atc aac gta ata      336
Asn Phe His Leu Arg Pro Arg Asp Leu Ile Ser Asn Ile Asn Val Ile
            80                  85                  90

gtt ctg gaa cta aag gga tct gaa aca aca ttc atg tgt gaa tat gct      384
Val Leu Glu Leu Lys Gly Ser Glu Thr Thr Phe Met Cys Glu Tyr Ala
        95                 100                 105

gat gag aca gca acc att gta gaa ttt ctg aac aga tgg att acc ttt      432
Asp Glu Thr Ala Thr Ile Val Glu Phe Leu Asn Arg Trp Ile Thr Phe
    110                 115                 120

tgt caa agc atc atc tca aca ctg act                                  459
Cys Gln Ser Ile Ile Ser Thr Leu Thr
125                 130
```

-continued

<210> SEQ ID NO 14
<211> LENGTH: 153
<212> TYPE: PRT
<213> ORGANISM: Homo sapiens

<400> SEQUENCE: 14

```
Met Tyr Arg Met Gln Leu Leu Ser Cys Ile Ala Leu Ser Leu Ala Leu
-20                 -15                 -10                  -5

Val Thr Asn Ser Ala Pro Thr Ser Ser Ser Thr Lys Lys Thr Gln Leu
             -1   1               5                  10

Gln Leu Glu His Leu Leu Leu Asp Leu Gln Met Ile Leu Asn Gly Ile
         15                  20                  25

Asn Asn Tyr Lys Asn Pro Lys Leu Thr Arg Met Leu Thr Phe Lys Phe
     30                  35                  40

Tyr Met Pro Lys Lys Ala Thr Glu Leu Lys His Leu Gln Cys Leu Glu
 45                  50                  55                  60

Glu Glu Leu Lys Pro Leu Glu Glu Val Leu Asn Leu Ala Gln Ser Lys
                 65                  70                  75

Asn Phe His Leu Arg Pro Arg Asp Leu Ile Ser Asn Ile Asn Val Ile
             80                  85                  90

Val Leu Glu Leu Lys Gly Ser Glu Thr Thr Phe Met Cys Glu Tyr Ala
         95                 100                 105

Asp Glu Thr Ala Thr Ile Val Glu Phe Leu Asn Arg Trp Ile Thr Phe
    110                 115                 120

Cys Gln Ser Ile Ile Ser Thr Leu Thr
125                 130
```

<210> SEQ ID NO 15
<211> LENGTH: 26
<212> TYPE: DNA
<213> ORGANISM: Artificial Sequence
<220> FEATURE:
<223> OTHER INFORMATION: Description of Artificial Sequence:PCR oligo

<400> SEQUENCE: 15

```
aactgcagat ggctaggctc tgtgct                                           26
```

<210> SEQ ID NO 16
<211> LENGTH: 26
<212> TYPE: DNA
<213> ORGANISM: Artificial Sequence
<220> FEATURE:
<223> OTHER INFORMATION: Description of Artificial Sequence:PCR oligo

<400> SEQUENCE: 16

```
gaagatcttc atttctcttc tctcag                                           26
```

<210> SEQ ID NO 17
<211> LENGTH: 26
<212> TYPE: DNA
<213> ORGANISM: Artificial Sequence
<220> FEATURE:
<223> OTHER INFORMATION: Description of Artificial Sequence:PCR oligo

<400> SEQUENCE: 17

```
aactgcagat ggcctcgccc tttgct                                           26
```

<210> SEQ ID NO 18
<211> LENGTH: 28
<212> TYPE: DNA
<213> ORGANISM: Artificial Sequence
<220> FEATURE:
<223> OTHER INFORMATION: Description of Artificial Sequence:PCR oligo

<400> SEQUENCE: 18
cgggatcctt attccttcct ccttaatc 28

<210> SEQ ID NO 19
<211> LENGTH: 25
<212> TYPE: DNA
<213> ORGANISM: Artificial Sequence
<220> FEATURE:
<223> OTHER INFORMATION: Description of Artificial Sequence:PCR oligo

<400> SEQUENCE: 19
gctctagatg gccctcctgt tccct 25

<210> SEQ ID NO 20
<211> LENGTH: 26
<212> TYPE: DNA
<213> ORGANISM: Artificial Sequence
<220> FEATURE:
<223> OTHER INFORMATION: Description of Artificial Sequence:PCR oligo

<400> SEQUENCE: 20
gcggatcctc aagatgagcc caggtc 26

<210> SEQ ID NO 21
<211> LENGTH: 36
<212> TYPE: DNA
<213> ORGANISM: Artificial Sequence
<220> FEATURE:
<223> OTHER INFORMATION: Description of Artificial Sequence: PCR oligo

<400> SEQUENCE: 21
acgcgtcgac atgtgtcctc agaagctaac catctc 36

<210> SEQ ID NO 22
<211> LENGTH: 34
<212> TYPE: DNA
<213> ORGANISM: Artificial Sequence
<220> FEATURE:
<223> OTHER INFORMATION: Description of Artificial Sequence: PCR oligo

<400> SEQUENCE: 22
gcggatccct aggatcggac cctgcaggga acac 34

<210> SEQ ID NO 23
<211> LENGTH: 37
<212> TYPE: DNA
<213> ORGANISM: Artificial Sequence
<220> FEATURE:
<223> OTHER INFORMATION: Description of Artificial Sequence: PCR oligo

<400> SEQUENCE: 23
catgccatgg gtcaatcacg ctacctcctc tttttgg 37

<210> SEQ ID NO 24
<211> LENGTH: 30
<212> TYPE: DNA
<213> ORGANISM: Artificial Sequence
<220> FEATURE:
<223> OTHER INFORMATION: Description of Artificial Sequence: PCR oligo

<400> SEQUENCE: 24
gcggatcctc aggcggagct cagatagccc 30

<210> SEQ ID NO 25
<211> LENGTH: 5469
<212> TYPE: DNA
<213> ORGANISM: Mus musculus
<220> FEATURE:
<221> NAME/KEY: CDS
<222> LOCATION: (1923)..(2393)
<220> FEATURE:
<221> NAME/KEY: sig_peptide
<222> LOCATION: (1923)..(1994)
<220> FEATURE:
<221> NAME/KEY: mat_peptide
<222> LOCATION: (1995)..(2393)

<400> SEQUENCE: 25

```
tcgcgcgttt cggtgatgac ggtgaaaacc tctgacacat gcagctcccg gagacggtca     60
cagcttgtct gtaagcggat gccgggagca gacaagcccg tcagggcgcg tcagcgggtg    120
ttggcgggtg tcggggctgg cttaactatg cggcatcaga gcagattgta ctgagagtgc    180
accatatgcg gtgtgaaata ccgcacagat gcgtaaggag aaaataccgc atcagattgg    240
ctattggcca ttgcatacgt tgtatccata tcataatatg tacatttata ttggctcatg    300
tccaacatta ccgccatgtt gacattgatt attgactagt tattaatagt aatcaattac    360
ggggtcatta gttcatagcc catatatgga gttccgcgtt acataactta cggtaaatgg    420
cccgcctggc tgaccgccca acgacccccg cccattgacg tcaataatga cgtatgttcc    480
catagtaacg ccaataggga ctttccattg acgtcaatgg gtggagtatt tacggtaaac    540
tgcccacttg gcagtacatc aagtgtatca tatgccaagt acgcccccta ttgacgtcaa    600
tgacggtaaa tggcccgcct ggcattatgc ccagtacatg accttatggg actttcctac    660
ttggcagtac atctacgtat tagtcatcgc tattaccatg gtgatgcggt tttggcagta    720
catcaatggg cgtggatagc ggtttgactc acggggattt ccaagtctcc accccattga    780
cgtcaatggg agtttgtttt ggcaccaaaa tcaacgggac tttccaaaat gtcgtaacaa    840
ctccgcccca ttgacgcaaa tgggcggtag gcgtgtacgg tgggaggtct atataagcag    900
agctcgttta gtgaaccgtc agatcgcctg gagacgccat ccacgctgtt ttgacctcca    960
tagaagacac cgggaccgat ccagcctccg cggccgggaa cggtgcattg gaacgcggat   1020
tccccgtgcc aagagtgacg taagtaccgc ctatagagtc tataggccca cccccttggc   1080
ttcttatgca tgctatactg tttttggctt ggggtctata cacccccgct tcctcatgtt   1140
ataggtgatg gtatagctta gcctataggt gtgggttatt gaccattatt gaccactccc   1200
ctattggtga cgatactttc cattactaat ccataacatg gctctttgcc acaactctct   1260
ttattggcta tatgccaata cactgtcctt cagagactga cacggactct gtatttttac   1320
aggatggggt ctcatttatt atttacaaat tcacatatac aacaccaccg tccccagtgc   1380
ccgcagtttt tattaaacat aacgtgggat ctccacgcga atctcgggta cgtgttccgg   1440
acatgggctc ttctccggta gcggcggagc ttctacatcc gagccctgct cccatgcctc   1500
cagcgactca tggtcgctcg gcagctcctt gctcctaaca gtggaggcca gacttaggca   1560
cagcacgatg cccaccacca ccagtgtgcc gcacaaggcc gtggcggtag ggtatgtgtc   1620
tgaaaatgag ctcggggagc gggcttgcac cgctgacgca tttggaagac ttaaggcagc   1680
ggcagaagaa gatgcaggca gctgagttgt tgtgttctga taagagtcag aggtaactcc   1740
cgttgcggtg ctgttaacgg tggagggcag tgtagtctga gcagtactcg ttgctgccgc   1800
gcgcgccacc agacataata gctgacagac taacagactg ttcctttcca tgggtctttt   1860
```

-continued

```
ctgcagtcac cgtccttaga tctagcctca accctgacta tcttccaggt cattgttcca   1920

ac atg gcc ctg tgg atc gac agg atg caa ctc ctg tct tgc att gca      1967
   Met Ala Leu Trp Ile Asp Arg Met Gln Leu Leu Ser Cys Ile Ala
                   -20                 -15                 -10

cta agt ctt gca ctt gtc aca aac agt gca cct act tca agt tct aca     2015
Leu Ser Leu Ala Leu Val Thr Asn Ser Ala Pro Thr Ser Ser Ser Thr
                -5                 -1   1               5

aag aaa aca cag cta caa ctg gag cat tta ctg ctg gat tta cag atg     2063
Lys Lys Thr Gln Leu Gln Leu Glu His Leu Leu Leu Asp Leu Gln Met
        10                  15                  20

att ttg aat gga att aat aat tac aag aat ccc aaa ctc acc agg atg     2111
Ile Leu Asn Gly Ile Asn Asn Tyr Lys Asn Pro Lys Leu Thr Arg Met
    25                  30                  35

ctc aca ttt aag ttt tac atg ccc aag aag gcc aca gaa ctg aaa cat     2159
Leu Thr Phe Lys Phe Tyr Met Pro Lys Lys Ala Thr Glu Leu Lys His
 40                 45                  50                  55

ctt cag tgt cta gaa gaa gaa ctc aaa cct ctg gag gaa gtg cta aat     2207
Leu Gln Cys Leu Glu Glu Glu Leu Lys Pro Leu Glu Glu Val Leu Asn
                60                  65                  70

tta gct caa agc aaa aac ttt cac tta aga ccc agg gac tta atc agc     2255
Leu Ala Gln Ser Lys Asn Phe His Leu Arg Pro Arg Asp Leu Ile Ser
            75                  80                  85

aat atc aac gta ata gtt ctg gaa cta aag gga tct gaa aca aca ttc     2303
Asn Ile Asn Val Ile Val Leu Glu Leu Lys Gly Ser Glu Thr Thr Phe
        90                  95                  100

atg tgt gaa tat gct gat gag aca gca acc att gta gaa ttt ctg aac     2351
Met Cys Glu Tyr Ala Asp Glu Thr Ala Thr Ile Val Glu Phe Leu Asn
    105                 110                 115

aga tgg att acc ttt tgt caa agc atc atc tca aca cta act             2393
Arg Trp Ile Thr Phe Cys Gln Ser Ile Ile Ser Thr Leu Thr
120                 125                 130

tgataattaa gtgcttccca cttaaaacat atcagggatc tcgactctag aggatcatcg   2453

cggccgctct agaccaggcg cctggatcca gatctgctgt gccttctagt tgccagccat   2513

ctgttgtttg cccctccccc gtgccttcct tgaccctgga aggtgccact cccactgtcc   2573

tttcctaata aaatgaggaa attgcatcgc attgtctgag taggtgtcat tctattctgg   2633

ggggtggggt ggggcagcac agcaaggggg aggattggga agacaatagc aggcatgctg   2693

gggatgcggt gggctctatg ggtacccagg tgctgaagaa ttgacccggt tcctcctggg   2753

ccagaaagaa gcaggcacat ccccttctct gtgacacacc ctgtccacgc ccctggttct   2813

tagttccagc cccactcata ggacactcat agctcaggag ggctccgcct tcaatcccac   2873

ccgctaaagt acttggagcg gtctctccct ccctcatcag cccaccaaac caaacctagc   2933

ctccaagagt gggaagaaat taaagcaaga taggctatta agtgcagagg gagagaaaat   2993

gcctccaaca tgtgaggaag taatgagaga aatcatagaa tttcttccgc ttcctcgctc   3053

actgactcgc tgcgctcggt cgttcggctg cggcgagcgg tatcagctca ctcaaaggcg   3113

gtaatacggt tatccacaga atcaggggat aacgcaggaa agaacatgtg agcaaaaggc   3173

cagcaaaagg ccaggaaccg taaaaaggcc gcgttgctgg cgtttttcca taggctccgc   3233

cccccctgacg agcatcacaa aaatcgacgc tcaagtcaga ggtggcgaaa cccgacagga   3293

ctataaagat accaggcgtt tccccctgga agctccctcg tgcgctctcc tgttccgacc   3353

ctgccgctta ccggatacct gtccgccttt ctcccttcgg gaagcgtggc gctttctcaa   3413

tgctcacgct gtaggtatct cagttcggtg taggtcgttc gctccaagct gggctgtgtg   3473

cacgaacccc ccgttcagcc cgaccgctgc gccttatccg gtaactatcg tcttgagtcc   3533
```

-continued

```
aacccggtaa gacacgactt atcgccactg gcagcagcca ctggtaacag gattagcaga   3593

gcgaggtatg taggcggtgc tacagagttc ttgaagtggt ggcctaacta cggctacact   3653

agaaggacag tatttggtat ctgcgctctg ctgaagccag ttaccttcgg aaaaagagtt   3713

ggtagctctt gatccggcaa acaaaccacc gctggtagcg gtggtttttt tgtttgcaag   3773

cagcagatta cgcgcagaaa aaaaggatct caagaagatc ctttgatctt ttctacgggg   3833

tctgacgctc agtggaacga aaactcacgt taagggattt tggtcatgag attatcaaaa   3893

aggatcttca cctagatcct tttaaattaa aaatgaagtt ttaaatcaat ctaaagtata   3953

tatgagtaaa cttggtctga cagttaccaa tgcttaatca gtgaggcacc tatctcagcg   4013

atctgtctat ttcgttcatc catagttgcc tgactccggg gggggggggc gctgaggtct   4073

gcctcgtgaa gaaggtgttg ctgactcata ccaggcctga atcgccccat catccagcca   4133

gaaagtgagg gagccacggt tgatgagagc tttgttgtag gtggaccagt tggtgatttt   4193

gaacttttgc tttgccacgg aacggtctgc gttgtcggga agatgcgtga tctgatcctt   4253

caactcagca aaagttcgat ttattcaaca aagccgccgt cccgtcaagt cagcgtaatg   4313

ctctgccagt gttacaacca attaaccaat tctgattaga aaaactcatc gagcatcaaa   4373

tgaaactgca atttattcat atcaggatta tcaataccat atttttgaaa aagccgtttc   4433

tgtaatgaag gagaaaactc accgaggcag ttccatagga tggcaagatc ctggtatcgg   4493

tctgcgattc cgactcgtcc aacatcaata caacctatta atttcccctc gtcaaaaata   4553

aggttatcaa gtgagaaatc accatgagtg acgactgaat ccggtgagaa tggcaaaagc   4613

ttatgcattt ctttccagac ttgttcaaca ggccagccat tacgctcgtc atcaaaatca   4673

ctcgcatcaa ccaaaccgtt attcattcgt gattgcgcct gagcgagacg aaatacgcga   4733

tcgctgttaa aaggacaatt acaaacagga atcgaatgca accggcgcag gaacactgcc   4793

agcgcatcaa caatattttc acctgaatca ggatattctt ctaatacctg gaatgctgtt   4853

ttcccgggga tcgcagtggt gagtaaccat gcatcatcag gagtacggat aaaatgcttg   4913

atggtcggaa gaggcataaa ttccgtcagc cagtttagtc tgaccatctc atctgtaaca   4973

tcattggcaa cgctaccttt gccatgtttc agaaacaact ctggcgcatc gggcttccca   5033

tacaatcgat agattgtcgc acctgattgc ccgacattat cgcgagccca tttataccca   5093

tataaatcag catccatgtt ggaatttaat cgcggcctcg agcaagacgt ttcccgttga   5153

atatggctca taacacccct tgtattactg tttatgtaag cagacagttt tattgttcat   5213

gatgatatat ttttatcttg tgcaatgtaa catcagagat tttgagacac aacgtggctt   5273

tccccccccc cccattattg aagcatttat cagggttatt gtctcatgag cggatacata   5333

tttgaatgta tttagaaaaa taaacaaata ggggttccgc gcacatttcc ccgaaaagtg   5393

ccacctgacg tctaagaaac cattattatc atgacattaa cctataaaaa taggcgtatc   5453

acgaggccct ttcgtc                                                    5469
```

<210> SEQ ID NO 26
<211> LENGTH: 157
<212> TYPE: PRT
<213> ORGANISM: Mus musculus

<400> SEQUENCE: 26

```
Met Ala Leu Trp Ile Asp Arg Met Gln Leu Leu Ser Cys Ile Ala Leu
                -20                 -15                 -10

Ser Leu Ala Leu Val Thr Asn Ser Ala Pro Thr Ser Ser Ser Thr Lys
```

-continued

```
           -5            -1   1             5

Lys Thr Gln Leu Gln Leu Glu His Leu Leu Leu Asp Leu Gln Met Ile
     10                  15                  20

Leu Asn Gly Ile Asn Asn Tyr Lys Asn Pro Lys Leu Thr Arg Met Leu
 25                  30                  35                  40

Thr Phe Lys Phe Tyr Met Pro Lys Lys Ala Thr Glu Leu Lys His Leu
                45                  50                  55

Gln Cys Leu Glu Glu Glu Leu Lys Pro Leu Glu Glu Val Leu Asn Leu
            60                  65                  70

Ala Gln Ser Lys Asn Phe His Leu Arg Pro Arg Asp Leu Ile Ser Asn
        75                  80                  85

Ile Asn Val Ile Val Leu Glu Leu Lys Gly Ser Glu Thr Thr Phe Met
     90                  95                 100

Cys Glu Tyr Ala Asp Glu Thr Ala Thr Ile Val Glu Phe Leu Asn Arg
105                 110                 115                 120

Trp Ile Thr Phe Cys Gln Ser Ile Ile Ser Thr Leu Thr
                125                 130
```

METHODS FOR TREATING CANCER USING INTERFERON-ω-EXPRESSING POLYNUCLEOTIDES

This application is a continuation of U.S. patent application Ser. No. 09/557,907, filed Apr. 21, 2000, now allowed, which is a continuation-in-part of U.S. patent application Ser. No. 09/196,313, filed Nov. 20, 1998, now abandoned, which claims the benefit of the following provisional applications: 60/067,087 filed Nov. 20, 1997; 60/079,914, filed Mar. 30, 1998; and 60/100,820, filed Sep. 15, 1998, all of which are incorporated herein by reference.

BACKGROUND OF THE INVENTION

1. Field of the Invention

The present invention relates to treatment of cancer in mammals. Generally, the present invention provides methods of treating cancer in a mammal by administering a polynucleotide construct comprising a polynucleotide encoding a cytokine. In addition, the present invention relates to the methodology for selective transfection of malignant cells with polynucleotides expressing therapeutic or prophylactic molecules in intra-cavity tumor bearing mammals. More specifically, the present invention provides a methodology for the suppression of an intra-cavity dissemination of malignant cells, such as intraperitoneal dissemination.

The present invention further relates generally to compositions and methods useful for in vivo polynucleotide-based polypeptide delivery into cells of vertebrates. More particularly, the present invention provides the use of sodium phosphate solutions in compositions and methods useful for direct polynucleotide-based polypeptide delivery into the cells of vertebrates.

2. Related Art

Cytokines have been demonstrated both in pre-clinical animal models as well as in humans to have potent anti-tumor effects. In particular IFN's have been tried for the treatment of a number of human concerns.

The interferons (IFNs) are a family of cytokines with potent anti-viral, antiproliferative, and immunomodulatory activities and play important roles in the body's defensive response to viruses, bacteria, and tumors (Baron, S. et al., *JAMA* 266:1375 (1991)). On the basis of antigenicity, biochemical properties, and producer cell, the interferon's have been divided into two classes, type I interferon and type II interferon. IFNα, IFNβ, IFNω, and IFNτ are type I interferons, and bind to the same α/β receptor. IFNγ is a type II interferon, and binds to the γ receptor (Pestka, S., *Ann. Rev. Biochem.* 56:727 (1987)). IFNα and IFNβ are naturally expressed in many cells upon viral infection. IFNγ is produced by activated T lymphocytes and natural killer (NK) cells. IFNτ is believed to possess hormone activity, and plays an important role in pregnancy in cattle, sheep, and related ruminants (Imakawa, K. et al., *Nature* 330:377 (1987); Stewart, H. J. et al., *J. Endocrinology* 115:R13 (1987)). Due to the pleiotropic activities of IFNs, these cytokines have been studied for their therapeutic efficacy in a number of diseases, particularly cancers and viral infectious diseases.

IFNω was discovered independently by three different groups in 1985 (Capon, D. J., et al., *Molec. Cell. Biol.* 5: 768-779 (1985), Feinstein, S. et al., *Molec. Cell. Biol* 5:510 (1985); and Hauptmann and Swetly, *Nucl. Acids Res.* 13: 4739-4749 (1985)). Unlike IFNα, for which at least 14 different functional nonallelic genes have been identified in man, IFNω is encoded by a single functional gene. IFNω genes are believed to be present in most mammals, but have not been found in dogs, rats or mice. The mature IFNω polypeptide is 172 amino acids and shares 60% sequence homology with the human IFNα's. Due to the sequence similarity with IFNα, IFNω was originally considered to be a member or a subfamily of IFNα, and was originally termed IFNα-$_{II}$. IFNω is a significant component (≈10%) of human leukocyte-derived interferon, the natural mixture of interferon produced after viral infection (Adolf, G. et al., *Virology* 175:410 (1990)). IFNω has been demonstrated to bind to the same α/β receptor as IFNα (Flores, I. et al., *J. Biol. Chem.* 266: 19875-19877 (1991)), and to share similar biological activities with IFNα, including anti-proliferative activity against tumor cells in vitro (Kubes, M. et al., *J. Interferon Research* 14:57 (1994) and immunomodulatory activity (Nieroda et al., *Molec. Cell. Differentiation* 4: 335-351 (1996)).

Recombinant IFNα polypeptide has been approved for use in humans for hairy cell leukemia, AIDS-related Kaposi's sarcoma, malignant melanoma, chronic hepatitis B and C, chronic myleogenous leukemia, and condylomata acuminata (Baron, S. et al., *JAMA* 266:1375 (1991)). However, for each of these indications, IFNα polypeptide must be administered repeatedly, often on a daily basis, for extended periods of time to maintain effective serum levels due to the short half-life (hours) of the polypeptide in the serum (Friedman, *Interferons: A Primer*, Academic Press, New York, pp. 104-107 (1981); Galvani and Cawley, *Cytokine Therapy*, Cambridge University Press, Cambridge, pp. 114-115 (1992)). Thus, in spite of producing clinical benefit for many disease conditions, the use of IFNα polypeptide is associated with acute and chronic side effects in most patients (Jones, *Cancer* 57: 1709-1715 (1986); and Quesda et al., *Blood* 68: 493-497 (1986)). The severity of the adverse reaction correlates with peak serum interferon levels.

Viral or plasmid vectors containing IFNα genes have been used in ex vivo therapy to treat mouse tumors. For example, tumor cells were transfected in vitro with viral or plasmid vectors containing an IFNα gene, and the transfected tumor cells were injected into mice (Belldegrun, A., et al., *J. Natl. Cancer Inst.* 85: 207-216 (1993); Ferrantini, M. et al., *Cancer Research* 53: 1107-1112 (1993); Ferrantini, M. et al., *J. Immunology* 153: 4604-4615 (1994); Kaido, T. et al., *Int. J. Cancer* 60: 221-229 (1995); Ogura, H. et al., *Cancer Research* 50: 5102-5106 (1990); Santodonato, L., et al., *Human Gene Therapy* 7:1-10 (1996); Santodonato, L., et al., *Gene Therapy* 4:1246-1255 (1997)). In another ex vivo study, cervical carcinoma and leukemia cells were transfected with a viral vector containing the interferon-consensus gene, and the transfected cells were injected into mice (Zhang, J.-F. et al., *Cancer Gene Therapy* 3: 31-38 (1996)). In all of these ex vivo studies, varying levels of anti-tumor efficacy, such as tumor regression and/or prolonged survival, have been observed.

Viral or plasmid vectors containing interferon genes have also been used in in vivo therapy for tumor-bearing mice. For example, a viral vector containing the interferon-consensus gene was injected into mice bearing transplanted MDA-MB-435 breast cancer, hamster melanoma, or K562 leukemia, and tumor regression was reported (Zhang, J.-F. et al., *Proc. Natl. Acad. Sci. USA* 93: 4513-4518 (1996)). In a similar study, a plasmid vector containing human IFNβ gene complexed with cationic lipid was injected intracranially into mice bearing a human glioma, and tumor regression was reported (Yagi, K. et al., *Biochemistry and Molecular Biology International* 32: 167-171 (1994)). In a murine model of renal cell carcinoma the direct intratumoral injection of an IL-2 plasmid DNA: lipid complex has been shown to result in complete tumor regression and a significant induction of a tumor specific CTL response increase in survival (Saffran et al., *Cancer Gene Therapy* 5: 321-330 (1998)).

Plasmid vectors containing cytokine genes have also been reported to result in systemic levels of the encoded cytokine and in some cases, biological effects characteristic of each cytokine in mice. For example, the intramuscular injection of plasmid DNA encoding either TGFβ, IL-2, IL-4, IL-5, or IFNα resulted in physiologically significant amounts in the systemic circulation of the corresponding cytokine polypeptide (Raz, E. et al., *Proc. Natl. Acad. Sci. USA* 90: 4523-4527 (1993); Raz, E. et al., *Lupus* 4: 266-292 (1995); Tokui, M. et al., *Biochem. Biophys. Res. Comm.* 233: 527-531 (1997); Lawson, C. et al., *J. Interferon Cytokine Res.* 17: 255-261 (1997); Yeow, W.-S. et al., *J. Immunol.* 160: 2932-2939 (1998)).

U.S. Pat. No. 5,676,954 reports on the injection of genetic material, complexed with cationic liposomes carriers, into mice. U.S. Pat. Nos. 4,897,355; 4,946,787; 5,049,386; 5,459,127; 5,589,466; 5,693,622; 5,580,859; 5,703,055; and International Patent Application No. PCT/US94/06069 (publication no. WO 94/29469) provide cationic lipids for use in transfecting DNA into cells and mammals. U.S. Pat. Nos. 5,589,466, 5,693,622, 5,580,859, 5,703,055, and international patent application no. PCT/US94/06069 (publication no. WO 04/9469) provide methods for delivering DNA-cationic lipid complexes to mammals.

Even though some viral vectors used in ex vivo and in vivo cancer therapy in murine models showed anti-tumor efficacy, the use of viral vectors to deliver interferon-expressing genes in vivo could induce anti-viral immune responses or result in viral integration into host chromosomes, causing disruption of essential host genes or activation of oncogenes (Ross et al., *Human Gene Therapy* 7: 1781-1790 (1996)).

For treatment of multiple metastatic carcinomas of a body cavity are treated using laparoscopy (Childers et al, *Gynecol. Oncol.* 59: 25-33, (1995)), catheterization (Naumann et al, *Gynecol. Oncol.* 50: 291-3, (1993)) or other access devices (Almadrones et al, *Semin. Oncol. Nurs.* 11: 194-202, (1995)). Treatment is usually by surgical removal of primary and large metastatic tumors and postoperative chemotherapy (Kigwawa et al, *Am. J. Clin. Oncol.* 17: 230-3, (1994); Markman et al, *J. Clin. Oncol.* 10: 1485-91, (1992)) or radiotherapy (Fjeld et al, *Acta. Obstet. Gynecol. Scand Suppl.* 155: 105-11, (1992)). Tumor recurrence is monitored by magnetic resonance imaging (Forstner et al, *Radiology* 196: 715-20, (1995)), ascites cytology (Clement, *Am. J. Clin. Pathol.* 103: 673-6, (1995); Forstner et al, *Radiology* 196: 715-20, 1995) and blood analyses (Forstner et al, *Radiology* 196: 715-20, (1995)). Many intraperitoneal (i.p.) cancers, such as ovarian cancer, eventually metastasize via the lymphatic system to the lungs or other vital organs, and the prognosis for the patient is very poor (Kataoka et al, *Nippon Sanka Fujinka Gakkai Zasshi* 46: 337-44, 1994; Hamilton, *Curr. Probl. Cancer* 16: 1-57, (1992)).

Human ovarian cancer is often diagnosed at an advanced stage when the effectiveness of surgery and chemotherapy are limited. The lack of effective treatment options for late-stage patients warrants the development of new treatment modalities for this disease. There have been several attempts to develop an effective immunotherapy for the treatment of ovarian cancer.

The early work in this area involved mouse studies in which bacteria-derived immunostimulants, such as *Bacillus Calmette-Guerin* (BCG) and *Corynebacterium parvum*, were injected i.p. as non-specific activators of the immune system. (Knapp and Berkowitz, *Am. J. Obstet. Gynecol.,* 128: 782-786, (1977); Bast et al., *J. Immunol.,* 123: 1945-1951, (1979); Vanhaelen, et al., *Cancer Research,* 41: 980-983, (1981); and Berek, et al., *Cancer Research,* 44, 1871-1875, (1984)). These studies generally resulted in a non-specific immune response that often did not prevent the growth of later tumors. In addition, if the bacterial antigens were injected more than 24 hours after tumor cell inoculation, there was minimal antitumor response, suggesting that treatment of late-stage ovarian cancer patients with this type of therapy would not be effective.

More recent studies in both mice and humans have involved the i.p. or intravenous (i.v.) administration of cytokine proteins as more specific activators of the immune response (Adachi, et al, *Cancer Immunol. Immunother.* 37: 1-6, (1993); Lissoni, et al, *Tumori.* 78: 118-20, (1992)). Treating murine ovarian tumors with a combination of recombinant IL-2 and GM-CSF proteins had some beneficial effect in inhibiting ascites production; however, IL-2 was only effective if it was combined with GM-CSF (Kikuchi, et al., *Cancer Immunol. Immunother.,* 43: 257-261, (1996)). Similarly, a combination of IL-2 and lymphokine-activated killer (LAK) cells was able to reduce i.p. sarcomas in mice, while IL-2 protein alone was not as effective (Ottow, et al., *Cellular Immunology,* 104: 366-376, (1987)). Human clinical trials evaluating IL-2 protein therapy of ovarian cancer patients indicated some antitumor effects (Chapman et al., *Investigational New Drugs,* 6:179-188, (1988); West et al., *N. Engl. J. Med.* 316:898-905, 1987; Lotze et al., *Arch. Surg.* 121:1373-1379, 1986; Benedetti Panici et al., *Cancer Treatment Review,* 16A:123-127, 1989; Beller et al., *Gynecol. Oncol.,* 34:407-412, 1989; Urba et al., *J. Natl. Cancer Inst.,* 81:602-611, 1989; Stewart et al., *Cancer Res.,* 50:6302-6310, 1990; Steis et al., *J. Clin. Oncol.,* 8:1618-1629, 1990; Lissoni et al., *Tumori,* 78:118-120, 1992; Sparano et al., *J. of Immunotherapy,* 16:216-223, 1994; Freedman et al., *J. of Immunotherapy,* 16:198-210, 1994; Edwards et al., *J. Clin. Oncol.,* 15:3399-3407, 1997).

Recent studies in mice have involved the injection of DNA constructs encoding "suicide" genes followed by treatment with prodrugs. This approach has successfully caused regression of some small tumors but has been less successful on larger tumor masses. (Szala, et al. *Gene Therapy* 3: 1025-1031, 1996; Sugaya, et al. *Hum Gene Ther* 7: 223-230 (1996)). In another study, liposome-mediated E1A gene therapy for mice bearing ovarian cancers that overexpress HER-2/neu resulted in reduced mortality among these tumor bearing mice. (Yu, et al. *Oncogene,* 11: 1383-1388 (1995)). Similarly, the successful treatment of murine ovarian carcinoma (MOT) has been demonstrated using cisplatin-induced gene transfer of DNA constructs encoding IFNγ via i.p. injection. (Son, *Cancer Gene Therapy* 4: 391-396 (1997)). However, this study demonstrated that tumors were poorly responsive to either the IFNγ gene or cisplatin alone, suggesting that the effectiveness of the cisplatin-based gene therapy protocol was mainly due to enhanced sensitization of cisplatin-exposed tumor cells to transfection by the IFNγ gene. (Son, *Cancer Gene Therapy* 4: 391-396, 1997).

Clearly, there is a need for superior therapeutic compositions and methods for treating mammalian cancer. Further, there is a need for an in vivo delivery system for IFNω. The present invention provides a simple and safe yet effective compositions and methods for treatment of mammalian cancer.

The present invention also solves the problems inherent in prior attempts to treat body cavity malignancies. The inventors show herein that the malignant cell dissemination into body cavities, such as into the peritoneal cavity during late stage ovarian cancer, can be suppressed simply by administering as few as two to six doses of a polynucleotide formulation directly into the body cavity. This treatment results in selective transfection of malignant cells, and subsequent long-term local production of an effective amount of therapeutic molecules.

The in vivo delivery of a polynucleotide (e.g., plasmid DNA) into vertebrate tissues has been shown to result in the cellular uptake and expression of the polynucleotide into a desired polypeptide (Wolff, J. A. et al., *Science* 247:1465-1468 (1990); Wheeler, C. J. et al., *Proc. Natl. Acad. Sci. USA* 93:11454-11459 (1996)). Potential human therapeutic uses of such polynucleotide-based polypeptide delivery include immune response induction and modulation, therapeutic polypeptide delivery, and amelioration of genetic defects. For example, a polynucleotide may encode an antigen that induces an immune response against an infectious pathogen or against tumor cells (Restifo, N. P. et al., *Folia Biol.* 40:74-88 (1994); Ulmer, J. B. et al., *Ann. NY Acad. Sci.* 772:117-125 (1995); Horton, H. M. et al., *Proc. Natl. Acad. Sci. USA* 96:1553-1558 (1999); Yagi, K. et al., *Hum. Gene Ther.* 10: 1975-1982 (1999)). The polynucleotide may encode an immunomodulatory polypeptide, e.g., a cytokine, that diminishes an immune response against self antigens or modifies the immune response to foreign antigens, allergens, or transplanted tissues (Qin, L. et al., *Ann. Surg.* 220:508-518 (1994); Dalesandro, J. et al., *J. Thorac. Cardiovasc. Surg.* 111: 416-421 (1996); Moffatt, M. and Cookson, W., *Nat. Med.* 2:515-516 (1996); Ragno, S. et al., *Arth. and Rheum.* 40:277-283 (1997); Dow, S. W. et al., *Hum. Gene Ther.* 10:1905-1914 (1999); Piccirillo, C. A. et al., *J. Immunol.* 161:3950-3956 (1998); Piccirillo, C. A. and Prud'homme, G. J., *Hum. Gene Ther.* 10: 915-1922 (1999)). For therapeutic polypeptide delivery, the polynucleotide may encode, for example, an angiogenic protein, hormone, growth factor, or enzyme (Levy, M. Y. et al., *Gene Ther.* 3:201-211 (1996); Tripathy, S. K. et al., *Proc. Natl. Acad. Sci. USA* 93:10876-10880 (1996); Tsurumi, Y. et al., *Circulation* 94:3281-3290 (1996); Novo, F. J. et al., *Gene Ther.* 4:488-492 (1997); Baumgartner, I. et al., *Circulation* 97:1114-1123 (1998); Mir, L. M. et al., *Proc. Natl. Acad. Sci. USA* 96:4262-4267 (1999)). For amelioration of genetic defects, the polynucleotide may encode normal copies of defective proteins such as dystrophin or cystic fibrosis transmembrane conductance regulator (Danko, I. et al., *Hum. Mol. Genet.* 2:2055-2061 (1993); Cheng, S. H. and Scheule, R. K., *Adv. Drug Deliv. Rev.* 30:173-184 (1998)).

However, the efficiency of a polynucleotide uptake and expression, especially when the polynucleotide is not associated with infectious agents, is relatively low. For example, Doh, S. G. et al., *Gene Ther.* 4:648-663 (1997) reports that the administration of plasmid DNA into mouse muscle results in the detectable transduction of an average of only 6%, e.g., about 234 out of approximately 4000, of the myofibers in the injected muscle. Wheeler, C. G. et al., ibid., showed that administration of plasmid DNA complexed with cationic lipid into a mouse lung results in the transduction of less than 1% of the lung cells.

Attempts have been made to increase the efficiency of in vivo polynucleotide administration into vertebrates using chemical agents or physical manipulations. Such chemical agents include cellular toxins such as bupivacaine or barium chloride (Wells, D. J., *FEBS Letters* 332:179-182 (1993); Vitadello, M. et al., *Hum. Gene. Ther.* 5:11-18 (1994); Danko, I. et al., *Hum. Mol. Genet.* 2:2055-2061 (1993)) which act to cause muscle damage followed by muscle regeneration by cell division which makes the cells more receptive to DNA entry (Thomason, D. B. and Booth, F. W., *Am. J. Physiol.* 258:C578-81 (1990)); polymers such as polyvinyl pyrollidine that coat the DNA and protect it from DNases (Mumper, R. J., et al., *Pharm. Res.* 13:701-709 (1996); Mumper R. J. et al., *J. Cont. Rel.* 52:191-203 (1998); Anwer, K. et al., *Pharm. Res.* 16:889-95 (1999)); bulking agents such as sucrose that are injected before DNA injection to help expand the spaces between muscle cells and therefore allow better distribution of the subsequently injected DNA (Davis, H. L. et al., *Hum. Gene Ther.* 4:151-159 (1993)); DNA binding agents such as histones or intercalaters that protect the DNA from DNases (Manthorpe, M. et al., *Hum. Gene Ther.* 4:419-431 (1993); Wolff, J. A., *Neuromuscul. Disord.* 7:314-318 (1997); WO 99/31262). Physical manipulations include removal of nerves that control muscle contraction (Wolff, J. A. et al., *BioTechniques* 11:575-485 (1991)); electroporation that electrically opens muscle cell pores allowing more DNA entry (Aihara, H. and Miyazaki, J., *Nature Biotechnol.* 16:867-870 (1998); Mir, L. M. et al., *CR Acad Sci. III* 321:893-899 (1998), Mir, L. M. et al., *Proc. Natl. Acad. Sci. USA* 96:4262-4267 (1999); Mathiesen, I., *Gene Ther.* 6:508-514 (1999); Rizzuto, G. et al., *Proc. Natl. Acad. Sci. USA* 96:6417-6422 (1999)); use of intravascular pressure (Budker, V. et al., *Gene Ther.* 5:272-276 (1998)); use of sutures coated with plasmid DNA (Labhasetwar, V. et al., *J. Pharm. Sci.* 87:1347-1350 (1998); Qin, Y. et al., *Life Sci.* 65:2193-2203 (1999)); use of sponges soaked with DNA as intramuscular depots to prolong DNA delivery (Wolff, J. A. et al. (1991), ibid.); use of special needle-based injection methods (Levy, M. Y. et al., *Gene Ther.* 3:201-211 (1996); Doh, S. G. et al. (1997), ibid.); and of needleless-injectors that propel the DNA into cells (Gramzinski, R. A. et al., *Molec. Med.* 4:109-118 (1998); Smith, B. F. et al., *Gene Ther.* 5:865-868 (1998); Anwer, K. et al. (1999) ibid.). In addition, Wolff, J. A. et al. (1991) ibid. and Manthorpe, M. et al. (1993) ibid. refers to conditions affecting direct gene transfer into rodent muscle in vivo.

WO99/64615 identifies the use of products and methods useful for delivering formulated nucleic acid molecules using electrical pulse voltage delivery. Examples include the formulation of plasmid DNA in a saline solution containing agents that promote better delivery of the plasmid DNA into cells in vivo when the formulation is delivered with an electrical pulse. Electrical pulse delivery often comprises electroporation where an electrical pulse is delivered to a tissue that is previously injected with a drug. Electroporation of a tissue causes transient interruption of cell membranes allowing more drug to enter the cell through the interruptions or "pores". The agents in the saline DNA solution that promote delivery of the DNA into electroporated tissues include propylene glycols, polyethylene glycols, poloxamers (block copolymers of propylene oxide and ethylene oxide), or cationic lipids. They claim that the way that these agents enhance delivery of the DNA into cells is by either protecting the DNA from degradation by DNases or by condensing the DNA into a smaller form, or both.

Many of these attempts to enhance tissue transduction have used agents that destroy muscle (bupivacaine, barium chloride) and actually lower expression (Norman, J. et al., *Methods in Molec. Med.* 29:185-196 (1999)); have to be pre-injected before the DNA (sucrose); are expensive organic polymers (polyvinyl pyrollidine), mutagens (intercalaters), antigenic proteins (histones) or devices that destroy muscle tissue (needless or needle-free injectors); or need to be inserted surgically (sutures, sponges, intravascular pressure). Furthermore, most of these methods may be expensive and not suitable or practical for human use.

On the other hand, little attention has been given to the use of alternative salt solutions and/or auxiliary agents in the pharmaceutical formulation as a way of enhancing the efficiency of a polynucleotide-based polypeptide delivery. Investigators in this field routinely use normal saline or phosphate buffered saline (PBS 0.9% (i.e., about 154 mM) NaCl and 10 mM Na-phosphate) solutions for polynucleotide delivery, e.g., by intramuscular injection, because they are physiologically isotonic, isoosmotic, stable, non-toxic, and also because they have been traditionally used for human intramuscular injections of other drugs. However, sodium phosphate, in the absence of saline, has been used in humans for delivery of non-polynucleotide-based drugs (e.g., small molecules) administered via the intramuscular or intravenous routes (See generally, *Physician's Desk Reference*. Medical Economics Co, Monyvale, N.J. (1998)).

Sodium or potassium phosphate have been reported to enhance Lipofectin™-mediated transfection of human osteosarcoma cells in vitro (Kariko, K., et al., *Biochim Biophys Acta* 1369:320-334 (1998)), and the use of RPMI cell culture medium buffered with $NaHCO_3/Na_2HPO_4$ were reported to be the best medium for forming DNA/cationic lipid complexes in vitro. (Kichler, A., et al., *Gene Ther.* 5:855-860 (1998)).

There remains a need in the art for a convenient and safe way of improving the effectiveness of in vivo polypeptide delivery via direct administration of a polynucleotide. Aqueous solutions of certain salts including sodium phosphate have been used in humans (i.e., intramuscular injection of various small molecule drugs), and detergents or surfactants as auxiliary agents are common additives in drugs administered into human tissues. However, the use of certain salts or auxiliary agents, or a combination thereof to improve the transduction, i.e., the entry into cells, and/or expression-enhancing efficiency of polynucleotides delivered in vivo is new.

SUMMARY OF THE INVENTION

The present invention is broadly directed to treatment of cancer by administering in vivo, into a tissue of a mammal suffering from cancer, a polynucleotide construct comprising a polynucleotide encoding a cytokine. The polynucleotide construct is incorporated into the cells of the mammal in vivo, and a therapeutically effective amount of a cytokine is produced in vivo, and delivered to tumor cells. Combinations of cytokine-encoding polynucleotides can be administered.

The present invention provides a pharmaceutical composition comprising about 1 ng to 20 mg of a non-infectious, non-integrating polynucleotide construct comprising a polynucleotide selected from the group consisting of (a) a polynucleotide that hybridizes under stringent conditions to the nucleotide sequence of SEQ ID No. 7 or the complement thereof, wherein the polynucleotide sequence encodes a polypeptide that has antiproliferative activity when added to NIH-OVCAR3 cells in vitro; (b) a polynucleotide that encodes a polypeptide comprising an amino acid sequence which, except for at least one but not more than 20 amino acid substitutions, deletions, or insertions, is identical to amino acids −23 to 172 or 1 to 172 in SEQ ID No. 8, wherein the polypeptide has antiproliferative activity when added to NIH-OVCAR3 cells in vitro; and (c) a polynucleotide that encodes a polypeptide comprising amino acids 86-172 in SEQ ID No. 8, wherein the polypeptide has antiproliferative activity when added to NIH-OVCAR3 cells in vitro; and any of the above group complexed with one or more cationic compounds selected from the group consisting of cationic lipids, cationic peptides, cationic proteins, cationic polymers, and mixtures thereof.

The present invention also provides a pharmaceutical composition obtained by complexing a polynucleotide selected from the group consisting of (a) a polynucleotide that hybridizes under stringent conditions to the nucleotide sequence of SEQ ID No. 7 or the complement thereof, wherein the polynucleotide sequence encodes a polypeptide that has antiproliferative activity when added to NIH-OVCAR3 cells in vitro; (b) a polynucleotide that encodes a polypeptide comprising an amino acid sequence which, except for at least one but not more than 20 amino acid substitutions, deletions, or insertions, is identical to amino acids −23 to 172 or 1 to 172 in SEQ ID No. 8, wherein the polypeptide has antiproliferative activity when added to NIH-OVCAR3 cells in vitro; (c) a polynucleotide that encodes a polypeptide comprising amino acids 86-172 in SEQ ID No. 8, wherein the polypeptide has antiproliferative activity when added to NIH-OVCAR3 cells in vitro, with one or more cationic compounds selected from the group consisting of cationic lipids, cationic peptides, cationic proteins, cationic polymers, and mixtures thereof.

The present invention also provides a method of treating cancer in a mammal, comprising administering into a tissue of the mammal a non-infectious, non-integrating polynucleotide construct comprising a polynucleotide encoding a cytokine, or an active fragment thereof, such that the polynucleotide is expressed in vivo, and such that the cytokine, or active fragment thereof, is delivered systemically to a tumor tissue in an amount effective to treat the cancer.

The present invention also provides a method of treating cancer in a mammal, comprising administering into a tissue of the mammal a non-infectious, non-integrating polynucleotide construct comprising a polynucleotide encoding a cytokine selected from the group consisting of interferon-ω, interferon-α, and a combination thereof, such that the polynucleotide or an active fragment thereof is expressed, and such that the cytokine is delivered locally to a tumor tissue in an amount effective to treat the cancer. Preferably, the polynucleotide construct is complexed with a cationic vehicle, more preferably, the cationic vehicle may be a cationic lipid, and most preferably, the cationic lipid may be mixed with a neutral lipid.

Another object of the invention is to provide a method of selectively transfecting malignant cells in a body cavity of a tumor-bearing mammal, comprising administering into the body cavity at least one non-infectious, non-integrating polynucleotide complexed with a cationic vehicle, such that the polynucleotide is expressed substantially in the malignant cells of the body cavity. Preferably, the cationic vehicle comprises one or more cationic lipids, and more preferably, the cationic vehicle comprises a cationic and neutral lipid mixture. In a preferred embodiment, the present invention is used to suppress peritoneal dissemination of malignant cells in a tumor-bearing mammal. In particular, the mammal may have ovarian cancer, or metastasis of ovarian cancer. Preferred polynucleotides may encode cytokines, or active fragments thereof. Most preferably, the polynucleotide may encode IL-2, or an active fragment thereof.

Compared to injection of recombinant cytokine polypeptides, the methods described herein have several important advantages. The present invention shows that in vivo transfection of cells with encoding polynucleotide, such as an IL-2 or IFNω, results in serum levels of the corresponding cytokine that have therapeutic effects, and yet are lower than the maximal serum levels typically required when cytokine polypeptides are injected. Further, injecting frequent high doses of cytokine polypeptides can produce debilitating side effects. The methods of the present invention provide cytokine therapy requiring less frequent injections of cytokine-encoding nucleic acids. The injection of polynucleotide constructs encoding cytokines produces sustained, low levels of biologically active cytokines that have beneficial effects, while minimizing adverse side effects.

Compared to the delivery of cytokine genes via a viral gene delivery vectors, the present method also has important advantages. Injection of non-viral vectors of the present method does not induce significant toxicity or pathological immune responses, as described, for example, in mice, pigs or monkeys (Parker, et al., *Human Gene Therapy* 6: 575-590 (1995); and San, et al., *Human Gene Therapy* 4: 781-788 (1993)). Thus, a non-viral vector is safer and can be repeatedly injected.

The present invention is further directed to compositions, and methods for using such compositions, for improving the effectiveness of polypeptide delivery into a vertebrate by administering in vivo, a polypeptide-encoding polynucleotide in an aqueous solution sodium phosphate. The polynucleotide is incorporated into the cells of the vertebrate in vivo, and encodes a detectable amount or a prophylactically or therapeutically effective amount, of a desired polypeptide.

The present invention further provides a composition selected from the group consisting of (a) a composition comprising about 1 ng to about 30 mg of a polynucleotide in aqueous solution, where the polynucleotide operably encodes a polypeptide within vertebrate cells in vivo; and sodium phosphate dissolved in the aqueous solution at a molar concentration from about 20 mM to about 300 mM, and reaction, association, or dissociation products thereof; and (b) a composition comprising: about 1 ng to about 30 mg of a polynucleotide in aqueous solution, where the polynucleotide operably encodes a polypeptide within vertebrate cells in vivo; sodium phosphate dissolved in the aqueous solution at a molar concentration from about 0.1 mM to about 150 mM, and reaction, association, or dissociation products thereof; and a cationic lipid suspended in said aqueous solution; where the aqueous solution is substantially free of chloride anion.

Another aspect of the present invention is a method for delivering a polypeptide into a vertebrate, comprising administering to the vertebrate a composition selected from the group consisting of (a) a composition comprising about 1 ng to about 30 mg of a polynucleotide in aqueous solution, where the polynucleotide operably encodes a polypeptide within vertebrate cells in vivo; and sodium phosphate dissolved in the aqueous solution at a molar concentration from about 20 mM to about 300 mM, and reaction, association, or dissociation products thereof; and (b) a composition comprising: about 1 ng to about 30 mg of a polynucleotide in aqueous solution, where the polynucleotide operably encodes a polypeptide within vertebrate cells in vivo; sodium phosphate dissolved in the aqueous solution at a molar concentration from about 0.1 mM to about 150 mM, and reaction, association, or dissociation products thereof; and a cationic lipid suspended in said aqueous solution; where the aqueous solution is substantially free of chloride anion; such that the polypeptide encoded by the delivered polynucleotide is expressed in the vertebrate, in an amount sufficient to be detectable.

Another aspect of the present invention is a method for delivering a therapeutic polypeptide into a vertebrate, comprising administering to a vertebrate in need of such a therapeutic polypeptide a composition selected from the group consisting of (a) a composition comprising about 1 ng to about 30 mg of a polynucleotide in aqueous solution, where the polynucleotide operably encodes a polypeptide within vertebrate cells in vivo; and sodium phosphate dissolved in the aqueous solution at a molar concentration from about 20 mM to about 300 mM, and reaction, association, or dissociation products thereof; and (b) a composition comprising: about 1 ng to about 30 mg of a polynucleotide in aqueous solution, where the polynucleotide operably encodes a polypeptide within vertebrate cells in vivo; sodium phosphate dissolved in the aqueous solution at a molar concentration from about 0.1 mM to about 150 mM, and reaction, association, or dissociation products thereof; and a cationic lipid suspended in said aqueous solution; where the aqueous solution is substantially free of chloride anion; such that a therapeutic polypeptide encoded by the delivered polynucleotide is expressed in the vertebrate, in a therapeutically effective amount.

The present invention also provides a method of producing antibodies to a polypeptide in a vertebrate, comprising administering to the vertebrate a composition selected from the group consisting of (a) a composition comprising about 1 ng to about 30 mg of a polynucleotide in aqueous solution, where the polynucleotide operably encodes a polypeptide within vertebrate cells in vivo; and sodium phosphate dissolved in the aqueous solution at a molar concentration from about 20 mM to about 300 mM, and reaction, association, or dissociation products thereof; and (b) a composition comprising: about 1 ng to about 30 mg of a polynucleotide in aqueous solution, where the polynucleotide operably encodes a polypeptide within vertebrate cells in vivo; sodium phosphate dissolved in the aqueous solution at a molar concentration from about 0.1 mM to about 150 mM, and reaction, association, or dissociation products thereof; and a cationic lipid suspended in said aqueous solution; where the aqueous solution is substantially free of chloride anion; such that a polypeptide encoded by the delivered polynucleotide is expressed in the vertebrate, in a sufficient amount to generate antibody to the encoded polypeptide in the vertebrate.

The present invention also provides a method of enhancing or modulating an immune response in a vertebrate in need of such an enhanced or modulated immune response, comprising administering to the vertebrate a composition selected from the group consisting of (a) a composition comprising about 1 ng to about 30 mg of a polynucleotide in aqueous solution, where the polynucleotide operably encodes a polypeptide within vertebrate cells in vivo; and sodium phosphate dissolved in the aqueous solution at a molar concentration from about 20 mM to about 300 mM, and reaction, association, or dissociation products thereof; and (b) a composition comprising: about 1 ng to about 30 mg of a polynucleotide in aqueous solution, where the polynucleotide operably encodes a polypeptide within vertebrate cells in vivo; sodium phosphate dissolved in the aqueous solution at a molar concentration from about 0.1 mM to about 150 mM, and reaction, association, or dissociation products thereof; and a cationic lipid suspended in said aqueous solution; where the aqueous solution is substantially free of chloride anion; such that an immunogenic and/or immunomodulatory polypeptide encoded by the delivered polynucleotide is expressed in the vertebrate, in a sufficient amount to induce a desired immune response in the vertebrate to prevent disease or treat disease, i.e., cure disease, reduce the severity of disease symptoms, or prolong the life of the vertebrate.

The invention further provides a method of delivering a physiologically or metabolically necessary polypeptide to a vertebrate incapable of making a functional form of the polypeptide, comprising administering to the vertebrate a composition selected from the group consisting of (a) a composition comprising about 1 ng to about 30 mg of a polynucleotide in aqueous solution, where the polynucleotide operably encodes a polypeptide within vertebrate cells in vivo; and sodium phosphate dissolved in the aqueous solution at a molar concentration from about 20 mM to about 300 mM, and reaction, association, or dissociation products thereof; and (b) a composition comprising: about 1 ng to about 30 mg of a polynucleotide in aqueous solution, where the polynucleotide operably encodes a polypeptide within vertebrate cells in vivo; sodium phosphate dissolved in the aqueous solution at a molar concentration from about 0.1 mM to about 150 mM, and reaction, association, or dissociation products thereof; and a cationic lipid suspended in said aqueous solution; where the aqueous solution is substantially free of chloride anion; such that a functional self polypeptide, i.e., a physiologically or metabolically necessary polypeptide encoded by the delivered polynucleotide is expressed in the vertebrate, in a sufficient amount to supply the vertebrate's requirements for the polypeptides.

The present invention also provides a pharmaceutical kit selected from the group consisting of: (a) a pharmaceutical kit comprising: a container or containers holding about 1 ng to about 30 mg of a polynucleotide which operably encodes a polypeptide within vertebrate cells in vivo; an amount of sodium phosphate which, when dissolved in a prescribed volume of distilled water, results in an aqueous solution with a molar concentration of sodium phosphate from about 20 mM to about 300 mM, and reaction, association, or dissociation products thereof; and optionally, an administration means and/or an instruction sheet; whereby the polynucleotide is provided in a prophylactically or therapeutically effective amount to treat a vertebrate; and (b) a pharmaceutical kit comprising: a container or containers holding about 1 ng to about 30 mg of a polynucleotide which operably encodes a polypeptide within vertebrate cells in vivo; an amount of sodium phosphate which, when dissolved in a prescribed volume of distilled water, results in an aqueous solution with a molar concentration of said salt from about 0.1 mM to about 150 mM, and reaction, association, or dissociation products thereof, and where the aqueous solution formed thereby is essentially free of chloride anion; a cationic lipid; and optionally, an administration means and/or an instruction sheet; whereby the polynucleotide is provided in a prophylactically or therapeutically effective amount. Any of components of the pharmaceutical kit can be provided in a single container, or in multiple containers packaged together.

The inventors have discovered that delivery of the compositions provided herein to a vertebrate results in much improved in vivo polypeptide expression over the delivery of existing nucleic acid-based compositions, e.g., compositions comprising polynucleotides which encode a polypeptide and an aqueous solution consisting of sterile water, normal saline (i.e., 154 mM sodium chloride), or phosphate buffered saline (i.e., 154 mM sodium chloride plus 10 mM sodium phosphate).

BRIEF DESCRIPTION OF THE FIGURES

A more complete appreciation of the invention and many of the attendant advantages thereof will be readily obtained as the same become better understood by reference to the following detailed description when considered in connection with the accompanying figures.

FIG. 2 shows the pharmacokinetics of hIFNω in the serum of C57BL/6 mice (FIG. 2A) and nude mice (FIG. 2B) after a single intramuscular (i.m.) injection of hIFNω plasmid DNA (VR4151). Mice were injected i.m. with 100 μg of VR4151. Following the intramuscular injection, mice were bled daily, and serum was collected and assayed for hIFNω polypeptide using an ELISA. Each point represents an average of four mice. In C57BL/6 mice, the single i.m. injection resulted in peak serum levels of 254 pg/ml on day 6 after injection, and serum levels were still detectable 14 days after injection (50 pg/ml) (FIG. 2A). In nude mice, the single i.m. injection resulted in peak serum levels of 648 pg/ml on day 7, and serum levels were still detectable 14 days after injection (134 pg/ml) (FIG. 2B).

FIG. 4 shows that systemic mIFNα, mIL-2 or mIL-12 plasmid DNA treatment reduces tumor volume (FIG. 4A) and mIFNα or mIL-12 plasmid DNA treatment increases survival (FIG. 4B) in the subcutaneous B16F10 melanoma model. C57BL/6 mice bearing subcutaneous B16F10 melanoma were injected with 100 μg of VR4111 (mIFNα), VR4001 (mIL-12), VR1110 (mIL-2), or VR1012 (control plasmid) (n=15-16 mice per group) twice per week for three weeks.

FIG. 5 shows that i.m. administration of hIFNω pDNA reduces tumor volume (FIG. 5A) and increases survival (FIG. 5B) in nude mice bearing human A431 epidermoid carcinoma tumors. Mice bearing human A431 tumors between 30-80 $mm^3$ were injected i.m. with 200 μg of either VR4151 (hIFNω plasmid) or VR1055 (control plasmid) twice per week for three weeks (n=15)

FIG. 7 shows that i.m. administration of mIFNα pDNA reduces intradermal M5076 primary tumor growth (FIG. 7A) as well as liver metastases (FIG. 7B) in C57BL/6 mice bearing murine M5076 reticulum cell sarcoma cells. Mice bearing M5076 tumors were injected i.m. with 100 μg of either VR4111 or VR1055 twice per week for three weeks, beginning on day 4 after tumor cell inoculation (n=10-13 mice per group).

FIG. 8 shows a comparison of different dosages and frequencies of mIFNα pDNA administration in the subcutaneous B16F10 melanoma model. C57BL/6 mice bearing subcutaneous B16F10 melanoma were injected i.m. with 50 μg or 100 μg of either VR4111 or VR1055 twice a week for 3 weeks beginning 4 days after tumor cell inoculation (n=10 mice per group). All groups treated with 100 μg of VR4111 showed significant reduction in tumor growth by day 21 (p=0.002) and significant enhancement in survival (p<0.008) with all treatments tested (FIGS. 8A and 8B). In mice treated with 50 μg VR4111, tumor growth was significantly reduced by day 21 ($p=0.005$), and survival was significantly increased ($p<0.003$) in the groups of mice that were injected twice per week or once per week. The group injected every other week with 50 μg VR4111 was not significantly different from the mice that received the control plasmid (FIGS. 8C and 8D).

FIG. 10 shows the results of experiments performed to evaluate the role of $CD4^+$ and $CD8^+$ T cells in the mIFNα DNA antitumor response. For depletion of $CD4^+$ and $CD8^+$ T cells, C57BL/6 mice bearing subcutaneous B16F10 melanoma tumors were injected i.p. with 500 μg of either the anti-CD4 mAb (clone GK1.5, rat IgG) (ATCC, Rockville, Md.) or anti-CD8 mAb (clone 2.43, rat IgG) (ATCC, Rockville, Md.) one day after each i.m. injection of 100 μg of either VR4111 or VR1055 twice per week for three weeks (n=10 mice per group). The mIFNα plasmid DNA therapy significantly reduced tumor growth ($p \leqq 0.002$) (FIG. 10A) and enhanced survival ($p \leqq 0.008$) (FIG. 10B) of both normal mice and mice depleted of $CD4^+$ T cells, suggesting that $CD4^+$ T cells were not required for the response. In contrast, mice depleted of $CD8^+$ T cells and injected with VR4111 had tumor volumes and survival that were not significantly different from mice treated with the control plasmid DNA, indicating a requirement for $CD8^+$ T cells in the antitumor response.

FIG. 11 shows that intratumoral hIFNω (VR4151) and hIFNα (VR4112) treatment reduces tumor volume in the human A375 melanoma model (FIG. 11A) and human NIH-OVCAR3 (FIG. 11B) in nude mice. Mice bearing subcutaneous tumor received direct intratumoral injections of a complex of DNA:DMRIE/DOPE (1:1 DNA:lipid mass ratio, 100 μg of plasmid DNA) for 6 consecutive days followed by an additional 5 treatments every other day for a total of 11 injections (A375 melanoma model), or for every other day for a total of 11 injections (NIH-OVCAR3 ovarian cancer model).

FIG. 12 shows that intratumoral mIFNα (VR4101) plasmid DNA treatment reduces tumor volume (FIG. 12A) and increases survival (FIG. 12B) in the subcutaneous B16F10 melanoma model in C57BL/6 mice. Mice received a subcutaneous implantation of $10^4$ B16F10 cells into the flank. Beginning at day 12 post tumor implant, mice received six consecutive intratumoral injections of a complex of pDNA: DMRIE/DOPE (1:1 DNA:DMRIE mass ratio, 100 μg of plasmid DNA).

FIG. 13 shows luciferase activity in peritoneal tissues and MOT ascites in mice after i.p. injection of luciferase DNA: lipid complex. The results show high levels of reporter gene expression in ascites but low levels in peritoneal tissue. MOT tumor-bearing C3H/HeN mice received i.p. injections of a complex of pDNA:DMRIE/DOPE (1:1 DNA:DMRIE mass ratio, 100 μg of plasmid DNA) on days 5 and 6 after tumor cell implant. Tissues were collected 1 day (FIG. 13A) or 3 days (FIG. 13B) following the DNA:lipid injection.

FIG. 14 shows serum levels of IL-2 after i.p. injection of either IL-2 pDNA or protein in MOT tumor bearing mice. The serum levels of IL-2 (FIG. 14B) were much lower than levels in ascites (FIG. 14A). Ascites and serum were collected at 4 hours and days 1, 2, 3, 6 and 10 post DNA or protein injection (5 mice for each time point), and analyzed for mIL-2 polypeptide using an ELISA.

FIG. 15 shows a significant reduction in MOT tumor growth ($p=0.01$) (FIG. 15A) and increased survival ($p=0.04$) (FIG. 15B) of mice treated with i.p. injection of IL-2 pDNA: lipid on days 5-10 after tumor cell injection. The DNA was complexed at either a 1:1 (FIG. 15B) or 5:1 (FIGS. 15C and 15D) DNA:DMRIE mass ratio (100 μg pDNA). Plasmid DNA without lipid Was not effective (FIGS.15E and 15F)

FIG. 16 shows that i.p. mIL-2 plasmid DNA (VR1110): lipid treatment inhibits tumor growth (FIG. 16A) and enhances survival (FIG. 16B) in the MOT tumor model in C3H/HeN mice. MOT tumor-bearing mice received three alternative-day i.p. injections of a complex of pDNA:DMRIE/DOPE (1:1 DNA:DMRIE mass ratio, 100 μg of plasmid DNA).

FIG. 17 shows a significant reduction in MOT tumor growth (FIG. 17A) and increased survival (FIG. 17B) of mice treated with i.p. injection of IL-2 DNA:lipid followed by debulking of tumor ascites. MOT tumor-bearing mice received six consecutive intraperitoneal injections of a complex of pDNA:DMRIE/DOPE (1:1 DNA:DMRIE mass ratio, 100 μg of pDNA) and debulked of 5 ml of tumor ascites 4 days after the last DNA:lipid injection (n=10).

FIG. 18 shows dose-response of mIL-2 pDNA (VR1110): lipid treatment in the MOT tumor model. C3H/HeN mice bearing MOT tumor were injected with 25, 50 or 100 μg of VR1110:DMRIE/DOPE on days 5, 8 and 11 after MOT tumor cell injection. In mice treated with 50 or 100 μg of VR1110, tumor growth (FIG. 18A) was significantly reduced ($p=0.002$) and survival (FIG. 18B) significantly enhanced ($p=0.01$) by day 15 post tumor cell inoculation compared to the control. Tumor-bearing mice treated with 25 μg of VR1110:lipid were not significantly different from the control mice for either tumor volume or survival (n=15).

FIG. 20 shows that i.p. mIFNα pDNA (VR4111):lipid treatment enhances survival (FIG. 20B) and reduces tumor growth (FIG. 20A) in the MOT tumor model in C3H/HeN mice. MOT tumor-bearing mice received three alternative-day i.p. injections of a complex of pDNA:DMRIE/DOPE (1:1 DNA:DMRIE mass ratio, 100 μg of plasmid DNA).

FIG. 21 shows the schematic contents of plasmid DNAs used in the examples that follow. All vectors contain a pUC19 origin of replication, human cytomegalovirus intron A, and the bacterial kanamycin resistance gene. "Lux" denotes the coding region encoding luciferase, from the firefly, *Photinus pyralis*; "CMV" denotes the human cytomegalovirus immediate early region—promoter and enhancer; "BGH" denotes the bovine growth hormone transcriptional terminator;

"LacZ" denotes the coding region encoding the β-galactosidase protein of *Escherichia coli*; "RSV" denotes the Rous sarcoma virus promoter and enhancer; "EPO" denotes the coding region encoding murine erythropoietin; "SEAP" denotes the coding region for secreted human placental alkaline phosphatase; "Rat preproinsulin" denotes the coding region for rat preproinsulin containing a point mutation to change histidine B10 (codon CAC) to aspartic acid (codon GAC), Abai, A. M., et al. *Human Gene Therapy* 10:2637-2649 (1999); "IFN-omega" denotes the coding region encoding human interferon-ω; "mRGB" denotes the modified rabbit β-globin transcriptional terminator; and "NP" denotes the coding region encoding the nucleoprotein of influenza virus A/PR/8/34. Intermediate and parental plasmids *VR1012, VR1255 and *VIJ were prepared as described by Manthorpe, M. et al., *Hum. Gene Ther.* 4:419-431 (1993), Hartikka, J. et al., *Hum. Gen. Ther.* 7:1205-1217 (1996), and Montgomery, D. L. et al., *DNA Cell Biol.* 12:777-783 (1993), respectively. VR1043 was derived from VR1012 by replacing the SacI-NdeI CMV promoter enhancer fragment with the RSV promotor enhancer.

Figure 22A:
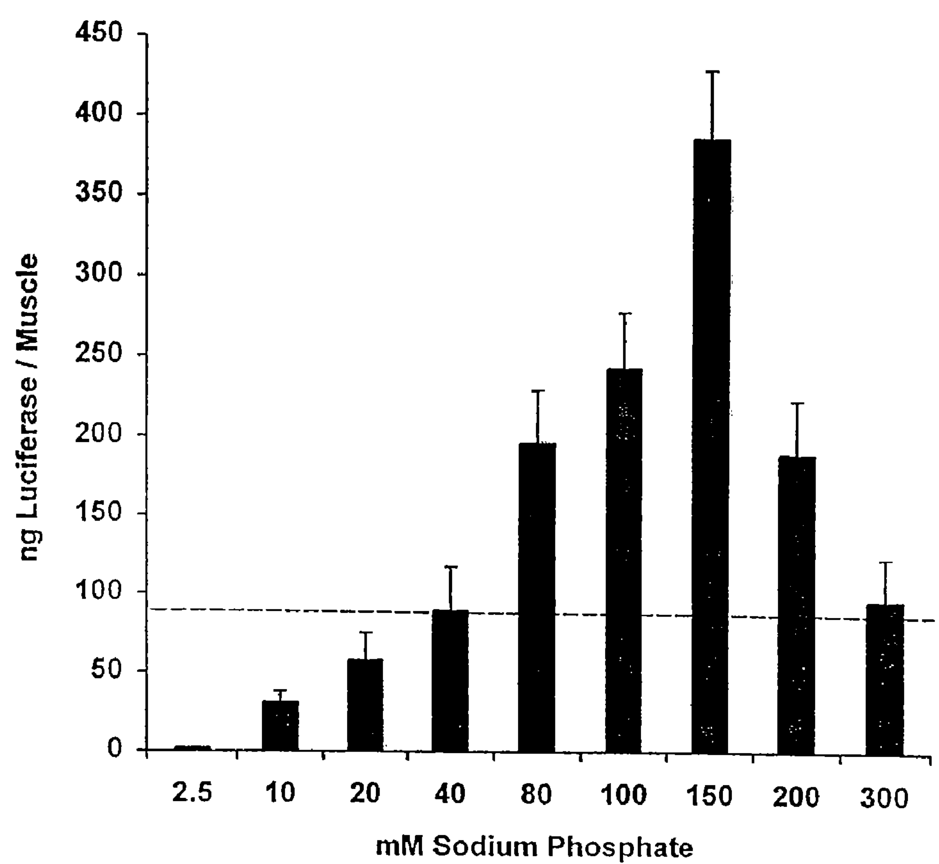

FIG. 22A is a bar graph demonstrating the effectiveness of sodium phosphate concentration on luciferase expression in mouse muscle. Fifty μg of plasmid VR1223 DNA per 50 μl sodium phosphate solution at the indicated molar concentrations was injected into mouse quadriceps and the muscles were extracted and assayed for enzyme activity 7 days later. Bars represent Standard Error of the Mean (n=50, 5 experiments each with n=10 per concentration). Peak expression occurred with DNA dissolved in 150 mM sodium phosphate, and yielded 386 ng luciferase per muscle which is 4.3-fold higher than the saline average (dashed line at 89 ng luciferase per muscle). The 80, 100, 150 and 200 mM sodium phosphate values were significantly higher than saline by Mann-Whitney rank sum test (p<0.05).

Figure 22B:
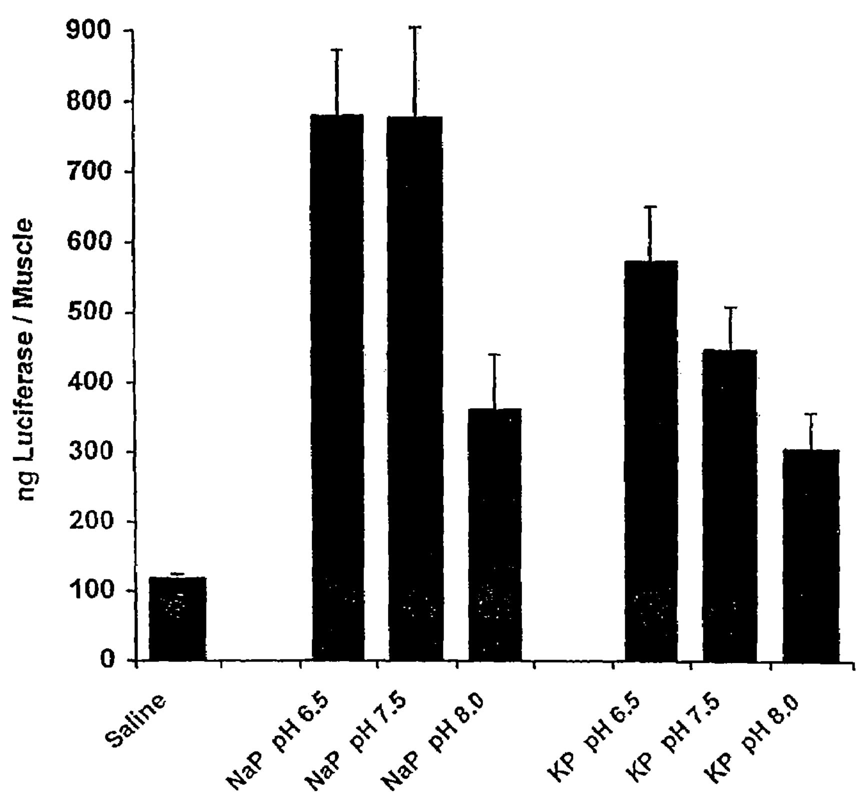

FIG. 22B is a bar graph demonstrating the effect of pH of the sodium phosphate and potassium phosphate solutions on luciferase expression in mouse muscle. Fifty μg of plasmid VR1223 DNA per 50 μl sodium phosphate and potassium phosphate solution at the indicated pH was injected into mouse quadriceps and the muscles were extracted and assayed for enzyme activity 7 days later. Bars represent Standard Error of the Mean (n=20 muscles per group).

Figure 22D:
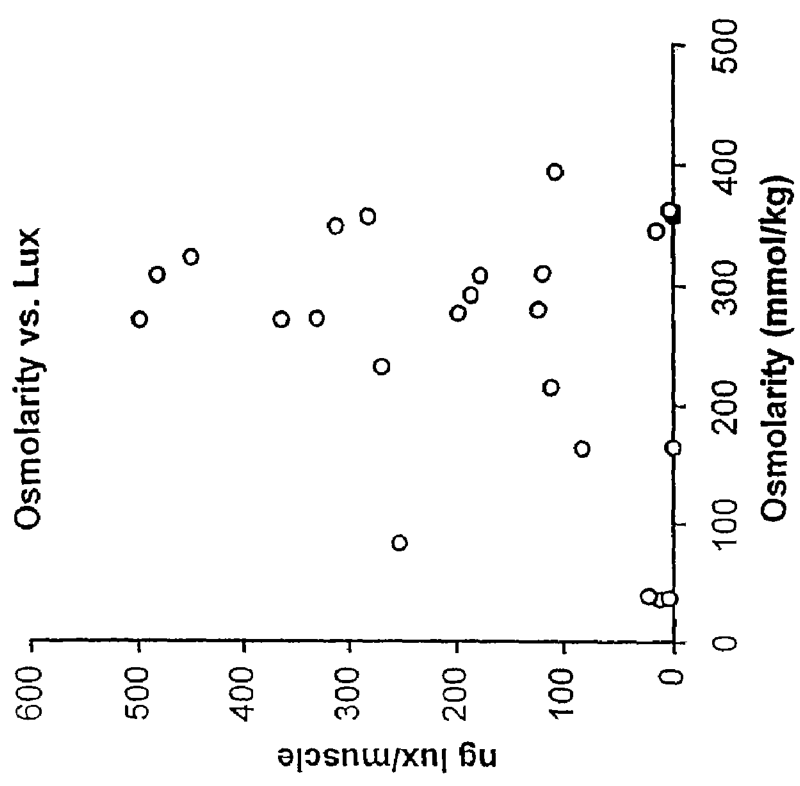
Figure 22C:
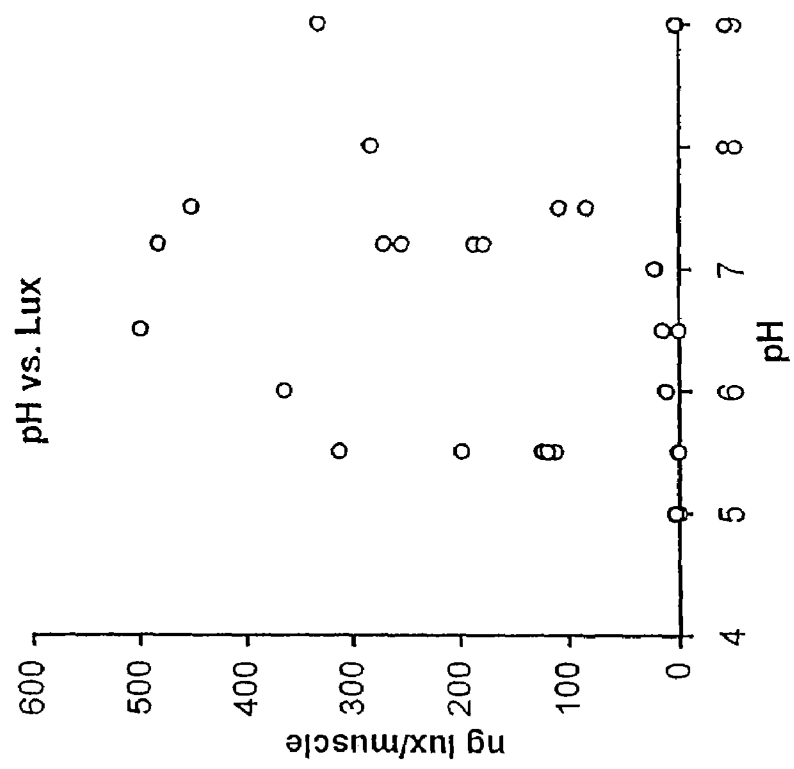

FIG. 22C is a graph plotting the effect of pH of the various salt solutions listed in Table 11-A on luciferase expression in mouse muscle.

FIG. 22D is a graph plotting the effect of osmolarity of the various salt solutions listed in Table 11-B on luciferase expression in mouse muscle.

Figure 23:
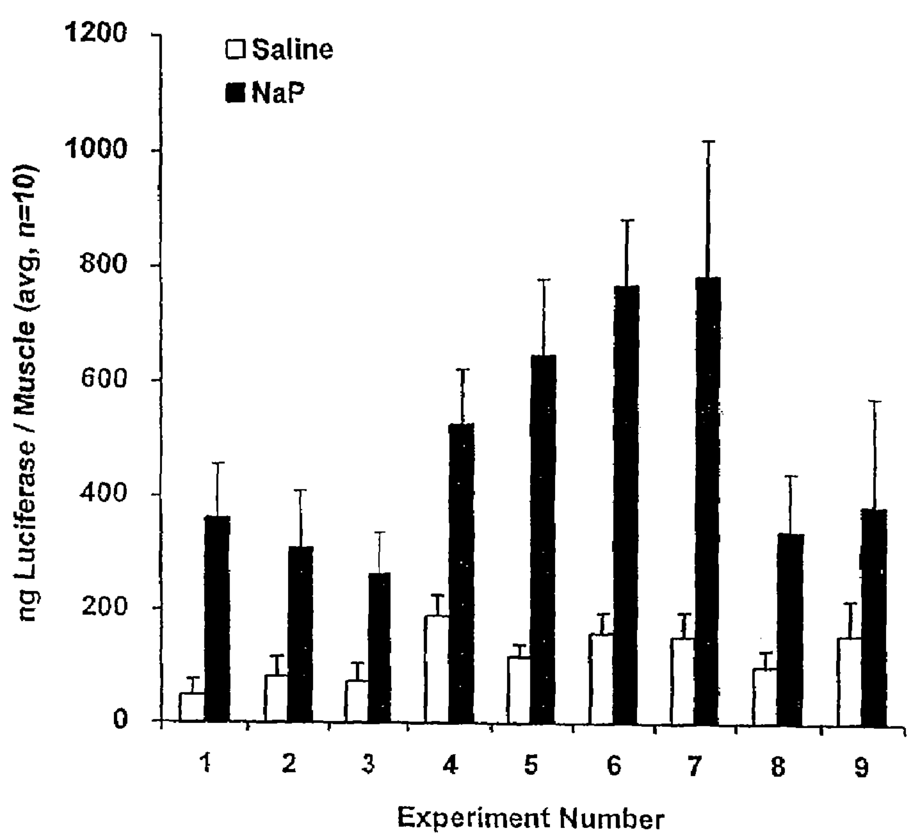

FIG. 23 is a bar graph demonstrating the reproducibility of the enhancement of luciferase expression in muscle upon delivery in 150 mM sodium phosphate. In each of nine experiments, ten quadriceps muscles in 5 mice per group were injected with 50 μg of plasmid VR1223 DNA dissolved in 50 μl saline or in 150 mM sodium phosphate (NaP). Bars represent the average ng luciferase per muscle for each experiment numbered 1 through 9. Error bars represent Standard Error of the Mean.

Figure 24:
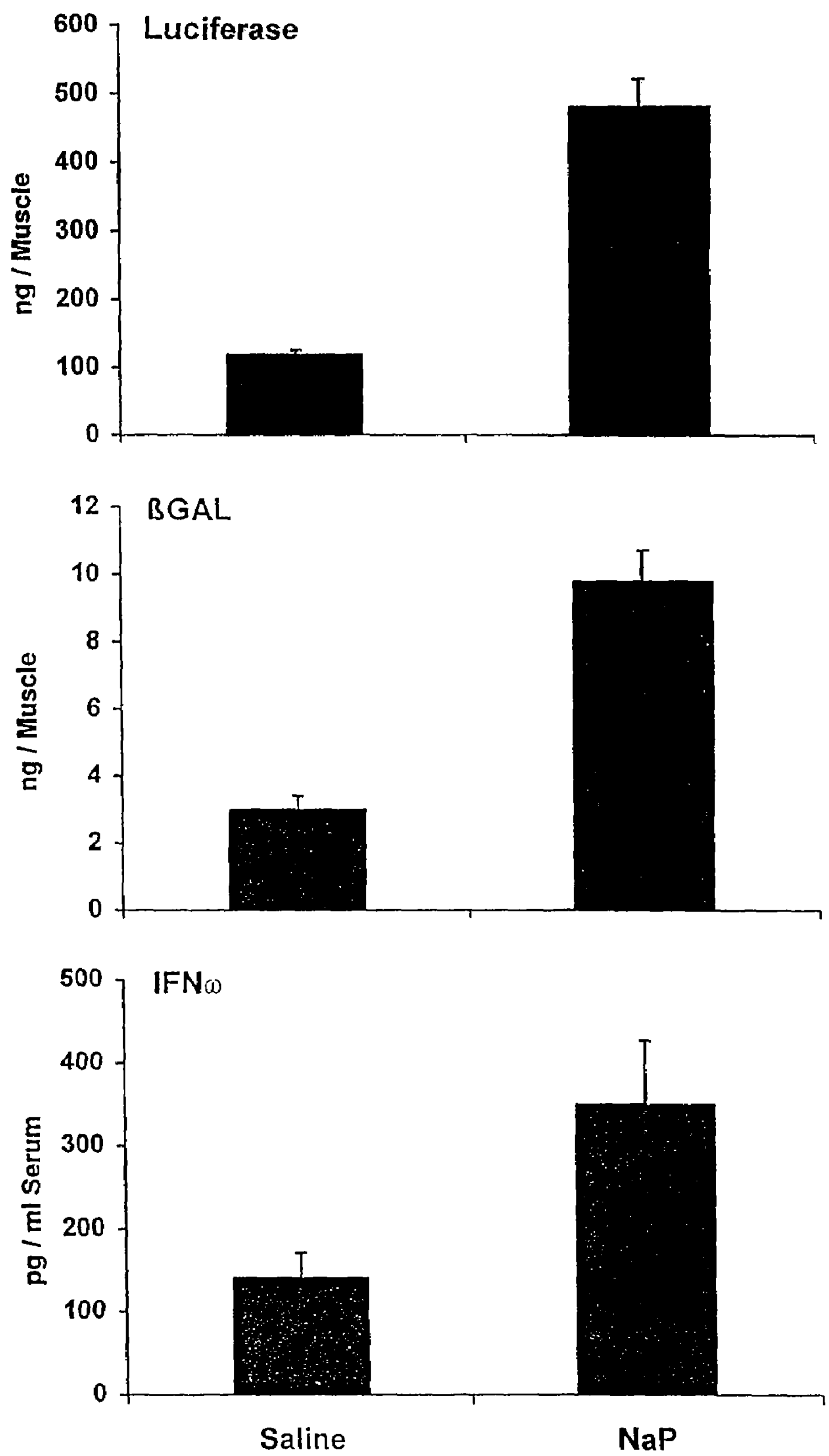

FIG. 24 shows the comparison of the effect of a 150 mM sodium phosphate solution on the expression of three reporter genes. Fifty μg of plasmid VR1223 (luciferase), 10 μg of plasmid VR1418 (β-galactosidase, or LacZ) or 50 μg of plasmid VR4151 (human IFNω) dissolved in 50 μl saline or in 150 mM sodium phosphate solution were injected into the quadriceps muscles of BALB/c mice. For luciferase and LacZ DNAs, the muscles were extracted and assayed 7 days later for enzyme activity. For IFN-ω DNA, serum was collected at 7 days after the injection and assayed for IFN-ω protein. Values are expressed as average ng of gene product per muscle or per ml serum. Bars represent Standard Error of the Mean. For luciferase, $n_{Saline}$=413, $n_{NaP}$=120; for β-galactosidase, $n_{Saline}$=119, $n_{NaP}$=180; for IFN-ω, $n_{Saline}$=10, $n_{NaP}$=9. The average expression in NaP was significantly higher than saline by Mann-Whitney rank sum test for luciferase (p=0.001), β-galactosidase (p=0.001) and IFN-ω (p=0.02).

Figure 25:
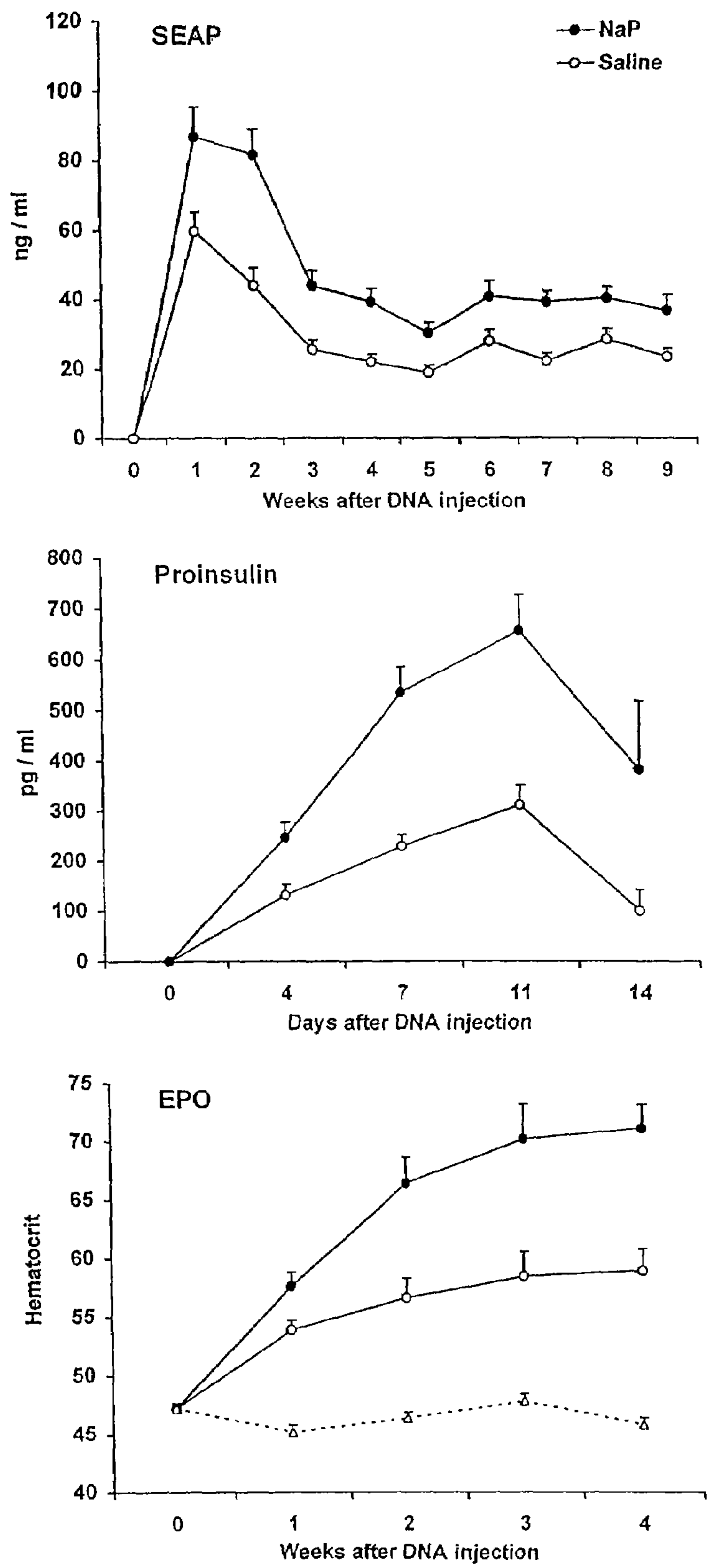

FIG. 25 shows long-term effects of a 150 mM sodium phosphate solution on the expression of secreted reporter gene products. Compositions comprising plasmids VR3301 encoding human placental alkaline phosphatase (SEAP), VR3502 encoding rat preproinsulin, and VR2901 encoding mouse erythropoietin, dissolved in saline or in 150 mM sodium phosphate, were injected bilaterally into mice as described in Example 1. At the indicated times after injections, serum was collected and assayed for SEAP or proinsulin expression, or hematocrits were measured as an indication of erythropoietin expression. Control mice injected with plasmid DNA encoding canine clotting Factor IX (open triangles in the lower graph) in 150 mM sodium phosphate exhibited an average hematocrit of 46. Bars represent Standard Error of the Mean (n=10). By the Mann-Whitney rank sum test, the sodium phosphate values were significantly different (p values all <0.007) from the saline values for each time point and for all three reporters.

Figure 26:
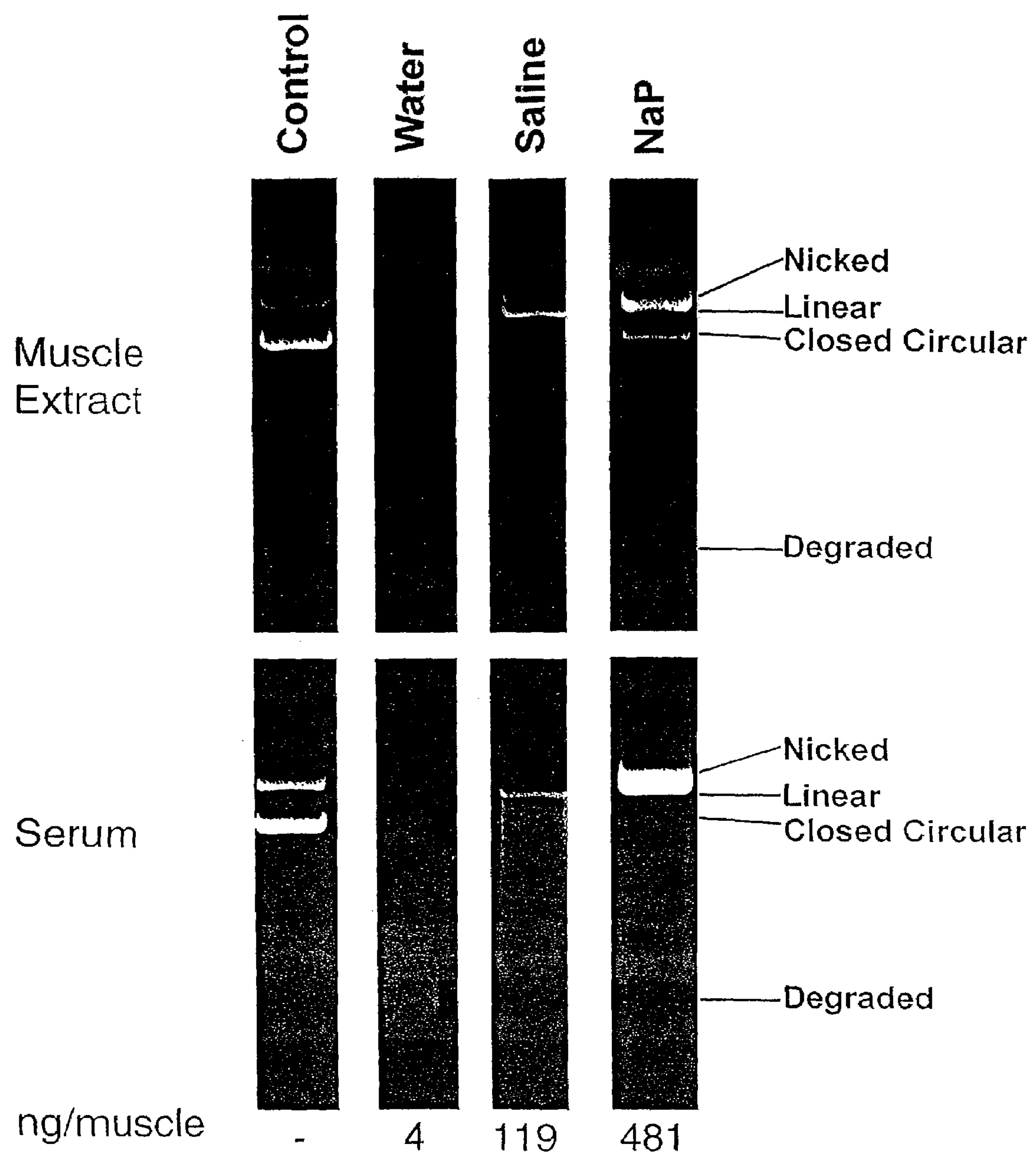

FIG. 26 shows the effect of a 150 mM sodium phosphate solution on DNA degradation in mouse muscle extract or serum. VR1255 plasmid DNA dissolved in each of 4 aqueous solutions was spiked with 10% (v/v) unbuffered mouse Muscle Extract or Serum and the spiked solutions were incubated for 2 hours at 37° C. The reactions were neutralized with SDS+EDTA and analyzed by agarose gel electrophoresis. The top row of four lanes are from the solutions spiked with muscle extract and the bottom row of lanes are from the solutions spiked with serum. The DNA samples from left to right are in: Control solution (pre-neutralized sample in water), Water, Saline, or NaP (150 mM sodium phosphate). On the right side of the right lane are indicated the position of the bands corresponding to nicked, linear, closed circular, and degraded plasmid DNA. The numbers at the bottom of the lower lanes are 7 day luciferase expression values taken from Tables 1 and 2 where DNA in the indicated vehicle was injected into muscle.

Figure 27:
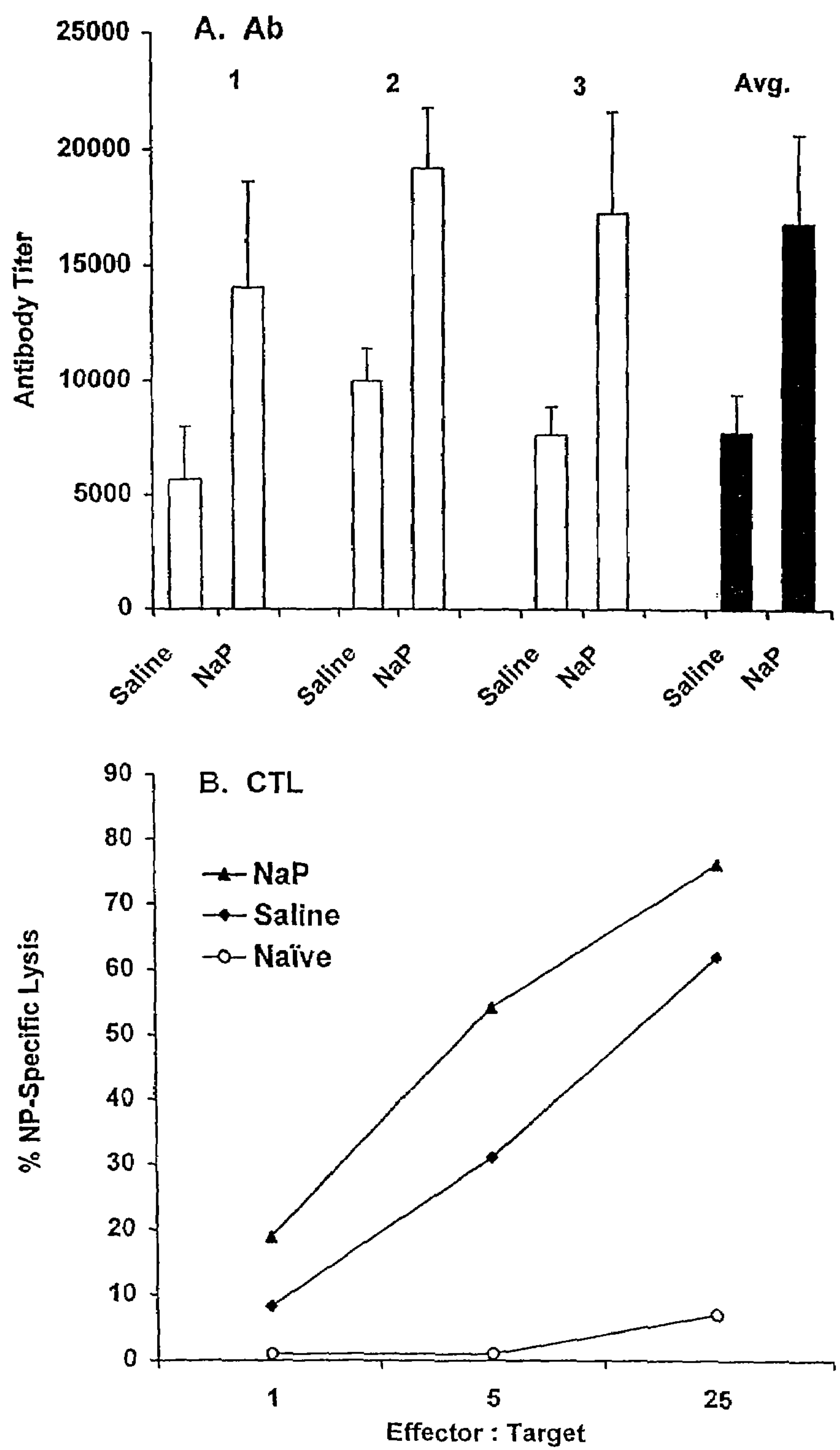

FIG. 27 shows the effects of a 150 mM sodium phosphate solution on DNA vaccination. Mice were vaccinated bilaterally in the quadriceps muscle with 5 μg of plasmid VR4700, encoding the influenza virus nucleoprotein, which was dissolved in 50 μl of saline or in 50 μl of 150 mM sodium phosphate on days 0 and 21. (A) Serum was collected at day 42 and assayed for anti-NP antibody titer by ELISA. Three separate experiments were performed with n=10 mice each, labeled 1-3. The average (Avg.) of all three experiments is indicated in the black bar. Values are expressed as anti-NP specific titer (n=10, 2 experiments with n=5). Error bars represent Standard Error of the Mean. Average anti-NP titers from NaP groups 1-3 were significantly different from the saline averages by Mann-Whitney rank sum test (p<0.04) as was the average titers from all 3 groups (p<0.001). (B) At day 60 the spleens were collected, dissociated and assayed for the presence of NP-specific cytolytic T lymphocyte activity. Splenocytes from unvaccinated mice served as controls ("Naïve"). Average % NP specific lysis from the saline and NaP groups were not significantly different by Mann Whitney rank sum test.

Figure 28:
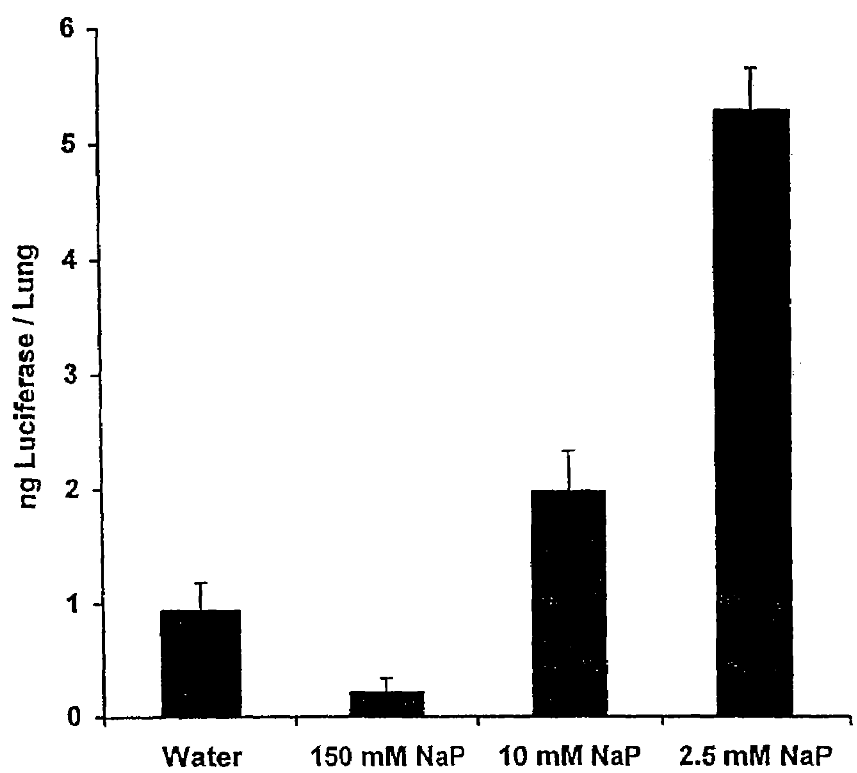

FIG. 28 shows the effects of sodium phosphate solutions on luciferase expression in lung following delivery of compositions comprising plasmid DNA encoding luciferase. Mouse lungs were intranasally instilled with compositions comprising 132 μg of plasmid VR1223 encoding luciferase, complexed with GAP-DLRIE/DOPE (1:1) cationic liposomes at a molar ratio of 4:1 DNA to lipid in water or in various aqueous solutions of sodium phosphate. The lungs were extracted 3 days later and assayed for luciferase activity. Values are expressed in ng luciferase per lung +/− Standard Error of the Mean ($n_{water}$ and $n_{2.5\ mM\ NaP}$=35; $n_{10\ mM\ NaP}$, and $n_{150\ mM\ NaP}$=15 with n=5 per each individual experiment). The 2.5 mM NaP solution averages were significantly different by Mann-Whitney rank sum test from all the other groups (p=<0.001).

DETAILED DESCRIPTION OF THE PREFERRED EMBODIMENTS

The present invention is broadly directed to treatment of cancer by administering in vivo, into a tissue of a mammal suffering from cancer, at least one polynucleotide construct comprising at least one polynucleotide encoding at least one cytokine, or at least one active fragment thereof. The polynucleotide construct is incorporated into the cells of the mammal in vivo, and a therapeutically effective amount of a cytokine is produced in vivo, and delivered to tumor cells. Combinations of cytokine-encoding polynucleotides can be administered.

The present invention provides a pharmaceutical composition comprising about 1 ng to 20 mg of a non-infectious, non-integrating polynucleotide construct comprising a polynucleotide selected from the group consisting of (a) a polynucleotide that hybridizes under stringent conditions to the nucleotide sequence of SEQ ID No. 7 or the complement thereof, wherein the polynucleotide sequence encodes a polypeptide that has antiproliferative activity when added to NIH-OVCAR3 cells in vitro; (b) a polynucleotide that encodes a polypeptide comprising an amino acid sequence which, except for at least one but not more than 20 amino acid substitutions, deletions, or insertions, is identical to amino acids −23 to 172 or 1 to 172 in SEQ ID No. 8, and wherein the polypeptide has antiproliferative activity when added to NIH-OVCAR3 cells in vitro; and (c) a polynucleotide that encodes a polypeptide comprising amino acids 86-172 in SEQ ID No. 8, wherein the polypeptide has antiproliferative activity when added to NIH-OVCAR3 cells in vitro; and one or more cationic compounds selected from the group consisting of cationic lipids, cationic peptides, cationic proteins, cationic polymers, and mixtures thereof. The pharmaceutical composition can be used to practice all of the methods of the present invention.

The present invention also provides a pharmaceutical composition obtained by complexing a polynucleotide selected from the group consisting of (a) a polynucleotide that hybridizes under stringent conditions to the nucleotide sequence of SEQ ID No. 7 or the complement thereof, wherein the polynucleotide sequence encodes a polypeptide that has antiproliferative activity when added to NIH-OVCAR3 cells in vitro; (b) a polynucleotide that encodes a polypeptide comprising an amino acid sequence which, except for at least one but not more than 20 amino acid substitutions, deletions, or insertions, is identical to amino acids −23 to 172 or 1 to 172 in SEQ ID No. 8, wherein the polypeptide has antiproliferative activity when added to NIH-OVCAR3 cells in vitro; and (c) a polynucleotide that encodes a polypeptide comprising amino acids 86-172 in SEQ ID No. 8, wherein the polypeptide has antiproliferative activity when added to NIH-OVCAR3 cells in vitro, with one or more cationic compounds selected from the group consisting of cationic lipids, cationic peptides, cationic proteins, cationic polymers, and mixtures thereof.

The pharmaceutical composition of the present invention can be a polynucleotide construct comprising a polynucleotide that hybridizes under stringent conditions to the nucleotide sequence of SEQ ID No. 7 or the complement thereof, wherein the polynucleotide sequence encodes a polypeptide that has antiproliferative activity when added to NIH-OVCAR3 cells in vitro, and one or more cationic compounds selected from the group consisting of cationic lipids, cationic peptides, cationic proteins, cationic polymers, and mixtures thereof Alternatively, the pharmaceutical composition of the present invention can be a polynucleotide construct comprising a polynucleotide that encodes a polypeptide comprising an amino acid sequence which, except for at least one but not more than 20 amino acid substitutions, deletions, or insertions, is identical to amino acids −23 to 172 or 1 to 172 in SEQ ID No. 8, wherein the polypeptide has antiproliferative activity when added to NIH-OVCAR3 cells in vitro, and one or more cationic compounds selected from the group consisting of cationic lipids, cationic peptides, cationic proteins, cationic polymers, and mixtures thereof. Alternatively, the pharmaceutical composition of the present invention can be a polynucleotide construct comprising a polynucleotide that encodes a polypeptide comprising amino acids 86-172 in SEQ ID No. 8, wherein the polypeptide has antiproliferative activity when added to NIH-OVCAR3 cells in vitro; and one or more cationic compounds selected from the group consisting of cationic lipids, cationic peptides, cationic proteins, cationic polymers, and mixtures thereof.

The pharmaceutical composition of the present invention comprises at least one polynucleotide construct comprising at least one polynucleotide encoding an IFNω, or an active fragment thereof Preferably, the polynucleotide construct contains a polynucleotide encoding a human IFNω. More preferably, IFNω is encoded by nucleotides 1 to 585 in SEQ ID No. 7 (corresponding to amino acids −23 to 172 in SEQ ID No. 8), or by nucleotides 70 to 585 in SEQ ID No. 7 (corresponding to amino acids 1 to 172 in SEQ ID No. 8). Most preferably, the polynucleotide construct is VR4151 in SEQ ID No. 4. The polynucleotide construct may be complexed with one or more cationic compounds selected from the group consisting of cationic lipids, cationic peptides, cationic proteins, cationic polymers, and mixtures thereof. Preferably, the polynucleotide construct is complexed with one or more cationic lipids. More preferably, the polynucleotide construct is complexed with one or more cationic lipids and one or more neutral lipids. Still more preferably, the cationic lipid is (±)-N-(2-hydroxyethyl)-N,N-dimethyl-2,3-bis(tetradecyloxy)-1-propaniminium bromide (DMRIE) and the neutral lipid is 1,2-dioleoyl-sn-glycero-3-phosphatidylethanolamine (DOPE) such that the mass ratio of polynucleotide construct to lipid is from about 10:1 and about 0.5:1. More preferably, the mass ratio of polynucleotide construct to lipid is from about 5:1 and about 1:1. Still more preferably, the mass ratio of polynucleotide construct to lipid is about 5:1.

Cytokine-encoding plasmids discussed herein include VR4102 (hIFNα in the VR1012 vector) (SEQ ID No. 1), VR4112 (hIFNα in the VR1055 vector) (SEQ ID No. 2), VR4150 (hIFNω in the VR1012 vector) (SEQ ID No. 3), VR4151 (hIFNω in the VR1055 vector) (SEQ ID No. 4), VR4101 (mIFNα in the VR1012 vector) (SEQ ID No. 5), VR4111 (mIFNα in the VR1055 vector) (SEQ ID No. 6), and VR1110 (mIL-2 in the VR1012 vector), VR1103 (hIL-2 in the VR1012 vector) (SEQ ID No: 25), VR4001 (mIL-12 in the VR1033 vector), and VR1700 (mGM-CSF in the VR1012 vector).

Cytokine-encoding cDNAs discussed herein include the cDNA for hIFNω (SEQ ID No. 7), the cDNA for hIFNα (SEQ ID No. 9), the cDNA for mIFNα (SEQ ID No. 11), the cDNA for hIL-2 (SEQ ID No. 13 and the coding portion of SEQ ID No. 25), the cDNA for mIL-2 (for example, as disclosed in Kashima et al., *Nature* 313:402-404 (1985), which is hereby incorporated by reference) the cDNA for mIL-12 (for example, as disclosed in Tone et al., *Eur. J. Immunol.* 26:1222-1227(1996), which is hereby incorporated by reference), and the cDNA for mGM-CSF (for example, as disclosed in Gough et al., *EMBO J.* 4:645-653 (1985), which is hereby incorporated by reference). Cytokine polypeptides discussed herein include hIFNω (SEQ ID No. 8), hIFNα (SEQ ID No. 10), mIFNα (SEQ ID No. 12), and hIL-2 (SEQ ID No. 14 and SEQ ID No. 26).

By "stringent conditions" is intended a hybridization by overnight incubation at 42° C. in a solution comprising: 50% formamide, 5×SSC (750 mM NaCl, 15 mM trisodium citrate), 50 mM sodium phosphate (pH 7.6), 5×Denhardt's solution, 10% dextran sulfate, and 20 μg/ml denatured, sheared salmon sperm DNA, followed by repeatedly washing the filters (at least three times) in 0.1×SSC and 0.1% sodium dodecyl sulfate (w/v) for 20 minutes at about 65° C.

By "active fragment" is intended a fragment of a cytokine that displays the antiproliferative activity of the mature or full length cytokine. For example, a full length hIFNω is set forth in amino acids −23 to 172 of SEQ ID No. 8. The corresponding mature hIFNω is set forth in amino acids 1 to 172 of SEQ ID No. 8. Active fragments of hIFNω include, but are not limited to a polypeptide comprising amino acids 86-172 in SEQ ID No. 8, a polypeptide comprising amino acids 61-172 in SEQ ID No. 8, a polypeptide comprising amino acids 41-172 in SEQ ID No. 8, and a polypeptide comprising amino acids 21-172 in SEQ ID No. 8. A full length hIFNα is set forth in amino acids −23 to 166 of SEQ ID No. 10. The corresponding mature hIFNα is set forth in amino acids 1 to 166 of SEQ ID No. 10. Active fragments of hIFNα include, but are not limited to a polypeptide comprising amino acids 83-166 in SEQ ID No. 10, a polypeptide comprising amino acids 61-166 in SEQ ID No. 10, a polypeptide comprising amino acids 41-166 in SEQ ID No. 10, and a polypeptide comprising amino acids 21-166 in SEQ ID No. 10. Full length hIL-2 is set forth in amino acids −20 to 133 of SEQ ID No. 14. The corresponding mature hIL-2 is set forth in amino acids 1 to 133 of SEQ ID No. 14. Active fragments of hIL-2 include, but are not limited to a polypeptide comprising amino acids 58 to 105 in SEQ ID No. 14, and a polypeptide comprising amino acids 20 to 126 in SEQ ID No. 14.

Assays of antiproliferative activity in vitro are well known to those of ordinary skill in the art. For example, one antiproliferation assay that can be used is to treat cultured cells, such as human ovarian NIH-OVCAR3 cells (ATCC, Rockville, Md.), with supernatants from human melanoma UM449 cells transfected with the polynucleotide construct containing a polynucleotide encoding an IFNω or an active fragment thereof. In this antiproliferation assay, NIH-OVCAR3 cells are cultured and plated in 96 well-tissue culture plates. The plates are incubated for 24 hours at 37° C. in a humidified 5% $CO_2$ atmosphere. Twenty μl of tissue culture supernatants from transfected UM449 cells are added to duplicate wells. An interferon reference standard (e.g., human leukocyte interferon, Sigma Chemical Co., St. Louis, Mo.) is included in each assay. The cells are incubated with the test samples or the interferon standard for an additional 72 hours at 37° C. To quantitate the effects on cell proliferation, 50 μl of XTT/ECR substrate (Cell Proliferation Kit, Boehringer Mannheim, Indianapolis, Ind.) is added to each well and the plates are incubated for an additional 24 hours at 37° C. prior to measurement of the $OD_{490}$. Other cell lines can be used in the antiproliferation assay. For example, any of the cells listed on Table 1 can be used. Another antiproliferation assay that can be used is provided in Nieroda, et al (*Mol. Cell. Differentiation* 4: 335-351 (1996)).

For treatment of cancer, a polynucleotide construct comprising a polynucleotide encoding a cytokine can be delivered locally, systemically or intra-cavity. In the "systemic delivery" embodiment of the invention, one or more polynucleotide construct comprising one or more polynucleotide encoding one or more cytokine is administered into a tissue such that the polynucleotide is expressed as the cytokine in vivo and the cytokine is released into the circulation, and such that a therapeutically effective amount of the cytokine is systemically delivered to the tumor. In this embodiment, the polynucleotide construct can be administered within ex vivo cells or associated with ex vivo cellular material. Preferably, the cytokine is an IFNω, IFNα, IFNτ, IFNγ, IFNβ, IL-1, IL-2, IL-4, IL-7, IL-12, IL-15, IL-18, GM-CSF, or any combination of these, or any combination of one or more of these and one or more additional cytokines. More preferably, the cytokine is an IFNα, IFNω, IL-2, or IL-12. Most preferably, the cytokine is an IFNα or IFNω. Examples of the combination are a polynucleotide encoding an IFNω and an IFNα; a polynucleotide encoding an IFNω and an IL-2; a polynucleotide encoding an IFNα and an IL-2; and a polynucleotide encoding an IFNω, an IFNα, and an IL-2. More preferably, the polynucleotide construct contains a polynucleotide encoding an IFNω and/or an IFNα. Even more preferably, the polynucleotide construct contains a polynucleotide encoding a human IFNω and/or a human IFNα. Even more preferably, the polynucleotide encodes a human IFNω. Preferably, the polynucleotide construct is administered free from ex vivo cells and free from ex vivo cellular material.

In this embodiment, administration can be into tissue including but not limited to muscle, skin, brain, lung, liver, spleen, bone marrow, thymus, heart, lymph nodes, blood, bone, cartilage, pancreas, kidney, gall bladder, stomach, intestine, testis, ovary, uterus, rectum, nervous system, eye, gland, or connective tissue. Preferably, the administration is into muscle tissue, i.e., skeletal muscle, smooth muscle, or myocardium, and the polynucleotide construct is naked. Most preferably, the muscle is skeletal muscle. For polynucleotide constructs in which the polynucleotide encoding a cytokine is DNA, the DNA can be operably linked to a cell-specific promoter that directs substantial transcription of the DNA only in predetermined cells.

By "naked" is meant that the polynucleotide construct is free from association with any delivery vehicle known in the art that can act to facilitate entry into cells, for example, from transfection-facilitating proteins, viral particles, liposomes, cationic lipids, and calcium phosphate precipitating agents.

As used herein, "ex vivo" cells are cells into which the polynucleotide construct is introduced, for example, by transfection, lipofection, electroporation, bombardment, or microinjection. The cells containing the polynucleotide construct are then administered in vivo into mammalian tissue. Such ex vivo polynucleotide constructs are well-known to those of ordinary skill in the art. For example, see Belldegrun, A., et al., *J. Natl. Cancer Inst.* 85: 207-216 (1993); Ferrantini, M. et al., *Cancer Research* 53: 1107-1112 (1993); Ferrantini, M. et al., *J. Immunology* 153: 4604-4615 (1994); Kaido, T., et al., *Int. J. Cancer* 60: 221-229 (1995); Ogura, H., et al., *Cancer Research* 50: 5102-5106 (1990); Santodonato, L., et al., *Human Gene Therapy* 7:1-10 (1996); Santodonato, L., et al.,

*Gene Therapy* 4:1246-1255 (1997); and Zhang, J.-F. et al., *Cancer Gene Therapy* 3: 31-38 (1996).

The polynucleotide construct is administered in a "cell-free" fashion when it is administered independently, i.e., free of ex vivo cells or ex vivo cellular material.

In the "local cytokine delivery" embodiment of the present invention, a polynucleotide construct comprising a polynucleotide encoding IFNω and/or IFNα is administered in vivo into or near a tumor of a mammal, such that the polynucleotide is incorporated into the cells of the tumor. Tumor cells subsequently express the interferon polypeptide in an amount effective to treat cancer.

In this embodiment, a polynucleotide construct comprising a polynucleotide encoding an IFNω and/or an IFNα can be administered into the tumor. Alternatively, the polynucleotide construct can be administered into non-tumor cells surrounding a tumor, near a tumor, or adjacent to a tumor, such that a therapeutically effective amount of an IFNω and/or an IFNα is produced in vivo near or within the tumor and is delivered to the malignant cells of the tumor. One way to provide local delivery of the polynucleotide construct is by administering intravenously a polynucleotide construct comprising a tumor-targeted promoter, wherein the polynucleotide is incorporated into the cells of the tumor and the cytokine is expressed in the tumor in an amount effective to treat cancer. Preferably, the polynucleotide construct is administered into the tumor.

In the "intra-cavity delivery" embodiment, the present invention provides a method of selectively transfecting malignant cells in a tumor-bearing body cavity of a mammal by introducing a polynucleotide construct into the body cavity, wherein the polynucleotide is incorporated into tumor cells and the tumor cells subsequently express the protein encoded by the polynucleotide in an amount effective to treat cancer. The polynucleotide construct is administered free from ex vivo cells and free from ex vivo cellular material.

A cavity is a space within the body that can confine a fluid volume for some period of time. The cavity can either be present in a normal animal, or it can be produced as a result of disease, surgery or trauma. Cavities in the normal animal include the peritoneum, the cerebrospinal fluid space, the ventricles of the brain, the plural space around lung, the bronchiolar airways, the nasal sinus, the bladder, the vagina, the ear, the synovium of various joints (knee, hip etc.), the internal network of salivary gland tissue, and the gastrointestinal tract including stomach. Surgical removal of tumor tissue can also produce a space which fits the definition of a cavity. An open wound produced by trauma or surgery and closed by suture can be defined as a cavity, and the area under a blister produced by an infection, abrasion or a burn also fits the definition.

There are special bioavailability considerations when a gene delivery system is administered into a cavity. First the fluid volume in the cavity can be substantially comprised of the vehicle in which the delivery system is suspended. Second, the delivery system can have particular access to cells that are either suspended in the cavity, or that are lining the surface of the cavity. Third, in some cases normally differentiated cells that are lining the cavity may be embedded in an extracellular matrix and, may not be accessible to the delivery system. Thus, the delivery system may preferentially transfect cells that are growing outside the normal extracellular matrix and avoid the cells that are growing within the extracellular matrix, conferring a kind of cell selectivity to the delivery system.

With respect to the first point, body fluids such as serum, have been shown to inhibit gene delivery systems. For example, the transfection activities of Lipofectin and LipofectAMINE are inhibited by serum. It is thought that serum factors bind to cationic lipid/DNA complexes and block their uptake into cells. In cavity models the endogenous fluid volume can be removed, the cavity can be washed, and the delivery system can be administered into the cavity in a vehicle that is compatible with optimal gene delivery efficacy. Thus the cavity model allows the investigator to create a fluid environment which allows for optimal gene delivery potency.

With respect to the second point, cells that are either floating in the cavity or are lining the surface of the cavity have preferential access to the delivery system and can be preferentially transfected relative to other cells in the body. Since the delivery system is confined within the cavity, peripheral cells in the body outside of the cavity will not be transfected. Thus, there is tissue targeting to the cells within the cavity. For example, gene delivery systems administered into the peritoneal cavity will have access to metastatic tumor cells derived from colon or ovarian cancers that are floating in the peritoneum or are attached to the surfaces of the peritoneum. Delivery systems administered into the plural space should transfect cancer cells in the plural effusion. Delivery systems administered into the cerebral spinal fluid should have access to metastatic cancer cells present there.

With respect to the third point, differentiated cells that are present in normal tissues are often embedded into an extracellular matrix. This matrix can be difficult to penetrate with large particulate delivery systems. Some cells, such as poorly differentiated tumor cells, that are present in cavities can grow outside of the normal extracellular matrix and are therefore more accessible to gene delivery systems. In this way the delivery system can preferentially transfect those cells that are growing outside of the extracellular matrix and not transfect those cells that are growing within the extracellular matrix. This is another form of in vivo, cell type specific targeting. Examples of normal cells that are not embedded in an extracellular matrix and are therefore more accessible to gene delivery systems are, bronchial airway cells, lung cells in the plural space, and ependimal cells lining the surface of the ventricles of the brain. Normal bladder cells that line the surface of the bladder are embedded in a tight extracellular matrix and are therefore not readily accessible to a gene delivery system delivered into the bladder, but tumor cells which grow up and out of the extracellular matrix into the bladder vesicle are accessible to gene delivery systems administered into the bladder vesicle. Thus normal bladder tissue would be expected to resist transfection whereas, bladder tumor would be expected to be transfectable.

A preferred application of the intra-cavity delivery embodiment is in the treatment of peritoneally disseminated cancers. More specifically, a mammal bearing peritoneal tumor may be injected i.p. with an effective amount of a polynucleotide complexed with a lipid in a physiologically acceptable diluent in a total volume sufficient to access the entire body cavity. The mammal may have tumor ascites in the peritoneal cavity as in an ovarian cancer. In the most preferred application, this methodology may be used in treating ovarian cancer of a human.

Debulking of tumor ascites is commonly performed on human ovarian cancer patients. Debulking involves removal of tumor ascites from the peritoneal cavity. In humans bearing ovarian tumor ascites, the ascites fluid would be debulked by insertion of a catheter i.p. followed by periodic draining of ascites fluid. It is contemplated that the tumor ascites would be debulked before and/or after the i.p. administration of the polynucleotide formulation of the present invention.

Transfection efficacy of the intra-cavity delivery embodiment may be determined by collecting the tumor ascites and serum at various times after the injection and performing diagnostic assays appropriate for the encoded molecule(s). Naturally, other means of determining tumor mass, growth, and viability may also be used to assess the effectiveness of the present invention.

Preferred polynucleotides for the intra-cavity delivery embodiment may encode not only immunogenic molecules such as cytokines (e.g., interleukins 1-18 and α/β/γ/ω-interferons, colony stimulating factors, e.g., G-CSF, GM-CSF, M-CSF, and tumor necrosis factors), but also chemokines (e.g., C-X-C and C-C), Class I and II histocompatibility antigens, costimulatory molecules (e.g., B7-1, B7-2, CAMs, and flt3 ligand), growth factors (e.g., epidermal growth factors, fibroblast growth factors, transforming growth factors and growth hormone), and the like. The polynucleotide may also encode bacterial antigens, viral glycoproteins, enzymes (e.g., lysozymes), recombinant antibodies, molecules that interfere with cellular adhesion, adhesion molecules, proliferation and vascular inhibitory factors, ribozymes, and antisense RNAs targeted toward key oncogenic or tumor growth proteins. Moreover, selective delivery of toxic peptides (e.g., ricin, diphtheria toxin, or cobra venom factor) or proteins capable of synthesizing toxic compounds (e.g. thymidine kinase and cytosine deaminase) to the malignant cells may have therapeutic benefits. The polynucleotide may also comprise a tumor suppressor gene (e.g., p53). Preferred polynucleotides encode cytokines. Preferred cytokines are IL-2, IFNω, and IFNα. IL-2 is most preferred.

For treatment of cancer by any of the above disclosed embodiments, any polynucleotide encoding an IFNω, or an active fragment thereof, can be used. For example, the polynucleotide construct can be a construct comprising a polynucleotide that hybridizes under stringent conditions to the nucleotide sequence of SEQ ID No. 7 or the complement thereof, wherein the polynucleotide sequence encodes a polypeptide that has antiproliferative activity when added to NIH-OVCAR3 cells in vitro, and one or more cationic compounds selected from the group consisting of cationic lipids, cationic peptides, cationic proteins, cationic polymers, and mixtures thereof Alternatively, the construct can be a polynucleotide construct comprising a polynucleotide that encodes a polypeptide comprising an amino acid sequence which, except for at least one but not more than 20 amino acid substitutions, deletions, or insertions, is identical to amino acids −23 to 172 or 1 to 172 in SEQ ID No. 8, wherein the polypeptide has antiproliferative activity when added to NIH-OVCAR3 cells in vitro, and one or more cationic compounds selected from the group consisting of cationic lipids, cationic peptides, cationic proteins, cationic polymers, and mixtures thereof. Alternatively, the construct can be a polynucleotide construct comprising a polynucleotide that encodes a polypeptide comprising amino acids 86-172 in SEQ ID No. 8, wherein the polypeptide has antiproliferative activity when added to NIH-OVCAR3 cells in vitro; and one or more cationic compounds selected from the group consisting of cationic lipids, cationic peptides, cationic proteins, cationic polymers, and mixtures thereof Preferably, IFNω is encoded by nucleotides 1 to 585 in SEQ ID No. 7 (corresponding to amino acids −23 to 172 in SEQ ID No. 8), or by nucleotides 70 to 585 in SEQ ID No. 7 (corresponding to amino acids 1 to 172 in SEQ ID No. 8). More preferably, the polynucleotide construct is VR4151.

For treatment of cancer, any polynucleotide encoding IFNα, or active fragment thereof, can also be used. For example, the polynucleotide construct can be a construct comprising a polynucleotide that hybridizes under stringent conditions to the nucleotide sequence of SEQ ID No. 9 or the complement thereof, wherein the polynucleotide sequence encodes a polypeptide that has antiproliferative activity when added to NIH-OVCAR3 cells in vitro, and one or more cationic compounds selected from the group consisting of cationic lipids, cationic peptides, cationic proteins, cationic polymers, and mixtures thereof Alternatively, the construct can be a polynucleotide construct comprising a polynucleotide that encodes a polypeptide comprising an amino acid sequence which, except for at least one but not more than 20 amino acid substitutions, deletions, or insertions, is identical to amino acids −23 to 166 or 1 to 166 in SEQ ID No. 10, wherein the polypeptide has antiproliferative activity when added to NIH-OVCAR3 cells in vitro, and one or more cationic compounds selected from the group consisting of cationic lipids, cationic peptides, cationic proteins, cationic polymers, and mixtures thereof. Alternatively, the construct can be a polynucleotide construct comprising a polynucleotide that encodes a polypeptide comprising amino acids 83-166 in SEQ ID No. 10, wherein the polypeptide has antiproliferative activity when added to NIH-OVCAR3 cells in vitro; and one or more cationic compounds selected from the group consisting of cationic lipids, cationic peptides, cationic proteins, cationic polymers, and mixtures thereof. Preferably, IFNα is encoded by nucleotides 1 to 567 in SEQ ID No. 9 (corresponding to amino acids −23 to 166 in SEQ ID No. 10), or by nucleotides 1 to 567 in SEQ ID No. 9 (corresponding to amino acids 1 to 166 in SEQ ID No. 10). Preferably, the polynucleotide construct is VR4112.

For polynucleotide constructs that do not contain a polynucleotide encoding IFNω, the polynucleotide construct is preferably a cell-free construct. For polynucleotide constructs that contain a polynucleotide encoding IFNω, the polynucleotide construct can be administered either within ex vivo cells or free of ex vivo cells or ex vivo cellular material. Preferably, the polynucleotide construct is administered free of ex vivo cells or ex vivo cellular material.

In the "local delivery" and "intra-cavity delivery" embodiments, the polynucleotide construct is preferably complexed with one or more cationic compounds. More preferably, the polynucleotide construct is complexed with one or more cationic lipids by ionic interaction. Generally, the complex then contacts the cell membrane and is transfected into the cell. This transfection mechanism is referred to as "lipofection," and is a highly efficient transfection procedure (Felgner, et al., *Proc. Natl. Acad. Sci. USA* 84:7413-7417, 1987); and Felgner, et al., *Nature* 337:387-388, 1989). Still more preferably, the polynucleotide construct is complexed with one or more cationic lipids and one or more neutral lipids.

For purposes of the present invention, lipid refers to a synthetic or naturally occurring compound that possesses both a lipophilic region and a polar region, commonly referred to as a head group. Preferred cationic compounds are cationic lipids. Cationic lipids are described in U.S. Pat. Nos. 4,897,355; 4,946,787; 5,049,386; 5,264,618; 5,279,833; 5,334,761; 5,429,127; 5,459,127; 5,589,466; 5,676,954; 5,693,622; 5,580,859; 5,703,055; and 5,578,475; and international publications WO 04/9469, WO 95/14381, 95/14651, 95/17373, 96/18372, 96/26179, 96/40962, 96/40963, 96/41873, and 97/00241, and documents cited therein. As illustrated in the above-cited patents and patent applications, cationic lipids comprise structural features that may be present in a variety of core molecular classes.

Examples of cationic lipids are 5-carboxyspermylglycine dioctadecylamide (DOGS) and dipalmitoyl-phophatidylethanolamine-5-carboxyspermylamide (DPPES). Cationic cholesterol derivatives are also useful, including {3β-[N-N',N'-dimethylamino)ethane]-carbomoyl}-cholesterol (DC-Chol). Dimethyldioctdecyl-ammonium bromide (DDAB), N-(3-aminopropyl)-N,N-(bis-(2-tetradecyloxyethyl))-N-methyl-ammonium bromide (PA-DEMO), N-(3-aminopropyl)-N,N-(bis-(2-dodecyloxyethyl))-N-methyl-ammonium bromide (PA-DELO), N,N,N-tris-(2-dodecyloxy)ethyl-N-(3-amino)propyl-ammonium bromide (PA-TELO), and $N^1$-(3-aminopropyl)((2-dodecyloxy)ethyl)-$N^2$-(2-dodecyloxy)ethyl-1-piperazinaminium bromide (GA-LOE-BP) can also be employed in the present invention.

Non-diether cationic lipids, such as DL-1,2-dioleoyl-3-dimethylaminopropyl-β-hydroxyethylammonium (DORI diester), 1-O-oleyl-2-oleoyl-3-dimethylaminopropyl-β-hydroxyethylammonium (DORI ester/ether), and their salts promote in vivo gene delivery. Preferred cationic lipids comprise groups attached via a heteroatom attached to the quaternary ammonium moiety in the head group. A glycyl spacer can connect the linker to the hydroxyl group.

Preferred cationic lipids are 3,5-(N,N-dilysyl)-diaminobenzoyl-3-(DL-1,2-dioleoyl-dimethylaminopropyl-β-hydroxyethylamine) (DLYS-DABA-DORI diester), 3,5-(N,N-di-lysyl)diamino-benzoylglycyl-3-(DL-1,2-dioleoyl-dimethylaminopropyl-β-hydroxyethylamine) (DLYS-DABA-GLY-DORI diester), and (±)-N-(2-hydroxyethyl)-N,N-dimethyl-2,3-bis(tetradecyloxy)-1-propaniminium bromide (DMRIE).

Also preferred are (±)-N,N-dimethyl-N-[2-(sperminecarboxamido)ethyl]-2,3-bis(dioleyloxy)-1-propaniminium pentahydrochloride (DOSPA), (±)-N-(2-aminoethyl)-N,N-dimethyl-2,3-bis(tetradecyloxy)-1-propaniminium bromide (β-aminoethyl-DMRIE or βAE-DMRIE) (Wheeler, et al., *Biochim. Biophys. Acta* 1280:1-11 (1996)), and (±)-N-(3-aminopropyl)-N,N-dimethyl-2,3-bis(dodecyloxy)-1-propaniminium bromide (GAP-DLRIE) (Wheeler, et al., *Proc. Natl. Acad. Sci. USA* 93:11454-11459 (1996)), which have been developed from DMRIE.

Other examples of DMRIE-derived cationic lipids that are useful for the present invention are (±)-N-(3-aminopropyl)-N,N-dimethyl-2,3-(bis-decyloxy)-1-propanaminium bromide (GAP-DDRIE), (±)-N-(3-aminopropyl)-N,N-dimethyl-2,3-(bis-tetradecyloxy)-1-propanaminium bromide (GAP-DMRIE), (±)-N-((N"-methyl)-N'-ureyl)propyl-N,N-dimethyl-2,3-bis(tetradecyloxy)-1-propanaminium bromide (GMU-DMRIE), (±)-N-(2-hydroxyethyl)-N,N-dimethyl-2,3-bis(dodecyloxy)-1-propanaminium bromide (DLRIE), and (±)-N-(2-hydroxyethyl)-N,N-dimethyl-2,3-bis-([Z]-9-octadecenyloxy)propyl-1-propaniminium bromide (HP-DORIE).

The lipids of the lipid-containing formulation can comprise a cationic lipid alone, or further comprise a neutral lipid such as cardiolipin, phosphatidylcholine, phosphatidylethanolamine, dioleoylphosphatidylcholine, dioleoylphosphatidyl-ethanolamine, 1,2-dioleoyl-sn-glycero-3-phosphatidylethanolamine (DOPE), sphingomyelin, and mono-, di- or tri-acylglycerol. Other additives, such as cholesterol, fatty acid, ganglioside, glycolipid, neobee, niosome, prostaglandin, sphingolipid, and any other natural or synthetic amphiphiles, can also be used. A preferred molar ratio of cationic lipid to neutral lipid in these lipid-containing formulations is from about 9:1 to about 1:9; an equimolar ratio is particularly preferred. The lipid-containing formulation can further comprise a lyso lipid (e.g., lyso-phosphatidylcholine, lysophosphatidyl-ethanolamine, or a lyso form of a cationic lipid).

More preferably, the cationic lipid is (±)-N-(2-hydroxyethyl)-N,N-dimethyl-2,3-bis(tetradecyloxy)-1-propaniminium bromide (DMRIE) and the neutral lipid is 1,2-dioleoyl-sn-glycero-3-phosphatidylethanolamine (DOPE) such that the mass ratio of polynucleotide construct to lipid is from about 10:1 and about 0.5:1. Still more preferably, the mass ratio of polynucleotide construct to lipid is from about 5:1 and about 1:1. Still more preferably, the mass ratio of polynucleotide construct to lipid is about 5:1.

Lipid-containing pharmaceutical composition for use in a complex with the polynucleotide construct of the present invention can also comprise cationic lipid together with an effective amount of a lysophosphatide. The lysophosphatide can have a neutral or a negative head group. Lysophosphatidylcholine and lysophosphatidyl-ethanolamine are preferred, and l-oleoyl lysophosphatidylcholine is particularly preferred. Lysophosphatide lipids are advantageously present in the lipid-containing formulation in a 1:2 ratio of lysolipid to cationic lipid. Lyso forms of a cationic lipid can also be used to promote polynucleotide delivery. These lyso forms are advantageously present in effective amounts up to about one-third of the total cationic lipid in the lipid-containing formulations.

In a formulation for preparing DNA:lipid complexes, the cationic lipid can be present at a concentration of between about 0.1 mole % and about 100 mole %, preferably about 5 mole % and 100 mole %, and most preferably between about 20 mole % and 100 mole %, relative to other formulation components present in the formulation. The neutral lipid can be present in a concentration of between zero and about 99.9 mole %, preferably zero and about 95 mole %, and most preferably zero and about 80 mole %. In order to produce lipid vesicles having a net positive charge, the quantity of the positively charged component must exceed that of the negatively charged component. The negatively charged lipid can be present at between zero and about 49 mole %, and preferably between zero and about 40 mole %. Cholesterol or a similar sterol can be present at between zero to about 80 mole %, and preferably zero and about 50 mole %.

The polynucleotide to be delivered can be solubilized in a buffer prior to mixing with lipid vesicles. Suitable buffers include, for example, phosphate buffered saline (PBS), normal saline, Tris buffer, and sodium phosphate vehicle (100-150 mM preferred). Insoluble polynucleotides can be solubilized in a weak acid or base, and then diluted to the desired volume with a neutral buffer such as PBS. The pH of the buffer is suitably adjusted, and moreover, a pharmaceutically acceptable additive can be used in the buffer to provide an appropriate osmolarity within the lipid vesicle.

A lipid solution comprising at least one amphipathic lipid can spontaneously assemble to form primary lipid vesicles, heterogeneous in size. Therefore, according to a preferred method, the lipids of the lipid-containing formulation, comprising at least one cationic lipid, are prepared by dissolution in a solvent such as chloroform and the mixture is evaporated to dryness as a film on the inner surface of a glass vessel. On suspension in an aqueous solvent, the amphipathic lipid molecules assemble themselves into primary lipid vesicles. These primary lipid vesicles may be reduced to a selected mean diameter by means of a freeze-thaw procedure. Vesicles of uniform size can be formed prior to drug delivery according to methods for vesicle production known to those in the art; for example, the sonication of a lipid solution as described by Felgner, et al (*Proc. Natl. Acad. Sci. USA* 84:7413-7417 (1987)) and U.S. Pat. No. 5,264,618.

The term "mammal" is intended to encompass a singular "mammal" and plural "mammals," and includes, but is not limited to humans; primate mammals such as apes, monkeys, orangutans, and chimpanzees; canine mammals such as dogs and wolves; feline mammals such as cats, lions, and tigers;

equine mammals such as horses, donkeys, deer, zebra, and giraffe; and bears. Preferably, the mammal is a human subject.

Tumor cell formation and growth, also known as "transformation," describes the formation and proliferation of cells that have lost their ability to control cellular division; that is the cells are cancerous. "Malignant cells" are defined as cells that have lost the ability to control the cell division cycle, leading to a transformed or cancerous phenotype.

The term "non-tumor tissue" is intended to include, but is not limited to non-tumor bearing tissues such as muscle, skin, brain, lung, liver, spleen, bone marrow, thymus, heart, lymph, blood, bone, cartilage, pancreas, kidney, gall bladder, stomach, intestine, testis, ovary, uterus, rectum, nervous system, eye, gland, or connective tissue. Preferably, the non-tumor tissue is muscle.

Preferably, the polynucleotide construct is delivered to the interstitial space of a tumor or of non-tumor tissues. "Interstitial space" comprises the intercellular, fluid, mucopolysaccharide matrix among the reticular fibers of organ tissues, elastic fibers in the walls of vessels or chambers, collagen fibers of fibrous tissues, or that same matrix within connective tissue ensheathing muscle cells or in the lacunae of bone. It is similarly the space occupied by the plasma of the circulation and the lymph fluid of the lymphatic channels.

The pharmaceutical composition and methods of the present invention can be used to treat a variety of mammalian cancers or tumors. Types of mammalian cancers and tumors that can be treated using the pharmaceutical composition and methods of the present invention include, but are not limited to all solid tumors, cutaneous tumors, melanoma, malignant melanoma, renal cell carcinoma, colorectal carcinoma, colon cancer, hepatic metastases of advanced colorectal carcinoma, lymphomas (including glandular lymphoma), malignant lymphoma, Kaposi's sarcoma, prostate cancer, kidney cancer, ovarian cancer, lung cancer, head and neck cancer, pancreatic cancer, mesenteric cancer, gastric cancer, rectal cancer, stomach cancer, bladder cancer, leukemia (including hairy cell leukemia and chronic myelogenous leukemia), breast cancer, non-melanoma skin cancer (including squamous cell carcinoma and basal cell carcinoma), hemangioma multiple myeloma, and glioma. Preferably, the cancer is melanoma, ovarian cancer, or metastases thereof.

By "treatment" is meant reduction in tumor size, a reduction in the rate of metastasis, and/or a slowing of tumor growth, and/or no worsening in disease over a specified period of time.

A systemic delivery embodiment can be particularly useful for treating nonlocalized tumors (i.e., leukemia and metastases of a variety of tumors), or a disease category that might be responsive to continuous exposure by the systemic route (i.e., myeloma, chronic myelogenous leukemia, lymphoma). A local delivery embodiment can be particularly useful for treating one disease condition that might be responsive to high local concentration (i.e., renal cell carcinoma, melanoma). For tumors involving body cavity of a mammal, "intra-cavity" embodiment is preferred. In particular, the use of this methodology is envisioned in treating cancers involving (i) the peritoneal cavity—pancreatic cancer, gastric cancer, ovarian cancer, mesenteric cancer, glandular lymphoma and metastatic melanoma; (ii) the thoracic cavity—lung cancer and glandular lymphoma; (iii) the rectal cavity—rectal cancer; (iv) the stomach cavity—stomach cancer; and (v) the urinary bladder vesicle—bladder cancer. When advantageous, systemic, local, and/or intra-cavity delivery can be combined, especially in a mammal having a primary site of tumor and one or more metastases.

An additional embodiment of the present invention is directed to combining any of the methods of the present invention with one or more additional cancer therapies including, but not limited to bone marrow transplant, cord blood cell transplant, surgery, chemotherapy, radiation therapy, and immunotherapy. The polynucleotide construct or pharmaceutical composition of the present invention can be administered prior to the commencement of one or more of the additional cancer therapies, during the practice of one or more of the additional cancer therapies, and after the end of one or more of the additional cancer therapies.

Types of bone marrow transplant include, but are not limited to autologous bone marrow transplant and heterologous (i.e., from a donor) bone marrow transplant.

Types of surgery include, but are not limited to surgery for breast cancer, prostate cancer, colon cancer, brain cancer, and head and neck cancer.

Chemotherapeutic agents include, but are not limited to alkylating agents, including mechlorethamine, cyclophosphamide, ifosfamide, melphalan, chlorambucil, dicarbazine, streptazocine, carmustine, lomustine, semustine, chlorozotocin, busulfan, triethylenemelamine, thiotepa, hexamethylmelamine; antimetabolites, including methotrexate; pyrimidine analogs, including fluorouracil, 5-fluorouracil, floxuridine (5'-fluoro-2'-deoxyuridine),idoxuridine, cytarabine, -phosphonoacetyl-L-aspartate, 5-azacytidine, azaribine, 6-azauridine, pyrazofuran, 3-deazauridine, acivicin; purine analogs, including thioguanine, mercaptopurine, azathioprine, pentostatin, erythrohydroxynonyladenine; vinca alkaloids, including vincristine and vinblastine; epipodophyllotoxins, including etoposide and teniposide; antibiotics, including dactinomycin, daunorubicin, doxorubicin, bleomycin sulfate, plicamycin, mitomycin; enzymes, including L-asparaginase; platinum coordination complexes, including cisplatin, carboplatin; hydroxyurea, procarbazine, mitotane; and hormones or related agents, including adrenocorticosteroids such as prednisone and prednisolone; aminoglutethimide; progestins such as hydroxyprogesterone caproate, medroxyprogesterone acetate, megesterol acetate, estrogens and androgens such as diethylstilbestrol, fluoxymesterone, ethynyl estradiol, antiestrogens such as tamoxifen, and gonadotropin-releasing hormone analogs such as leuprolide.

The present invention also provides kits for use in treating cancer comprising an administration means and a container means containing one or more cytokine-expressing polynucleotide constructs in a sterile environment. Also provided are kits for use in treating cancer comprising an administration means and a container means containing one or more cytokine-expressing polynucleotide constructs and one or more cationic compounds in a sterile environment. Examples of cationic compounds are described above. The cytokine-expressing polynucleotide constructs and the cationic compounds may be in the same container means or in separate container means. Preferably, the polynucleotide construct is in the amount of 1 ng to 20 mg.

Container means include glass containers, plastic containers, or strips of plastic or paper. In one embodiment, the container means is a syringe and the administration means is a plunger. In another embodiment, the administration means is a catheter.

The cytokine encoded by the polynucleotide construct of the kit of the present invention can be an IFN$\omega$ and one or more additional cytokines, including any of the cytokines described herein. Preferably, the cytokine is IFN$\omega$ and/or an IFN$\alpha$. The construct can be in the form of a pharmaceutical composition and can contain a pharmaceutically acceptable carrier. Pharmaceutical compositions are described above.

The kit can further comprise a pharmaceutically acceptable carrier in a separate container means.

The kit can further comprise an instruction sheet for administration of the composition into a mammal. The components of the polynucleotide composition are preferably provided as a liquid solution, such as a suspension, a solution, or an emulsion; or in lypholized form as a dried powder or a cake. If the polynucleotide construct is provided in lypholized form, preferably the kit further comprises a container means containing a suitable vehicle, such as sterile pyrogen-free water, for reconstitution of the lypholized polynucleotide construct, or any buffer described herein, including PBS, normal saline, Tris buffer, and sodium phosphate vehicle.

The term "cytokine" refers to polypeptides, including but not limited to interleukins (e.g., IL-1, IL-2, IL-3, IL-4, IL-5, IL-6, IL-7, IL-8, IL-9, IL-10, IL-11, IL-12, IL-13, IL-14, IL-15, IL-16, IL-17, and IL-18), α interferons (e.g, IFNα), β interferons (e.g., IFNβ), γ interferons (e.g., IFNγ), ω interferon (IFNω), τ interferons (IFNτ), colony stimulating factors (CSFs, e.g., CSF-1, CSF-2, and CSF-3), granulocyte-macrophage colony stimulating factor (GMCSF), epidermal growth factor (EGF), fibroblast growth factors (FGFs, e.g., acidic fibroblast growth factor, basic fibroblast growth factor, FGF-1, FGF-2, FGF-3, FGF-4, and FGF-5), transforming growth factor (TGF, e.g., TGFα and TGFβ), platelet-derived growth factor (PDGF), tumor necrosis factors (TNFs, e.g., TNF-α and TNF-β), and insulin-like growth factors (IGFs, e.g, IGF-I and IGF-II).

A "polypeptide" refers to any translation product of a polynucleotide, regardless of the size of the translation product, and regardless of whether the translation product is post-translationally modified (e.g., glycosylated) or not.

The polynucleotide construct of the present invention, whether complexed with cationic vehicle or not, can be administered by any suitable route of administration, including intramuscularly, subcutaneously, intravenously, transdermally, intranasally, by inhalation, or transmucosally (i.e., across a mucous membrane). Similarly, the pharmaceutical composition of the present invention can by administered by any suitable route, including intramuscularly, into or near a tumor, into a cavity (e.g., intraperitoneally), subcutaneously, intravenously, transdermally, intranasally, by inhalation, or transmucosally (i.e., across a mucous membrane).

Any mode of administration can be used so long as the mode results in the expression of one or more cytokines in an amount sufficient to decrease the tumorigenicity of the cancer bearing mammal. This includes needle injection, catheter infusion, biolistic injectors, particle accelerators (i.e., "gene guns"), pneumatic "needleless" injectors (e.g., MedEJet, PedoJet, Bioject), gelfoam sponge depots, other commercially available depot materials, osmotic pumps (e.g., Alza minipumps), oral or suppositorial solid (tablet or pill) pharmaceutical formulations, and decanting or topical applications during surgery. Preferred methods include needle injection and catheter infusion.

A "polynucleotide construct" is a polynucleotide molecule that carries genetic information for encoding one or more molecules, preferably, cytokines. The polynucleotide material delivered to the cells in vivo can take any number of forms. It can contain the entire sequence or only a functionally active fragment of a cytokine gene.

The polynucleotide construct comprises at least one polynucleotide (e.g., DNA, RNA, ribozyme, phosphorothioate, or other modified nucleic acid) encoding one or more molecules. Preferred molecules are cytokines. The polynucleotide can be provided in linear, circular (e.g. plasmid), or branched form; and double-stranded or single-stranded form. The polynucleotide can involve a conventional phosphodiester bond or a non-conventional bond (e.g., an amide bond as in peptide nucleic acid (PNA)). The choice of polynucleotide encoding a cytokine will depend on the desired kinetics and duration of expression. When long term delivery of the polynucleotide construct is desired, the preferred polynucleotide is DNA. Alternatively, when short term delivery is desired, the preferred polynucleotide is mRNA. RNA will be rapidly translated into polypeptide, but will be degraded by the target cell more quickly than DNA. In general, because of the greater resistance of circular DNA molecules to nucleases, circular DNA molecules will persist longer than linear polynucleotides, and they will be less likely to cause insertional mutation by integrating into the target genome.

In one embodiment, the polynucleotide sequence encoding one or more cytokines is RNA. Most preferably, the RNA is messenger RNA (mRNA). Methods for introducing RNA sequences into mammalian cells is described in U.S. Pat. No. 5,580,859. A viral alphavector, a non-infectious vector useful for administering RNA, may be used to introduce RNA into mammalian cells. Methods for the in vivo introduction of alphaviral vectors to mammalian tissues are described in Altman-Hamamdzic, S., et al., *Gene Therapy* 4: 815-822 (1997). Preferably, the polynucleotide sequence encoding one or more cytokines is DNA. In a DNA construct, a promoter is preferably operably linked to the polynucleotide encoding a cytokine. The promoter may be a cell-specific promoter that directs substantial transcription of the DNA only in predetermined cells. Other transcription control elements, besides a promoter, can be included in the polynucleotide construct to direct cell-specific transcription of the DNA.

An operable linkage is a linkage in which a polynucleotide sequence encoding a cytokine is connected to one or more regulatory sequence in such a way as to place expression of the cytokine sequence under the influence or control of the regulatory sequence(s). Two DNA sequences (such as a coding sequence and a promoter region sequence linked to the 5' end of the coding sequence) are operably linked if induction of promoter function results in the transcription of mRNA encoding the desired polypeptide and if the nature of the linkage between the two DNA sequences does not (1) result in the introduction of a frame-shift mutation, (2) interfere with the ability of the expression regulatory sequences to direct the expression of the polypeptide, antisense RNA, or (3) interfere with the ability of the DNA template to be transcribed. Thus, a promoter region would be operably linked to a DNA sequence if the promoter was capable of affecting transcription of that DNA sequence.

Preferably, the polynucleotide construct is a circular or linearized plasmid containing non-infectious nucleotide sequence. A linearized plasmid is a plasmid that was previously circular but has been linearized, for example, by digestion with a restriction endonuclease. The polynucleotide sequence encoding a cytokine may comprise a sequence which directs the secretion of the polypeptide.

"Non-infectious" means that the polynucleotide construct does not infect mammalian cells. Thus, the polynucleotide construct can contain functional sequences from non-mammalian (e.g., viral or bacterial) species, but the construct does not contain non-mammalian nucleotide sequences that facilitate infection of the construct into mammalian cells.

"Non-integrating" means that the polynucleotide construct does not integrate into the genome of mammalian cells. The construct can be a non-replicating DNA sequence, or specific replicating sequences genetically engineered to lack the ability to integrate into the genome. The polynucleotide construct does not contain functional sequences that facilitate integration of the cytokine-encoding polynucleotide sequence into the genome of mammalian cells.

The polynucleotide construct is assembled out of components where different selectable genes, origins, promoters, introns, 5' untranslated (UT) sequence, terminators, polyadenylation signals, 3' UT sequence, and leader peptides, etc. are put together to make the desired vector. The precise nature of the regulatory regions needed for gene expression can vary between species or cell types, but shall in general include, as necessary, 5' non-transcribing and 5' non-translating (non-coding) sequences involved with initiation of transcription and translation respectively, such as the TATA box, capping sequence, CAAT sequence, and the like, with those elements necessary for the promoter sequence being provided by the promoters of the invention. Such transcriptional control sequences can also include enhancer sequences or upstream activator sequences, as desired.

The polynucleotide construct can be an expression vector. A typical mammalian expression vector contains the promoter element, which mediates the initiation of transcription of mRNA, the polypeptide coding sequence, and signals required for the termination of transcription and polyadenylation of the transcript. Additional elements include enhancers, Kozak sequences and intervening sequences flanked by donor and acceptor sites for RNA splicing. Highly efficient transcription can be achieved with the early and late promoters from SV40, the long terminal repeats (LTRS) from retroviruses, e.g., RSV, HTLVI, HIVI, MPSV and the immediate early promoter of the cytomegalovirus (CMV IEP). However, cellular elements can also be used (e.g., the human actin promoter, metallothionein promoter). In humans, CMV IEP is preferred. Suitable expression vectors for use in practicing the present invention include, for example, vectors such as PSVL and PMSG (Pharmacia, Uppsala, Sweden), pRSVcat (ATCC 37152), pSV2dhfr (ATCC 37146) and pBC12MI (ATCC 67109), VR1012, VR1055, and pcDNA3 (Invitrogen, San Diego, Calif.). All forms of DNA, whether replicating or non-replicating, which do not become integrated into the genome, and which are expressible, are within the methods contemplated by the invention.

The vector containing the DNA sequence (or the corresponding RNA sequence) which can be used in accordance with the invention can be a eukaryotic expression vector. Techniques for obtaining expression of exogenous DNA or RNA sequences in a host are known. See, for example, Korman, et al., *Proc. Nat. Acad Sci*. (*USA*) 84:2150-2154 (1987).

Secretion of a cytokine from a cell can be facilitated by a leader or secretory signal sequence. In a preferred embodiment, either the native leader sequence of a cytokine is used, or a functional derivative of that sequence that retains the ability to direct the secretion of the peptide that is operably linked to it. Alternatively, a heterologous mammalian leader sequence, or a functional derivative thereof, may be used. For example, the wild-type leader sequence may be substituted with the leader sequence of human tissue plasminogen activator or mouse β-glucuronidase.

For the methods of the present invention, a single polynucleotide construct containing more than one polynucleotide sequences encoding one or more molecules, or more than one polynucleotide constructs each containing polynucleotide sequences encoding one or more molecules may be co-injected or sequentially injected. For example, a single polynucleotide construct containing one polynucleotide encoding an interferon and another polynucleotide encoding an additional cytokine or an immunomodulatory molecule, i.e., MHC class I antigen, tumor antigen, and co-stimulatory molecule, can be injected. Alternatively, two polynucleotide construct can be injected where one encodes a cytokine to enhance anti-tumor efficacy of the other gene product. For example, an IFNω, IFNα, IL-12 or IL-2-expressing polynucleotide construct can be co-injected with a polynucleotide construct encoding a different cytokine. More specifically, an IL-2 expressing plasmid could be co-injected with a G-CSF or GM-CSF expressing plasmid. Alternatively, one or more plasmids could be administered initially and other plasmid(s) could be administered subsequently at various time intervals. Combination of the present invention with therapeutic agents such as lymphokine-activated killer cells (LAK) and tumor-infiltrating lymphocytes (TIL) is also envisioned.

It will be recognized in the art that some amino acid sequences of the polypeptides described herein can be varied without significant effect on the functional activity of the polypeptides. If such differences in sequence are contemplated, it should be remembered that there will be critical areas on the polypeptide which determine activity. Such variations include deletions, insertions, inversions, repeats, and type substitutions. Guidance concerning which amino acid changes are likely to be phenotypically silent can be found in Bowie, J. U., et al., "Deciphering the Message in Protein Sequences: Tolerance to Amino Acid Substitutions," (*Science* 247:1306-1310 (1990)). Compositions within the scope of the invention can be assayed according to the anti-proliferation assay described herein. Amino acids that are critical for cytokine activity can also be determined by structural analysis such as crystallization, nuclear magnetic resonance or photoaffinity labeling (Smith, et al., *J. Mol. Biol.* 224:899-904 (1992) and de Vos, et al. *Science* 255:306-312 (1992)).

The present invention further relates to using variants of the cytokine-encoding polynucleotide, which encode portions, analogs or derivatives of the cytokine. Variants may occur naturally, such as a natural allelic variant. By an "allelic variant" is intended one of several alternate forms of a gene occupying a given locus on a chromosome of an organism. *Genes II*, Lewin, B., ed., John Wiley & Sons, New York (1985). Non-naturally occurring variants may be produced using art-known mutagenesis techniques.

Alterations in the coding regions may produce conservative or non-conservative amino acid substitutions, deletions or additions. Especially preferred among these are silent substitutions, additions and deletions, which do not alter the properties and activities of the cytokine or portions thereof. Also especially preferred in this regard are conservative substitutions. For example, aromatic amino acids that can be conservatively substituted for one another include phenylalanine, tryptophan, and tyrosine. Hydrophobic amino acids that can be conservatively substituted for one another include leucine, isoleucine, and valine. Polar amino acids that can be conservatively substituted for one another include glutamine and asparagine. Basic amino acids that can be conservatively substituted for one another include arginine, lysine, and histidine. Acidic amino acids that can be conservatively substituted for one another include aspartic acid and glutamic acid. Small amino acids that can be conservatively substituted for one another include alanine, serine, threonine, methionine, and glycine.

Substitutions, deletions, or insertions can be made outside of the region encoding the shortest active fragment of the cytokine, without affecting the activity of the cytokine. Further, mutated proteins (or muteins) often retain a biological activity that is similar to that of the naturally occurring protein. For example, Gayle and coworkers (*J. Biol. Chem.* 268: 22105-22111 (1993)) conducted an extensive mutational analysis of the human cytokine IL-1α. They used random mutagenesis to generate over 3,500 individual IL-1α mutants with an average of 2.5 amino acid changes per mutein over the entire length of the molecule. Multiple mutations were examined at every possible amino acid and, on average, each mutein's amino acid sequence was 98.4% identical to that of naturally occurring IL-1α. The investigators observed that most of the molecule could be mutated with little effect on either binding or biological activity, and that 75% of the molecule may not contribute significantly to the biological activity of the molecule.

Similarly, Gronenborn and colleagues (*FEBS Letters* 231: 135-138 (1988)) analyzed the receptor binding activity of six mutant IL-1α polypeptides. Each mutant contained a single amino acid alteration from the naturally occurring IL-1α polypeptide and was examined under four sets of experimental conditions. In this study, the investigators found very little difference between the receptor binding activity of the mutants and naturally occurring IL-1α.

Further, Zurawski and colleagues (*EMBO J.* 12: 5113-5119 (1993)) studied residues 41-142 of mIL-2 by generating 1,090 muteins. The extent of the mutagenesis was such that there was an average of 11 different amino acid substitutions per naturally occurring amino acid residue, with the exception of the extreme N- and C-termini and residues 31-40. The mIL-2 muteins were assayed for specific activity and compared to that of naturally occurring mIL-2. The degree to which the specific activity was antagonized by a previously characterized mIL-2 mutant was also assessed. The investigators observed that in the 149 residue mIL-2 protein, only 23 residues are important for interaction with IL-2R, 18 residues are presumed to be part of the structural core, and three additional residues are important for structure. 98 mIL-2 residues (or 65% of the protein) were assigned as relatively unimportant residues.

The polynucleotide and amino acid sequences encoding an IFNω include the sequences for the complete IFNω and the mature IFNω set forth in U.S. Pat. No. 4,917,887; European Patent Publication No. 0 170 204 B1; and Capon, D. J., et al., *Molec. Cell. Biol.* 5: 768-779 (1985); Hauptmann, R. and P. Swetly, *Nucl. Acids Res.* 13: 4739-4749 (1985); Adolf, G. R., et al., *Biochim. Biophys. Acta* 1089: 167-174 (1991); Mege, D., et al., *J. Interf. Res.* 11: 341-350 (1991); Charlier, M., et al., *J. Interf. Res.* 13 313-322 (1993); Hughes, A. L., *J. Mol. Evol.* 41: 539-548 (1995); and Roberts, R. M., et al., *Prog. Nucl. Acid Res. Molec. Biol.* 56:287-325, edited by W. E. Cohn, Academic Press (1997).

The polynucleotide and amino acid sequences encoding IFNα include the sequences for the complete IFNα and the mature IFNα set forth in U.S. Pat. Nos. 4,530,901; 4,695,543; 4,695,623; 4,748,233; 4,892,743; 4,897,471; 4,973,479; 4,975,276; and 5,098,703; and in Pestka, S., *Methods Enzymol.* 119: 3-14 (1986); Hughes, A. L., *J. Mol. Evol.* 41: 539-548 (1995); and Roberts, R. M., et al., *Prog. Nucl. Acid Res. Molec. Biol.* 56:287-325, edited by W. E. Cohn, Academic Press (1997).

The polynucleotide and amino acid sequences encoding an IL-2 include the sequences for the complete human IL-2 and mature IL-2 set forth in Lupker, J. et al., EP 0307285-A3 (1989), U.S. Pat. No. 5,641,665, Maeda et al., *Biochem. Biophys. Res. Commun.* 115:1040-1047 (1983), Mita et al., *Biochem. Biophys. Res. Commun.* 117:114-121 (1983), Taniguchi et al., *Nature* 302:305-310 (1983), Devos et al., *Nucleic Acid Res.* 11:4307-4323 (1983), Fujita et al., *Proc. Natl. Acad. Sci. USA* 80:74347-7441 (1983), Clark et al., *Proc. Natl. Acad. Sci. USA* 81:2543-2547 (1984) and Cullen, *DNA* 7:645-650 (1988).

The polynucleotide sequences encoding an IFNω, an IFNα, and an IL-2 also include sequences that encode the complete polypeptide encoded by the nucleotide sequences set forth in SEQ ID Nos. 7, 9 and 13, respectively, and the mature polypeptides encoded by nucleotide sequences set forth in SEQ ID Nos. 7, 9 and 13, respectively. The polynucleotide sequences encoding IL-2 further includes the sequence that encodes the complete IL-2 polypeptide encoded by the nucleotide sequence set forth in SEQ ID No. 25, shown as SEQ ID No. 26.

Thus, a polynucleotide sequence encoding a polypeptide of the present invention can encode a polypeptide having one to twenty amino acid substitutions, deletions or insertions, either from natural mutations or human manipulation, relative to the full length or mature IFNα, IFNω, or IL-2. Preferably, no more than one to fifteen substitutions, deletions or insertions are present, relative to the full length or mature IFNα, IFNω, or IL-2 (excluding the signal sequence). More preferably, no more than one to ten substitutions, deletions or insertions are present. Still more preferably, no more than one to five substitutions, deletions or insertions are present.

Determining an effective amount of substance to be delivered can depend upon a number of factors including, for example, the chemical structure and biological activity of the substance, the age and weight of the mammal, the precise condition requiring treatment and its severity, and the route of administration. The precise amount, number of doses, and timing of doses will be determined by the attending physician or veterinarian.

If the polynucleotide construct of the present invention is administered as a pharmaceutical composition, the pharmaceutical composition can be formulated according to known methods for preparing pharmaceutical compositions, whereby the substance to be delivered is combined with a pharmaceutically acceptable carrier vehicle. Suitable vehicles and their preparation are described, for example, in Remington's Pharmaceutical Sciences, 16$^{th}$ Edition, A. Osol, Ed., Mack Publishing Co., Easton, Pa. (1980), and Remington's Pharmaceutical Sciences, 19$^{th}$ Edition, A. R. Gennaro, Ed., Mack Publishing Co., Easton, Pa. (1995).

The pharmaceutical composition can be in the form of an emulsion, gel, solution, suspension, or other form known in the art. Optionally, it can contain one or more lipids as described above. In addition, the pharmaceutical composition can also contain pharmaceutically acceptable additives including, for example, diluents, binders, stabilizers, and preservatives. Administration of pharmaceutically acceptable salts of the polynucleotides described herein is preferred. Such salts can be prepared from pharmaceutically acceptable non-toxic bases including organic bases and inorganic bases. Salts derived from inorganic bases include sodium, potassium, lithium, ammonium, calcium, magnesium, and the like. Salts derived from pharmaceutically acceptable organic non-toxic bases include salts of primary, secondary, and tertiary amines, basic amino acids, and the like.

For aqueous pharmaceutical compositions used in vivo, sterile pyrogen-free water is preferred. Such formulations will contain an effective amount of the substance together with a suitable amount of vehicle in order to prepare pharmaceutically acceptable compositions suitable for administration to a human or animal.

A pharmaceutical composition can be in solution form, or alternatively, in lyophilized form for reconstitution with a suitable vehicle, such as sterile, pyrogen-free water. Both liquid and lyophilized forms will comprise one or more agents, preferably buffers, in amounts necessary to suitably adjust the pH of the injected solution.

The container in which the pharmaceutical formulation is packaged prior to use can comprise a hermetically sealed container enclosing an amount of the lyophilized formulation or a solution containing the formulation suitable for a pharmaceutically effective dose thereof, or multiples of an effective dose. The pharmaceutical formulation is packaged in a sterile container, and the hermetically sealed container is designed to preserve sterility of the pharmaceutical formulation until use. Optionally, the container can be associated with administration means and or instruction for use.

It will be apparent to one skilled in the art, in view of the following detailed description and the claims appended hereto, that various substitutions and modifications may be made to the present invention without departing from the scope of the invention as claimed.

The present invention is broadly directed to compositions and methods for improving the effectiveness of polypeptide delivery into a vertebrate by administering a polynucleotide encoding the polypeptide to the vertebrate's cells in vivo. Such compositions comprise a polypeptide-encoding polynucleotide and sodium phosphate dissolved in an aqueous solution. In one preferred embodiment, about 1 ng to about 30 mg of a polynucleotide is dissolved in a solution of about 20 mM to about 300 mM sodium phosphate. In another preferred embodiment, about 1 ng to about 30 mg of a polynucleotide is associated with a cationic lipid in an aqueous solution of about 0.1 to about 150 mM sodium phosphate. In this embodiment, the aqueous solution is substantially free of chloride anion.

In this manner, the present invention provides a method of enhancing the level of polypeptide expression from delivered polynucleotides in vivo and/or facilitating uptake of the polynucleotides by vertebrate cells. Delivery methods utilizing the compositions of the present invention significantly enhance the levels of in vivo transfection and in vivo polypeptide expression compared with traditional methods, i.e., delivery of a polypeptide-encoding polynucleotide in a solution of normal saline (about 154 mM NaCl) or phosphate buffered saline ("PBS": about 154 mM NaCl, about 10 mM sodium phosphate at pH 7).

It is to be noted that the term "a" or "an" entity, refers to one or more of that entity; for example, "a polynucleotide," is understood to represent one or more polynucleotides. As such, the terms "a" (or "an"), "one or more," and "at least one" can be used interchangeably herein.

The term "vertebrate" is intended to encompass a singular "vertebrate" as well as plural "vertebrates," and comprises mammals and birds, as well as fish, reptiles, and amphibians.

The terms "saline" or "normal saline" as used herein refer to an aqueous solution of about 145 mM to about 155 mM sodium chloride, preferably about 154 mM sodium chloride. The terms "phosphate buffered saline" or "PBS" refer to an aqueous solution of about 145 mM to about 155 mM sodium chloride, preferably about 154 mM sodium chloride, and about 10 mM sodium phosphate, at a pH ranging from about 6.0 to 8.0, preferably at a pH ranging from about 6.5 to about 7.5, most preferably at pH 7.0.

As used herein, an "ion," an "ionic molecule," or an "ionic compound refers to a charged molecule or compound. A "cation," a "cationic molecule, or a "cationic compound" refers to a positively charged molecule or compound, for example $Na^+$. An "anion," an "anionic molecule," or an "anionic compound" refers to a negatively charged molecule or compound, for example, $HPO_4^{2-}$ or $H_2PO_4^-$. Cations and anions may have any number of positive or negative charges, respectively, i.e., they may be monovalent like $Na^+$ or multivalent, e.g., divalent such as $Ca^{2+}$, or trivalent such as $Al^{3+}$. Anions can be either inorganic or organic, examples of the latter being pyruvate or citrate anions.

Salts and Associated Formulations

Certain embodiments of the present invention comprise the salt sodium phosphate. As used herein, a "salt" of the present invention is a compound having a positively charged cation, C, and a negatively charged anion, A. A salt may be in a solid crystalline form, but preferably for the present invention, is dissolved in an aqueous solution, i.e., liquid water. As used herein, "sodium phosphate" can be either the monobasic form, e.g., $Na_2HPO_4$, or the dibasic form, e.g., $NaH_2PO_4$, but a mixture of the two, resulting in a desired pH, is most preferred. Accordingly, as used herein the term "sodium phosphate" refers to a mixture of the dibasic and monobasic forms of the salt to reach a given pH.

The pH values for the sodium phosphate solution of the present invention can range from about pH 4 to about pH 10, depending on the properties of the particular salt solution. These pH values include about pH 4, about pH 4.5, about pH 5, about pH 5.5., about pH 6, about pH 6.5, about pH 7, about pH 7.5. about pH 8, about pH 8.5, about pH 9, about pH 9.5, and about pH 10. As used herein, the term "about" when referring to pH values indicates that the pH value may vary by as much as 0.4 pH units in either direction due to, for example, standard error or equipment error. Preferred pH values for a solution of sodium phosphate are from about pH 6 to about pH 8. More preferred pH values for a solution of sodium phosphate range from about pH 6.5 to about pH 7.5. Even more preferred pH values for a solution of sodium phosphate or potassium phosphate range from about 6.8 to about 7.4.

Sodium phosphate is preferably dissolved in aqueous solution at a concentration which enhances entry of a polypeptide-encoding polynucleotide into vertebrate cells in vivo, and/or enhances polypeptide expression, relative to saline, PBS, or water.

Certain embodiments of the present invention are drawn to compositions comprising about 1 ng to about 30 mg of a polynucleotide in aqueous solution, where the polynucleotide operably encodes a polypeptide within vertebrate cells in vivo; and sodium phosphate dissolved in the aqueous solution at a molar concentration from about 20 mM to about 300 mM, and reaction, association, or dissociation products thereof. The present invention is further drawn to methods to use such a composition, methods to make such a composition, and pharmaceutical kits.

The term "sodium phosphate dissolved in aqueous solution at a given molar concentration" means that the molecular mass, e.g., in grams, of a crystallized form of sodium phosphate required to produce a given volume of a solution of a given molar concentration is calculated based on the molecular weight of the particular crystalline form. That amount of crystals is weighed out using standard laboratory procedures, the crystals are added to a volume of water or other aqeuous solution which is slightly less than the final desired volume, the liquid is mixed until the crystals are fully dissolved, and then the volume of the liquid is brought up to the final desired volume.

The term "reaction, association, or dissociation products thereof" refers to any ionic interactions which may be formed in the aqueous solution once the salt crystals are dissolved. For example, once sodium phosphate is dissolved in an aqueous solution, the cations and anions disassociate and are free in solution to interact with other cations or anions that may be present in the solution, including, for example, a negatively-charged polynucleotide molecule. The interactions taking place in a complex aqueous sodium phosphate solution, except for the precipitation of insoluble salt complexes, are transient and reversible, and cannot be precisely predicted at any point in time. Therefore, once an aqueous solution comprising sodium phosphate at a certain molar concentration is prepared, the interactions in the solution may include reaction products other than the interaction of the cation and anion which composed the sodium phosphate crystals that were added to the solution as described above.

Preferably in the present embodiment, sodium phosphate is dissolved in aqueous solution at a molar concentration ranging from about 25 mM to about 290 mM, from about 30 mM to about 280 mM, from about 35 mM to about 270 mM, from about 40 mM to about 260 mM, from about 45 mM to about 255 mM, from about 50 mM to about 250 mM, from about 55 mM to about 245 mM, from about 60 mM to about 240 mM, from about 65 mM to about 235 mM, from about 70 mM to about 230 mM, from about 75 mM to about 225 mM, from about 80 mM to about 220 mM, from about 85 mM to about 215 mM, from about 90 mM to about 210 mM, from about 95 mM to about 205 mM, from about 100 mM to about 200 mM, from about 105 mM to about 195 mM, from about 110 mM to about 190 mM, from about 115 mM to about 185 mM, from about 120 mM to about 180 mM, from about 125 mM to about 175 mM, from about 130 mM to about 170 mM, from about 135 mM to about 165 mM, from about 140 mM to about 160 mM, and from about 145 mM to about 155 mM.

More preferably in the present embodiment, sodium phosphate is dissolved in aqueous solution at a molar concentration of about 20 mM, about 25 mM, about 30 mM, about 35 mM, about 40 mM, about 45 mM, about 50 mM, about 55 mM, about 60 mM, about 65 mM, about 70 mM, about 75 mM, about 80 mM, about 85 mM, about 90 mM, about 95 mM, about 100 mM, about 105 mM, about 110 mM, about 115 mM, about 120 mM, about 125 mM, about 130 mM, about 135 mM, about 140 mM, about 145 mM, about 150 mM, about 155 mM, about 160 mM, about 165 mM, about 170 mM, about 175 mM, about 180 mM, about 185 mM, about 190 mM, about 200 mM, about 205 mM, about 210 mM, about 215 mM, about 220 mM, about 225 mM, about 230 mM, about 235 mM, about 240 mM, about 245 mM, about 250 mM, about 255 mM, about 260 mM, about 265 mM, about 270 mM, about 275 mM, about 280 mM, about 285 mM, about 290 mM, about 295 mM, and about 300 mM.

Even more preferably in the present embodiment, sodium phosphate is dissolved in aqueous solution at a molar concentration of about 100 to about 200 mM. Most preferably, sodium phosphate is dissolved in aqueous solution at a molar concentration of about 150 mM.

As used herein, a phrase such as "a molar concentration of about 150 mM" refers to the range of molar concentrations approaching 150 mM to the best approximation obtainable by one of ordinary skill in the art using standard laboratory equipment and methods. For example, "the salt sodium phosphate dissolved in aqueous solution of about 150 mM," prepared using ordinary laboratory balances and measuring glassware, and using generally accepted techniques, may range anywhere from approximately 145 mM to approximately 155 mM based on the standard error inherent in preparing chemical solutions. Such a standard error range would be well understood by one of ordinary skill in the art to be equivalent to "about 150 mM."

According to the present embodiment, compositions comprising about 1 ng to about 30 mg of a polynucleotide in aqueous solution and sodium phosphate dissolved in the aqueous solution at a molar concentration from about 20 mM to about 300 mM as described above may further comprise chloride ion, represented by the symbol $Cl^-$, in the aqueous solution at a molar equivalent concentration of 0 (zero) mM to about 125 mM. By "molar equivalent" is meant the molar concentration of chloride ion in solution, as opposed to the molar concentration of the salt added to the aqueous solution. For example, chloride ion may be added to the aqueous solution as part of certain salt crystals dissolved in the solution, such as sodium chloride (NaCl) or calcium chloride ($CaCl_2$). Each mole of sodium chloride crystals added to an aqueous solution will add one mole equivalent of chloride ion to the solution, where each mole of calcium chloride crystals added to an aqueous solution will add two mole equivalents of chloride ion to the solution. Alternatively, chloride ion may be added to the aqueous solution as part of an acid or base such as hydrogen chloride or ammonium chloride.

Preferably, chloride ion is present in the aqueous solution at a molar equivalent concentration ranging from 0 mM to about 120 mM, from 0 mM to about 115 mM, from 0 mM to about 110 mM, from 0 mM to about 105 mM, from 0 mM to about 100 mM, from 0 mM to about 95 mM, from 0 mM to about 90 mM, from 0 mM to about 85 mM, from 0 mM to about 80 mM, from 0 mM to about 75 mM, from 0 mM to about 70 mM, from 0 mM to about 65 mM, from 0 mM to about 60 mM, from 0 mM to about 55 mM, from 0 mM to about 50 mM, from 0 mM to about 45 mM, from 0 mM to about 40 mM, from 0 mM to about 35 mM, from 0 mM to about 30 mM, from 0 mM to about 25 mM, from 0 mM to about 20 mM, from 0 mM to about 15 mM, from 0 mM to about 10 mM, or from 0 mM to about 5 mM.

More preferably, chloride ion is present in the aqueous solution at a molar concentration of about 120 mM, about 115 mM, about 110 mM, about 105 mM, about 100 mM, about 95 mM, about 90 mM, about 85 mM, about 80 mM, about 75 mM, about 70 mM, about 65 mM, about 60 mM, about 55 mM, about 50 mM, about 45 mM, about 40 mM, about 35 mM, about 30 mM, about 25 mM, about 20 mM, about 15 mM, about 10 mM, about 5 mM, or 0 mM.

Most preferably, the aqueous solution is substantially free of chloride ion. As used herein, the phrase "substantially free of chloride ion" indicates that the amount of chloride ion added into the composition is insubstantial and that the addition cannot alter the transcription- and/or expression-enhancing activity of the composition at a significant level. The phrase "essentially free of chloride ion" indicates that no chloride ion is intentionally added to the composition. However, some chloride ion may be present due to, for example, impurities in other components of the composition.

In certain embodiments, described in more detail below, compositions of the present invention may further comprise one or more transfection facilitating materials including, but not limited to, materials such as cationic lipids, calcium phosphate, alum, gold, tungsten, or other metal particles, peptides, proteins, and polymers. However, compositions of the present embodiment, which comprise a polynucleotide in aqueous solution and sodium phosphate dissolved in the aqueous solution at a molar concentration from about 20 mM to about 300 mM as described above, are preferably free of cationic lipids.

Accordingly a preferred embodiment of the present invention is a composition comprising: about 1 ng to about 30 mg of a polynucleotide in aqueous solution, where the polynucleotide operably encodes a polypeptide within vertebrate cells in vivo; sodium phosphate dissolved in the aqueous solution at a molar concentration from about 20 mM to about 300 mM, and reaction, association, or dissociation products thereof; where the composition is free of cationic lipids.

Further embodiments of the present invention are drawn to compositions comprising: about 1 ng to about 30 mg of a polynucleotide in aqueous solution, where the polynucleotide operably encodes a polypeptide within vertebrate cells in vivo; sodium phosphate dissolved in the aqueous solution at a molar concentration from about 0.1 mM to about 150 mM, and reaction, association, or dissociation products thereof; a cationic lipid suspended in said aqueous solution; and where the aqueous solution is substantially free of chloride anion. The present invention is further drawn to methods to use such a composition, methods to make such a composition, and pharmaceutical kits.

Preferably, sodium phosphate is dissolved in aqueous solution at a molar concentration ranging from about 0.1 mM to about 145 mM, from about 0.1 mM to about 140 mM, from about 0.1 mM to about 135 mM, from about 0.1 mM to about 130 mM, from about 0.1 mM to about 125 mM, from about 1 mM to about 120 mM, from about 1 mM to about 115 mM, from about 1 mM to about 110 mM, from about 1 mM to about 105 mM, from about 1 mM to about 100 mM, from about 1 mM to about 95 mM, from about 1 mM to about 90 mM, from about 1 mM to about 85 mM, from about 1 mM to about 80 mM, from about 1 mM to about 75 mM, from about 1 mM to about 70 mM, from about 1 mM to about 65 mM, from about 1 mM to about 60 mM, from about 1 mM to about 55 mM, from about 1 mM to about 50 mM, from about 1 mM to about 45 mM, from about 1 mM to about 40 mM, from about 1 mM to about 35 mM, from about 1 mM to about 30 mM, from about 1 mM to about 25 mM, from about 1 mM to about 20 mM, from about 1 mM to about 15 mM, from about 1 mM to about 10 mM, from about 1 mM to about 5 mM, from about 1 mM to about 4.0 mM, from about 1 mM to about 3.0 mM, or from about 1 mM to about 2.5 mM.

More preferably, sodium phosphate is dissolved in aqueous solution at a molar concentration of about 145 mM, about 140 mM, about 135 mM, about 130 mM, about 125 mM, about 120 mM, about 115 mM, about 110 mM, about 105 mM, about 100 mM, about 95 mM, about 90 mM, about 85 mM, about 80 mM, about 75 mM, about 70 mM, about 65 mM, about 60 mM, about 55 mM, about 50 mM, about 45 mM, about 40 mM, about 35 mM, about 30 mM, about 25 mM, about 20 mM, about 15 mM, about 10 mM, about 5 mM, about 4.0 mM, about 3.0 mM, about 2.5 mM, about 2.0 mM, about 1.5 mM, about 1.0 mM, about 0.5 mM, or about 0.1 mM.

Even more preferably, sodium phosphate is dissolved in aqueous solution at a molar concentration of about 1 mM to 10 mM, with about 2.5 mM being most preferred.

Those embodiments of the present invention comprising sodium phosphate dissolved in the aqueous solution at a molar concentration from about 0.1 mM to about 150 mM, and which are substantially free of chloride ion also comprise a cationic lipid suspended in the aqueous solution. Cationic lipids are described in more detail above. While not being bound by theory, cationic lipids are thought to interact with anionic polynucleotide molecules in solution, and the complexes formed thereby are thought to have an improved ability to enter into vertebrate cells.

That sodium phosphate and sodium phosphate solutions disclosed herein were effective in increasing expression of polypeptides encoded by polynucleotides delivered to vertebrate cells in vivo relative to saline or PBS was unexpected in view of results showing that other salt solutions have no enhancing effect on expression of polypeptides encoded by polynucleotides delivered to vertebrate cells in vivo, or even hinder such expression. For example, the following salt solutions had no ability to enhance, relative to a salt solution consisting essentially of normal saline, the entry of polynucleotides into vertebrate cells in vivo, and/or the in vivo expression of polypeptides encoded by such polynucleotides: 150 mM potassium chloride, 150 mM magnesium chloride, 150 mM calcium chloride, 150 mM zinc chloride, 150 mM ferrous chloride, 150 mM magnesium phosphate, 150 mM calcium phosphate, 150 mM aluminum phosphate, 150 mM ferric phosphate, 150 mM sodium citrate, and 150 mM sodium oxalate. See Table 10.

Polynucleotides

The present invention covers the delivery to a vertebrate of a polypeptide-encoding polynucleotide in a detectable amount. Preferably, the encoded polypeptide is expressed in vivo in the vertebrate in an amount sufficient to provide an immunogenic, immunomodulatory, therapeutic, or corrective effect to a vertebrate in need of such treatment.

The term "nucleic acid" is intended to encompass a singular "nucleic acid" as well as plural "nucleic acids," and refers to an isolated molecule or construct, e.g., virus genomes (preferably non-infectious), messenger RNA (mRNA), plasmid DNA (pDNA), or derivatives of pDNA (e.g., minicircles as described in (Darquet, A-M et al., *Gene Therapy* 4:1341-1349 (1997)) comprising a polynucleotide. A nucleic acid may be provided in linear (e.g., mRNA), circular (e.g., plasmid), or branched form as well as double-stranded or single-stranded forms. A nucleic acid may comprise a conventional phosphodiester bond or a non-conventional bond (e.g., an amide bond, such as found in peptide nucleic acids (PNA)).

The term "polynucleotide" refers to any one or more nucleic acid segments, e.g., DNA or RNA fragments, present in a nucleic acid or construct. Two or more polynucleotides of the present invention can be present in a single nucleic acid construct, e.g., on a single plasmid, or in separate nucleic acid constructs, e.g., on separate plasmids. Furthermore, any polynucleotide may encode a single polypeptide, e.g., a single antigen, cytokine, or regulatory polypeptide, or may encode more than one polypeptide, e.g., a polynucleotide may encode two or more polypeptides. In addition, a polynucleotide may encode a regulatory element such as a promoter or a transcription terminator, or may encode a specific element of a polypeptide or protein, such as a secretory signal peptide or a functional domain.

Nucleic acids and/or polynucleotides of the present invention, e.g., plasmid DNA, derivatives of plasmid DNA, mRNA, linear DNA, viral genomes, or polynucleotide fragments contained therein may be formulated into any of the various compositions and may be used in any of the methods disclosed herein. For aqueous compositions used in vivo, use of sterile pyrogen-free water is preferred. Such formulations will contain an effective amount of a polynucleotide together with sodium phosphate as disclosed herein, in order to prepare pharmaceutically acceptable compositions suitable for optimal administration to a vertebrate. Insoluble polynucleotides may be solubilized in a weak acid or weak base, and then diluted to the desired volume, for example, with an aqueous solution of the present invention. The pH of the solution may be adjusted as appropriate. In addition, a pharmaceutically acceptable additive can be used to provide an appropriate osmolarity. Such additives are within the purview of one skilled in the art.

The amount of a polynucleotide included in a composition of the present invention depends on many factors, including the age and weight of the subject, the delivery method and route, the type of treatment desired, and the type of polynucleotide being administered. In general, a composition of the present invention includes from about 1 ng to about 30 mg of a polynucleotide, more preferably, from about 100 ng to about 10 mg of a polynucleotide.

Certain preferred compositions of the present invention may include about 1 ng of a polynucleotide, about 5 ng of a polynucleotide, about 10 ng of a polynucleotide, about 50 ng of a polynucleotide, about 100 ng of a polynucleotide, about 500 ng of a polynucleotide, about 1 μg of a polynucleotide, about 5 μg of a polynucleotide, about 10 μg of a polynucleotide, about 50 μg of a polynucleotide, about 100 μg of a polynucleotide, about 150 μg of a polynucleotide, about 200 μg of a polynucleotide, about 250 μg of a polynucleotide, about 300 μg of a polynucleotide, about 350 μg of a polynucleotide, about 400 μg of a polynucleotide, about 450 μg of a polynucleotide, about 500 μg of a polynucleotide, about 550 μg of a polynucleotide, about 600 μg of a polynucleotide, about 650 μg of a polynucleotide, about 700 μg of a polynucleotide, about 750 μg of a polynucleotide, about 800 μg of a polynucleotide, about 850 μg of a polynucleotide, about 900 μg of a polynucleotide, about 950 μg of a polynucleotide, about 1 mg of a polynucleotide, about 5 mg of a polynucleotide, about 10 mg of a polynucleotide, about 15 mg of a polynucleotide, about 20 mg of a polynucleotide, about 25 mg of a polynucleotide, and about 30 mg of a polynucleotide.

The choice of polynucleotide form depends in part on the desired kinetics and duration of expression. When long-term expression of the polypeptide encoded by the polynucleotide is desired, the preferred form is DNA, preferably plasmid DNA. Alternatively, when short-term expression of the polypeptide encoded by the polynucleotide is desired, the preferred form is RNA, preferably messenger RNA, since RNA is rapidly translated into polypeptide, but is degraded more quickly than DNA.

In one embodiment, a polynucleotide of the present invention is RNA. Preferably in this embodiment, the RNA is in the form of messenger RNA (mRNA). Methods for introducing RNA sequences into vertebrate cells is described in U.S. Pat. No. 5,580,859, the disclosure of which is incorporated herein by reference in its entirety.

Alternatively, the RNA is in the form of an RNA virus genome. Preferably an RNA virus genome of the present invention is noninfectious, (i.e., does not result in the production of infectious virus particles in vertebrate cells). Suitable RNA virus genomes include, but are not limited to, alphavirus genomes, picornavirus genomes, and retrovirus genomes. Methods for the in vivo introduction of non-infectious viral genomes to vertebrate tissues are well known to those of ordinary skill in the art and are described, e.g., in Altman-Hamamdzic, S., et al., *Gene Therapy* 4, 815-822 (1997), in U.S. Pat. No. 4,980,289, Dec. 25, 1990, and in Miller, A. D., et al., *Meth. Enzymol.* 217:581-599 (1993), the disclosures of which are incorporated herein by reference in their entireties. Viral replicons, i.e., non-infectious RNA virus genomes packaged in a viral coat, e.g., a picornavirus coat or an alphavirus coat, are also useful for efficient administration of RNA. See, e.g., U.S. Pat. No. 5,766,602, U.S. Pat. No. 5,614,413, and PCT Publication No. WO 95/07994, the disclosures of which are incorporated herein by reference in their entireties.

Preferably, the polynucleotide is DNA. In the case of DNA, a polynucleotide encoding a polypeptide is normally operably associated with a promoter. The promoter may be a cell-specific promoter that directs substantial transcription of the DNA only in predetermined cells. Other transcription control elements, besides a promoter, for example enhancers, operators, repressors, and transcription termination signals, can be operably associated with the polynucleotide to direct cell-specific transcription.

An operable association is when a polynucleotide encoding a gene product, e.g., a polypeptide, is associated with one or more regulatory sequences in such a way as to place expression of the molecule under the influence or control of the regulatory sequence(s). Two DNA fragments (such as a polypeptide-coding polynucleotide and a promoter associated with the 5' end of the polynucleotide) are "operably associated" if induction of promoter function results in the transcription of mRNA encoding the desired gene product and if the nature of the linkage between the two DNA fragments does not (1) result in the introduction of a frame-shift mutation, (2) interfere with the ability of the expression regulatory sequences to direct the expression of the gene product, or (3) interfere with the ability of the DNA template to be transcribed. Thus, a promoter region would be operably associated with a polynucleotide encoding a polypeptide if the promoter was capable of effecting transcription of that polynucleotide.

A variety of transcription control regions are known to those skilled in the art. Preferred transcription control regions include those which function in vertebrate cells, such as, but not limited to, promoter and enhancer segments from cytomegaloviruses (preferably the immediate early promoter, preferably in conjunction with intron-A), simian virus 40 (preferably the early promoter), retroviruses (such as Rous sarcoma virus), and picornaviruses (particularly an internal ribosome entry site, or IRES, also referred to as a CITE sequence). Other preferred transcription control regions include those derived from vertebrate genes such as actin, heat shock protein, bovine growth hormone and rabbit β-globin, as well as other sequences capable of controlling gene expression in eukaryotic cells. Additional suitable transcription control regions include tissue-specific promoters and enhancers as well as lymphokine-inducible promoters (e.g., promoters inducible by interferons or interleukins).

Preferably, a DNA polynucleotide of the present invention is part of a circular or linearized plasmid which is preferably non-infectious (i.e., does not result in the production of infectious virus particles in vertebrate cells), and nonintegrating (i.e., does not integrate into the genome of vertebrate cells). A linearized plasmid is a plasmid that was previously circular but has been linearized, for example, by digestion with a restriction endonuclease.

Alternatively, DNA virus genomes may be used to administer DNA polynucleotides into vertebrate cells. Preferably a DNA virus genome of the present invention is noninfectious, (i.e., does not result in the production of infectious virus particles in vertebrate cells), and nonintegrating (i.e., does not integrate into the genome of vertebrate cells). Suitable DNA virus genomes include herpesvirus genomes, adenovirus genomes, adeno-associated virus genomes, and poxvirus genomes. References citing methods for the in vivo introduction of non-infectious virus genomes to vertebrate tissues are well known to those of ordinary skill in the art, and are cited supra.

Polynucleotides of the present invention may be associated with additional polynucleotides which encode secretory or signal peptides, which direct the secretion of the polypeptide encoded by the polynucleotide of the present invention. Those of ordinary skill in the art are aware that polypeptides secreted by vertebrate cells normally have a signal peptide which is cleaved from the complete polypeptide to produce a secreted "mature" form of the polypeptide.

Polypeptides

Compositions of the present invention may be used to deliver a wide variety of polypeptides to a vertebrate in need of any given polypeptide. Suitable polypeptides include, but are not limited to: therapeutic polypeptides, antigenic polypeptides, immunogenic polypeptides, immunomodulatory polypeptides, functional self polypeptides, and other functional polypeptides.

As used herein, a "therapeutic polypeptide" is a polypeptide which when delivered to a vertebrate, treats, i.e., cures, ameliorates, or lessens the symptoms of, a given disease in that vertebrate, or alternatively, prolongs the life of the vertebrate by slowing the progress of a terminal disease. As used herein, an "immunomodulatory polypeptide" is a polypeptide which, when delivered to a vertebrate, can alter, enhance, suppress, or regulate an immune response in a vertebrate. Immunomodulatory polypeptides are a subset of therapeutic polypeptides. Therapeutic and immunomodulatory polypeptides of the present invention include, but are not limited to, cytokines, chemokines, lymphokines, ligands, receptors, hormones, apoptosis-inducing polypeptides, enzymes, antibodies, and growth factors. Examples include, but are not limited to granulocyte macrophage colony stimulating factor (GM-CSF), granulocyte colony stimulating factor (G-CSF), macrophage colony stimulating factor (M-CSF), colony stimulating factor (CSF), interleukin 2 (IL-2), interleukin-3 (IL-3), interleukin 4 (IL-4), interleukin 5 (IL-5), interleukin 6 (IL-6), interleukin 7 (IL-7), interleukin 8 (IL-8), interleukin 10 (IL-10), interleukin 12 (IL-12), interleukin 15 (IL-15), interleukin 18 (IL-18), interferon alpha (IFNα), interferon beta (IFNβ), interferon gamma (IFNγ), interferon omega (IFNω), interferon tau (IFNτ), interferon gamma inducing factor I (IGIF), transforming growth factor beta (TGF-β), RANTES (regulated upon activation, normal T-cell expressed and presumably secreted), macrophage inflammatory proteins (e.g., MIP-1 alpha and MIP-1 beta), *Leishmania* elongation initiating factor (LEIF), platelet derived growth factor (PDGF), tumor necrosis factor (TNF), growth factors, e.g., epidermal growth factor (EGF), vascular endothelial growth factor (VEGF), fibroblast growth factor, (FGF), nerve growth factor (NGF), brain derived neurotrophic factor (BDNF), neurotrophin-2 (NT-2), neurotrophin-3 (NT-3), neurotrophin-4 (NT-4), neurotrophin-5 (NT-5), glial cell line-derived neurotrophic factor (GDNF), ciliary neurotrophic factor (CNTF), erythropoietin (EPO), and insulin.

Therapeutic polypeptides of the present invention may be used to treat diseases such as Parkinson's disease, cancer, and heart disease. In addition, therapeutic polypeptides may be used to treat autoimmune disorders such as multiple sclerosis; Sjogren's syndrome; sarcoidosis; insulin dependent diabetes mellitus; autoimmune thyroiditis; arthritis (e.g.), osteoarthritis, rheumatoid arthritis, reactive arthritis, and psoriatic arthritis; ankylosing spondylitis; and scleroderma. Also, therapeutic polypeptides of the present invention can be used to treat acute and chronic inflammatory disorders, to promote wound healing, and to prevent rejection after transplantation of cells, tissues, or organs.

Therapeutic polypeptides of the present invention, for example, neurotrophic factors (NTFs), may be used to promote the survival, maintenance, differentiation, repair, regeneration, and growth of cells in the brain, spinal cord, and peripheral nerves. Suitable NTFs include, but are not limited to, NGF, BDNF, the Neurotrophins or NTs such as NT-2, NT-3, NT-4, NT-5, GDNF, CNTF, as well as others. The administration of purified recombinant NTFs represents a clinical strategy for treatment of such acute and chronic nervous system disorders. Such disorders include, but are not limited to mechanical or chemical brain or spinal cord injury, Parkinson's Disease, Alzheimer's Disease and other dementias, Amyotrophic Lateral Sclerosis and Multiple Sclerosis.

Therapeutic polypeptides of the present invention, for example, growth factors, may be used to promote wound healing. Useful growth factors include, but are not limited to FGF, and EGF.

Therapeutic polypeptides of the present invention may be used to promote cell suicide (termed "apoptosis"). Suitable apoptotic polypeptides include the BAX protein. Alternatively, therapeutic polypeptides of the present invention may be used to prevent apoptosis. Suitable apoptosis antagonists include the BAX antagonist Bcl-2. A disease which may be treated with apoptosis-inhibiting polypeptides is Muscular Dystrophy (MD), where patients have a defective protein called Dystrophin. Dystrophin is required for proper muscle function. The non-defective, normal Dystrophin may act as an antigen if delivered via plasmid DNA to patients with MD. In this case, muscle cells transduced with DNA encoding normal Dystrophin would be recognized by the immune system and killed by Dystrophin-specific T cell based responses. Such T cell based killing is known to kill cells by inducing apoptosis. If the normal, and potentially immunogenic, Dystrophin could be delivered into muscle cells along with Bcl-2 or other apoptosis-preventing protein, one would expect that CTL would be unable to kill the muscle cells. This reasoning applies to many genetic diseases where treatment involves delivery of a "normal", and therefore potentially immunogenic, copy of a protein.

As used herein, a "functional self polypeptide" is a polypeptide which is required for normal functioning of a vertebrate, but because of, e.g., genetic disease, cancer, environmental damage, or other cause, is missing, defective, or non-functional in a given individual. A composition of the present invention is used to restore the individual to a normal state by supplying the necessary polypeptide. Examples of functional self polypeptides include insulin, dystrophin, cystic fibrosis transmembrane conductance regulator, granulocyte macrophage colony stimulating factor, granulocyte colony stimulating factor, macrophage colony stimulating factor colony stimulating factor, interleukin 2, interleukin-3, interleukin 4, interleukin 5, interleukin 6, interleukin 7, interleukin 8, interleukin 10, interleukin 12, interleukin 15, interleukin 18, interferon alpha, interferon beta, interferon gamma, interferon omega, interferon tau, interferon gamma inducing factor I, transforming growth factor beta, RANTES, Flt-3 ligand, macrophage inflammatory proteins, platelet derived growth factor, tumor necrosis factor, epidermal growth factor, vascular epithelial growth factor, fibroblast growth factor, insulin-like growth factors I and II, insulin-like growth factor binding proteins, nerve growth factor, brain derived neurotrophic factor, neurotrophin-2, neurotrophin-3, neurotrophin-4, neurotrophin-5, glial cell line-derived neurotrophic factor, ciliary neurotrophic factor, and erythropoietin. Examples of diseases or disorders that may be treated with functional self polypeptides include, but are not limited to: diabetes, muscular dystrophy, multiple sclerosis, Parkinson's disease, Alzheimer's disease, arthritis, sickle cell anemia, and hemophilia.

As used herein, an antigenic polypeptide or an immunogenic polypeptide is a polypeptide which, when introduced into a vertebrate, reacts with the immune system molecules of the vertebrate, i.e., is antigenic, and/or induces an immune response in the vertebrate, i.e., is immunogenic. It is quite likely that an immunogenic polypeptide will also be antigenic, but an antigenic polypeptide, because of its size or conformation, may not necessarily be immunogenic. Examples of antigenic and immunogenic polypeptides include, but are not limited to, polypeptides from infectious agents such as bacteria, viruses, parasites, or fungi, allergens such as those from pet dander, plants, dust, and other environmental sources, as well as certain self polypeptides, for example, tumor-associated antigens.

Antigenic and immunogenic polypeptides of the present invention can be used to prevent or treat, i.e., cure, ameliorate, lessen the severity of, or prevent or reduce contagion of viral, bacterial, fungal, and parasitic infectious diseases, as well as to treat allergies.

In addition, antigenic and immunogenic polypeptides of the present invention can be used to prevent or treat, i.e., cure, ameliorate, or lessen the severity of cancer including, but not limited to, cancers of oral cavity and pharynx (i.e., tongue, mouth, pharynx), digestive system (i.e., esophagus, stomach, small intestine, colon, rectum, anus, anal canal, anorectum, liver, gallbladder, pancreas), respiratory system (i.e., larynx, lung), bones, joints, soft tissues (including heart), skin, melanoma, breast, reproductive organs (i.e., cervix, endometirum, ovary, vulva, vagina, prostate, testis, penis), urinary system (i.e., urinary bladder, kidney, ureter, and other urinary organs), eye, brain, endocrine system (i.e., thyroid and other endocrine), lymphoma (i.e., hodgkin's disease, non-hodgkin's lymphoma), multiple myeloma, leukemia (i.e., acute lymphocytic leukemia, chronic lymphocytic leukemia, acute myeloid leukemia, chronic myeloid leukemia).

Examples of viral antigenic and immunogenic polypeptides include, but are not limited to, adenovirus polypeptides, alphavirus polypeptides, calicivirus polypeptides, e.g., a calicivirus capsid antigen, coronavirus polypeptides, distemper virus polypeptides, Ebola virus polypeptides, enterovirus polypeptides, flavivirus polypeptides, hepatitis virus (AE) polypeptides, e.g., a hepatitis B core or surface antigen, herpesvirus polypeptides, e.g., a herpes simplex virus or varicella zoster virus glycoprotein, immunodeficiency virus polypeptides, e.g., the human immunodeficiency virus envelope or protease, infectious peritonitis virus polypeptides, influenza virus polypeptides, e.g., an influenza A hemagglutinin, neuraminidase, or nucleoprotein, leukemia virus polypeptides, Marburg virus polypeptides, orthomyxovirus polypeptides, papilloma virus polypeptides, parainfluenza virus polypeptides, e.g., the hemagglutinin/neuraminidase, paramyxovirus polypeptides, parvovirus polypeptides, pestivirus polypeptides, picorna virus polypeptides, e.g., a poliovirus capsid polypeptide, pox virus polypeptides, e.g., a vaccinia virus polypeptide, rabies virus polypeptides, e.g., a rabies virus glycoprotein G, reovirus polypeptides, retrovirus polypeptides, and rotavirus polypeptides.

Examples of bacterial antigenic and immunogenic polypeptides include, but are not limited to, *Actinomyces* polypeptides, *Bacillus* polypeptides, *Bacteroides* polypeptides, *Bordetella* polypeptides, *Bartonella* polypeptides, *Borrelia* polypeptides, e.g., *B. burgdorferi* OspA, *Brucella* polypeptides, *Campylobacter* polypeptides, *Capnocytophaga* polypeptides, *Chlamydia* polypeptides, *Clostridium* polypeptides, *Corynebacterium* polypeptides, *Coxiella* polypeptides, *Dermatophilus* polypeptides, *Enterococcus* polypeptides, *Ehrlichia* polypeptides, *Escherichia* polypeptides, *Francisella* polypeptides, *Fusobacterium* polypeptides, *Haemobartonella* polypeptides, *Haemophilus* polypeptides, e.g., *H. influenzae* type b outer membrane protein, *Helicobacter* polypeptides, *Klebsiella* polypeptides, L-form bacteria polypeptides, *Leptospira* polypeptides, *Listeria* polypeptides, *Mycobacteria* polypeptides, *Mycoplasma* polypeptides, *Neisseria* polypeptides, *Neorickettsia* polypeptides, *Nocardia* polypeptides, *Pasteurella* polypeptides, *Peptococcus* polypeptides, *Peptostreptococcus* polypeptides, *Pneumococcus* polypeptides, *Proteus* polypeptides, *Pseudomonas* polypeptides, *Rickettsia* polypeptides, *Rochalimaea* polypeptides, *Salmonella* polypeptides, *Shigella* polypeptides, *Staphylococcus* polypeptides, *Streptococcus* polypeptides, e.g., *S. pyogenes* M proteins, *Treponema* polypeptides, and *Yersinia* polypeptides, e.g., *Y. pestis* F1 and V antigens.

Examples of fungal immunogenic and antigenic polypeptides include, but are not limited to, *Absidia* polypeptides, *Acremonium* polypeptides, *Alternaria* polypeptides, *Aspergillus* polypeptides, *Basidiobolus* polypeptides, *Bipolaris* polypeptides, *Blastomyces* polypeptides, *Candida* polypeptides, *Coccidioides* polypeptides, *Conidiobolus* polypeptides, *Cryptococcus* polypeptides, *Curvalaria* polypeptides, *Epidermophyton* polypeptides, *Exophiala* polypeptides, *Geotrichum* polypeptides, *Histoplasma* polypeptides, *Madurella* polypeptides, *Malassezia* polypeptides, *Microsporum* polypeptides, *Moniliella* polypeptides, *Mortierella* polypeptides, *Mucor* polypeptides, *Paecilomyces* polypeptides, *Penicillium* polypeptides, *Phialemonium* polypeptides, *Phialophora* polypeptides, *Prototheca* polypeptides, *Pseudallescheria* polypeptides, *Pseudomicrodochium* polypeptides, *Pythium* polypeptides, *Rhinosporidium* polypeptides, *Rhizopus* polypeptides, *Scolecobasidium* polypeptides, *Sporothrix* polypeptides, *Stemphylium* polypeptides, *Trichophyton* polypeptides, *Trichosporon* polypeptides, and *Xylohypha* polypeptides.

Examples of protozoan parasite immunogenic and antigenic polypeptides include, but are not limited to, *Babesia* polypeptides, *Balantidium* polypeptides, *Besnoitia* polypeptides, *Cryptosporidium* polypeptides, *Eimeria* polypeptides, *Encephalitozoon* polypeptides, *Entamoeba* polypeptides, *Giardia* polypeptides, *Hammondia* polypeptides, *Hepatozoon* polypeptides, *Isospora* polypeptides, *Leishmania* polypeptides, *Microsporidia* polypeptides, *Neospora* polypeptides, *Nosema* polypeptides, *Pentatrichomonas* polypeptides, *Plasmodium* polypeptides, e.g., *P. falciparum* circumsporozoite (PfCSP), sporozoite surface protein 2 (PfSSP2), carboxyl terminus of liver state antigen 1 (PfLSA1 c-term), and exported protein 1 (PfExp-1), *Pneumocystis* polypeptides, *Sarcocystis* polypeptides, *Schistosoma* polypeptides, *Theileria* polypeptides, *Toxoplasma* polypeptides, and *Trypanosoma* polypeptides.

Examples of helminth parasite immunogenic and antigenic polypeptides include, but are not limited to, *Acanthocheilonema* polypeptides, *Aelurostrongylus* polypeptides, *Ancylostoma* polypeptides, *Angiostrongylus* polypeptides, *Ascaris* polypeptides, *Brugia* polypeptides, *Bunostomum* polypeptides, *Capillaria* polypeptides, *Chabertia* polypeptides, *Cooperia* polypeptides, *Crenosoma* polypeptides, *Dictyocaulus* polypeptides, *Dioctophyme* polypeptides, *Dipetalonema* polypeptides, *Diphyllobothrium* polypeptides, *Diplydium* polypeptides, *Dirofilaria* polypeptides, *Dracunculus* polypeptides, *Enterobius* polypeptides, *Filaroides* polypeptides, *Haemonchus* polypeptides, *Lagochilascaris* polypeptides, *Loa* polypeptides, *Mansonella* polypeptides, *Muellerius* polypeptides, *Nanophyetus* polypeptides, *Necator* polypeptides, *Nematodirus* polypeptides, *Oesophagostomum* polypeptides, *Onchocerca* polypeptides, *Opisthorchis* polypeptides, *Ostertagia* polypeptides, *Parafilaria* polypeptides, *Paragonimus* polypeptides, *Parascaris* polypeptides, *Physaloptera* polypeptides, *Protostrongylus* polypeptides, *Setaria* polypeptides, *Spirocerca* polypeptides *Spirometra* polypeptides, *Stephanofilaria* polypeptides, *Strongyloides* polypeptides, *Strongylus* polypeptides, *Thelazia* polypeptides, *Toxascaris* polypeptides, *Toxocara* polypeptides, *Trichinella* polypeptides, *Trichostrongylus* polypeptides, *Trichuris* polypeptides, *Uncinaria* polypeptides, and *Wuchereria* polypeptides.

Examples of ectoparasite immunogenic and antigenic polypeptides include, but are not limited to, polypeptides (including protective antigens as well as allergens) from fleas; ticks, including hard ticks and soft ticks; flies, such as midges, mosquitos, sand flies, black flies, horse flies, horn flies, deer flies, tsetse flies, stable flies, myiasis-causing flies and biting gnats; ants; spiders, lice; mites; and true bugs, such as bed bugs and kissing bugs.

Examples of tumor-associated antigenic and immunogenic polypeptides include, but are not limited to, tumor-specific immunoglobulin variable regions (e.g., B cell lymphoma idiotypes), GM2, Tn, sTn, Thompson-Friedenreich antigen (TF), Globo H, Le(y), MUC1, MUC2, MUC3, MUC4, MUC5AC, MUC5B, MUC7, carcinoembryonic antigens, beta chain of human chorionic gonadotropin (hCG beta), HER2/neu, PSMA, EGFRvIII, KSA, PSA, PSCA, GP100, MAGE 1, MAGE 2, TRP 1, TRP 2, tyrosinase, MART-1, PAP, CEA, BAGE, MAGE, RAGE, and related proteins.

Also included as polypeptides of the present invention are fragments, derivatives, analogs, or variants of the foregoing polypeptides, and any combination of the foregoing polypeptides. Additional polypeptides may be found, for example in "*Foundations in Microbiology*," Talaro, et al., eds., McGraw-Hill Companies (October, 1998), Fields, et al., "*Virology,*" 3d ed., Lippincott-Raven (1996), "*Biochemistry and Molecular Biology of Parasites*," Marr, et al., eds., Academic Press (1995), and Deacon, J., "*Modern Mycology*," Blackwell Science Inc (1997), which are incorporated herein by reference.

Transfection Facilitating Materials

Compositions of the present invention can also include one or more transfection facilitating materials that facilitate delivery of polynucleotides to the interior of a cell, and/or to a desired location within a cell. Examples of the transfection facilitating materials include, but are not limited to lipids, preferably cationic lipids; inorganic materials such as calcium phosphate, alum (aluminum sulfate), and metal (e.g., gold or tungsten) particles (e.g., "powder" type delivery solutions); peptides, including cationic peptides, targeting peptides for selective delivery to certain cells or intracellular organelles such as the nucleus or nucleolus, and amphipathic peptides, i.e. helix forming or pore forming peptides; basic proteins, such as histones; asialoproteins; viral proteins (e.g., Sendai virus coat protein); pore-forming proteins; and polymers, including dendrimers, star-polymers, "homogenous" poly-amino acids (e.g., poly-lysine, poly-arginine), "heterogenous" poly-amino acids (e.g., mixtures of lysine & glycine), co-polymers, polyvinylpyrrolidinone (PVP), and polyethylene glycol (PEG). Furthermore, those auxiliary agents of the present invention which facilitate and enhance the entry of a polynucleotide into vertebrate cells in vivo, may also be considered "transfection facilitating materials."

Certain embodiments of the present invention may include lipids as a transfection facilitating material, including cationic lipids (e.g., DMRIE, DOSPA, DC-Chol, GAP-DLRIE), basic lipids (e.g., steryl amine), neutral lipids (e.g., cholesterol), anionic lipids (e.g., phosphatidyl serine), and zwitterionic lipids (e.g., DOPE, DOPC), as described above. However, certain compositions and methods of the present invention, e.g., those including or utilizing compositions comprising a sodium phosphate dissolved in an aqueous solution at a molar concentration from about 20 mM to about 300 mM, are preferably substantially free of cationic lipids.

Certain other compositions and methods of the present invention, e.g., those including or utilizing compositions comprising a sodium phosphate dissolved in aqeuous solution at a molar concentration from about 0.1 mM to about 150 mM, where the aqueous solution is substantially free of chloride anion, always include cationic lipids as transfection facilitating agents. While not being bound by theory, cationic lipids are believed to bind effectively to negatively charged polynucleotides, thereby facilitating entry of the polynucleotide into cells. The use of cationic lipids is especially effective in the delivery of polynucleotides to non-muscle tissues, e.g., pulmonary tissues, tumor tissues, skin, peritoneum, tissues of digestive system, or vascular tissues.

In the embodiments including cationic lipids, the polynucleotide construct(s) are combined with lipids by mixing, for example, a plasmid DNA solution and a solution of cationic lipid:co-lipid liposomes. Preferably, the concentration of each of the constituent solutions is adjusted prior to mixing such that the desired final plasmid DNA/cationic lipid:co-lipid ratio and the desired plasmid DNA final concentration will be obtained upon mixing the two solutions. For example, if the desired final solution is to be 150 mM sodium phosphate, the various components of the composition, e.g., plasmid DNA, cationic lipid:co-lipid liposomes, and any other desired auxiliary agents, transfection facilitating materials, or additives are each prepared in 150 mM sodium phosphate and then simply mixed to afford the desired complex.

Alternatively, if the desired final solution is to be, e.g., 150 mM sodium phosphate, certain components of the composition, e.g., the auxiliary agent and/or cationic lipid:co-lipid liposomes, is prepared in a volume of water which is less than that of the final volume of the composition, and certain other components of the composition, e.g., the plasmid DNA, is prepared in a solution of sodium phosphate at a higher concentration than 150 mM, in a volume such that when the components in water are added to the components in the sodium phosphate solution, the final composition is in an aqueous solution of 150 mM sodium phosphate. For example, the plasmid DNA could be prepared in 300 mM sodium phosphate at one half the final volume, the auxiliary agent and/or cationic lipid:co-lipid liposome is prepared in water at one half the final volume, and then these two elements are mixed together to produce the final composition.

The cationic lipid:co-lipid liposomes are preferably prepared by hydrating a thin film of the mixed lipid materials in an appropriate volume of aqueous solvent by vortex mixing at ambient temperatures for about 1 minute. The thin films are prepared by admixing chloroform solutions of the individual components to afford a desired molar solute ratio followed by aliquoting the desired volume of the solutions into a suitable container. The solvent is removed by evaporation, first with a stream of dry, inert gas (e.g. argon) followed by high vacuum treatment.

A transfection facilitating material can be used alone or in combination with one or more other transfection facilitating materials. Two or more transfection facilitating materials can be combined by chemical bonding (e.g., covalent and ionic such as in lipidated polylysine, PEGylated polylysine) (Toncheva, V., et al., *Biochim. Biophys. Acta* 1380(3):354-368 (1998)), mechanical mixing (e.g., free moving materials in liquid or solid phase such as "polylysine+cationic lipids") (Gao, X., and Huang, L., *Biochemistry* 35:1027-1036 (1996); Trubetskoy, V. S., et al., *Biochem. Biophys. Acta* 1131:311-313 (1992)), and aggregation (e.g., co-precipitation, gel forming such as in cationic lipids+poly-lactide co-galactide, and polylysine+gelatin).

Other Additives

Other hydrophobic and amphiphilic additives, such as, for example, sterols, fatty acids, gangliosides, glycolipids, lipopeptides, liposaccharides, neobees, niosomes, prostaglandins and sphingolipids, may also be included in the compositions of the present invention. In such compositions, these additives may be included in an amount between about 0.1 mol % and about 99.9 mol % (relative to total lipid).

Preferably, these additives comprise about 1-50 mol % and, most preferably, about 2-25 mol %. Preferred additives include lipopeptides, liposaccharides and steroids.

Methods and Administration

The present invention further provides methods for delivering a polypeptide into a vertebrate, which comprise administering to the vertebrate a composition as described herein; such that upon administration of the composition, the polypeptide is expressed in the vertebrate, in an amount sufficient to be detectable. Methods to detect polypeptides expressed in a vertebrate are well known to those of ordinary skill in the art and include, but are not limited to, serological methods to detect the polypeptide in serum, e.g., western blotting, staining tissue sections by immunohistochemical methods, measuring an immune response generated by the vertebrate against the polypeptide, and measuring the activity of the polypeptide. Certain of these methods are disclosed in the Examples, below.

The present invention further provides a method for delivering a therapeutic polypeptide into a vertebrate, comprising administering to a vertebrate in need of the therapeutic polypeptide a composition as described herein. In this method, the composition comprises a polynucleotide encoding a therapeutic polypeptide. Upon administration of the composition according to this method, the needed therapeutic polypeptide is expressed in the vertebrate in a therapeutically effective amount.

Similarly, the present invention provides a method of enhancing or modulating an immune response in a vertebrate in need of such an enhanced or modulated immune response, comprising administering to the vertebrate a composition as described herein. In this method, the composition contains a polynucleotide encoding an immunogenic and/or immunomodulatory polypeptide. Upon administration of the composition according to this method, the needed immunogenic and/or immunomodulatory polypeptide is expressed in the vertebrate, in a sufficient amount to induce and/or modify a desired immune response in the vertebrate to prevent disease, cure disease, reduce the severity of disease symptoms, or prolong the life of the vertebrate.

Also, the present invention provides a method of enhancing or modulating an immune response in a healthy vertebrate for large-scale antibody production, comprising administering to the vertebrate a composition as described herein. In this method, the composition contains a polynucleotide encoding an immunogenic and/or immunomodulatory polypeptide. Upon administration of the composition according to this method, the immunogenic and/or immunomodulatory polypeptide is expressed in the vertebrate, in a sufficient amount to produce a vigorous antibody response in the vertebrate. The antibodies thus produced are then recovered from the vertebrate by, for example, the collection of serum, milk, or saliva. Such antibodies may be useful for research or diagnostic purposes, or for additional therapies in vertebrates in need of such therapies. For example, passive antibody treatment using antibodies produced by this method may prevent disease, cure disease, reduce the severity of disease symptoms, or prolong the life of a vertebrate.

Moreover, the present invention further provides a method of delivering a physiologically or metabolically necessary polypeptide to a vertebrate incapable of making a functional form of the polypeptide, comprising administering to the vertebrate a composition as disclosed herein. According to this method, the composition contains a polynucleotide encoding a functional self polypeptide. Upon administration of the composition according to this method, the needed functional self polypeptide is expressed in the vertebrate, in a sufficient amount to supply the vertebrate's requirements for the polypeptide.

An important aspect of the present invention is that use of the claimed compositions in any of the above methods allows the skilled artisan to reduce the amount of polynucleotide included in the composition relative to methods utilizing existing compositions, e.g., those which formulate the polynucleotide in saline or water. Even though the amount of polynucleotide is reduced, sufficient protein expression occurs in the treated vertebrate. Such a reduction in polynucleotide will significantly reduce the cost of producing compositions of the present invention. Accordingly, one embodiment of the present invention is a method to reduce the amount of polynucleotide required to obtain a desired clinical response in a vertebrate, comprising administering to the vertebrate a composition as disclosed herein.

In any of the methods disclosed herein, it is preferred that the composition be delivered to a mammal. More preferably, the mammal is a human.

Administration of the compositions of the present invention according to any of the above methods can be accomplished according to any of various methods known in the art. For example, U.S. Pat. No. 5,676,954, incorporated herein by reference in its entirety, reports on the injection of genetic material, complexed with cationic lipid carriers, into mice. Also, U.S. Pat. Nos. 5,589,466, 5,693,622, 5,580,859, 5,703,055, and PCT international patent application PCT/US94/06069 (WO 94/29469), the disclosures of which are incorporated herein by reference in their entireties, provide methods for delivering compositions comprising naked DNA, or DNA cationic lipid complexes to vertebrates.

More specifically, the compositions of the present invention may be administered to any tissue of a vertebrate, including, but not limited to, muscle, skin, brain tissue, lung tissue, liver tissue, spleen tissue, bone marrow tissue, thymus tissue, heart tissue, e.g., myocardium, endocardium, and pericardium, lymph tissue, blood tissue, bone tissue, pancreas tissue, kidney tissue, gall bladder tissue, stomach tissue, intestinal tissue, testicular tissue, ovarian tissue, uterine tissue, vaginal tissue rectal tissue, nervous system tissue, eye tissue, glandular tissue, tongue tissue, and connective tissue, e.g., cartilage.

Furthermore, the compositions of the present invention may be administered to any internal cavity of a vertebrate, including, but not limited to, the lungs, the mouth, the nasal cavity, the stomach, the peritoneal cavity, the intestine, any heart chamber, veins, arteries, capillaries, lymphatic cavities, the uterine cavity, the vaginal cavity, the rectal cavity, joint cavities, ventricles in brain, spinal canal in spinal cord, and the ocular cavities.

Preferably, the compositions comprising sodium phosphate dissolved in aqueous solution at a molar concentration from about 20 mM to about 300 mM are delivered to muscle, either skeletal muscle or cardiac muscle, and those embodiments comprising sodium phosphate dissolved in aqueous solution at a molar concentration from about 0.1 mM to about 150 mM and a cationic lipid are administered to lung tissue. Preferred modes for administration to lung tissue are disclosed in Wheeler, C. J., et al., *Proc. Natl. Acad. Sci. USA* 93:11454-11459 (1996), which is incorporated herein by reference in its entirety.

According to the disclosed methods, compositions of the present invention are preferably administered by intramuscular (i.m.), subcutaneous (s.c.), or intrapulmonary routes. Other suitable routes of administration include intratracheal, transdermal, interdermal, intraocular, intranasal, inhalation, transmucosal (i.e., across a mucous membrane), intracavity (e.g., oral, vaginal, rectal, nasal, peritoneal, ventricular, or intestinal), and intravenous (i.v.) administration.

Any mode of administration can be used so long as the mode results in the expression of the desired peptide or protein, in the desired tissue, in an amount sufficient to be detectable, and/or prophylactically or therapeutically effective. Administration means of the present invention include needle injection, catheter infusion, biolistic injectors, particle accelerators (e.g., "gene guns" or pneumatic "needleless" injectors) Med-E-Jet (Vahlsing, H., et al., *J. Immunol. Methods* 171,11-22 (1994)), Pigjet (Schrijver, R., et al., *Vaccine* 15, 1908-1916 (1997)), Biojector (Davis, H., et al., *Vaccine* 12, 1503-1509 (1994); Gramzinski, R., et al., *Mol. Med.* 4, 109-118 (1998)), AdvantaJet (Linmayer, I., et al., *Diabetes Care* 9:294-297 (1986)), Medi-jector (Martins, J., and Roedl, E. *J. Occup. Med.* 21:821-824 (1979)), gelfoam sponge depots, other commercially available depot materials (e.g., hydrogels), osmotic pumps (e.g., Alza minipumps), oral or suppositorial solid (tablet or pill) pharmaceutical formulations, topical skin creams, and decanting, use of polynucleotide coated suture (Qin, Y., et al., *Life Sciences* 65, 2193-2203 (1999)) or topical applications during surgery. The preferred modes of administration are intramuscular needle-based injection and pulmonary application via catheter infusion. Each of the references cited in this paragraph is incorporated herein by reference in its entirety.

Determining an effective amount of a composition depends upon a number of factors including, for example, the chemical structure and biological activity of the substance, the age and weight of the subject, the precise condition requiring treatment and its severity, and the route of administration. Based on the above factors, determining the precise amount, number of doses, and timing of doses are within the ordinary skill in the art and will be readily determined by the attending physician or veterinarian.

Compositions of the present invention can be formulated according to known methods. Suitable preparation methods are described, for example, in *Remington's Pharmaceutical Sciences,* 16$^{th}$ Edition, A. Osol, ed., Mack Publishing Co., Easton, Pa. (1980), and *Remington's Pharmaceutical Sciences,* 19$^{th}$ Edition, A. R. Gennaro, ed., Mack Publishing Co., Easton, Pa. (1995), both of which are incorporated herein by reference in their entireties. Although the composition is preferably administered as an aqueous solution, it can be formulated as an emulsion, gel, solution, suspension, lyophilized form, or any other form known in the art. According to the present invention, if the composition is formulated other than as an aqueous solution, it will require resuspension in an aqueous solution prior to administration. In addition, the composition may contain pharmaceutically acceptable additives including, for example, diluents, binders, stabilizers, and preservatives.

For aqueous compositions used in vivo, the use of sterile pyrogen-free water is preferred. Such formulations will contain an effective amount of a polynucleotide together with a suitable amount of an aqueous solution in order to prepare pharmaceutically acceptable compositions suitable for administration to a vertebrate Pharmaceutical Kits The present invention also provides kits for use in delivering a polypeptide to a vertebrate. Each kit includes a container holding about 1 ng to about 30 mg of a polynucleotide which operably encodes a polypeptide within vertebrate cells in vivo. Furthermore, each kit includes either (a) an amount of sodium phosphate which, when dissolved in a prescribed volume of distilled water, results in an aqueous solution with a molar concentration of said salt from about 20 mM to about 300 mM, and reaction, association, or dissociation products thereof; and optionally, an administration means; whereby the polynucleotide is provided in a prophylactically or therapeutically effective amount to treat a vertebrate; or (b) an amount of sodium phosphate which, when dissolved in an prescribed volume of distilled water, results in an aqueous solution with a molar concentration of said salt from about 0.1 mM to about 150 mM, and reaction, association, or dissociation products thereof, and where the aqueous solution formed thereby is essentially free of chloride anion; a cationic lipid; and optionally, an administration means; whereby the polynucleotide is provided in a prophylactically or therapeutically effective amount. Any of the components of pharmaceutical kits (a) or (b) can be provided in a single container or in multiple containers. Preferably, the kit includes from about 1 ng to about 30 mg of a polynucleotide, more preferably, the kit includes from about 100 ng to about 10 mg of a polynucleotide.

Any suitable container or containers may be used with pharmaceutical kits. Examples of containers include, but are not limited to, glass containers, plastic containers, or strips of plastic or paper.

Each of the pharmaceutical kits may further comprise an administration means. Means for administration include, but are not limited to syringes and needles, catheters, biolistic injectors, particle accelerators, i.e., "gene guns," pneumatic "needleless" injectors, gelfoam sponge depots, other commercially available depot materials, e.g., hydrogels, osmotic pumps, and decanting, polynucleotide coated sutures, skin patches, or topical applications during surgery.

The kit can further comprise an instruction sheet for administration of the composition to a vertebrate. The polynucleotide components of the composition are preferably provided as a liquid solution or they may be provided in lyophilized form as a dried powder or a cake. If the polynucleotide is provided in lyophilized form, the dried powder or cake may also include any salts, auxiliary agents, transfection facilitating agents, and additives of the composition in dried form. Such a kit may further comprise a container with an exact amount of sterile pyrogen-free water, for precise reconstitution of the lyophilized components of the composition.

The container in which the composition is packaged prior to use can comprise a hermetically sealed container enclosing an amount of the lyophilized formulation or a solution containing the formulation suitable for a pharmaceutically effective dose thereof, or multiples of an effective dose. The composition is packaged in a sterile container, and the hermetically sealed container is designed to preserve sterility of the pharmaceutical formulation until use. Optionally, the container can be associated with administration means and/or instruction for use.

EXAMPLES

Having now generally described the invention, the same will become more readily understood by reference to the following specific examples which are included herein for purposes of illustration only and are not intended to be limiting unless otherwise specified.

Described herein are: 1) the in vitro characterization of biological activities of and IFNs delivered by plasmid DNA (anti-proliferative activity and anti-viral activity in vitro); 2) in vivo expression of cytokines following in vivo administration of cytokine-expressing pDNA; and 3) the in vivo characterization of anti-tumor activity of cytokines in murine models of solid and metastatic tumors following intratumoral, intramuscular or intra-cavity administration of cytokine-encoding pDNA.

The cytokine-encoding polynucleotide constructs have potent anti-proliferative activity in vitro. Moreover, the in vivo anti-tumor activities of IFNω, IFNα, IL-2, and IL-12 are herein demonstrated in multiple murine tumor models including nude mice bearing subcutaneous human tumors, or in immunocompetent mice bearing murine solid and metastatic tumors. Intratumoral, intramuscular, or intraperitoneal injection of the cytokine-encoding plasmids is shown to result in a statistically significant slowing of tumor growth and/or a statistically significant increase in survival. In addition to the potent antitumor effects of the cytokine plasmids delivered via intratumoral or intramuscular injection, this is the first in vivo demonstration of anti-tumor activity for human interferon-ω. Moreover, the in vivo antitumor activity of IL-2 in the treatment of peritoneally disseminated cancers, such as ovarian metastatic melanoma is also demonstrated.

Example 1

Construction of Expression Vectors

Three basic eukaryotic expression plasmid vectors, termed VR1012, VR1055 and VR1033 were used in the construction of all plasmids used in the following examples. The blank plasmids, VR1012 and VR1055 differ only in transcriptional termination sequences. The backbone of both plasmids is derived from pUC19, with the beta-lactamase (ampicillin resistance) gene replaced by the aminoglycoside acetyltransferase (kanamycin resistance) gene from pET9a (Novagen, Madison, Wis.). Both plasmids direct eukaryotic gene expression from a cassette containing the human cytomegalovirus immediate early I (CMV IE) gene promoter/enhancer, CMV IE 5' untranslated (UT) sequence, and intron A. Following these regulatory elements is a cloning polylinker for insertion of polypeptide coding sequences. Following the polylinker in VR1012 is the 3' UT sequence from the bovine growth hormone gene for polyadenylation and transcriptional termination. In VR1055, the transcriptional terminator region includes a polyadenylation and termination signals derived from the rabbit b-globin gene. VR1033 is identical to VR1012, except that it contains a cap-independent translational enhancer from the encephalomyocarditis virus within the cloning polylinker sequence. This sequence allows the production of two different polypeptides from a single expressed mRNA.

Plasmid VR4101 (murine interferon α (mIFNα)) was constructed by cloning the murine interferon α cDNA into the vector VR1012 vector. The cDNA was obtained by amplifying the coding sequence from the plasmid RSV-"1 (Kelly, K. A. and P. M. Pitha, *Nucl. Acids Res.* 13: 805-823 (1985); Kelly, K. A. and P. M. Pitha, *Nucl. Acids Res.* 13: 825-839 (1985)), which was provided by Dr. Paula Pitha-Rowe of Johns Hopkins University. Plasmid VR4111 was constructed by transferring the coding sequences from VR4101 to the VR1055 cloning vector. The oligonucleotide primers used for polymerase chain reaction (PCR) were 5'-AACTGCA-GATGGCTAGGCTCTGTGCT-3' (SEQ ID No. 15) and 5'-GAAG-ATCTTCATTTCTCTTCTC-TCAG-3' (SEQ ID No. 16). Reaction conditions were 30 cycles of 94° C. for 1 minute (denaturing), 58° C. for 2 minutes (annealing), and 72° C. for 1 minute (extension).

Plasmid VR4102 (human interferon α (hIFNα)) was constructed by cloning the human interferon α cDNA into the VR1012 vector. The cDNA was obtained by amplifying the coding sequence from human genomic DNA prepared from a fresh blood sample. Plasmid VR4112 was constructed by transferring the coding sequence sequences from VR4102 to the VR1055 cloning vector. Genomic DNA was isolated using the QIAamp Blood Kit (Qiagen, Inc.). The oligonucleotide primers used for PCR were 5'-AACTGCAGATGGC-CTC-GCCCTTTGCT-3' (SEQ ID No. 17) and 5'-CGG-GATCCTTATTCCTTC-CTCCTTAATC-3' (SEQ ID No. 18). Reaction conditions were 30 cycles of 94° C. for 1 minute (denaturing), 58° C. for 2 minutes (annealing), and 72° C. for 1 minute (extension).

Plasmid VR4150 (human interferon ω (hIFNω)) was constructed by cloning the human IFNω cDNA into the VR1012 cloning vector. The cDNA was obtained by amplifying the coding sequence from human genomic DNA prepared from a fresh blood sample. Plasmid VR4151 (SEQ ID No. 1) was constructed by transferring the coding sequences from VR4150 to the VR1055 cloning vector. The oligonucleotide primers used for PCR were 5'-GCTCTAGATGGCCCTCCT-GTTCCCT-3' (SEQ ID No. 19) and 5'-GCGG-ATCCTCAA-GATGAGCCCAGGTC-3' (SEQ ID No. 20). Reaction conditions were 30 cycles of 94° C. for 1 minute (denaturing), 58° C. for 2 minutes (annealing), and 72° C. for 1 minute (extension).

Plasmid VR1110 (murine interleukin-2 (mIL-2)) was constructed by cloning modified murine IL-2 cDNA into the VR1012 vector. The 5' UT sequence and the two amino acids of the leader peptide were replaced with the rat insulin II gene 5' UT sequence and coding region of the first six amino acids of the rat preproinsulin leader peptide. The IL-2 cDNA was then cloned into the BamHI site of VR1012.

Plasmid VR1103 (human interleukin-2 (hIL-2)) is identical to VR1110 with the exception that the murine IL-2 cDNA was replaced with the cDNA for human IL-2 (Parker et. al. 1996).

Plasmid VR4001 (murine interleukin-12 (mIL-12)) was constructed by cloning the cDNA's encoding the two murine subunits p35 and p40 into the VR1033 vector. Both cDNA's were obtained by amplifying the coding sequences from plasmids provided by Dr. Thomas Gajewski of The University of Chicago (J. Immun., 154:5637; J. Immun., 156:1095). The oligonucleotides used for PCR of p35 were 5'-CAT GCC ATG GGT CAA TCA CGC TAC CTC CTC TTT TTG G-3' (SEQ ID No. 23) and 5'-GCG GAT CCT CAG GCG GAG CTC AGA TAG CCC-3' (SEQ ID No. 24). The oligonucleotides used for PCR of p40 were 5'-ACG CGT CGA CAT GTG TCC TCA GAA GCT AAC CAT CTC-3' (SEQ ID No. 21) and 5'-GCG GAT CCC TAG GAT CGG ACC CTG CAG GGA ACA C-3' (SEQ ID No. 22). Reaction conditions were 30 cycles of 94° C. for 1 minute (denaturing), 58° C. for 2 minutes (annealing), and 72° C. for 1 minute (extension).

Plasmids VR1223 (luciferase) was constructed by cloning cytoplasmic luciferase gene into the VR1012 vector (Hartikka et al., *Hum. Gene Ther.* 7:1205-1217, 1996). The source of the cytoplasmic luciferase gene found in VR1223 was the plasmid termed pSP-luc+ which was purchased from Promega. An AvrII-XbaI restriction fragment encoding the luciferase cDNA was transferred from pSP-luc+ to VR1012 to make VR1223.

Plasmid VR1412 (β-galactosidase) was constructed by cloning cytoplasmic β-gal gene into the VR1012 vector (Doh et al., *Gene Ther.* 4:648-663).

Plasmid VR1332 was constructed by inserting a SalI-BamHI fragment encoding chloramphenicol acetyltransferase (CAT) from pBS-CAT (Promega) into SalI/BamHI-cut VR1012 vector (Hartikka et al., *Hum. Gene Ther.* 7:1205-1217 (1996)).

Example 2

Purification of pDNA pDNA was transformed into *Escherichia coli* DH10B-competent cells and grown in Terrific Broth (Sambrook, J. et al., in: *Molecular Cloning. A laboratory manual*, Cold Spring Harbor Laboratory Press, Cold Spring Harbor, N.Y., p. A.2 (1989)) complemented with 50 μg/ml kanamycin in a 1 Liter shaker flask. Cells were harvested by centrifugation at the end of the exponential growth phase (approximately 16 hr), typically yielding 10 grams of biomass net weight per liter. Covalently closed circular pDNA was isolated by a modified lysis procedure (Horn, N. A. et al., *Human Gene Therapy* 6: 565-573 (1995)) followed by standard double CsCl-ethidium bromide gradient ultracentrifugation with an average yield of approximately 5 mg per liter. Plasmids were ethanol precipitated and resolubilized in saline at 4° C. and dialyzed against saline. Endotoxin content was determined by the *Limulus* Amebocyte Lysate assay (Associates of Cape Cod, Inc., Falmouth, Mass.). All plasmid preparations were free of detectable RNA. Endotoxin levels were less than 0.6 Endotoxin Units/μg of plasmid DNA. The spectrophotometric A260/A280 ratios were between 1.75 and 2.0.

Example 3

In Vitro Evaluation of Biological Activity of IFNω and IFNα

To assure that the interferon plasmid DNA used in the following examples encoded biologically active interferon, cell proliferation and antiviral assays were performed. All culture medium used in this and following examples was obtained from Life Technologies (Gaithersburg, Md.), and all serum was obtained from HyClone (Logan, Utah).

UM449 cells (American Type Culture Collection, Rockville, Md.) were plated at a concentration of $2\times10^5$ cells per well in a 6 well plate and incubated for 24 hours. Plasmid DNA and the lipid, DMRIE/DOPE (1:1) were each diluted to a concentration of 1 mg in 0.5 ml Optimem medium (Life Technologies, Gaithersburg, Md.). The lipid DMRIE/DOPE consists of the cationic lipid (±)-N-(2-hydroxyethyl)-N,N-dimethyl-2,3-bis(tetradecyloxy)-1-propanaminium bromide (DMRIE) and the neutral lipid dioleoylphosphatidylethanolamine (DOPE) at a 1:1 mol:mol ratio (Feigner et al., *J. Biol. Chem.* 269:2550-2561, 1994). DMRIE/DOPE has been shown to be effective for both in vitro (Feigner et al., *J. Biol. Chem.* 269:2550-2561, 1994) and in vivo transfection (Stopeck et al., *J. Clin. Oncol.* 15:341-349, 1997 and Rubin et al., *Gene Ther.* 4:419-425, 1997). The lipid mixture and the DNA mixture were then gently mixed. Medium was removed from the cells which were rinsed gently with PBS, followed by addition of the DNA:lipid mixture (1 ml/well). After incubating the cells for 4-5 h at 37° C., one ml of Optimem with 30% fetal calf serum (FCS) was added to each well. Following an overnight incubation at 37° C., one ml of Optimem with 10% FCS was added to each well. Tissue culture supernatants were collected 48 h after the start of the in vitro transfection.

a. Antiproliferative Activity

To evaluate the antiproliferative and hence, anti-tumor activity of IFNω and IFNα, supernatants from the above described UM449 cells transfected with the interferon or control plasmid DNA were tested in a cell proliferation assay of murine or human tumor cell lines (ATCC, Rockville, Md.) using the Boehringer Mannheim (Indianapolis, Ind.) Cell Proliferation Kit II (XTT). Murine or human tumor cells were plated in 96 well plates at the desired concentration (cell concentration varied with each cell line evaluated, for example, at a concentration of $5\times10^3$ cells/ml for B16F10 cells and $5\times10^4$ cells/ml for the Cloudman S91 and glioma 261 cells). The plates were incubated at 37° C. for 24 hours followed by addition of tissue culture supernatants from UM449 cells in vitro transfected with either interferon plasmid DNA or control plasmid DNA. As a positive control for mIFNα plasmid DNA, mIFNα protein (ICN Pharmaceuticals Inc., Costa Mesa, Calif.) was serially diluted and added to the wells. For the hIFN plasmid DNA, an interferon reference standard (human leukocyte interferon, Sigma Chemical Co., St. Louis, Mo.) was included in each assay. Following a 24-72 hour incubation, at 37° C., 50 μl of XTT/ECR substrate was added to each well. Plates were incubated for 6-24 hours at 37° C. and the optical density (OD) at 490 nm was determined. Increasing amounts of interferon result in inhibition of cell proliferation and a reduction in the $OD_{490}$. The percent reduction in cell proliferation due to addition of the supernatants was determined by the formula:

$$1-\frac{\begin{array}{c}OD_{490}\text{ of cells incubated with}\\ \text{interferon plasmid DNA supernatants}\end{array}}{\begin{array}{c}OD_{490}\text{ of cells incubated with}\\ \text{control plasmid DNA supernatants}\end{array}}\times 100$$

As shown in Table 1, both human interferons displayed the characteristic potent anti-proliferative activity against a wide variety of human tumor cell lines, with the most sensitive line being the NIH-OVCAR3 ovarian line and the least sensitive being the SK-OV-3 ovarian line. Also, the supernatants from the mIFNα pDNA (VR4111)-transfected UM449 cells inhibited the proliferation of murine B16F10 melanoma (generous gift from Dr. Suzuki at the University of Texas, Galveston, Tex.), murine Cloudman melanoma S91 (American Type Culture Collection, Rockville, Md.), and murine glioma 261 cell lines (Division of Cancer Treatment Tumor Repository, National Cancer Institute, Frederick Cancer Research and Development Center, Frederick, Md.) by 40, 42 and 17%, respectively.

TABLE 1

IFNω (VR4150) and IFNα (VR4102) in vitro biological assay: anti-proliferation activity against human tumor cell lines

| | % reduction in cell proliferation (compared to control plasmid DNA supernatants) | |
|---|---|---|
| Cell line (tissue type) | Interferon ω | Interferon α |
| NIH-OVCAR3 (ovarian) | 60 | 43 |
| SCC-4 (squamous) | 36 | 36 |
| ACHN (renal) | 41 | 35 |
| A431 (epidermoid) | 24 | 19 |
| SCC-15 (squamous) | 29 | 29 |
| U87MG (glioblastoma) | 36 | 30 |
| A375 (melanoma) | 24 | 21 |
| PC3 (prostate) | 20 | 22 |
| UMUC3 (bladder) | 14 | 6 |
| A549 (lung) | 17 | 15 |
| MCF7 (breast) | 18 | 18 |
| SK-OV-3 (ovarian) | <10 | <10 |

b. Antiviral Activity

An antiviral assay was performed to evaluate the ability of the supernatants from the interferon plasmid DNA-transfected cells to protect murine L929 cells or human A549 cells from infection by murine encephalomyocarditis (EMC) virus (Assay performed at IIT Institute, Chicago, Ill.). In vitro transfections were performed as described above and supernatants were collected from cells transfected with either VR4151 (hIFNω)), VR4112 (hIFNα), VR4111 (mIFNα) or VR1055 (control). Antiviral activity of the supernatants was performed by IIT Research Institute (Chicago, Ill.). The antiviral assay evaluated the degree of protection of either human A549 or murine L929 cells from infection with murine encephalomyocarditis (EMC) virus. Briefly, $2.5\times10^4$ L929 cells were plated into 96-well plates and incubated for 24 h. Tissue culture supernatants were serially diluted and added to the L929 cells which were incubated for another 24 h. Supernatants were then removed from the wells, the cells were washed and murine EMC virus was added to each well at a multiplicity of infection of 0.04. Assay plates were incubated further for 24 h followed by removal of supernatants, washing of wells, fixation with 5% formalin and staining with 1% crystal violet. Samples with interferon activity protected the cells from virus infection, resulting in darkly stained cell monolayers.

Supernatants from UM449 cells transfected with VR4151, VR4112, or VR4111 had antiviral activity of 30,000, 3,000 or 30 Units/ml, respectively, on human A549 cells. When evaluated for antiviral activity on the murine L929 cell line, supernatants from UM449 cells transfected with VR4151, VR4112, or VR4111 had antiviral activity of 300, 1000 and 30,000 Units/ml, respectively (Table 2) showing species specificity of the hIFNs for human cells and mIFNs for mouse cells.

TABLE 2

Antiviral Activity of interferon Plasmid DNA

| | Interferon (Units/ml) | |
|---|---|---|
| Plasmid | Human cell line | Murine cell line |
| VR4151 | 30,000 | 300 |
| VR4112 | 3,000 | 1,000 |
| VR4111 | 30 | 30,000 |

Example 4

Systemic Interferon Therapy; Intramuscular Administration of Cytokine-Expressing Plasmids Cell Lines and Tumor Models Murine B16F10 cells were grown in RPMI-1640 (Gibco-BRL) and 5% fetal bovine serum (FBS). Murine Cloudman S91 cells were grown in Ham's F-10 medium with 25 mM Hepes, 0.1 mM, non-essential amino acids, 1 mM sodium pyruvate, 0.05 mM β-mercaptoethanol, 2.5% FBS and 12.5% horse serum. Human melanoma UM449 cells were grown in RPMI 1640 with 10% FBS.

Murine glioma 261 tumor fragments and M5076 reticulum cell sarcoma cells were obtained from the Division of Cancer Treatment Tumor Repository (National Cancer Institute, Frederick Cancer Research and Development Center, Frederick, Md.). The glioma 261 tumor fragments (2 $mm^3$) were initially implanted into the inguinal region of C57BL/6 mice using a 13 g trocar (Popper Sons, Inc., New Hyde Park, N.Y.). Tumors which grew in the mice were used to establish a tumorigenic cell line. Minced tumor fragments were placed in Iscove's tissue culture medium with 10% FBS. Glioma 261 tumor cells began to attach to the flasks after several days, and the cells were propagated using standard tissue culture techniques. The M5076 cells were grown as ascites in C57BL/6 mice and frozen in liquid nitrogen. Human A431 cells were obtained from the American Type Culture Collection and were grown in DMEM and 10% FBS.

C57BL/6, DBA/2, nude (nu/nu) and beige-nude (bg/nu/xid) female mice between the ages of 6-8 weeks were obtained from Harlan Sprague Dawley (San Diego, Calif.). All animal experiments in this and the following examples were conducted in accordance with Vical's Institutional Animal Care and Use Committee as well as the standards set forth in the National Research Council guidelines concerning animal care and use.

To establish subcutaneous B16F10 melanoma tumors, C57BL/6, nude or nude-beige mice were injected subcutaneously on the flank with $10^4$ B16F10 cells. The Cloudman melanoma model was established by subcutaneous injection of $10^5$ Cloudman S91 cells on the flank of DBA/2 mice and the glioma 261 model was established by subcutaneous injection of $5\times10^4$ glioma 261 cells on the flank of C57BL/6 mice. To establish human epidermoid carcinomas, nude mice were injected subcutaneously on the flank with $5\times10^3$ A431 cells.

To establish intradermal M5076 tumors and liver metastases thereof, C57BL/6 mice were injected intradermally with $10^5$ M5076 reticulum cell sarcoma cells. In this model, primary intradermal tumors spontaneously metastasize to the liver. On day 29 after tumor cell injection, mice were sacrificed, livers removed and fixed in 10% buffered formalin (Fisher Scientific, Pittsburgh, Pa.), and the liver nodules were counted.

To establish lung metastases of B16F10 melanoma, C57BL/6 mice were injected intravenously with $2\times10^4$ B16F10 cells. On day 25 after tumor cell injection, the mice were sacrificed, lungs removed and fixed in 10% buffered formalin, and the lung nodules were counted.

To monitor the primary tumor growth, tumor sizes were determined 2-3 times per week by measuring with calipers (l×w×h), and tumor volumes were determined using the formula: tumor volume ($mm^3$)=0.52(l×w×h).

Tumor volume was analyzed using the Mann-Whitney U non-parametric Statistical Test to identify groups having significantly different mean weights. Mouse survival was analyzed using a Kaplan-Meier survival plot followed by a Logrank (Mantel-Cox) test to identify significant differences in survival between groups. Differences were considered statistically significant when the p value was less than or equal to 0.05.

Intramuscular Injections

Fifty to 100 μg of plasmid DNA in 50 μl of saline was injected into the rectus femoris muscle of each hind leg for a total DNA dose of 100 to 200 μg. The muscle injections were performed using a 300 μl sterile tuberculin syringe fitted with a 28G ½ needle (Becton Dickenson) and a plastic collar cut from a 200 μl micropipette tip. The collar length was adjusted to limit the needle from penetrating further than 2 mm into the rectus femoris muscle.

Serum Levels of Interferon Following Intramuscular Injection of Interferon Plasmid DNA Serum samples from C57BL/6 mice injected intramuscularly with either VR4111 (mIFNα plasmid) or VR1055 (control plasmid DNA) were analyzed in a mIFNα ELISA (n=10). For the ELISA, 96-well plates (Immulon 4HBX high binding plates from Dynex Technologies, Chantilly, Va.) were coated with rat anti-mouse IFNα monoclonal antibody (mAb) from Caltag Laboratories (Burlingame, Calif.) at a concentration of 5 μg/ml in 100 mM sodium carbonate buffer, pH 9.5 (50 μl per well). Plates were incubated with the coating mAb for 16 hours at 4° C. The plates were then washed 3 times with a wash buffer (phosphate-buffered saline (PBS)), pH 7.2 and 0.05% Tween-20 (Sigma, St. Louis, Mo.)). The plates were blocked in PBS containing 3% bovine serum albumin (BSA, Sigma) and 0.05% Tween-20 (400 μl per well) and incubated for 24 hours at 4EC followed by washing three times with wash buffer.

Serum samples (10 μl) from mice injected intramuscularly with VR4111 (mIFNα) were mixed with 40 μl of assay buffer (PBS, 1% BSA, 0.05% Tween-20) and the mixture was added to each assay well. The positive control was mIFNα polypeptide (Biosource International, Camarillo, Calif.), which was serially diluted in assay buffer and 50 μl was added to the positive control wells. The negative control was serum from mice injected intramuscularly with VR1055. After adding the test samples and controls, the plates were incubated for 16 hours at 4° C. The plates were then washed 6 times with wash buffer, followed by addition of a sheep anti-mouse IFNα polyclonal antibody (pAb) (Biosource International, Camarillo, Calif.). The PAb was added at a 1:500 dilution in assay buffer (50 μl per well) and the plates were incubated for 5 hours at room temperature.

Following incubation with the pAb, the plates were washed six times with wash buffer followed by addition of anti-sheep IgG conjugated with peroxidase (Sigma) at a 1:5000 dilution in assay buffer (50 μl per well) and incubated for 1 hour at room temperature. The plates were washed 6 times with wash buffer and 200 μl of 3,3',5,5'-tetramethylbenzidine liquid substrate (TMB) (Sigma Chemical Co.) was added per well. Plates were incubated at room temperature for 30 minutes, followed by determination of the optical density of the wells at 650 nm. A standard curve was generated by plotting the ng/ml of mIFNα polypeptide versus the optical density at 650 nm. The concentration of mIFNα in the test serum samples was determined from the linear portion of the mIFNα standard curve. The sensitivity of the mIFNα ELISA was 50 ng/ml.

C57BL/6 mice injected intramuscularly with VR4111 had detectable serum levels of mIFNα after 5 intramuscular injections of 100 μg VR4111 (twice a week for two weeks, followed by one injection the next week). The average serum level of mIFNα after 5 intramuscular injections of VR4111 was 1465 ng/ml (average of 16 mice). At the time of this study, no commercial mIFNα ELISA kit had been developed. Since sensitivity of the in-house mIFNα ELISA is 50 ng/ml, lower serum levels of mIFNα could exist in the mice at earlier timepoints, but we were unable to detect this in our ELISA.

To determine the serum levels of hIFNω, C57BL/6 or nude mice received a single intramuscular injection of 100 μg of VR4151 (hIFNω plasmid DNA) or VR1055 (control plasmid DNA) (50 μg per leg bilaterally) in the rectus femoris. Serum samples were collected daily over a two week period and analyzed in the hIFNω ELISA kit (Alexis, San Diego, Calif.) which was sensitive to 2 pg/ml. Serum samples were collected from 4-5 mice per day. In the C57BL/6 mice, measurable serum levels of hIFNω were detected as early as one day after injection (69 pg/ml) (FIG. 2A). In these mice, peak serum levels were found six days after injection (254 pg/ml) and expression continued out to day 14 (50 pg/ml), the final timepoint of the study.

In nude mice, serum levels of IFNω were found as early as one day after injection (133 pg/ml). Peak serum levels were found on day 7 (648 pg/ml) and expression continued out to day 14 (134 pg/ml), the final time point of the study (FIG. 2B). Thus, interferon could be detected in the serum after a single intramuscular injection of an interferon-encoding plasmid DNA.

Systemic Interferon Treatment Inhibits Primary Tumor Growth

As shown in FIGS. 3-5 and FIG. 7A, mice bearing different tumors were found to significantly benefit from intramuscular injection of different cytokines. To test the efficacy of IFNα plasmid, C57BL/6 mice bearing subcutaneous B16F10 melanoma, subcutaneous glioma 261, or intradermal M5076 tumors, or DBA/2 mice bearing subcutaneous Cloudman melanoma were injected with 100 μg either of VR4111 (mIFNα) or VR1055 (control), twice per week for three weeks, beginning on day 4 after tumor cell injection (n=8-10 mice per group). In all three subcutaneous tumor models, the mice treated intramuscularly with VR4111 had a significant reduction in tumor volume ($p<0.05$) (FIGS. 3A, 3C, and 3E), and a significant enhancement of survival ($p<0.02$) compared to the mice that received the control plasmid (FIGS. 3B, 3D, and 3F). In the intradermal tumor model, mice treated with intramuscular VR4111 had a significant reduction in primary tumor volume ($p<0.001$) compared to the mice that received the control plasmid (FIG. 7A).

To compare the efficacy of IL-2, IL-12 to IFNα plasmids, C57BL/6 mice bearing subcutaneous B16F10 melanoma were injected with 100 μg of VR4111 (mIFNα), VR4001 (mIL-12), VR1110 (mIL-2), or VR1012 (control) (n=15-16 mice per group) twice per week for three weeks. Mice receiving intramuscular injections of VR4111 had a significant reduction in tumor growth ($p<0.0002$) (FIG. 4A) by day 17 as well as a significant increase in survival ($p=0.00001$) (FIG. 4B). By day 28 of the study, 100% of the VR4111-treated mice were still alive, compared to only 20% of the VR1012-treated mice. Mice treated with VR1110 had a modest reduction in tumor growth by day 17 ($p<0.02$) (FIG. 4A) but did not have an increase in survival compared to the VR1012-treated mice (FIG. 4B). Mice treated with VR4001 also had a modest reduction in tumor growth by day 17 ($p<0.03$) (FIG. 4A) as well as a significant increase in survival ($p=0.02$) (FIG. 4B). By day 28, 55% of the mice treated with VR4001 were alive, compared to 20% of the VR1012-treated mice.

To test the efficacy of IFNω, mice bearing human A431 tumors between 30-80 $mm^3$ were injected intramuscularly with 200 μg of either VR4151 (hIFNω) or VR1055 (control) twice per week for three weeks (n=15). Mice bearing subcutaneous A431 tumors and injected intramuscularly with VR4151 had a significant reduction in tumor volume ($p<0.05$) (FIG. 5A) and a significant increase in survival ($p<0.05$), compared to the mice that received the control plasmid (FIG. 5B).

Systemic mIFNα Plasmid DNA Treatment Inhibits the Growth of Tumor Metastases

Figure 1:
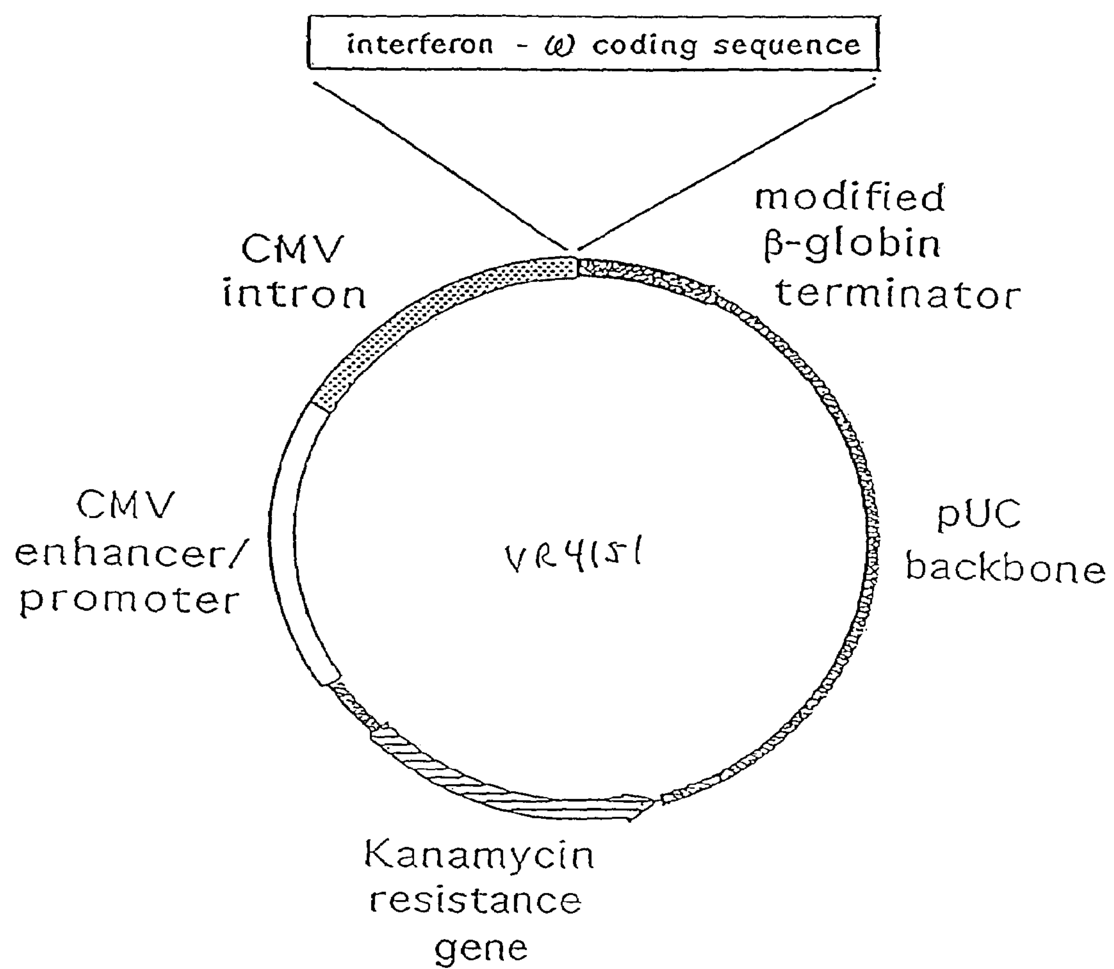
FIG. 1 shows the plasmid map of VR4151 (SEQ ID No. 4). The cytomegalovirus immediate-early gene promoter enhancer and 5' untranslated sequences (5' UTR+intron A) drive the expression of the human interferon ω coding sequence. The transcriptional terminator region includes polyadenylation and termination signals derived from the rabbit β-globin gene.
Figure 3:
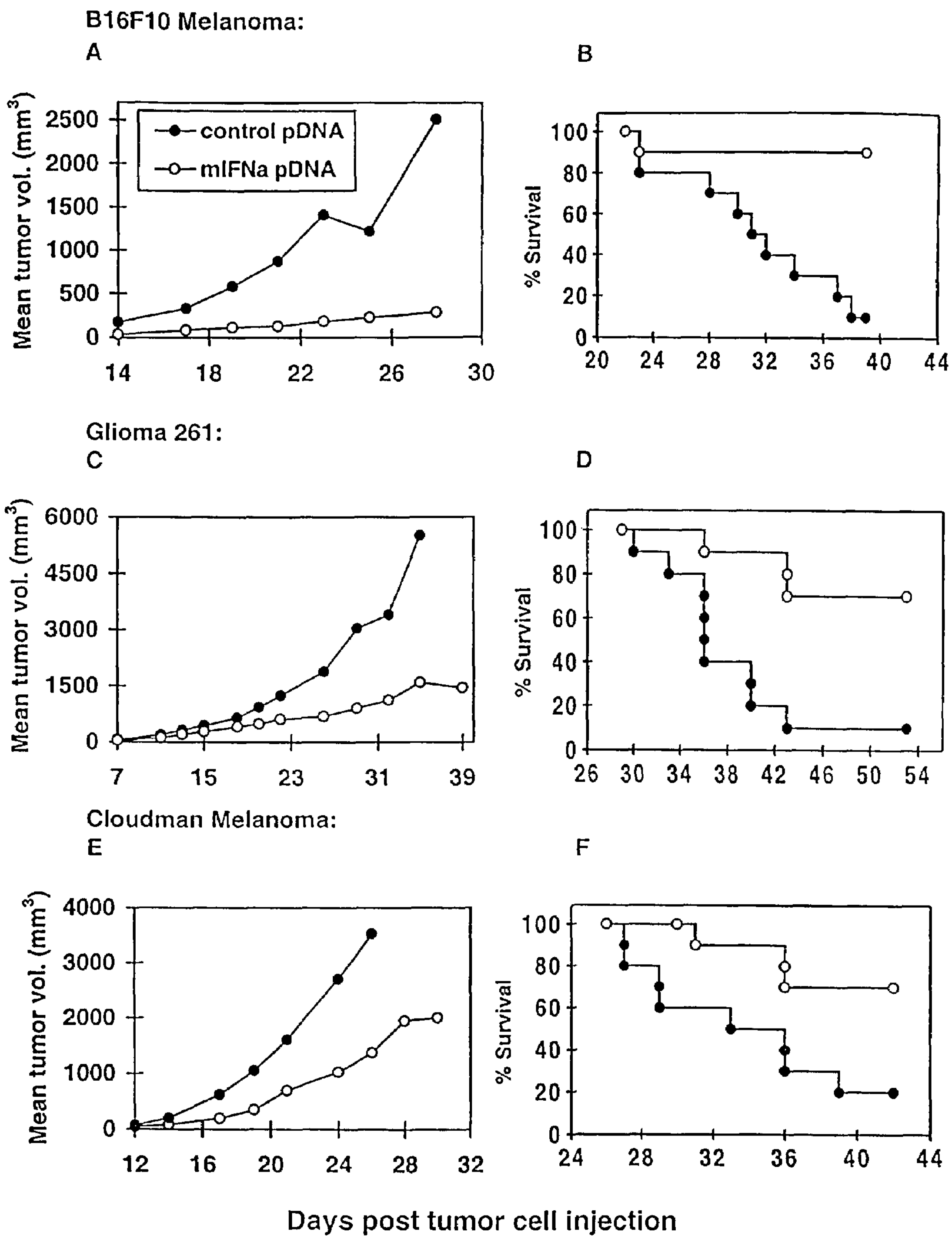
FIG. 3 shows that systemic mIFNα treatment reduces tumor volume (FIGS. 3A, 3C, and 3E) and increases survival (FIGS. 3B, 3D, and 3F) in three murine tumor models. C57BL/6 mice bearing subcutaneous B16F10 melanoma (FIGS. 3A and 3B), subcutaneous glioma 261 (FIGS. 3C and 3D), or DBA/2 mice bearing subcutaneous Cloudman melanoma (FIGS. 3E and 3F) were injected with 100 μg either of VR4111 (mIFNα plasmid) or VR1055 (control plasmid), twice per week for three weeks, beginning on day 4 after tumor cell injection (n=8-10 mice per group).
Figure 6:
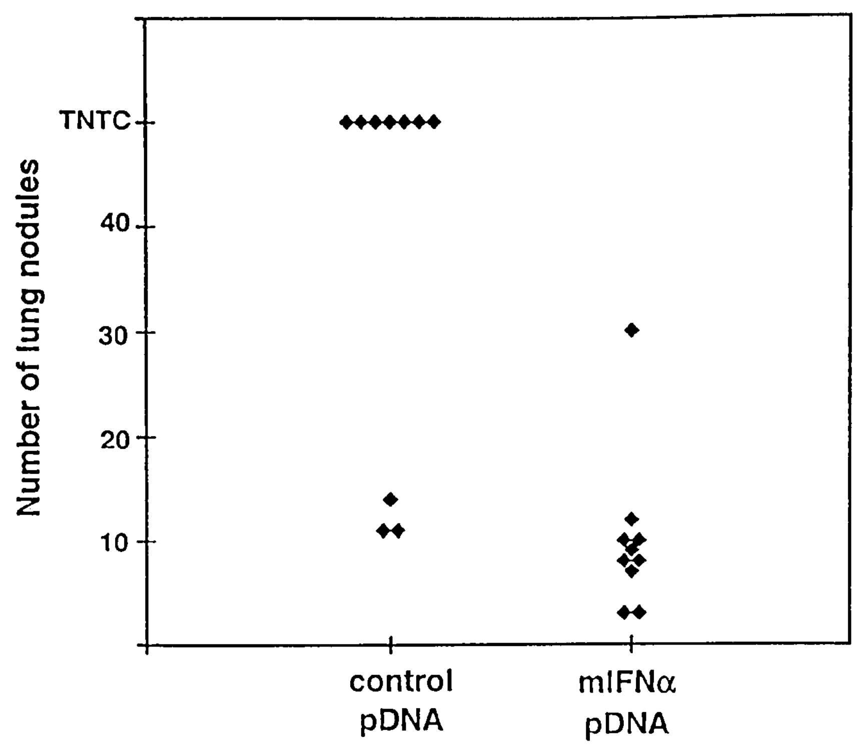
FIG. 6 shows that i.m. administration of mIFNα pDNA reduces B16F10 melanoma lung metastases in C57BL/6 mice. Mice bearing lung metastases of B16F10 melanoma were injected i.m. with 100 μg of either VR4111 or VR1055 twice per week for three weeks, beginning on day 4 after tumor cell injection (n=10 mice per group). "TNTC" means too numerous to count as seen in the control group.

As shown in FIG. 6 and FIG. 7, mice bearing different tumor metastases were found to significantly benefit from intramuscular injection of IFNα. C57BL/6 mice bearing lung metastases of B16F10 melanoma were injected intramuscularly with 100 μg of either VR4111 (mIFNα) or VR1055 (control) twice per week for three weeks, beginning on day 4 after tumor cell injection (n=10). On day 25 after tumor cell injection, the mice were sacrificed, lungs removed and fixed in 10% buffered formalin (Fisher Scientific, Pittsburgh, Pa.) followed by counting of lung nodules.

While 70% of the control plasmid-treated mice had lung nodules that were too numerous to count, 80% of the mice treated with mIFNα plasmid DNA had 10 or fewer nodules (FIG. 6). TNTC denotes lungs with nodules that were too numerous to count.

In the liver metastases model, C57BL/6 mice bearing intradermal M5076 murine reticulum sarcoma were injected intramuscularly with 100 μg of either VR4111 or VR1055 twice per week for three weeks, beginning on day 4 after tumor cell injection (n=10-13 mice per group). On day 29 after tumor cell injection, the mice were sacrificed, livers removed and fixed in 10% buffered formalin (Fisher Scientific, Pittsburgh, Pa.) followed by counting of liver nodules.

While the control plasmid-treated mice had a mean of 190 hepatic tumor nodules or had nodules that were too numerous to count, mIFNα plasmid DNA-treated mice had a mean of 35 hepatic tumor nodules (FIG. 7B).

These results demonstrate that intramuscular injection of mIFNα plasmid DNA can effectively inhibit the growth of both primary and metastatic lesions. Thus, for patients with metastatic disease, intramuscular administration of therapeutic plasmid DNAs would be advantageous for the treatment of undiagnosed or inaccessible metastatic lesions.

Regimen Optimization of mIFNα Therapy in the B16F10 Melanoma Model

A regimen optimization study was conducted to evaluate the antitumor efficacy of fewer injections and/or a lower dose of VR4111 (mIFNα) in the subcutaneous B16F10 melanoma model. C57BL/6 mice were injected with either 100 or 50 μg of VR4111 or VR1055 over a 6 week period (n=10). Mice received intramuscular injections either twice per week, once per week or once every other week. All intramuscular injections began four days after the initial subcutaneous B16F10 tumor cell injection. Mice which received intramuscular injections of 100 μg of VR4111 at any of the time courses had a significant reduction in tumor volume ($p \leqq 0.005$) and a significant increase in survival ($p=0.007$) (FIGS. 8A and 8B). The mice which received the 100 μg dose of VR4111 once every other week for 6 weeks had a total of only three intramuscular injections with significant antitumor efficacy. In contrast, mice receiving the 50 μg dose of VR4111 revealed a dose response based on the frequency of injection. While mice injected with 50 μg of VR4111 once or twice per week had a significant reduction in tumor volume ($p \leqq 0.03$), and a significant increase in survival ($p=0.002$), mice injected only once every other week did not have a significant antitumor response for either tumor growth or survival (FIGS. 8C and 8D).

Mechanism of mIFNα Antitumor Effect

To investigate the role of natural killer (NK) and T cells in mediating the antitumor effect of systemically delivered mIFNα, VR4111 or VR1055 was administered intramuscularly to nude mice (which are T cell deficient) and to beige-nude mice (which are NK and T cell deficient) bearing subcutaneous B16F10 melanoma tumors. Beginning on day 4 after injection of $10^4$ B16F10 cells, 50 μg of plasmid DNA in 50 μl of saline was injected into the rectus femoris muscle of each hind leg for a total DNA dose of 100 μg twice per week for three weeks (n=15 mice per group).

Figure 9:
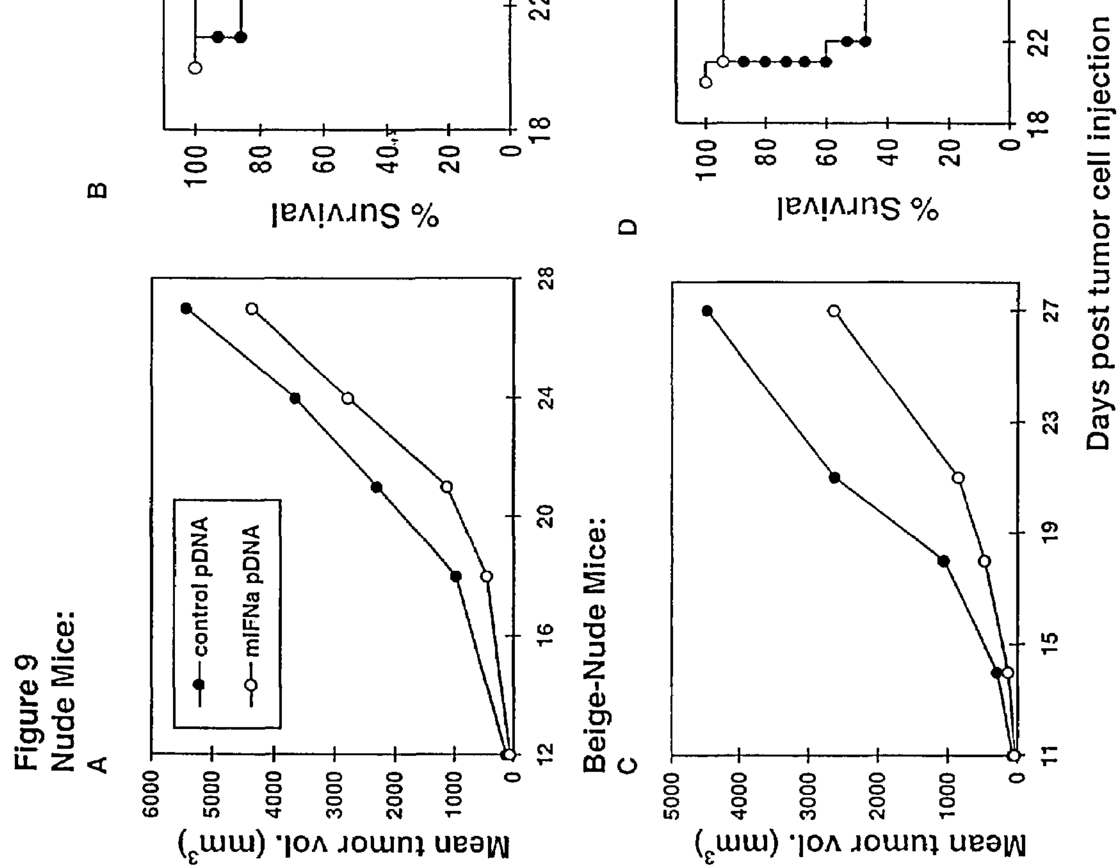
FIG. 9 shows the results of experiments performed to determine the role of NK and T cells in the antitumor response induced by mIFNα plasmid DNA. Nude mice (T cell deficient) (FIGS. 9A and 9B), and beige-nude mice (NK and T cell deficient) (FIGS. 9C and 9D) bearing subcutaneous B16F10 melanoma tumors were injected i.m. with 100 μg of either VR4111 or VR1055 twice per week for three weeks, beginning on day 4 after tumor cell injection (n=15 mice per group). No significant reduction in tumor volume or increase in survival was found for nude or nude-beige mice treated with VR4111, suggesting that T cells are involved in the mIFNα antitumor response.

There was neither a significant reduction in tumor volume nor enhancement of survival in the nude mice (FIGS. 9A and 9B) or beige-nude mice (FIGS. 9C and 9D). These results suggest that T cells may be required for the mIFNα antitumor response. NK cells appeared not to be required for the antitumor effect since nude mice ($NK^+$) did not have a greater antitumor response compared to the beige-nude mice ($NK^-$).

To further explore the role of T cells in the antitumor effect of mIFNα DNA therapy, C57BL/6 mice bearing subcutaneous B16F10 tumors were injected with depleting doses of monoclonal antibodies (mAbs) specific for either $CD4^+$ or $CD8^+$ T cells. For depletion of T cell subsets, anti-CD4 (clone GK1.5, rat IgG) and anti-CD8 (clone 2.43, rat IgG) hybridomas (American Type Culture Collection, Rockville, Md.) were used to generate the corresponding mAb. The anti-CD8 hybridoma was grown as ascites in nude mice and the mAbs were purified from ascites using ion exchange chromatography (Harlan Bioproducts for Science, San Diego, Calif.). The anti-CD4 hybridoma was grown in vitro with Dulbecco's Modified Eagle Medium, 10% fetal bovine serum and low IgG. The anti-CD4 mAb was purified from tissue culture supernatant by ammonium sulfate precipitation to 30%. The protein pellet was resolubilized and extensively dialyzed in Dulbecco's $Ca^{2+}/Mg^{2+}$-free phosphate-buffered saline (Zymed Laboratories Inc., San Francisco, Calif.).

Beginning on day 4 after subcutaneous injection with $10^4$ B16F10 cells, mice were injected intramuscularly with 100 μg of either VR4111 or VR1055 twice per week for three weeks. For depletion of $CD4^+$ and $CD8^+$ T cells, mice were injected intraperitoneally with 500 μg of either the anti-CD4 mAb (clone GK1.5, rat IgG) or anti-CD8 mAb (clone 2.43, rat IgG) one day prior to each intramuscular DNA injection (n=10 mice per group). Control tumor-bearing mice were injected intraperitoneally with 500 μg of normal rat IgG (Simga Chemical Co., St. Louis, Mo.) (n=10). To assure complete depletion, sentinel mice were injected according to the same regimen, and once per week, spleens were collected, dissociated and assessed for the presence of $CD4^+$ and $CD8^+$ T cells. Spleen cells were stained with FITC-conjugated anti-CD4 and PE-conjugated anti-CD8 mAbs (Pharmingen, San Diego, Calif.) and analyzed by flow cytometry (Cytometry Research Services, San Diego, Calif.). The depletion of $CD4^+$ and $CD8^+$ T cells was consistently greater than 98%, as determined by cytometry.

The mIFNα DNA therapy significantly reduced tumor growth ($p \leqq 0.002$) and enhanced survival ($p \leqq 0.008$) of both normal mice and mice depleted of $CD4^+$ T cells, compared to mice injected with control plasmid and treated with normal IgG (FIGS. 10A and 10B). These results suggest that $CD4^+$ T cells are not required for the mIFNα antitumor effect. In contrast, mice depleted of $CD8^+$ T cells and injected with mIFNα DNA displayed tumor volumes and survival profiles that were not significantly different from mice treated with the control plasmid (FIGS. 10A and 10B). This result suggests that $CD8^+$ cells are involved in the mIFNα antitumor response.

Example 5

Local Interferon Therapy: Intratumoral Administration of Interferon Plasmids The anti-tumor activity of IFNω and IFNα was evaluated in vivo in nude mice bearing subcutaneous human ovarian (NIH-OVCAR3) or human melanoma (A375) (nude/human/xenograft model), or in C57BL/6 mice bearing murine melanoma (B16F10) tumors following intratumoral administration of DNA complexed with a cationic lipid.

Cell Lines and Tumor Models

Athymic nude (nu/nu) and C57/BL/6 mice between the ages of 6-10 weeks were obtained from Harlan Sprague Dawley (San Diego, Calif.).

Human A375 melanoma cells and human NIH-OVCAR3 ovarian carcinoma cells were obtained from the American Type Culture Collection (Rockville, Md.), and grown in Dulbecco's modified Eagle's medium (GibcoBRL, Gaithersburg, Md.) supplemented with 10% FBS. B16F10 cells were a generous gift from Dr. Suzuki at the University of Texas (Galveston, Tex.). Cells were grown in RPMI-1640 (Gibco-BRL) and 5% fetal bovine serum (FBS).

To establish subcutaneous A375 melanoma tumors and subcutaneous NIH-OVCAR3 ovarian tumors, athymic nude/nude mice (10 mice/group) were injected subcutaneously with $5\times10^6$ A375 cells and $5\times10^7$ NIH-OVCAR3 cells respectively. To establish subcubaneous murine B16F10 melanoma tumors, C57BL/6 mice were injected subcutaneously with $10^4$ B16F10 cells.

Mice were monitored for tumor growth and survival. Tumor sizes were determined 3 times per week by measuring with calipers (l×w×h) and tumor volumes were determined using the formula: tumor volume ($mm^3$)=0.52 (l×w×h). Statistical analysis was done as described in Example 4.

Local Interferon Plasmid DNA Inhibits Tumor Growth

Established subcutaneous A375 human melanoma and NIH-OVCAR3 human ovarian carcinoma tumors in nude mice were transfected in vivo by intratumoral administration of pDNA/DMRIE/DOPE (DNA:lipid) complexes (n=10). When tumors became palpable (80-300 $mm^3$, at day 27 post tumor cell implant for the A375 cells, and at day 41 post tumor cell implant for the NIH-OVCAR3 cells), mice were injected intratumorally with 100 μg of VR4112 (hIFNα), VR4151 (hIFNω), VR1055 (control) or VR1012 (control) complexed with DMRIE/DOPE (1:1 DNA:DMRIE mass ratio). Tumor bearing animals were treated intratumorally with DNA:lipid for 6 consecutive days followed by 5 treatments every other day for a total of 11 treatments (A375 melanoma model), or every other day for a total of 11 treatments (NIH-OVCAR3 ovarian cancer model).

As shown in FIG. 11A, in the A375 model of melanoma, the direct intratumoral injection of VR4151:lipid complex for 6 consecutive days, followed by 5 additional injections every other day (100 μg plasmid DNA/injection, total of 11 injections), resulted in a statistically significant slowing of tumor growth, as compared to the control ($p<0.03$, days 40-44).

As shown in FIG. 2B, in the NIH-OVCAR3 model of ovarian cancer, the direct intratumoral injection of VR4151: lipid complex every other day for a total of 11 injections (100 μg plasmid DNA/injection), resulted in sustained and statistically significant reduction in tumor growth as compared to the control plasmid control ($p<0.001$-0.05, Days 45-65). A similar treatment regimen with VR4112:lipid was found to have a moderate effect on tumor growth which only reached statistical significance vs. the control plasmid at two timepoints during the study ($p<0.05$, days 53 and 57).

As shown in FIG. 12A, in the B16F10 melanoma model, direct intratumoral injection of mIFNα resulted in decrease in tumor volume. Once palpable tumors were established (80-300 $mm^3$) on day 12 after tumor cell injection in C57BL/6 mice bearing subcutaneous B16F10 melanoma tumors, mice were injected intratumorally with 100 μg of either VR4101 (mIFNα) or VR1012 (control) complexed with the cationic lipid, DMRIE/DOPE at a DNA/DMRIE mass ratio of 1:1 in a 100 μl volume. Mice received six consecutive intratumoral injections of either VR4101 or VR1012 (n=10 mice per group). As shown in FIG. 12A, although not statistically significant, intratumoral injection of VR4101 resulted in a 54% reduction in tumor volume by day 19 of the study. As shown in FIG. 12B, a significant increase in survival ($p=0.02$) was found for the VR4101-treated mice, compared to the mice that received VR1012.

Example 6

Local Cytokine Therapy: Intraperitoneal Administration of Cytokine-Expressing Plasmids The goal of this example is to show that the present invention provides an effective method of treating malignant tumors of murine ovarian carcinoma via intraperitoneal (i.p.) injection of cytokine-expressing plasmid DNA. Since late-stage ovarian carcinoma is usually limited to the peritoneal cavity, it was envisioned that continuous secretion of a cytokine in this cavity would produce beneficial anti-tumor immune response. In particular, the present example clearly shows that the ovarian cancer therapy by intraperitoneal injection of a cytokine-expressing plasmid DNA:lipid complexes (1) results in sustained levels of the cytokine in the ascites, avoiding the need for frequent injections of the protein (in contrast to intraperitoneal injection of recombinant cytokine wherein the cytokine level declines shortly after injection), (2) targets tumor ascites, rather than peritoneal tissues (suggesting that systemic cytokine side effects should be reduced using this method), (3) inhibits tumor growth and enhances survival, and (4) can be combined with debulking of tumor ascites to enhance the antitumor effect.

Cell Lines and Tumor Models

As a model for human ovarian cancer, the murine ovarian teratocarcinoma (MOT) model in C3H/HeN mice was used. MOT exhibits many of the characteristics of late-stage human ovarian cancer including peritoneal spread, production of tumor ascites and tumor cell blockage of lymphatics (Ozols et al., 1979 and Fekete et al., 1952).

Murine ovarian teratocarcinoma (MOT) cells were obtained from Dr. Robert Knapp and Dr. Robert C. Bast at the Dana-Farber Cancer Center (Boston, Mass.). The MOT cells ($10^5$) were grown by serial intraperitoneal (i.p) transplantation in C3H/HeN mice and a stock of the cells was frozen in liquid nitrogen.

CTLL-2 cells were obtained from the American Type Culture Collection (ATCC, Rockville, Md.) and were grown in RPMI 1640 with glutamine, 1% sodium pyruvate, 1% penicillin-streptomycin (Life Technologies, Gaithersburg, Md.), 10% fetal bovine serum (HyClone, Logan, Utah) and 10 U/ml murine IL-2 (Boehringer Mannheim, Indianapolis, Ind.).

C3H/HeN and nude (nu/nu) female mice between the ages of 6-10 weeks were obtained from Harlan Sprague Dawley (San Diego, Calif.). All animal experiments were conducted in accordance with Vical's Institutional Animal Care and Use Committee as well as the standards set forth in the National Research Council guidelines concerning animal care and use.

To establish i.p. MOT tumors, C3H/HeN mice were injected i.p. with $10^5$ MOT cells in 100 ul of medium. In the MOT tumor model, tumor growth is typically monitored by weighing the mice which reflects the increase in volume of tumor ascites (Berek et al., *Cancer Res.,* 44:1871-1875, 1984). The nude mouse study were performed in the same manner as the studies in C3H/HeN mice with injection i.p. of $10^5$ MOT cells and monitoring the weight of the mice. Statistical analysis on mouse weight and survival was done as described in Example 4.

Preparation of Plasmid DNA:Lipid Complexes and Intraperitoneal Injection

To yield a pDNA:DMRIE mass ratio of 1:1, 100 μg of VR1110 (mIL-2) was diluted in 500 ul 0.9% saline (Radix Labs, Eau Claire, Wis.), DMRIE/DOPE lipid (100 μg DMRIE) was diluted in 500 ul of 0.9% saline in a separate vial, and the pDNA and cationic lipid were combined and vortexed for 5 seconds. To yield a pDNA:DMRIE mass ratio of 5:1, 500 μg of mIL-2 pDNA was diluted in 500 ul 0.9% saline (Radix Labs, Eau Claire, Wis.), DMRIE/DOPE lipid (100 μg DMRIE) was diluted in 500 ul of 0.9% saline in a separate vial, and the pDNA and cationic lipid were combined and vortexed for 5 seconds.

The 1 ml pDNA:DMRIE/DOPE (DNA:lipid) complex was injected i.p. into mice bearing i.p. MOT tumors on various days after tumor cell implant. Control MOT tumor-bearing mice received i.p. injections of VR1012 (control):lipid at the same ratio (1:1 pDNA:DMRIE, 100 μg pDNA) and were injected i.p. on the same days as the cytokine-expressing or reporter gene treatment groups.

Intraperitoneal Injection of Plasmid DNA:Lipid Results in Targeted Expression in Tumor Ascites The pDNA:lipid therapy was evaluated for the ability to target malignant cells within a cavity. C3H/HeN mice were injected i.p. with $10^5$ MOT cells followed by i.p. injection of 100 μg of VR1223 (luciferase):lipid (1:1 pDNA:DMRIE mass ratio) on days 5 and 6 after tumor cell implant. Control MOT tumor-bearing mice were injected i.p. with 100 μg of either VR1012:lipid or VR1223 without lipid on days 5 and 6 after MOT tumor cell injection. An additional group of control mice did not receive MOT tumor cells and were injected i.p. with VR1223:lipid on the same days as the other treatment groups (n=3). Three days later the mice were euthanized and tumor ascites and tissues (liver, kidney, spleen, diaphragm, intestine and ovary) were collected. Luciferase was extracted from the tissues by freeze-thawing and grinding of the samples in cell lysis reagent (Promega, Madison, Wis.) as previously described (Hartikka et al., *Hum. Gene Ther.,* 7:1205-1217, 1996). The tumor ascites was diluted 1:5 in cell lysis reagent followed by three cycles of freeze-thaw and collection of supernatant from the cell lysate. Samples were read in a microplate luminometer (Dynatech, Chantilly, Va.) following addition of luciferase substrate (Promega, Madison, Wis.). The relative light units (RLU) of the samples were determined from a standard curve using purified firefly luciferase (Analytical Luminescence Laboratory, Sparks, Md.). The protein concentration of each sample was determined using the BCA protein assay kit (Pierce Chemical Company, Rockford, Ill.). Luciferase levels were expressed as RLU per mg of protein. There may be a decrease in IL-2 pDNA expression from day 1 to day 3 post DNA injection.

On day three, tumor ascites had 900,000 RLU of luciferase/mg, while diaphragm and ovary tissue had only 327 and 16 RLU/mg (FIG. 13). Kidney, liver, spleen and intestinal tissue had no detectable luciferase activity. These results suggest that i.p. injection of pDNA:lipid complexes appears to target the tumor ascites in the peritoneal cavity with limited or negligible transfection of surrounding tissues. Luciferase detected in the diaphragm and ovary tissue was only found in MOT tumor-bearing mice injected with VR1223:lipid. When naive non-tumor bearing mice were injected with the same DNA:lipid complex, no luciferase activity was found in any of the tissues (data not shown). These results suggest that the low levels of luciferase in the diaphragm and ovary in MOT tumor-bearing mice may reflect metastases of tumor cells to these tissues. Tumor-bearing mice injected with luciferase pDNA without cationic lipid had no luciferase activity in either tumor ascites or surrounding tissues, indicating that lipid is required for optimal in vivo transfection of ovarian tumor ascites. Mice injected with VR1012:lipid had no detectable luciferase activity in either tumor ascites or tissues.

A follow-up study investigated the specific cell type in the ovarian tumor ascites that was transfected after i.p. injection of a reporter gene pDNA:DMRIE/DOPE complex. On days 5 and 6 after tumor cell implant ($10^5$ cells), C3H/HeN mice were injected i.p. with 100 μg of VR1412 (β-galactosidase (β-gal)):lipid, VR1012:lipid (1:1 DNA:DMRIE mass ratio), or with VR1412 without cationic lipid (n=3 mice per group). One day later the mice were sacrificed and the tumor ascites was collected. The ascites was spun at 2500 rpm for 2 minutes to pellet the cells, and the supernatant was removed. The tumor cells were fixed in 10% buffered formalin (Fisher Scientific, Pittsburgh, Pa.), placed in a cryomold containing OCT embedding medium (VWR, S. Plainfield, N.J.), frozen in isopentane and then stored at −70° C. The embedded and frozen samples were then cryostat sectioned (5 um), further fixed (0.5% glutaraldehyde in PBS), washed (PBS), stained with X-gal reagent (1 mg/ml X-gal diluted in PBS containing 5 mM potassium ferricyanide, 5 mM potassium ferrocyanide, and 1 mM magnesium chloride), washed again (PBS), and counterstained with hematoxylin and eosin. (The samples were cryostat sectioned and stained by Pathology Associates (Frederick, Md.).)

The ascites from mice treated with either VR1012 or VR1412 without lipid had no β-gal activity in the samples. In contrast, the tumor ascites from mice injected with VR1412: lipid had β-gal staining primarily in the tumor cells (data not shown). In a few slides, several macrophages and lymphocytes were also positive for β-gal while neutrophils were negative for β-gal.

Intraperitoneal Injection of IL-2 pDNA:Lipid Results in Sustained Expression of IL-2 in Tumor Ascites A time-course study was done to determine the length of time that IL-2 could be detected after multiple i.p. injections of IL-2 pDNA:lipid or a single i.p. injection of either IL-2 protein or IL-2 pDNA:lipid in mice bearing i.p. ovarian tumor ascites. Beginning on day 5 after tumor cell injection, mice were injected multiple times with VR1110 (mIL-2):lipid or a single time with VR1110:lipid or IL-2 protein. Mice were sacrificed at various times and ascites and serum were analyzed for IL-2 levels. Ascites was collected from the sacrificed mice, the samples were spun at 14,000 rpm for 2 minutes and the supernatant was harvested. Blood was collected from the mice on the same day as the ascites collection and the serum was separated from blood cells by allowing the blood to clot in serum separator tubes (Microtainer, Becton Dickinson, Franklin Lakes, N.J.) followed by centrifugation at 14,000 rpm for 10 minutes and collection of the serum supernatant. IL-2 concentration (pg/ml) in the ascites and serum samples was determined using a murine IL-2 ELISA (R & D Systems, Minneapolis, Minn.). Since the volume of tumor ascites increases over time, the volume of ascites was also determined for each mouse. The total concentration of IL-2 in ascites was determined using the formula: IL-2 pg/ml×ml of ascites=pg IL-2/total ascites. Serum IL-2 concentrations were reported as pg/ml.

IL-2 in Serum and Ascites after Multiple Injections of IL-2 pDNA:Lipid.

Beginning on day 5 after tumor cell injection, mice were injected with VR1110:lipid for either 2, 4 or 6 consecutive days or with control VR1012:lipid for 6 consecutive days (100 μl of plasmid DNA complexed with 100 μl DMRIE/DOPE at 1:1 mass ratio in a total volume of 1 ml). An additional group of mice received VR1110 that was not complexed with DMRIE/DOPE. Every two days for up to 17 days after the DNA:lipid injections, 3-4 mice were sacrificed per treatment group and ascites and serum were collected and analyzed using mIL-2 ELISA assay as described above.

Two injections of VR1110:lipid (100 μl DNA per day, 1:1 DNA:cationic lipid mass ratio) into mice bearing i.p. MOT ovarian tumors yielded high levels of IL-2 protein in the tumor ascites. One day after VR1110:lipid i.p. injection, 28,000 pg/ml of IL-2 was measured in the tumor ascites (Table 3). IL-2 expression in the ascites continued for over two weeks after DNA:lipid injection with 750 pg/ml detected 17 days after the last pDNA:lipid injection. Mice injected with either four or six consecutive injections of VR1110:lipid also had high levels of IL-2 in the tumor ascites; however, due to the very high expression levels after more frequent VR1110:lipid injections, IL-2-mediated side effects were noted in the mice which did not survive beyond day 9 or 13 after DNA injection. In contrast, two consecutive injections of VR1110 plus DMRIE/DOPE did not cause observable IL-2 side effects yet IL-2 expression levels remained high for over 2 weeks. The IL-2 expressed after i.p. DNA:lipid injection of MOT-bearing mice appeared to remain localized in the peritoneal cavity as the IL-2 serum levels after VR1110:lipid i.p. injection were always less than 10% of the levels in the tumor ascites. Injection of VR1110 without lipid yielded very low levels of IL-2 in ascites and serum (0-32 pg/ml). Injection of the control vector, VR1012, resulted in only background levels of IL-2.

days 1, 2, 3, 6 and 10 post DNA or protein injection. Ascites and serum were collected and analyzed using mIL-2 ELISA assay as described above.

Mice injected i.p. with IL-2 protein had peak levels of IL-2 in ascites (10 ng) at 4 hours after injection of IL-2 and a 1000-fold reduction in IL-2 one day later (0.009 ng) (FIG. 14A). In contrast, mice injected with IL-2 pDNA:lipid had peak IL-2 levels in ascites 2 days after injection (64 ng) and only a 2.6 fold reduction in IL-2 by 10 days after injection (25 ng) (FIG. 14A). These results indicate that mice receiving IL-2 pDNA:lipid have more sustained levels of IL-2 in the ascites compared to mice receiving IL-2 protein. Tumor-bearing mice injected i.p. with either VR1012:lipid or VR1110 without cationic lipid had no IL-2 in the tumor ascites. In a related study, MOT tumor-bearing mice injected i.p. with 10-fold less VR1110:lipid (10 μg DNA) still had detectable IL-2 in the tumor ascites 11 days after the VR1110: lipid injection (data not shown).

Serum levels of IL-2 after either i.p. protein or DNA injection reflected a similar pattern as that found in tumor ascites; however, the serum IL-2 levels were markedly reduced compared to the ascites IL-2 levels. Four hours after protein injection, IL-2 in the serum was 2.4 ng/ml and negligible by one day after protein injection. Serum levels of IL-2 one day after VR1110:lipid injection was 1 ng/ml and undetectable by 6 days after the injection (FIG. 14B). These results suggest

TABLE 3

| Treatment | Days post tumor cell injection | | | | | | | | |
|---|---|---|---|---|---|---|---|---|---|
| | 7 | 9 | 11 | 13 | 15 | 17 | 19 | 21 | 23 |
| | mIL-2 concentration in ascites (pg/ml) | | | | | | | | |
| VR1110 (mIL-2) without DM/DP, 6 injs. | 28 | 12 | 0 | 1 | 0 | 1 | 0 | | |
| VR1012 (control) + DM/DP, 6 injs. | 0 | 0 | 8 | 0 | 0 | 1 | 43 | | |
| VR1110 (mIL-2) + DM/DP, 6 injs. | | | 7196 | 7716 | 7824 | 3895 | 3200 | | |
| VR1110 (mIL-2) + DM/DP, 4 injs. | | 3524 | 4187 | 5968 | 3050 | 3984 | 2392 | 441 | |
| VR1110 (mIL-2) + DM/DP, 2 injs. | 28882 | 4750 | 11725 | 8047 | 1246 | 1445 | 1407 | 774 | 753 |
| | mIL-2 concentration in serum (pg/ml) | | | | | | | | |
| VR1110 (mIL-2) without DM/DP, 6 injs. | 0 | 4 | 0 | 32 | 0 | 0 | 0 | | |
| VR1012 (control) + DM/DP, 6 injs. | 0 | 0 | 0 | 0 | 0 | 0 | 62 | | |
| VR1110 (mIL-2) + DM/DP, 6 injs. | | | 66 | 85 | 34 | 5 | 4 | | |
| VR1110 (mIL-2) + DM/DP, 4 injs. | | 114 | 81 | 40 | 10 | 3 | 2 | 0 | |
| VR1110 (mIL-2) + DM/DP, 2 injs. | 625 | 418 | 181 | 76 | 6 | 0 | 1 | 0 | 0 |

IL-2 in Serum and Ascites after Single Injection of pDNA: Lipid Injection Compared to Protein Injection.

Five days after i.p. injection of $10^5$ MOT tumor cells, C3H/HeN mice were injected with 100 μg of either VR1110:lipid or VR1012:lipid (1:1 DNA:DMRIE mass ratio) or with 100 μg of VR1110 without lipid. For the IL-2 protein-treated group, mice were injected with 1 μg recombinant murine IL-2 protein (R & D Systems, Minneapolis, Minn.). The pDNA: lipid, pDNA alone, or recombinant protein was injected i.p. in a total volume of 1 ml saline per mouse. Five mice from each group were sacrificed beginning at 4 hours and continuing on that the majority of the IL-2 after either IL-2 protein or pDNA:lipid delivery remains in the peritoneal cavity.

Intraperitoneal Injection of IL-2 Plasmid DNA:Lipid Inhibits Tumor Growth and Enhances Survival Six consecutive-day treatments. The plasmid DNA:lipid therapy was evaluated for the ability to reduce tumor growth and to increase survival of mice with MOT tumors. On day 5 after MOT tumor cell injection, mice were injected i.p. with 100 μg of either VR1110 or VR1012, both complexed with DMRIE/DOPE. The plasmid DNA was complexed at either a 5:1 or 1:1 DNA:DMRIE mass ratio. An additional treatment group received VR1110 that was not complexed with lipid. A total volume of 1 ml DNA:lipid or DNA alone in physiological saline was injected i.p. The DNA treatments occurred over 6 consecutive days, beginning on day 5 (days 5-10). MOT tumor growth was measured by weighing the mice. All treatment groups consisted of 10 mice per group.

The high IL-2 expression level in ascites was accompanied by significant antitumor effects. Mice treated with VR1110:lipid on days 5-10 after tumor cell injection had a significant reduction in MOT tumor growth compared to the mice treated with the VR1012:lipid (p=0.01) (FIG. 15A). A significant enhancement in survival was also found for mice injected i.p. with VR1110:lipid (p=0.05) (FIG. 15B).

Complexing the pDNA with a cationic lipid seemed necessary for the antitumor effect as treatment of tumor-bearing mice with VR1110 without lipid was not effective (FIGS. 15E and 15F). Furthermore, a 1:1 DNA:cationic lipid mass ratio was found to be more effective at reducing tumor burden and increasing survival than a 5:1 DNA:cationic lipid mass ratio (FIGS. 15C and 15D).

Three alternative-day treatments. C3H/HeN mice bearing i.p. MOT tumor ascites were injected i.p. with VR1110:lipid or with VR1012:lipid (100 μg DNA) on days 5, 8 and 11 after tumor cell implant. By day 14 post tumor cell injection, mice treated with VR1110:lipid had a significant reduction in mean weight (p=0.001) compared to the mice treated with the control pDNA:lipid (FIG. 16A). In addition, a significant increase in survival (p=0.008) was found for the VR1110:lipid-treated mice compared to the mice treated with the VR1012:lipid (FIG. 16B). By day 26 post tumor cell injection, none of the mice treated with the VR1012 were still alive, while 50% of the mice treated with VR1110:lipid remained alive. By day 55 post tumor cell injection, 20% of the mice treated with VR1110:lipid appeared to be tumor-free.

Whether the IL-2 pDNA:lipid antitumor effect required T cells was investigated by implanting nude mice with i.p. MOT tumors followed by same VR1110:lipid regimen used in the C3H/HeN tumor-bearing mice (DNA treatment on days 5, 8 and 11 after tumor cell implant). No significant antitumor effect was found for the nude mice treated with VR1110:lipid suggesting that T cells may be required for the antitumor effect (data not shown).

IL-2 Plasmid DNA:Lipid Antitumor Effect Enhanced by Debulking of Tumor Ascites

Debulking of tumor ascites is commonly performed on human ovarian cancer patients. A similar procedure was performed in the mice bearing MOT tumors and treated with VR1110:lipid. Mice bearing MOT tumors and injected i.p. with 100 ul DNA:lipid on days 5-10 as described above (1:1 DNA:lipid mass ratio), were also debulked of tumor ascites on day 14 after tumor cell injection (4 days after the last DNA:lipid injection). Mice were debulked of 5 ml of tumor ascites by insertion of a 22 G needle attached to a 5 ml syringe and removal of 5 ml of fluid. The mice were anesthetized with methoxyflurane during the debulking procedure. All treatment groups in this experiment consisted of 8-10 mice per group.

Debulking of ovarian tumor ascites in mice previously treated with IL-2 plasmid DNA:lipid further enhanced the efficacy of the treatment resulting in a significant reduction in tumor growth (p=0.01) and an increase in survival. Forty four percent of the IL-2 plasmid DNA:lipid-treated and debulked mice were alive on day 57 vs. 17% of the plasmid control-treated and debulked mice (FIG. 17). These results show that plasmid-mediated gene therapy in combination with conventional procedures such as debulking of tumor ascites may hold promise for future treatment of human ovarian cancer.

Dose-Response of IL-2 pDNA:Lipid

A dose-response study was initiated to determine the minimum dose of VR1110:lipid that could still result in a significant antitumor effect. C3H/HeN mice were injected with 25, 50 or 100 μg of IL-2 pDNA:lipid on days 5, 8 and 11 after MOT tumor cell injection. A control group of MOT tumor-bearing mice were injected with 100 μg of VR1012 complexed with lipid. By day 15 post tumor cell injection, mice treated with either the 50 or 100 μg dose of VR1110 complexed with lipid had a significant inhibition of tumor growth (p=0.002) compared to the mice treated with the VR1012:lipid (FIG. 18A). A significant increase in survival (p=0.01) was also found for the mice treated with either the 50 or 100 μg dose of VR1110:lipid (FIG. 18B). On day 25, none of the mice treated with the VR1012:lipid survived, while the mice injected with 50 or 100 μg of VR1110:lipid had 27 and 33% survival, respectively. By day 37, mice treated with 50 or 100 μg of VR1110:lipid had 20 and 27% survival, respectively. Tumor-bearing mice treated with 25 μg of VR1110 complexed with lipid were not significantly different from the control mice for either tumor volume or survival.

Cytokine Profile of Ovarian Tumor Ascites

Since i.p. injection of IL-2 pDNA:lipid into mice bearing i.p. MOT tumors resulted in high levels of IL-2 expression in the ascites, it was of interest to determine whether the IL-2 therapy initiated a cytokine cascade in the tumor ascites. C3H/HeN mice were injected i.p. with $10^5$ MOT cells. On days 5, 8 and 11 after tumor cell implant, the mice were injected i.p. with either VR1110:lipid or VR1012:lipid (1:1 pDNA:DMRIE mass ratio) or received no treatment after the MOT tumor cell injection. Two days after each injection of pDNA:lipid (days 7, 10 and 13 after tumor cell implant), 5 mice per group were sacrificed and the tumor ascites was collected. The total volume of ascites was determined per mouse. The ascites samples were spun at 14,000 rpm for 2 minutes followed by collection of the supernatants. The ascites supernatants were assayed for the concentration of the cytokines: IL-2, IL-4, IL-6, IL-10, IL-12, granulocyte-macrophage colony stimulating factor (GM-CSF), interferon gamma (IFNγ) and tumor necrosis factor alpha (TNFα) using ELISA (R & D Systems, Minneapolis, Minn.). The concentration of transforming growth factor beta (TGFβ) in the ascites was assayed using the TGF$\beta_2$ Emax Immunoassay System (Promega, Madison, Wis.). The amount of cytokine in the tumor ascites was calculated using the formula: cytokine concentration in pg/ml×ml of total ascites=pg of cytokine/total ascites.

Figure 19:
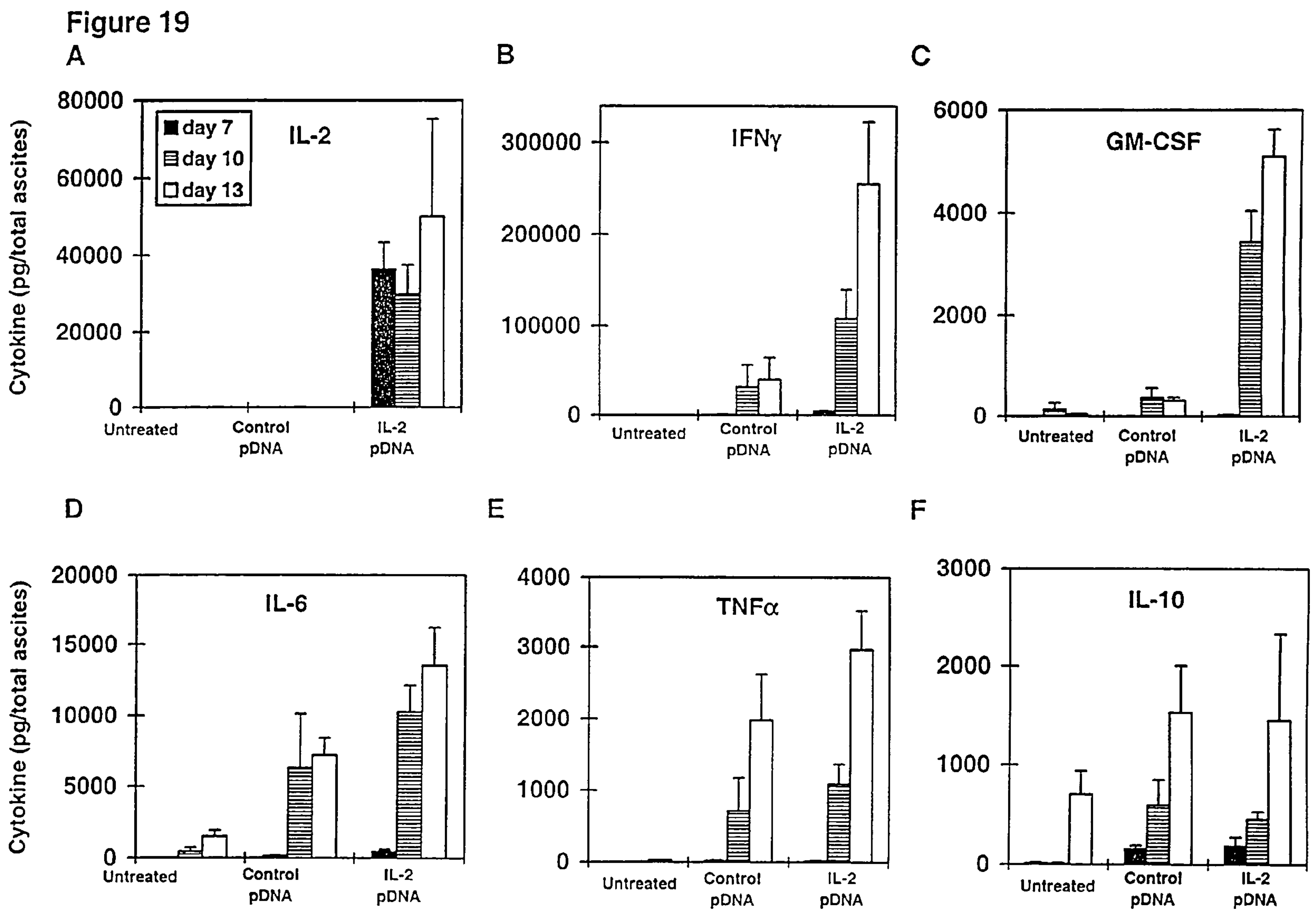
FIG. 19 shows the cytokine profile of ovarian tumor ascites in C3H/HeN mice MOT tumor model following mIL-2 pDNA (VTR1110):lipid treatment. Mice received i.p. injections of a complex of pDNA/DMRIE/DOPE (1:1 DNA/DMRIE mass ratio, 100 μg of plasmid DNA) on days 5, 8 and 11 after tumor cell implant. Two days after each injection, mice were sacrificed (5 mice for each time point), and the ascites were collected and analyzed for IL-2 (FIG. 19A), IFNγ (FIG. 19B), GM-CSF (FIG. 19C), IL-6 (FIG. 19D), TNFα (FIG. 19E) and IL-10 (FIG. 19F) concentration. The level of IL-2 (days 7, 10 and 13) as well as IFNγ and GM-CSF (days 10 and 13) were markedly elevated suggesting that IL-2 upregulates IFNγ and GM-CSF production.

As expected, tumor-bearing mice injected i.p. with VR1110:lipid had a marked increase in IL-2 levels with negligible levels in untreated tumor-bearing mice or mice injected with the VR1012:lipid (FIG. 19A). The levels of IFNγ and GM-CSF were also markedly elevated in the mice treated with VR1110:lipid (FIGS. 19B and 19C). The IFNγ and GM-CSF levels in these mice increased on days 10 and 13 after tumor cell injection but not on the day 7 timepoint suggesting that this could be due to IL-2 secretion. Some non-specific increase in IFNγ was also found in the ascites of tumor-bearing mice after injection of the VR1012:lipid; however, by day 13, the levels of IFNγ in the tumor-bearing mice treated with VR1110:lipid were 6-fold higher than in the mice treated with VR1012:lipid suggesting that expression of IL-2 upregulates IFNγ production.

Levels of IL-6, TNFα and IL-10 were increased in both the IL-2 pDNA:lipid group as well as the control pDNA:lipid group suggesting that pDNA:lipid complexes may non-specifically stimulate production of these particular cytokines in the tumor ascites (FIGS. 19D, 19E, and 19F). No differences were found for IL-4, IL-12 or TGFβ in the ascites from any of the groups and levels of these cytokines were low (0-300 pg/ml for IL-4 and IL-12 and 0-2000 pg/ml for TGFβ, data not shown). For all of the cytokines evaluated, mice treated with control pDNA without lipid, IL-2 pDNA without lipid or with lipid alone had similar cytokine levels as the untreated mice.

Intraperitoneal Injection of IFNα pDNA:Lipid Enhances Survival

C3H/HeN mice were injected i.p. with $10^5$ MOT cells to establish ovarian i.p. tumors. The mice then received i.p. injections of 100 μg of VR4111 (mIFNα) or VR1012 (control) complexed with DMRIE:DOPE cationic lipid at a 1:1 DNA:DMRIE mass ratio in a total volume of 1 ml saline. The mice received the i.p. injections of pDNA:lipid on days 5, 8 and 11 after tumor cell injection. The mice were weighed 3-6 times per week. Fifteen mice were included in each treatment group.

Mice bearing i.p. MOT tumors and treated with i.p. VR4111:lipid had a significant increase in survival ($p<0.006$) compared to the mice receiving the control plasmid (FIG. 20B). No significant reduction in tumor volume was found for the VR4111:lipid-treated mice (FIG. 20A).

Example 7

Selective Transfection of Malignant Cells in Murine Intraperitoneal Melanoma Tumor Model The anti-tumor effect of DNA formulations with or without lipids in mouse i.p. melanoma model have been evaluated in the present example.

Cell Line and Tumor Model

B16F10 mouse melanoma cells were grown in vitro in DMEM and 10% FCS. Two hundred thousand B16F10 mouse melanoma cells were implanted i.p. in C57BL/6 mice in 1-3 ml saline using a 28 G ½ needle and without puncturing internal organs.

Preparation of Plasmid DNA:Lipid Complexes

The plasmid DNA-cationic lipid formulations were prepared just prior to use. Equal volumes of DNA and DMRIE:DOPE (1:1) were mixed by swirling to achieve a target concentration of 0.5 mg DNA/ml, 100 μg DMRIE/ml and 0.12 mg DOPE/ml as previously described (Parker et al, 1996; Saffran et al, 1998). The other cationic lipids were mixed similarly so that the mass ratio of DNA to cationic lipid was 5:1 and the cationic lipid to DOPE molar ratio was 1:1. The formulated material was then vortexed at high speed for 30 seconds and kept at room temperature until dose administration.

CAT Assay

Tumor or other tissues were collected, immediately frozen in liquid nitrogen and ground into a powder using a reversible drill as described (Manthorpe, M., Hartikka, J., Vahlsing, H. L. and Sawdey, M. Quantification of plasmid DNA transfection in vivo. In Gene Quantification. F. Ferre, ed. Birkhauser, Boston, Mass., 1998 in press.). The dry frozen powder was thawed and extracted in lysis buffer and high speed supernates assayed for CAT activity using a two-phase partition assay as described (Sankaran, L., Analytical Biochemistry 200: 180-186 (1992)).

Cationic Lipids Enhances Tumor Transfection

C57BL/6 mice were injected i.p. with 200,000 B16F10 murine melanoma cells, and seven days later, injected i.p. with CAT pDNA (VR1332):DMRIE/DOPE. Two days later, tumor tissues were collected, extracted, and assayed for CAT activity.

As shown in Table 4, DNA alone transfected tumor, but DMRIE:DOPE increased transfection by 78 fold (from 2,326 to 182,052).

TABLE 4 pgs CAT per gm of tumor tissue collected (n = 4 to 6 mice as indicated); saline values subtracted

| Mouse # | DNA only | DNA:DMRIE | DMRIE, no DNA |
|---|---|---|---|
| 1 | 0 | 82,600 | 0 |
| 2 | 307 | 137,551 | 0 |
| 3 | 706 | 220,600 | 0 |
| 4 | 791 | 287,458 | 0 |
| 5 | 5,892 | | 0 |
| 6 | 6,258 | | |
| Average | 2,326 | 182,052 | 0 |
| Std Error | 1,306 | 52,140 | 0 |
| Fold higher | 1 | 78 | 0 |

Selective Transfection of Tumor Cells

Normal animal. Normal, non-tumor bearing BALB/c mice were injected i.p. with 1 mg/2 ml VR1332, with or without a cationic lipid, and with or without the neutral lipid, DOPE. Two days later, selected i.p. tissues (liver, lung, kidney, spleen, mesentery) were collected, extracted, and assayed for CAT activity.

As shown in Table 5, normal intraperitoneal organs were not at all transfected or transfected very little with a variety of cationic lipids: There was a low level transfection of mesentery tissues, and a moderate transfection of 1 of 5 spleens (the one transfected spleen may have been punctured by the injection needle).

TABLE 5

Average pgs CAT per gm of tumor tissue (avg., n = 5 mice) Saline background values have been subtracted

| ORGANS | DNA only | +DMRIE | +βAE-DMRIE | +GAP-DLRIE |
|---|---|---|---|---|
| Liver | 0 | 0 | 0 | 0 |
| Lung | 0 | 0 | 0 | 0 |
| Kidney | 0 | 0 | 0 | 0 |
| Spleen | 0 | 2,563(0)* | 0 | 0 |
| Mesentery | 370 | 1,549 | 1,866 | 1,127 |

| ORGANS | +DOSPA | +DMRIE, no DOPE | +βAE-DMRIE, no DOPE |
|---|---|---|---|
| Liver | 0 | 0 | 0 |
| Lung | 0 | 0 | 0 |
| Kidney | 0 | 0 | 0 |
| Spleen | 0 | 0 | 0 |
| Mesentery | 600 | 1,091 | 3,604 |

*one mouse with a CAT value; the rest = 0

Tumor-bearing animal compared to normal animal. C57BL/6 mice were injected i.p. with 200,000 B16F10 murine melanoma cells, and seven days later, injected i.p. with VR1332 with or without cationic lipid/DOPE. Two days later, selected i.p. tissues (liver, lung, kidney, spleen, mesentery) were collected, extracted, and assayed for CAT activity.

As shown in Table 6, tumor tissues were transfected at high levels with pDNA complexed with cationic lipid/DOPE. Normal i.p. organs were not transfected well compared to i.p. tumor tissues.

TABLE 6

| Average pgs CAT per gm of tumor tissue (n = 5 mice); saline values subtracted | | | |
|---|---|---|---|
| ORGANS | DNA only | DNA + DMRIE:DOPE | DNA + DMRIE:DOPE normal mice no tumors |
| Tumor | 0 | 200,195 | n/a |
| Liver | 0 | 0 | 0 |
| Lung | 0 | 0 | 0 |
| Kidney | 0 | 0 | 0 |
| Spleen | 493 | 0 | 0 |
| Mesentery | 6,795 | nd | 2,562 |
| Ovary | nd | nd | 0 |

Dose Response

C57BL/6 mice were injected i.p. with 200,000 B16F10 murine melanoma cells, and seven days later, injected i.p. with 0.15 or 1.5 mgs of VR1332 with or without cationic lipid/DOPE in 3 ml saline. Two days later, tumor tissues were collected, extracted, and assayed for CAT activity.

As shown in Table 7, a higher dose of DNA transfected tumor tissues better than a lower dose. Also, DMRIE transfected better than the two other cationic lipids tested.

TABLE 7

| Average pgs CAT per gm of tumor tissue (n = 5 mice); saline values subtracted | | | | |
|---|---|---|---|---|
| DNA DOSE | DNA only | +DMRIE | +GAP-DMRIE | +PA-DELO |
| 1.5 mgs | 16,592 | 1,270,466 | 524,006 | 581,616 |
| 0.15 mgs | 1,937 | 131,089 | 47,866 | 99,797 |

Testing a Variety of Cationic Lipids

C57BL/6 mice were injected i.p. with 200,000 B16F10 murine melanoma cells, and seven days later, injected i.p. with 1 mg of VR1332 with or without cationic lipid/DOPE in 3 ml saline. Two days later, tumor tissues were collected, extracted, and assayed for CAT activity.

As shown in Table 8, all cationic lipids tested increased transfection level, and DMRIE was one of three preferred cationic lipids.

TABLE 8

| Average pgs CAT per gm of tumor tissue (n = 5 mice); saline values have been subtracted | | | |
|---|---|---|---|
| CL:DOPE | Run 1 | Run 2 | Average |
| None | 6,247 | not done | 6,247 |
| GAP-DDRIE | 20,816 | 7,027 | 13,922 |
| GMU-DMRIE | 9,355 | 52,888 | 31,122 |
| HP-DORIE | 36,615 | 26,795 | 31,705 |
| DOSPA | 33,494 | 57,026 | 45,260 |
| PA-TELO | 63,326 | 32,681 | 48,004 |
| GA-LOE-BP | 59,729 | 63,528 | 61,629 |
| GAP-DMRIE | 80,760 | 63,002 | 71,881 |
| PA-DELO | 73,692 | 82,265 | 77,979 |
| GAP-DLRIE | 77,553 | 107,629 | 92,591 |
| DMRIE | 77,128 | 122,225 | 99,677 |
| DLRIE | 122,999 | 128,225 | 125,612 |
| PA-DEMO | 155,369 | 154,884 | 155,127 |

In sum, the success of the intra-cavity delivery embodiment of the present invention is also exemplified in the murine melanoma tumor model. Following i.p. injection of a polynucleotide, transfection occurs predominantly in tumor tissues, and normal intraperitoneal organs, such as liver, lung, and kidney are poorly transfected, if at all, with the polynucleotide formulation.

The following examples demonstrate the surprising finding that compositions comprising polypeptide-encoding polynucleotides and certain salts and/or auxiliary agents can enhance subsequent gene expression when administered into murine tissues.

Materials and Methods

The following materials and methods apply generally to all the examples disclosed herein. Specific materials and methods are disclosed in each example, as necessary.

Preparation of the Pharmaceutical Compositions

All salts used in the following examples are available from Sigma Chemical Corporation (Sigma, St. Louis, Mo.). Detergents used in the following examples are available from Sigma, Roche Molecular Biochemicals (Indianapolis, Ind.), BASF (Mount Olive, N.J.), and Amresco (Solon, Ohio). Purified plasmid DNA was ethanol precipitated and resuspended in water. Salt solutions were prepared as 300 mM stock solutions and dilutions were made using sterile USP water (Baxter, Deerfield, Ill.).

Preparation of Plasmid DNAs

FIG. 21 depicts the major structural and regulatory elements contained in each plasmid. The gene for *Photinus pyralis* (firefly) luciferase was subcloned from the pSP-LuC vector (available from Promega, Madison, Wis.) into the VR1012 vector (Manthorpe, M., et al., *Hum. Gene Ther.* 4:419-431 (1993)) to make VR1223 or VR1255 (Hartikka, J., et al., *Hum. Gene Ther.* 7:1205-1217 (1996)). The RSV promoter-regulated VR1418 LacZ vector was made by subcloning the LacZ gene from the VR1412 vector (Doh, S. G., et al., *Gene Ther.* 4:648-663 (1997)) into VR1043, itself derived by replacing the CMV control elements of VR1012 with RSV control elements. The mouse erythropoietin (EPO) was obtained by PCR as described (Tripathy, S. K., et al., *Proc. Natl. Acad. Sci. USA* 93:10876-10880 (1996)) and subcloned into the VR1012 vector to produce VR2901. The secreted form of the human placental alkaline phosphatase (SEAP) gene was subcloned from pSEAP2-Basic (available from Clonetech, Palo Alto, Calif.) into the VR1012 backbone vector to make VR3301. The rat preproinsulin coding sequence was obtained from reverse transcription of rat pancreatic preproinsulin poly(A) mRNA as described (Abai, A. M., et al., *Hum. Gene Ther.* 10:2637-2649 (1999)) and subcloned into the VR1012 backbone vector to produce VR3502. The human IFN-ω coding sequence was obtained by amplifying the coding sequence from human genomic DNA prepared from DNA of fresh human blood. The mouse IFN-α gene was a generous gift from Paula Pitha-Rowe (Johns Hopkins University). The IFN-ω and IFN-α genes were subcloned into the VR1055 vector to produce, respectively VR4151 and VR4111 as described (Horton, H. M., et al., *Proc. Natl. Acad. Sci. USA* 96:1553-1558 (1999)). The luciferase gene in VR1255 was replaced with the influenza A/PR/8/34 nucleoprotein gene as described (Ulmer, J. B., et al., *Ann. N.Y. Acad. Sci.* 772:117-125 (1995)) to yield VR4700.

Plasmid DNA Purification

Plasmid DNA was transformed into *Escherichia coli* DH5α competent cells and highly purified covalently closed circular plasmid DNA was isolated by a modified lysis procedure (Horn, N. A., et al., *Hum. Gene Ther.* 6:565-573 (1995)) followed by standard double CsCl-ethidium bromide gradient ultracentrifugation (Sambrook, J., et al., *Molecular Cloning: A Laboratory Manual,* 2nd Ed., Cold Spring Harbor Laboratory Press, Plainview, N.Y. (1989)). Alternatively, SEAP and preproinsulin encoding plasmid DNAs were purified using Giga columns from Qiagen (Valencia, Calif.) according to the kit instructions. All plasmid preparations were free of detectable chromosomal DNA, RNA and protein impurities based on gel analysis and the bicinchoninic protein assay (Pierce Chem. Co., Rockford Ill.). Endotoxin levels were measured using Limulus Amebocyte Lysate assay (LAL, Associates of Cape Cod, Falmouth, Mass.) and were less than 0.6 Endotoxin Units/mg of plasmid DNA. The spectrophotometric $A_{260}/A_{280}$ ratios of the DNA solutions were typically above 1.8. Plasmids were ethanol precipitated and resuspended in water at 4° C. until completely dissolved. DNA was stored at −20° C. until use. DNA was diluted by mixing it with 300 mM salt solutions and by adding appropriate amount of USP water to obtain 1 mg/ml plasmid DNA in the desired salt at the desired molar concentration.

Injections of Plasmid DNA

The quadriceps muscles (or tibialis anterior muscles for SEAP plasmids) of restrained awake mice (female 6-12 week old BALB/c or Nude, nu/nu, from Harlan Sprague Dawley, Indianapolis, Ind.) were injected with 50 μg of DNA in 50 μl solution using a disposable sterile, plastic insulin syringe and 28G ½ needle (Becton-Dickinson, Franklin Lakes, N.J., Cat. No. 329430) fitted with a plastic collar cut from a micropipette tip, all as previously described (Hartikka, J., et al., *Hum. Gene Ther.* 7:1205-1217 (1996)). The tissues were extracted and assayed as described in Manthorpe, M., et al., "Quantification of plasmid DNA expression in vivo," in *Gene Quantification*, Ferre, F., ed., F. Birkhäuser, Boston, Mass. (1998), pp. 343-368. Briefly, tissues were rapidly collected and frozen, they were combined with and frozen into a lysis buffer, the tissue was then pulverized with a drill bit run in reverse direction, the resulting powder was thawed, and was extracted two times with extraction buffer. Nude mice were injected with VR3301 DNA bilaterally on three consecutive days for a total of 300 μg DNA per mouse. Lungs were instilled with 132 μg plasmid DNA complexed with GAP-DLRIE/DOPE in solution and extracted all as described (Wheeler, C. J., et al., *Proc Natl Acad Sci USA* 93:11454-11459 (1996)).

Animal care throughout the study was in compliance with the "Guide for the Use and Care of Laboratory Animals", Institute of Laboratory Animal Resources, Commission on Life Sciences, National Research Council, National Academy Press, Washington, D.C., 1996 as well as with Vical's Institutional Animal Care and Use Committee.

Enzyme Assays

Luciferase activity was assayed using a Dynatech model ML2250 microplate luminometer (Chantilly, Va.) as previously described (Hartikka, J., et al., *Hum. Gene Ther.* 7:1205-1217 (1996)). The luciferase content of the samples was calculated from Relative Light Units using a standard curve of purified firefly luciferase (Analytical Luminescence Laboratory, Sparks, Md., Cat. No. 2400), which was diluted in pooled extract from uninjected muscles to control for quenching. Luciferase values were expressed as ng luciferase per muscle. The level of β-galactosidase expression in muscle extracts was quantified using a chemiluminescent assay according to the manufacturer's instructions (Roche Molecular Biochemicals, Indianapolis, Ind., Cat. No. 1758241). A standard curve, prepared in pooled extract from uninjected muscles, was included on each plate using the β-galactosidase enzyme standard included in the kit.

Sera from nude mice injected with VR3301 were collected at various times post-injection. Five μl of serum was mixed with 15 μl distilled $H_2O$ and placed into individual wells of a 96 well plate (e.g., Costar EIA/RIA A/2 #3690, available from Corning, Inc). A serial dilution of EIA grade calf intestinal alkaline phosphatase (CIP, available from Roche Molecular Biochemicals, cat. # 567 744) in PBS containing 0.05% Bovine Serum Albumin (BSA) was used to produce a standard curve. Samples were assayed in duplicate. Plates were sealed, incubated at 65° C. for 30 min and spun for 5 min at 4000 rpm at room temperature. Each well received 100 μl substrate solution containing 1 mg/ml para-nitrophenyl phosphate (PNPP, available from Roche Molecular Biochemicals, cat. # 107 905) and 1 mM $MgCl_2$ in 1M diethanolamine, pH 9.8. The samples were analyzed using a Molecular Devices Opti Max plate reader (Sunnyvale, Calif.). The plate reader was pre-warmed to 37° C. and a standard kinetic program was used to assay the samples at a wavelength of 405 nm for 30 min.

NP, Proinsulin, and β-galactosidase ELISA

Sera were collected at different times before and after plasmid DNA injections. Ninety-six well plates (available from Corning Incorporated, Acton, Mass., Cat. No. 3690) were coated with 36 ng/50 μl of Borate Buffered Saline (BBS)/well of NP purified from recombinant baculoviral extracts (available from Imgenix Corporation), commercial rat proinsulin (available from Crystal Chem, Chicago, Ill.) or 5 μl/50 μl of β-galactosidase protein (available from Sigma). The plates were stored overnight at +4° C. and the wells washed twice with Borate Buffered Saline Tween (BBST) (89 mM Boric Acid+90 mM NaCl, pH 8.3+234 mM NaOH supplemented with 0.05% Tween 20® (v/v)). The wells were then incubated 90 minutes with BB (BBST in which the Tween was replaced with 5% non-fat milk in 1×BBS) and washed twice with BBST again. Two-fold serial dilutions of mouse serum in BB starting at 1:20 were made in successive wells and the solutions were incubated for 2 hours at room temperature. Wells were then rinsed four times with BBST. Sera from mice hyperimmunized with VR4700 NP, VR3502, or VR1412 plasmid DNA were used as a positive control and pre-immune sera were used as negative controls.

To detect specific antibodies, alkaline phosphatase conjugated goat anti-mouse IgG-Fc (e.g., from Jackson Immunoresearch Laboratories, Inc. West Grove, Pa., Cat. No. 115-055-008) diluted 1:5000 in BBS were added at 100 μg/well and the plates were incubated at room temperature for 2 hours. After 4 washings in BBST, the substrate (1 mg/ml p-nitrophenyl phosphate, e.g., from Calbiochem-Novabiochem Corp., San Diego, Calif., Cat. No. 4876 in 50 mM sodium bicarbonate buffer, pH 9.8 and 1 mM $MgCl_2$) was incubated for 90 min at room temperature and absorbance readings were performed at 405 nm. The titer of the sera was determined by using the reciprocal of the last dilution still giving a signal two times above background. Background was established using pre-immune serum diluted 1:20. Serum concentrations of human IFN-ω were measured using a commercially available kit with a detection limit of 2 pg/ml (available from Alexis Corp., San Diego, Calif.).

Hematocrit Measurements

Hematocrits were measured by centrifugation of blood obtained from the retro-orbital cavity of mice. Blood samples were collected in 75 μl heparinized capillary tubes and analyzed using HemaSTAT II microhematocrit centrifuge (Separation Technology, Inc., Altamone Springs, Fla.).

Histology

For whole muscle staining, quadriceps were fixed for 3 hours at room temperature in 2% paraformaldehyde in PBS, washed 3 times for 20 min each in PBS and incubated for 18 hours at 37° C. in a solution containing 2 mM $MgCl_2$, 5 mM potassium ferricferrocyanide and 1 mg/ml 5-bromo-4-chloro-3-indoyl-β-D-galactosidase (available from Life Technologies, Inc. (LTI), Gaithersberg, Md.) in PBS. After incubation, the muscles were washed 3 times for 10 min each in 3% dimethyl sulfoxide in PBS and stored in PBS at 4° C. until analysis. To prepare stained tissue cross sections, quadriceps were snap-frozen in liquid nitrogen-cooled isopentane, cut in half, embedded in OCT medium (available from VWR, McGraw Park, Ill.) and 10 μm sections were cut using a Jung Frigocut Model 2800E cryostat (Leica, Foster City, Calif.). Sections were collected on 1% gelatin coated glass slides, brought to room temperature and stained for 2 hours at 37° C. in the same reagent as for whole mounts above except that the beta-galactosidase reagent concentration was 200 μg/ml. The sections were then counterstained with Harris hematoxylin in acetic acid, rinsed in tap water, dehydrated and mounted in Permount (Fisher, Fair Lawn, N.J.). The number of β-galactosidase positive cells per muscle was determined by light microscopy in muscle cross-sections as described (Doh, S. G., et al., *Gene Ther.* 4:648-663 (1997)).

Splenocyte CTL Stimulation Cultures

To generate CTL effector cells from plasmid DNA immunized BALB/c mice, splenocytes were stimulated in culture for 5 days with $NP_{147-155}$ peptide (TYQRTRALV) pulsed, irradiated splenocytes from naïve BALB/c mice. For the stimulation cultures, splenocytes from naive mice were γ-irradiated with 3200 Rads and pulsed with 10 μM of the H-$2K^d$ restricted $NP_{147-155}$ peptide for 40 min at 37° C. Then, $2.5\times10^7$ test splenocytes from DNA immunized mice were incubated at 37° C. in 5.5% $CO_2$ with an equal number of irradiated, pulsed splenocytes from naive mice in 25 $cm^2$ flasks containing 25 ml RPMI 1640 media with L-glutamine and 25 mM HEPES supplemented with 10% fetal bovine serum, penicillin (100 U/ml), streptomycin (100 μg/ml) and $5.5\times10^{-5}$ M β-mercaptoethanol). Tissue culture reagents are all available from LTI. After 24 hours of culture, recombinant murine IL-2 was added to a final concentration of 1 U/ml.

$^{51}Cr$ Release Assay

To measure specific lysis of $NP_{147-155}$ peptide pulsed target cells by CTL effector cells, P815 cells (available from the American Type Culture Collection, Manassas, Va.) were labeled with $Na_2{}^{51}CrO_4$ (NEN Life Scientific Products, Inc., Boston, Mass.). Aliquots of $^{51}Cr$ labeled cells were either pulsed with 10 μM $NP_{147-155}$ or were used unpulsed. For the CTL assay, stimulated splenocytes were serially diluted in 96 well round bottom microtiter plates (available from ICN Biomedicals, Inc., Aurora, Ohio). Target cells were added in a final volume of 100 μl/well. After incubation for 5 hours at 37° C. in 5.5% $CO_2$, 100 μl of RPMI 1640 complete media was added to each well, the plates were centrifuged and 100 μl/well was removed for analysis in a Cobra II gamma counter (Packard Instruments Co., Downers Grove, Ill.). The percentage of specific lysis was calculated as % specific lysis=(a−b/c−b)100 where a is the average cpm released in the presence of effectors, b is the average spontaneous cpm released from target cells incubated in media only and c is the maximum cpm released from target cells in the presence of 1% Triton X-100™.

DNase Inhibition Assay

Quadriceps muscles were harvested from naive mice as previously described (Hartikka, J., et al., *Hum. Gene Ther.* 7:1205-1217 (1996)). Ten muscles were pooled and ground at 4° C. without adding buffer using a Duall tissue grinder with ground glass pestle (Kontes Glass Co., Vineland, N.J.), centrifuged at 13,000×g for 20 min, and the supernatant was collected and stored at −20° C. Serum was collected from 10 naïve mice by orbital sinus puncture, pooled and stored at 4° C. For the assay, VR1255 DNA was diluted to 0.25 μg/ml in the respective solution, mixed with 0.1 volume of muscle extract or serum, and incubated at 37° C. for 2 hours. The samples were neutralized by adding an equal volume of 2% sodium dodecyl sulfate+50 mM EDTA, and 4 μl of each sample was analyzed by electrophoresis on 0.8% agarose Tris Acetate EDTA gels with ethidium bromide staining.

Statistical Evaluations

All statistical comparisons from tissue expression data were performed using the non-parametric Mann-Whitney rank sum test (SigmaStat version 2.03, Jandel Scientific Software, San Rafael, Calif.) and where indicated by the standard Student T-Test. Differences by all statistical methods were considered statistically significant when the p value was less than 0.05.

Example 8

Effect of Various Solutions Containing Sodium Chloride and Sodium Phosphate on Luciferase Plasmid DNA Expression in Murine Muscles The purpose of the present example is to demonstrate the ability of certain salt solutions to increase the levels of plasmid DNA expression when injected into muscle compared with plasmid DNAs formulated in normal saline.

Mouse quadriceps muscles were injected with 50 μg of plasmid VR1223, encoding luciferase, dissolved in 50 μl of either water, saline, PBS, saline plus 100 mM sodium phosphate, 100 mM NaCl, or 100 mM NaCl plus 50 mM sodium phosphate. The muscles were extracted and assayed for luciferase activity 7 days later. The results are shown in Table 9. When the plasmid was dissolved in distilled water, luciferase expression was 25-times lower than when the plasmid was dissolved in saline (4 vs. 119 ng lux/muscle). Injection of the plasmid dissolved in PBS (i.e., saline plus 10 mM sodium phosphate) elicited a marginal, but statistically higher 1.6-fold expression level than saline (186 vs. 119 ng luciferase per muscle, p=0.02). Delivery of the plasmid in a hypertonic solution containing saline plus 100 mM sodium phosphate reduced expression to the level obtained using saline alone (117 vs. 119 ng lux/muscle). A hypoosmotic 100 mM NaCl solution yielded the same expression as isoosmotic saline (112 vs 119 ng lux/muscle), but restoration of osmolarity by the addition of 50 mM sodium phosphate to the 100 mM NaCl increased expression by 1.8 fold (112 vs 203 ng lux/muscle, p=0.03). Thus, sodium phosphate increased luciferase expression.

Example 9

Effect of the Molar Concentration of Sodium Phosphate and pH on Luciferase Plasmid DNA Expression in Murine Muscles The effect of sodium phosphate concentration and pH on the level of luciferase expression from injected plasmid DNA in murine muscles was tested as follows. Plasmid VR1223 DNA was dissolved in solutions containing different concentrations of sodium phosphate in the absence of NaCl, and these were tested for day 7 luciferase expression in quadriceps muscle as described in Example 1 above. The molar concentrations of sodium phosphate tested ranged from 2.5 mM to 300 mM. The averaged data from 5 separate experiments are shown in FIG. 22A. Peak expression occurred when the plasmid DNA was dissolved in 150 mM sodium phosphate, which yielded 386 ng luciferase per muscle which is 4.3-fold higher than the average expression level observed when the DNA is dissolved in saline (indicated by the dashed line at 89 ng luciferase per muscle, p<0.001). The expression levels observed when the DNA was dissolved in 80 mM, 100 mM, 150 mM, and 200 mM sodium phosphate solutions were significantly higher than saline by Mann-Whitney rank sum test ($p<0.05$). Injection of plasmid DNA dissolved in solutions having sodium phosphate concentrations below 40 mM (in the absence of added chloride ion) or above 300 mM resulted in luciferase expression levels equal to or lower than those seen with saline.

To examine the effect of pH, plasmid VR1223 was dissolved in 150 mM sodium phosphate or potassium phosphate at pHs of 6.5, 7.5 or 8.0 and was tested for day 7 expression in quadriceps muscle as described in Example 1 above. The results indicated that an optimal pH of about 6.5 to 7.5, with pH 8.0 being suboptimal (FIG. 22B).

Example 10

Effect of Alternate Salt Solutions on Luciferase Plasmid DNA Expression in Murine Muscles In this example, injection of plasmid DNA encoding luciferase dissolved in 150 mM solutions of various salts which vary either the cation or the anion of normal saline were compared with saline for their ability to stimulate luciferase expression in murine muscle. The results are shown in Table 10.

Table 10A shows the effect on luciferase expression when the plasmid DNA is dissolved in a solution of a salt where the sodium cation in saline is replaced with other cations. Plasmid VR1223 dissolved in the various solutions was tested for day 7 expression in quadriceps muscle as described in Example 1 above. Two salts, $ZnCl_2$ and $FeCl_2$, were only tested in 2 or 3 mice since these salts appeared to cause pain. Solutions containing divalent cations, e.g., magnesium ($Mg^{2+}$), calcium ($Ca^{2+}$), zinc ($Zn^{2+}$) and ferrous iron ($Fe^{2+}$), greatly decreased expression while the solution containing the monovalent cation potassium ($K^+$) elicited the same expression as the monovalent sodium cation ($Na^+$).

Table 10B shows the effect on luciferase expression when the plasmid DNA is dissolved in a solution of a salt where the sodium cation in sodium phosphate was replaced with various other cations. Plasmid VR1223 dissolved in the various solutions was tested for day 7 expression in quadriceps muscle as described in Example 1 above. Just as replacing the sodium cation in saline with potassium cation did not affect luciferase expression, replacing the sodium cation in sodium phosphate with potassium cation also had no effect. Thus, a solution of 150 mM potassium phosphate stimulated expression just as well as solution of 150 mM sodium phosphate when both were compared with saline. When plasmid DNA was dissolved in 150 mM solutions of dibasic or monobasic sodium phosphate (not adjusted for pH), luciferase expression was only slightly stimulated over saline. The best stimulation of expression occurred when the plasmid DNA was dissolved in a 150 mM solution of sodium or potassium phosphates which is a mixture of the dibasic and monobasic forms balanced to achieve the desired pH (in this case, pH 7.0). Other phosphate salts tested, i.e., when the cation was $Mg^{3+}$, $Ca^{3+}$, Aluminum ($Al^{3+}$) or ferric iron ($Fe^{3+}$) resulted in inhibited expression relative to saline.

Table 10C shows the effect on luciferase expression when the plasmid DNA is dissolved in a solution of a salt where the phosphate anion in 150 mM sodium phosphate was replaced with various other anions. Plasmid VR1223 dissolved in the various solutions was tested for day 7 expression in quadriceps muscle as described in Example 1 above. Injection of the plasmid DNA in solutions of the sodium salts of acetate, pyruvate, bicarbonate and sulfate all increased luciferase expression compared with saline. Sodium citrate yielded the same luciferase expression as saline but sodium oxalate inhibited luciferase expression. Thus, according to Table 10C, stimulatory effects of various 150 mM salt solutions can be ranked in order of their relative enhancement of luciferase expression as follows: sodium phosphate=potassium phosphate=sodium acetate>sodium pyruvate=sodium bicarbonate=sodium sulfate>saline=potassium chloride=sodium citrate. The rest of the solutions tested inhibited expression compared with saline.

The effects of osmolarity and pH on the ability of certain salt solutions to enhance luciferase expression in murine muscle was tested as follows. The osmolarity and pH of each salt solution (150 mM concentration unless otherwise indicated) shown in Tables 11-A and 11-B were measured and plotted vs. the 7-day luciferase expression level obtained with that solution (FIGS. 22C and 2D). The pH values and osmolarities of the various salt solutions, as well as the relative 7-day luciferase expression observed when plasmid VR1223 was dissolved in each solution and injected into murine muscle, are shown in Table 11-A and 11-B. The osmolarity graph (FIG. 22D) revealed that solutions with osmolarities between 271 and 349 mmol/kg generally yielded the highest expression levels but exceptions included 50 & 100 mM sodium phosphate at 83 and 270 mmol/kg (respective expression levels 2.1 and 2.3 fold those of saline at 310 mmol/kg) and sodium citrate at 394 mmol/kg (expression level was the same as with saline). The 150 mM sodium phosphate solution yielded an expression level that was 4-fold higher than that of saline, yet both solutions had the same osmolarity (310 vs. 308 mmol/kg, respectively). The pH graph (FIG. 22C) revealed that the highest expression levels were generally obtained with solutions at pH 6.0 to 7.5. However, some exceptions were sodium sulfate, pH=5.5, and sodium bicarbonate, pH 9.0, which yielded expression levels that were 2.6 and 2.8-fold, respectively, over saline at pH 5.5. Furthermore, the magnesium phosphate solution had a pH=7.0 but yielded an expression level lower than saline.

The reproducibility of enhanced luciferase DNA expression when the plasmid DNA is dissolved in a solution of 150 mM sodium phosphate was tested as follows. Nine different experiments were carried out to test luciferase expression levels when plasmid VR1223 was dissolved in 150 mM sodium phosphate for injection into mouse skeletal muscle. In each of the experiments, 10 quadriceps muscles were injected with 50 μg of plasmid VR1223 in 50 μl of either saline or 150 mM sodium phosphate. Muscles were collected and assayed for luciferase expression at 7 days. The averaged results for each experiment are shown in FIG. 23. Compared with saline, sodium phosphate enhanced luciferase expression in all 9 experiments, with the enhancement ranging from 2.5-fold (156 vs. 384 ng lux/muscle for Exp. #9) to 7.3-fold (49 vs. 362 ng lux/muscle in Exp. # 1). In these replicate experiments, the average enhancement by sodium phosphate for all 9 experiments was 4.1-fold (120 vs. 490 ng luciferase/muscle).

Example 11

Expression of β-galactosidase and Human Interferon-Omega Following Intramuscular Injection of Plasmid DNA is Enhanced When the Plasmid is Injected in a Sodium Phosphate Solution The effect of a sodium phosphate solution on the expression of polypeptides other than luciferase following intramuscular injection of plasmid DNAs encoding the polypeptides was examined as follows. Plasmids encoding non-secreted β-galactosidase (VR1418) and secreted human interferon-omega (IFN-ω; VR4151) in saline or 150 mM sodium phosphate were injected into mouse quadriceps as described in the materials and methods and Example 1. Muscle extracts were assayed for β-galactosidase and the serum was assayed for circulating levels of IFN-ω. The 7 day post-DNA injection protein expression data, including luciferase plasmid DNA run in parallel for comparison, are shown in FIG. 24. Injection of the plasmid DNAs dissolved in 150 mM sodium phosphate enhanced expression of all three proteins over saline. Compared with saline, injection of plasmid DNA in 150 mM sodium phosphate enhanced expression of luciferase in muscle by 4.8-fold (769 vs. 159 ng/muscle; $p<0.001$), β-galactosidase in muscle by 3.3-fold (9.8 vs. 3.0 ng/muscle; $p=0.001$) and serum IFN-ω levels by 2.5-fold (0.35 vs. 0.14 ng ml serum; $p=0.020$).

Plasmid DNA dissolved in PBS, run in parallel, elicited statistically equivalent expression as saline for the plasmids encoding β-galactosidase and IFN plasmids (data not shown).

Plasmid DNA VR1418 encoding β-galactosidase was dissolved in sodium phosphate solutions at the various molar concentrations tested in Example 2. Quadriceps muscles were injected with 50 μl of each solution containing 10 μg of plasmid VR1418, and the muscles were tested for 7-day expression levels. As with luciferase expression, as shown in Example 2, 150 mM sodium phosphate was the optimal molar concentration for β-galactosidase expression (data not shown). This similar effect occurred despite the fact that the β-galactosidase gene on VR1418 is driven by an RSV promoter, rather than the CMV promoter which drives expression of luciferase on plasmid VR1223 and IFN-ω on plasmid VR4151, and despite the fact that 10 μg of plasmid DNA was injected per muscle rather than 50 μg.

Example 12

Expression of Human Placental Alkaline Phosphatase, Rat Proinsulin and Mouse Erythropoietin Following Intramuscular Injection of Plasmid DNA is Enhanced When the Plasmid is Injected in a Sodium Phosphate Solution Three different plasmid DNAs encoding a secreted form of human placental alkaline phosphatase (SEAP; VR3301), rat preproinsulin (VR3502) or mouse erythropoietin (EPO; VR2901) were injected into mouse skeletal muscle in saline or 150 mM sodium phosphate solutions as described in the Materials and Methods and in Example 1. The mice were monitored over time for blood levels of SEAP or proinsulin or for hematocrits. The results are shown in FIG. 25. In the case of SEAP, plasmid DNA was injected into the tibialis anterior muscles, and nude mice were used to prevent an immune response to the foreign transgene product. The kinetics of blood SEAP levels from mice injected with DNA dissolved in both saline and 150 mM sodium phosphate were similar. SEAP protein expression rose to a peak level at 7 days, then declined to 40-45% of the maximum expression level where it remained for two months. The Sodium phosphate solution significantly enhanced SEAP expression by 1.4 to 1.8-fold compared with saline ($n=15$; p 0.002 to 0.037) over the time course. A parallel experiment using PBS showed expression to be statistically equivalent to that obtained with saline (data not shown). Thus, injection of plasmid DNA dissolved in a 150 mM sodium phosphate solution resulted in a higher level of sustained expression than when dissolved in saline.

Plasmid DNA encoding rat preproinsulin, dissolved in either 150 mM sodium phosphate or saline, was injected into the muscles of immunocompetent mice. Injection of the plasmid DNA in the sodium phosphate solution enhanced expression over a 2 week period by 1.9 to 3.8-fold compared with saline ($n=10$; $p<0.01$). Proinsulin expression eventually declined to very low levels in both groups, possibly due to the generation of measurable anti-proinsulin antibodies (data not shown).

Plasmid DNA encoding mouse EPO, dissolved in either 150 mM sodium phosphate or saline, was injected into the muscles of immunocompetent mice. Hematocrit levels, which correlate with the expression of erythropoeitin, rose steadily over 4 weeks. Control mice injected with 20 μg of DNA encoding canine Factor IX exhibited a constant hematocrit averaging 48. Injection of plasmid DNA dissolved in 150 mM sodium phosphate solution resulted in higher hematocrit levels than the injection of plasmid DNA dissolved in saline at all the time points tested. This enhancement ranged from 1.4 to 2.1-fold ($n=10$; $p=0.02$-$0.001$).

Example 13

Histological Analysis of Muscle Tissues Injected with Plasmid DNA Encoding β-galactosidase Dissolved in Either Sodium Phosphate or Saline Individual muscle cells were examined for β-galactosidase expression as follows. Twenty-six BALB/c quadriceps muscles each were injected with 50 μg of plasmid VR1412 DNA (expressing β-galactosidase) in 50 μl of either saline or 150 mM sodium phosphate, according to the methods disclosed in the Materials and Methods and in Example 1. The muscles were collected 7 days later and stained for β-galactosidase. A quantitative analysis of β-galactosidase-stained fibers using previously detailed methods (Doh, S. G., et al., *Gene Ther.* 4:648-663 (1997)) revealed a significantly greater number of β-galactosidase-stained myofiber cells in the sodium phosphate group than in the saline group. Cell counts of sections taken from the midline of 20 muscles (10 muscles for each group) revealed that the sodium phosphate group contained more β-galactosidase-positive myofiber cells than did the saline group (average of 108+/−21 vs. 186+/−43 myofiber cells/muscle section; $p=0.02$; $n=10$). Thus, plasmid DNA dissolved in 150 mM sodium phosphate apparently has an enhanced ability to transduce muscle cells relative to plasmid DNA dissolved in saline.

Example 14

Sodium Phosphate Inhibits Muscle DNase Activity

While not being bound by theory, the inventors believe that one mechanism by which sodium phosphate could enhance plasmid DNA expression in muscle is by preventing or inhibiting DNA degradation. To assess this possibility, aliquots of plasmid DNA in various aqueous solutions were spiked with mouse muscle extract or serum as described in the materials and methods section, above. The reactions were incubated for 2 hours at 37° C. in the presence of water, saline or 150 mM sodium phosphate. After incubation, DNA degradation was analyzed by agarose gel electrophoresis. The results are shown in FIG. 26. Incubation of plasmid DNA in water with 10% v/v muscle extracts or serum resulted in the complete degradation of the DNA. Compare lanes 1 vs. 2 in FIG. 26. A significant amount of the DNA was protected in the presence of both saline and sodium phosphate. However, the sodium phosphate solution protected the DNA considerably better than did saline. Compare lanes 3 and 4 in FIG. 26; note the presence of remaining closed circular form in the muscle extract and the remaining nicked form in the serum for the DNA in the sodium phosphate solution. Similar results were obtained in replicate experiments. This inhibition of DNA degradation correlates with the increase in gene expression observed for DNA injected into muscle (compare ng luciferase expression values taken form Tables I and II and shown at the bottom of each lane in FIG. 26 with the presence of nicked and closed circular DNA).

Example 15

Plasmid DNA Immunization Utilizing a Sodium Phosphate Solution

The effect of sodium phosphate on the elicitation of an immune response upon injection of plasmid DNA encoding an immunogen was examined as follows. Mice were vaccinated intramuscularly with plasmid VR4700, encoding the influenza nucleoprotein. The DNA was dissolved in either saline or 150 mM sodium phosphate. The mice were monitored for the presence of circulating anti-NP antibodies and for an NP-specific cytotoxic T lymphocyte response (CTL). The antibody data at 6 weeks and CTL data at 9 weeks post-vaccination are shown in FIG. 27. FIG. 27A shows that in three replicate experiments (labeled 1-3, n=10 mice per experiment), the sodium phosphate solution enhanced serum anti-NP antibody titers compared with saline solution. The enhancement by sodium phosphate was significant in all 3 experiments ($p<0.04$) as well as in the average of all three experiments ($p<0.001$). Plasmid VR VR4700, injected in PBS, was run in parallel and the antibody titers were not statistically different from the plasmid injected in saline (data not shown). FIG. 27B shows that anti-NP specific CTL activity was statistically similar ($p>0.05$) in the saline and 150 mM sodium phosphate group. A repeat set of CTL experiments showed the same result (data not shown).

Example 16

Polypeptide Expression in a Non-Muscle Tissue is Enhanced by Use of a Sodium Phosphate Solution and a Cationic Lipid for Delivery of Plasmid DNA The effect of a sodium phosphate solution on the enhancement of polypeptide expression from plasmid DNA delivered to a non-muscle tissue using a cationic lipid was evaluated as follows. Mouse lungs were instilled with plasmid VR1223 encoding luciferase combined with the cationic lipid GAP-DLRIE and co-lipid DOPE in water or selected concentrations of sodium phosphate as described in the Materials and Methods above. The use of DNA lipid complexes in water and collection at day 3 were previously found to yield peak lung transfection (Wheeler, C. J., et al., *Proc Natl Acad Sci USA* 93:11454-11459 (1996); Sawa, T., et al., *Hum. Gene Ther* 7:933-941 (1996)). The results are shown in FIG. 8. The level of luciferase expression in lung when the plasmid/lipid mixture was delivered to the lung in water (0.94 ng lux/lung) is comparable with published reports (Wheeler, C. J., et al., *Proc Natl Acad Sci USA* 93:11454-11459 (1996)) and is considerably below the level of expression obtained in muscle tissue using the same vectors without lipid. Unlike with muscle, when the plasmid/lipid mixture was delivered to the lung in a 150 mM sodium phosphate solution, luciferase expression was inhibited compared with water (0.22 vs. 0.94 ng lux/lung; $p<0.001$). However, when the plasmid/lipid mixture was delivered to the lung in a 2.5 mM sodium phosphate solution, luciferase expression was enhanced by 5.5-fold compared with water (5.2 vs. 0.94 ng lux/lung; $p<0.001$). Intermediate to these values, when the plasmid/lipid mixture was delivered to the lung in a 10 mM sodium phosphate solution, luciferase expression was enhanced compared with water, but not as much as with 2.5 mM sodium phosphate. When the plasmid/lipid mixture was delivered to the lung in saline, luciferase expression was inhibited compared with water (0.14 ng lux/lung; data not shown). Thus, sodium phosphate enhances luciferase expression upon delivery of a plasmid DNA/lipid mixture in lung, but does so at a much lower sodium phosphate molar concentration than is effective in muscle.

TABLE 9

Effects of Selected Sodium Chloride Vehicles on Lucifrease Plasmid DNA expression in Muscle

| ng Lux per Muscle | ±Std. Error | n | Fold Saline | Salt Solution |
|---|---|---|---|---|
| 4 | 1 | 30 | 0.03 | Double-distilled water |
| 119 | 6 | 413 | 1.0 | 150 mM Sodium Chloride (saline) |
| 186 | 11 | 357 | 1.6 | 150 mM Sodium Chloride (saline) + 10 mM Sodum Phosphate (PBS) |
| 117 | 64 | 20 | 1.0 | 150 mM Sodum Chloride (saline) + 100 mM Sodium Phosphate |
| 112 | 38 | 20 | 0.9 | 100 mM Sodium Chloride |
| 203 | 42 | 40 | 1.7 | 100 mM Sodium Chloride + 50 mM Sodium Phosphate |

TABLE 10

Effects of Selected Vehicles on Lucifrease Plasmid DNA expression in Muscle

| ng Lux/ Muscle | ±Std. Error | n | Fold Saline | Salt Solution | Formula |
|---|---|---|---|---|---|
| | | | | A. Chloride Salts at 150 mM | |
| 119 | 6 | 413 | 1.0 | Sodium Chloride | NaCl |
| 124 | 32 | 10 | 1.0 | Potassium Chloride | KCl |
| 1 | 0.4 | 10 | <0.1 | Magnesium Chloride | $MgCl_2 \cdot 6H_2O$ |
| 0.3 | 0.2 | 10 | <0.1 | Calcium Chloride | $CaCl_2 \cdot 2H_2O$ |
| 0.1 | 0.1 | 6 | <0.1 | Zinc Chloride | $ZnCl_2$ |
| 0.0 | 0.0 | 4 | <0.1 | Ferrous Chloride | $FeCl_2 \cdot 4H_2O$ |
| | | | | B. Phosphate salts at 150 mM | |
| 481 | 36 | 120 | 4.0 | Sodium Phosphate | $NaH_2PO_4$/ $K_2HPO_4$ |
| 282 | 56 | 20 | 2.4 | Sodium Phosphate -- dibasic | $Na_2HPO_4$ |
| 198 | 44 | 20 | 1.7 | Sodium Phosphate -- monobasic | $Na_2HPO_4$ |
| 449 | 40 | 20 | 3.8 | Potassium Phosphate | $KH_2PO_4/K_2HPO_4$ |
| 22 | 6 | 8 | 0.2 | Magnesium Phosphate | $MgHPO_4 \cdot 3H_2O$ |
| 12 | 2 | 8 | 0.1 | Calcium Phosphate | $CaHPO_4$ |
| 4 | 1 | 8 | <0.1 | Aluminum Phosphate | $AlPO_4$ |
| 0.4 | 0 | 10 | <0.1 | Ferric Phosphate | $FePO_4$ |

TABLE 10-continued

Effects of Selected Vehicles on Lucifrease Plasmid DNA expression in Muscle

| ng Lux/ Muscle | ±Std. Error | n | Fold Saline | Salt Solution | Formula |
|---|---|---|---|---|---|
| C. Sodium salts at 150 mM | | | | | |
| 119 | 6 | 413 | 1.0 | Sodium Chloride | NaCl |
| 481 | 36 | 120 | 4.0 | Sodium Phosphate | $NaH_2PO_4$/ $Na_2HPO_4$ |
| 498 | 119 | 10 | 4.1 | Sodium Acetate | $C_2H_3O_2Na•3H_2O$ |
| 364 | 64 | 19 | 3.1 | Sodium Pyruvate | $C_3H_3O_3Na$ |
| 330 | 47 | 20 | 2.8 | Sodium Bicarbonate | $NaHCO_2$ |
| 312 | 83 | 10 | 2.6 | Sodium Sulfate | $NaSO_4$ |
| 90 | 25 | 14 | <0.1 | Sodium Citrate | $C_6H_5Na_3O•2H_2O$ |
| 15 | 2 | 8 | <0.1 | Sodium Oxalate | $C_2O_4Na_2$ |

TABLE 11-A

| Salt | PH | lux |
|---|---|---|
| Zinc Chloride | 5.0 | 0.1 |
| Ferrous Chloride | 5.0 | 0.0 |
| Aluminum Phosphate | 5.0 | 4 |
| 150 mM NaCl (Saline) | 5.5 | 119 |
| 100 mM NaCl | 5.5 | 112 |
| Potassium Chloride | 5.5 | 124 |
| Magnesium Chloride | 5.5 | 1 |
| Calcium Chloride | 5.5 | 0.3 |
| Sodium Chloride | 5.5 | 119 |
| NaP-monobasic | 5.5 | 198 |
| Sodium Sulfate | 5.5 | 312 |
| Calcium Phosphate | 6.0 | 12 |
| Sodium Pyruvate | 6.0 | 364 |
| Ferric Phosphate | 6.5 | 0.4 |
| Sodium Acetate | 6.5 | 498 |
| Sodium Oxalate | 6.5 | 15 |
| Magnesium Phosphate | 7.0 | 22 |
| Saline + 10 mM Na—P (PBS) | 7.2 | 186 |
| 75 mM NaCl + 75 mM Na—P | 7.2 | 177 |
| 50 mM Sodium Phosphate | 7.2 | 254 |
| 100 mM Sodium Phosphate | 7.2 | 270 |
| 150 mM Sodium Phosphate | 7.2 | 481 |
| Sodium Phosphate | 7.2 | 481 |
| Potassium Phosphate | 7.5 | 449 |
| Sodium Citrate | 7.5 | 108 |
| 50 mM Sodium Citrate | 7.5 | 83 |
| NaP-dibasic | 8.0 | 282 |
| Sodium Pyrophosphate | 9.0 | 3 |
| Sodium Bicarbonate | 9.0 | 330 |

TABLE 11-B

| Salt | Osm | lux |
|---|---|---|
| Calcium Phosphate | 36 | 12 |
| Aluminum Phosphate | 37 | 4 |
| Magnesium Phosphate | 39 | 22 |
| 50 mM Sodium Phosphate | 83 | 254 |
| 50 mM Sodium Citrate | 164 | 83 |
| Ferric Phosphate | 165 | 0.4 |
| 100 mM NaCl | 215 | 112 |
| 100 mM Sodium Phosphate | 232 | 270 |
| Sodium Acetate | 271 | 498 |
| Sodium Pyruvate | 271 | 364 |
| Sodium Bicarbonate | 727 | 330 |
| NaP-monobasic | 277 | 198 |
| Potassium Chloride | 280 | 124 |
| 150 mM NaCl + 10 mM Na—P (PBS) | 292 | 186 |
| 75 mM NaCl + 75 mM Na—P | 308 | 177 |
| 150 mM Sodium Phosphate | 308 | 481 |
| 150 mM NaCl (Saline) | 310 | 119 |
| Potassium Phosphate | 323 | 449 |
| Sodium Oxalate | 346 | 15 |
| Sodium Sulfate | 349 | 312 |
| NaP-dibasic | 357 | 282 |
| Zinc Chloride | 358 | 0.1 |
| Magnesium Chloride | 360 | 1 |
| Calcium Chloride | 362 | 0.3 |
| Ferrous Chloride | 362 | 0.0 |
| Sodium Pyrophosphate | 363 | 3 |
| Sodium Citrate | 394 | 108 |

It clear that the invention may be practiced otherwise than as particular described in the foregoing description and examples.

Numerous modifications and variations of the present invention are possible in light of the above teachings and, therefore, are within the scope of the appended claims.

The entire disclosure of all publications (including patents, patent application, journal articles, laboratory manuals, books, or other documents) cited herein are hereby incorporated by reference.

What is claimed is

1. A method of treating cancer or metastasis thereof in a mammal, comprising:

administering into a muscle tissue of said mammal a non-infectious, non-integrating DNA encoding interferon-omega, or an active fragment thereof, through operable association with one or more transcription control elements, wherein said DNA is administered free from ex vivo cells;

such that the interferon-omega encoded by said DNA is expressed in vivo, and such that said interferon-omega is present in the blood stream of said mammal in an amount effective to treat said cancer, or metastasis thereof.

2. The method of claim 1, wherein said cancer is selected from the group consisting of renal cell carcinoma, colorectal carcinoma, lymphoma, Kaposi's sarcoma, melanoma, prostate cancer, ovarian cancer, lung cancer, liver cancer, head and neck cancer, bladder cancer, uterine cancer, bone cancer, leukemia, breast cancer, non-melanoma skin cancer, glioma, solid cutaneous tumor, epidermoid carcinoma, metastases of any of thereof, and combinations of any of thereof.

3. The method of claim 1, wherein said DNA is administered intramuscularly.

4. The method of claim 1, wherein said interferon ω is a polypeptide comprising amino acids 1 to 172 in SEQ ID NO:8.

5. The method of claim 4, wherein said interferon ω is a polypeptide comprising amino acids −23 to 172 in SEQ ID NO:8.

6. The method of claim 1, wherein said DNA is VR4151 (SEQ ID NO:4).

7. The method of claim 1, wherein said DNA is dissolved in an aqueous solution.

8. The method of claim 7, further comprising sodium phosphate dissolved in said aqueous solution at a molar concentration ranging from about 20 mM to about 300 mM.

9. The method of claim 1, wherein said DNA is administered free from association with transfection-facilitating proteins, viral particles, liposomes, cationic lipids, and calcium phosphate precipitating agents.

10. The method of claim 1, wherein said DNA is administered as a complex of said DNA and one or more cationic compounds selected from the group consisting of cationic lipids, cationic peptides, cationic proteins, cationic polymers other than lipids or peptides, and mixtures thereof.

11. The method of claim 10, wherein said complex further comprises one or more neutral lipids.

12. A method of treating cancer, or metastasis thereof, in a mammal, comprising:

(a) the method of claim 1 in combination with one or more additional cancer treatment methods selected from the group consisting of surgery, radiation therapy, chemotherapy, immunotherapy, and gene therapy.

13. A pharmaceutical composition comprising about 1 ng to 20 mg of a non-infectious, non-integrating polynucleotide construct comprising a polynucleotide selected from the group consisting of:

(a) a polynucleotide that hybridizes under stringent conditions to the nucleotide sequence of SEQ ID No. 7 or the complement thereof, wherein said polynucleotide sequence encodes a polypeptide that has antiproliferative activity when added to NIH-OVCAR3 cells in vitro;

(b) a polynucleotide that encodes a polypeptide comprising an amino acid sequence which, except for at least one but not more than 20 amino acid substitutions, deletions, or insertions, is identical to amino acids −23 to 172 or 1 to 172 in SEQ ID No. 8, wherein said polypeptide has antiproliferative activity when added to NIH-OVCAR3 cells in vitro; and (c) a polynucleotide that encodes a polypeptide comprising amino acids 86 to 172 in SEQ ID No. 8, wherein said polypeptide has antiproliferative activity when added to NIH-OVCAR3 cells in vitro;

wherein said polynucleotide is dissolved in an aqueous solution; and sodium phosphate dissolved in said aqueous solution at a molar concentration ranging from about 20 mM to about 300 mM, and reaction, association, or dissociation products thereof.

14. A pharmaceutical composition obtained by complexing about 1 ng to 20 mg of a non-infectious, non-integrating polynucleotide construct comprising a polynucleotide selected from the group consisting of:

(a) a polynucleotide that hybridizes under stringent conditions to the nucleotide sequence of SEQ ID No. 7 or the complement thereof, wherein said polynucleotide sequence encodes a polypeptide that has antiproliferative activity when added to NIH-OVCAR3 cells in vitro;

(b) a polynucleotide that encodes a polypeptide comprising an amino acid sequence which, except for at least one but not more than 20 amino acid substitutions, deletions, or insertions, is identical to amino acids −23 to 172 or 1 to 172 in SEQ ID No. 8, wherein said polypeptide has antiproliferative activity when added to NIH-OVCAR3 cells in vitro; and (c) a polynucleotide that encodes a polypeptide comprising amino acids 86-172 of SEQ ID No. 8, and wherein said polypeptide has antiproliferative activity when added to NIH-OVCAR3 cells in vitro;

wherein said polynucleotide is dissolved in an aqueous solution; and sodium phosphate dissolved in said aqueous solution at a molar concentration ranging from about 20 mM to about 300 mM, and reaction, association, or dissociation products thereof.

15. The method of claim 14, wherein said polynucleotide is DNA operably linked to a promoter.

16. A method of treating cancer in a mammal, comprising:

administering into a tissue of said mammal a non-infectious, non-integrating polynucleotide in aqueous solution, wherein said polynucleotide encodes a cytokine, or an active fragment thereof, selected from the group consisting of an interferon ω, and a combination of an interferon ω and an interferon α, and an active fragment of any of thereof; and sodium phosphate dissolved in said aqueous solution at a molar concentration ranging from about 20 mM to about 300 mM, and reaction, association, or dissociation products thereof;

such that said cytokine is delivered to a tumor in a therapeutically effective amount.

17. A method of treating cancer in a mammal, comprising: administering into a body cavity of said mammal a non-infectious, non-integrating polynucleotide construct comprising a polynucleotide encoding interferon-omega, or an active fragment thereof, such that the interferon-omega is delivered to a tumor in a therapeutically effective amount.

18. The method of claim 17, wherein said construct is free from association with transfection-facilitating proteins, viral particles, and calcium phosphate precipitating agents.

19. The method of claim 17, wherein said construct is administered as a complex of said construct and one or more cationic lipids.

20. The method of claim 19, wherein said complex further comprising one or more neutral lipids.

21. A method of selectively transfecting malignant cells in a body cavity of a mammal, comprising: administering into a body cavity of said mammal a non-infectious, non-integrating polynucleotide construct comprising a polynucleotide encoding interferon-omega, or an active fragment thereof, such that said interferon-omega is delivered substantially to and expressed in malignant cells within said body cavity.

22. The method of claim 21, wherein said construct is free from association with transfection-facilitating proteins, viral particles, and calcium phosphate precipitating agents.

23. The method of claim 21, wherein said construct is administered as a complex of said construct and one or more cationic lipids.

24. The method of claim 23, wherein said complex further comprising one or more neutral lipids.

25. A composition comprising:

(a) about 1 ng to about 30 mg of a polynucleotide in aqueous solution which operably encodes an interferon-omega polypeptide upon delivery to vertebrate cells in vivo;

(b) sodium phosphate dissolved in said aqueous solution at a molar concentration ranging from about 20 mM to about 300 mM, and reaction, association, or dissociation products thereof.

26. The composition of claim 25, further comprising a transfection facilitating agent selected from the group consisting of calcium phosphate, alum, gold, tungsten, or other metal particles, peptides, proteins, and polymers.

27. A method for delivering a polypeptide to a vertebrate, comprising administering into a tissue or cavity of said vertebrate the composition of claim 25;

wherein said polypeptide is expressed in the vertebrate in an amount sufficient to be detectable.

28. A method for delivering a therapeutic polypeptide to a vertebrate, comprising administering into a tissue or cavity of said vertebrate in need of the therapy provided by said polypeptide the composition of claim 25;

wherein said polypeptide is a therapeutic polypeptide, and wherein said therapeutic polypeptide is expressed in the vertebrate in a therapeutically effective amount.

29. A method of enhancing or modulating a vertebrate immune response comprising administering into a tissue or cavity of a vertebrate in need of such an enhanced or modulated immune response the composition of claim 25;

wherein said polypeptide is an immunogenic or immunomodulatory polypeptide, and wherein said immunogenic or immunomodulatory polypeptide is expressed in the vertebrate in a sufficient amount to induce a desired immune response.

30. A pharmaceutical kit comprising:

(a) a container holding about 1 ng to about 30 mg of a polynucleotide which operably encodes an interferon-omega polypeptide within vertebrate cells in vivo; and (b) an amount of sodium phosphate which, when dissolved in an prescribed volume of distilled water, results in an aqueous solution with a molar concentration of said salt from about 20 mM to about 300 mM, or reaction, association, or dissociation products thereof;

whereby said polynucleotide is provided in a prophylactically or therapeutically effective amount to treat a vertebrate.

* * * * *